United States Patent
Cheung et al.

(10) Patent No.: US 6,747,002 B2
(45) Date of Patent: *Jun. 8, 2004

(54) PHARMACOKINETIC AND PHARMACODYNAMIC MODELING OF ERYTHROPOIETIN ADMINISTRATION

(75) Inventors: Wing Cheung, Warren, NJ (US); David Gibson, Bassersdorf (CH); Christine Cote, Skillman, NJ (US); Els Vercammen, Dietlikon (CH)

(73) Assignee: Ortho-McNeil Pharmaceutical, Inc., Raritan, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/569,612

(22) Filed: May 10, 2000

(65) Prior Publication Data

US 2003/0198691 A1 Oct. 23, 2003

Related U.S. Application Data

(60) Provisional application No. 60/133,418, filed on May 11, 1999.

(51) Int. Cl.⁷ ................... A61K 38/19; C97K 14/505
(52) U.S. Cl. ............................... 514/8; 530/351
(58) Field of Search ............... 514/8; 530/351; 930/90; 702/19; 703/11

(56) References Cited

U.S. PATENT DOCUMENTS

| | | | |
|---|---|---|---|
| 4,732,889 A | 3/1988 | Cynshi et al. | 514/8 |
| 4,748,600 A | 5/1988 | Urquhart | 368/10 |
| 5,354,934 A | 10/1994 | Pitt et al. | 514/8 |
| 5,416,071 A | 5/1995 | Igari et al. | 514/8 |
| 5,541,158 A | 7/1996 | Vance et al. | 514/8 |
| 5,674,534 A | 10/1997 | Zale et al. | 424/501 |
| 5,739,277 A | 4/1998 | Presta et al. | 530/326 |

FOREIGN PATENT DOCUMENTS

| | | |
|---|---|---|
| EP | 0 902 085 A1 * | 3/1999 |
| JP | 2-96535 | 4/1990 |

OTHER PUBLICATIONS

Salmonson, "Pharmacokinetic and Pharmacodynamic Studies on Recombinant Human Erythropoietin", Scandinavian Journal of Urology and Nephrology, (1990), suppl. 129, pp. 1–66.*

Salmonson, T., "Pharmacokinetic and Pharmacodynamic Studies on Recombinant Human Erythropoietin," *J. Uro. Nephrol. Suppl.* 1990 0(129), pp 1–66. BIOSIS No. 1990:49718, Abstract only.

Matsushia, et al., "A computer program (PPMODELS) with NeXTSTEP for clcutating distribution of drugs based on physiological pharmacokinetic model," Sch. Med., Kanazawa Univ 1996 22(2) pp 123–132 Abstract only.

Physicians Desk Reference, 51rst ed. (1997) pp 489–495 Medical Economics Company. Inc., Montvale NJ.

Wichmann, et al., "A mathematical model of erythropoiesis in mice and rats," *Cell Tiissue Kinet.* (1989) 22(1) pp 31–49.

Colburn, et al., "Pharmacokinetic Analysis of Drug Concentration Data Obtained during Repetitive Drug Administration," *J. Pharmaceutical Sci.* (1977) 66(4) pp 530–533.

Walton, et al., "Computer support for determining drug dose systematic review and meta–analysis." *Brit. Medical Journal* (1999) 318 pp 984–990.

McMahon, et al. "Pharmackinetics and effects of recombinant human erythropoietin after intravenous and subcutaneous injections in healthy volunteers," *Blood* (1990) 76(9) pp1718–1722.

Hu, Chuanpu, et al. "Comparison of Some Control Strategies for Three–Compartment PK/PD Models," *J. of Pharacokinetics and Biopharmaceutics,* Biopharmaceutics 1994 22(6) 525–550.

Gobburu "Role of dosage regimen in controlling indirect pharmacodynamic responses," *Adv. Drug Delivery Reviews,* (1998) 33 pp 221–233.

Port, R. E. et al., "Predicting the time course of hemoglobin in children treated with erythropoietin for renal anaemia," *Br. J. Clin. Pharmacol* (1998) 46(5) pp 461–466.

* cited by examiner

*Primary Examiner*—Marjorie Moran
(74) *Attorney, Agent, or Firm*—Preston Gates Ellis & Rouvelas Meeds LLP

(57) ABSTRACT

The present invention relates to systems and methods for obtaining optimized EPO dosage regimens for a desired pharmacodynamic/pharmacokinetic response. The system includes choosing one or more EPO dosage regimens, then using a PK/PD model to determine the pharmacodynamic/pharmacokinetic profile of one or more EPO dosage regimens, and finally selecting one of the EPO dosage regimens for administration to achieve the desired pharmacodynamic/pharmacodynamic response based on the EPO profile.

30 Claims, 99 Drawing Sheets

PHARMACOKINETIC PARAMETERS FOR INTRAVENOUS AND SUBCUTANEOUS EPO DOSES

| PARAMETER | ESTIMATE | CV% |
|---|---|---|
| $V_{max}$ (IU/hr) | 138.5 | |
| $K_m$ (IU/l) | 20940 | |
| $V_d$ (l/kg) | 0.0558 | |
| $k_a$ (hr$^{-1}$) | 0.0219 | 4.836 |
| Fr | 0.131 | 7.291 |
| $\tau$ (Lower doses, hr) | 44 | |
| $\tau$ (Higher doses, hr) | 60 | |

FIG. 3

BIOAVAILABILITY VALUES FOR SUBCUTANEOUS EPO

| DOSE (IU/kg) | F (fitted) | F (linear regression) | F (deconvolution) |
|---|---|---|---|
| 300 | 0.464 | 0.463 | 0.36 |
| 450 | 0.614 | 0.50 | 0.56 |
| 600 | 0.535 | 0.538 | 0.51 |
| 900 | 0.651 | 0.613 | 0.61 |
| 1200 | 0.631 | 0.688 | 0.57 |
| 1350 | 0.748 | 0.752 | 0.73 |
| 1800 | 0.823 | 0.836 | 0.83 |
| 2400 | 1.00 | 0.987 | 1.00 |

FIG. 8

PHARMACODYNAMIC PARAMETERS FOR SUBCUTANEOUS EPO EFFECTS

|  | PARAMETER | ESTIMATE |
|---|---|---|
| ESTIMATED: | Ks (cells/l/hr) | $0.3709 \times 10^{10}$ |
|  | SC50 (IU/l) | 22.58 |
|  | TP (hr) | 81.96 |
| FIXED: |  |  |
|  | $R_L$ (hr) | 72 |
|  | $RCB_L$ (hr) | 2880 |
|  | Hb (pg/cell) | 29.5 |
|  | Threshold (=SC50; IU/l) | 22.58 |

FIG.13

| Study Type/Description | Study Identifier | Ref No. |
|---|---|---|
| Pharmacokinetics/Pharmacodynamics<br>    Single-center, open-label, parallel design, randomized study conducted in 36 healthy subjects (36 enrolled and analyzed for safety; 34 completed and analyzed for pharmacokinetic and pharmacodynamic [PK/PD]). Subjects were randomized to two treatment groups and received Epoetin alfa as either the standard cancer regimen (150 IU/kg s.c. t.i.w.) or a weekly fixed dose regimen (40,000 IU s.c. q.w.) for 4 wk. | EPO-PHI-373<br>(Pivotal) | 1 |
| Pharmacokinetics/Pharmacodynamics<br>    Single-center, open-label, parallel design, randomized study conducted in 49 healthy subjects (49 enrolled and analyzed for safety; 46 completed and analyzed for PK/PD). Subjects were randomized to two treatment groups and received Epoetin alfa as either the standard cancer regimen (150 IU/kg s.c. t.i.w.) or a weekly fixed dose regimen (40,000 IU s.c. q.w.) for 4 wk. | EPO-PHI-370<br>(Supportive) | 2 |
| Pharmacokinetics/Pharmacodynamics<br>    Open-label, randomized, placebo controlled, parallel-group, single-center study conducted in 32 subjects (32 enrolled and analyzed for safety; 30 completed and analyzed for PK/PD). Subjects were randomized into three treatment groups (N = 5 each) to receive one of the six treatments (450-, 900-, 1350-, and 1800-IU/kg single s.c. dose, and 150-IU/kg s.c. t.i.w. for 4 wk). | EPO-PHI-358<br>(Pilot exploratory) | 3 |
| Pharmacokinetics/Pharmacodynamics<br>    Open-label, randomized, placebo controlled, parallel-group, single-center study conducted in 30 subjects. Subjects were randomized into six treatment groups (N = 5 each) to receive one of the six treatments (300-, 600-, 1200-, and 2400-IU/kg single s.c. dose, and 600-IU/kg s.c. q.w. for 4 wk). | EPO-PHI-359<br>(Pilot exploratory) | 4 |

FIG. 17

| Applicant: | The R.W. Johnson Pharmaceutical Research Institute | | | | | | | |
|---|---|---|---|---|---|---|---|---|
| Drug: | Epoetin Alfa Once Weekly Dosing | | | | | | | |
| NDA No.: | Insert NDA No. | | | | | | | |

| Study No (Ref No.) | Study Type | Dosage Form(s) Study Design | Dose | Batch No. Plant/Date Manufactured | No. of Subjects | Related IND or NDA No.s | Submission Date | Applicant Conclusion | Previous Agency Responses on Study with Date of Correspondence |
|---|---|---|---|---|---|---|---|---|---|
| RWJPRI Clinical Study EPO-PHI-373 (1) | s.c. | 10,000 IU/ml solution for s.c. injection (Formula FD 22512-000-T-45) | 150 IU/kg t.i.w. s.c. administration for 4 wk | 10,000 IU/ml formulation: 99KS077 Manufactured at Cilag AG Switzerland in Oct 1999 | 36 enrolled 34 analyzed | NA | NA | Despite the difference in total exposure of erythropoietin in serum (AUC of Epoetin alfa) after the 150-IU/kg t.i.w. and the 40,000-IU q.w. dosing regimens, the hemoglobin responses to the two regimens were similar. | |
| | | 40,000 IU/ml solution for s.c. injection (Formula FD 22512-000-AA-45) | 40,000 IU q.w. s.c. administration for 4 wk | 40,000 IU/ml formulation: 99KS091 Manufactured at Cilag AG Switzerland in Oct 1999 | | | | | |
| | | Single-center, open-label, parallel-design, randomized study in healthy subjects. Two parallel treatment groups: 150 IU/kg s.c. t.i.w. x 4 wk and 40,000 IU q.w. x 4 wk. | | | | | | | |

FIG. 18A

| Applicant: | The R.W. Johnson Pharmaceutical Research Institute | | | | | | | |
|---|---|---|---|---|---|---|---|---|
| Drug: | Epoetin Alfa Once Weekly Dosing | | | | | | | |
| NDA No.: | Insert NDA No. | | | | | | | |

| Study No (Ref No.) | Study Type | Dosage Form(s) Study Design | Dose | Batch No. Plant/Date Manufactured | No. of Subjects | Related IND or NDA No.s | Submission Date | Applicant Conclusion | Previous Agency Responses on Study with Date of Correspondence |
|---|---|---|---|---|---|---|---|---|---|
| RWJPRI Clinical Study EPO-PHI-370 (2) | s.c. | 10,000 IU/ml solution for s.c. injection (Formula FD 22512-000-C-45) 40,000 IU/ml solution for s.c. injection (Formula FD 22512-000-AC-45) Single-center, open-label, parallel-design, randomized study in healthy subjects. Two parallel treatment groups: 150 IU/kg s.c. t.i.w. x 4 wk and 40,000 IU q.w. x 4 wk. | 150 IU/kg t.i.w. s.c. administration for 4 wk 40,000 IU q.w. s.c. administration for 4 wk | 10,000 IU/ml formulation: Lot D000123 Manufactured at Amgen Inc. Thousand Oaks, CA 40,000 IU/ml formulation: Lot D000175 Manufactured at Amgen Inc. Thousand Oaks, CA | 49 enrolled 46 analyzed | IND BB-IND-2318 | Protocol 01 Jul 1999 Ammended Protocols | Despite the difference in total exposure of erythropoietin in serum (AUC of Epoetin alfa) after the 150-IU/kg t.i.w. and the 40,000-IU q.w. dosing regimens, the hemoglobin responses to the two regimens were similar. | |

| Applicant: | | The R.W. Johnson Pharmaceutical Research Institute | | | | | |
|---|---|---|---|---|---|---|---|
| Drug: | | Epoetin Alfa Once Weekly Dosing | | | | | |
| NDA No.: | | Insert NDA No. | | | | | |
| Study No (Ref No.) | Study Type | Dosage Form(s) Study Design | Dose | Batch No. Plant/Date Manufactured | No. of Subjects | Related IND or NDA No.s | Submission Date | Applicant Conclusion | Prevous Agency Responses on Study with Date of Correspondence |
| RWJPRI Clinical Study EPO-PHI-358 (3) | s.c. | 40,000 IU/ml solution for s.c. administration (Formula FD 22512-000-J-45)<br><br>Open-label, randomized, placebo controlled, parallel-group, single center study conducted in 32 subjects (32 enrolled and analyzed for safety; 30 completed and analyzed for PK/PD). Subjects were randomized into six treatment | Single s.c. dose: 450, 900, 1350, 1800 IU/kg<br><br>Multiple s.c. dose: 150 IU/kg t.i.w. for 4 wk | 5C903J, Manufactured at Hoffman La-Roche, Basel Switzerland; March 1995 | 32 enrolled 30 analyzed | IND BB-IND-2318 | Protocol 06 May 1996<br><br>Amended Protocol 06 May 1996 | Pharmacological response to Epoetin alfa is a function of dose and dosing regimen. The absorption rate of Epoetin alfa after subcutaneous administration was independent of dose. Clearance of Epoetin alfa was dose-dependent - it decreased with increasing dose. There was an increasing trend of AUC of reticulocytes with AUC of Epoetin alfa for single doses. A continuous pharmacological response (a continuous production of reticulocytes and sustained elevation of | |

1/2

| Applicant:<br>Drug:<br>NDA No.: | The R.W. Johnson Pharmaceutical Research Institute<br>Epoetin Alfa Once Weekly Dosing<br>Insert NDA No. | | | | | | | |
|---|---|---|---|---|---|---|---|---|
| Study No<br>(Ref No.) | Study<br>Type | Dosage Form(s)<br>Study Design | Dose | Batch No.<br>Plant/Date<br>Manufactured | No. of<br>Subjects | Related<br>IND or<br>NDA No.s | Submission<br>Date | Applicant<br>Conclusion | Previous Agency<br>Responses on Study with<br>Date of Correspondence |
| | | groups (N = 5 each) to receive one of the six treatments (placebo 450, 900, 1350, and 1800 IU/kg single dose, and 150 IU/kg t.i.w. for 4 wk). | | | | | | hemoglobin) requires Epoetin alfa serum concentration to be maintained continuously (such as after 150 IU/kg t.i.w. dosing regimen) or intermittently (such as after the 600-IU/kg q.w. dosing regimen) above endogenous level. | 1/2 |

| Applicant: | | The R.W. Johnson Pharmaceutical Research Institute | | | | | | |
|---|---|---|---|---|---|---|---|---|
| Drug: | | Epoetin Alfa Once Weekly Dosing | | | | | | |
| NDA No.: | | Insert NDA No. | | | | | | |
| Study No (Ref No.) | Study Type | Dosage Form(s) Study Design | Dose | Batch No. Plant/Date Manufactured | No. of Subjects | Related IND or NDA No.s | Submission Date | Applicant Conclusion | Previous Agency Responses on Study with Date of Correspondence |
| RWJPRI Clinical Study EPO-PHI-359 (4) | s.c. | 40,000 IU/ml solution for s.c. administration (Formula FD 22512-000-J-45) Open-label, randomized, placebo controlled, parallel-group, single center study conducted in healthy subjects. Subjects were randomized into six treatment groups (N = 5 each) to receive one of the six treatments (placebo 300, | Single s.c. dose: 300, 600, 1200, 2400 IU/kg Multiple s.c. doses: 600 IU/kg q.w. for 4 wk | 5C903J, Manufactured at Hoffman La-Roche, Basel Switzerland; March 1995 | 30 enrolled 30 analyzed | IND BB-IND-2318 | 06 May 1996 | Pharmacological response to Epoetin alfa is a function of dose and dosing regimen. The absorption rate of Epoetin alfa after subcutaneous administration was independent of dose. Clearance of Epoetin alfa was dose-dependent - it decreased with increasing dose. There was an increasing trend of AUC of reticulocytes with AUC of Epoetin alfa for single doses. A continuous pharmacological response (a continuous production of reticulocytes and sustained elevation of | |

| Applicant: | The R.W. Johnson Pharmaceutical Research Institute | | | | | | | |
|---|---|---|---|---|---|---|---|---|
| Drug: | Epoetin Alfa Once Weekly Dosing | | | | | | | |
| NDA No.: | Insert NDA No. | | | | | | | |
| Study No (Ref No.) | Study Type | Dosage Form(s) Study Design | Dose | Batch No. Plant/Date Manufactured | No. of Subjects | Related IND or NDA No.s | Submission Date | Applicant Conclusion | Previous Agency Responses on Study with Date of Correspondence |
| | | 600, 1200, 2400 IU/kg and 600 IU/kg q.w. for 4 wk). | | | | | | hemoglobin) requires Epoetin alfa serum concentration to be maintained continuously (such as after 150 IU/kg t.i.w. dosing regimen) or intermittently (such as after the 600-IU/kg q.w. dosing regimen) above endogenous level. | |

| Applicant: | The R.W. Johnson Pharmaceutical Research Institute | | | | | |
|---|---|---|---|---|---|---|
| Drug: | Epoetin Alfa Once Weekly Dosing | | | | | |
| NDA No.: | Insert NDA No. | | | | | |

| Study | Dose | $C_{max}$ (mIU/mL) | $t_{max}$ (h) | $AUC^a$ (mIU·h/mL) | CL/F (mL/h/kg) | $t_{1/2}$ (h) |
|---|---|---|---|---|---|---|
| Single Subcutaneous Dose Administration | | | | | | |
| EPO359 | 300 IU/kg | 429 ± 86 (20.0%) | 22.8 ± 8.1 (36.5%) | 20056 ± 4138 (20.6%) | 15.5 ± 3.1 (20.2%) | 68.2 ± 52.2 (76.6%) |
| EPO358 | 450 IU/kg | 1263 ± 290 (23.0%) | 15.6 ± 5.8 (37.0%) | 45498 ± 12342 (27.1%) | 10.4 ± 2.6 (24.9%) | 24.2 ± 3.2 (13.2%) |
| EPO359 | 600 IU/kg | 1263 ± 486 (38.5%) | 27.6 ± 9.1 (33.0%) | 55475 ± 16384 (29.5%) | 11.8 ± 4.2 (35.5%) | 29.3 ± 9.4 (32.0%) |
| EPO358 | 900 IU/kg | 2235 ± 599 (26.8%) | 22.2 ± 12.7 (57.0%) | 103154 ± 28024 (27.2%) | 9.36 ± 2.97 (31.7%) | 36.0 ± 13.5 (37.3%) |
| EPO359 | 1200 IU/kg | 2256 ± 710 (31.4%) | 26.4 ± 7.8 (29.4%) | 119932 ± 44217 (36.9%) | 11.2 ± 4.2 (37.7%) | 78.5 ± 95.4 (122%) |
| EPO358 | 1350 IU/kg | 3755 ± 879 (23.4%) | 23.4 ± 8.8 (37.8%) | 174193 ± 41417 (23.8%) | 8.23 ± 2.57 (31.3%) | 33.4 ± 2.4 (7.2%) |
| EPO358 | 1800 IU/kg | 4370 ± 1673 (38.3%) | 28.8 ± 7.8 (27.2%) | 258600 ± 101175 (39.1%) | 7.64 ± 2.22 (29.1%) | 32.4 ± 8.4 (25.9%) |
| EPO359 | 2400 IU/kg | 6819 ± 764 (11.2%) | 25.2 ± 6.2 (24.7%) | 429441 ± 32139 (7.5%) | 5.61 ± 0.44 (7.8%) | 43.6 ± 25.9 (59.5%) |
| Multiple Subcutaneous Dose Administration | | | | | | |
| EPO358 Wk 4 | 150 IU/kg t.i.w. | 252 ± 71 (28.0%) | NA | 16582 ± 4256 (25.7%) | 28.7 ± 7.8 (27.1%) | 25.9 ± 7.1 (27.2%) |
| EPO359 Wk 1 | 600 IU/kg q.w. | 1502 ± 384 (25.6%) | 21.6 ± 6.1 (28.5%) | 63439 ± 10893 (17.2%) | 9.70 ± 1.8 (18.1%) | 28.3 ± 7.5 (26.3%) |
| EPO359 Wk 4 | 600 IU/kg q.w. | 1278 ± 213 (16.6%) | 24.0 ± 8.7 (36.4%) | 50725 ± 6774 (13.4%) | 12.0 ± 1.6 (13.2%) | 28.1 ± 7.0 (24.9%) |

FIG. 19

| Applicant: | The R.W. Johnson Pharmaceutical Research Institute |
| --- | --- |
| Drug: | Epoetin Alfa Once Weekly Dosing |
| NDA No.: | Insert NDA No. |

| Study | Dose | $C_{max}$ (mIU/mL) | $t_{max}$ (h) | AUC[a] (mIU·h/mL) | CL/F (mL/h/kg) | $t_{1/2}$ (h) |
| --- | --- | --- | --- | --- | --- | --- |
| | | Single Subcutaneous Dose Administration | | | | |
| EPO370 Wk 4 | 150 IU/kg t.i.w. | 191 ± 100 (52.3%) | NA | 13446 ± 4374 (32.5%) | 37.1 ± 12.3 (33.1%) | 31.8 ± 13.4 (42.1%) |
| EPO370 Wk 4 | 40,000 IU q.w. | 785 ± 427 (54.4%) | 18 ± 5 (29.4%) | 30084 ± 13516 (44.9%) | 23.2 ± 10.8 (46.5%) | 39.3 ± 7.1 (18.1%) |
| EPO373 Wk 4 | 150 IU/kg t.i.w. | 143 ± 54 (37.8%) | NA | 8587 ± 1521 (17.7%) | 54.1 ± 10.1 (18.7%) | 19.4 ± 8.1 (41.5%) |
| EPO373 Wk 4 | 40,000 IU q.w. | 861 ± 445 (51.7%) | 16 ± 8 (45.6%) | 25747 ± 9062 (35.2%) | 24.7 ± 7.2 (29.1%) | 15.0 ± 6.1 (40.9%) |

[a] AUC(0-168h) during a dose week for multiple dose regimens and AUC(0-672h) during the 4-wk of study period for single doses.

NA = Not applicable

| Applicant: | The R.W. Johnson Pharmaceutical Research Institute | | | |
|---|---|---|---|---|
| Drug: | Epoetin Alfa Once Weekly Dosing | | | |
| NDA No.: | Insert NDA No. | | | |

| Study No. Primary Supportive (Ref. No.) | Type of Biological Fluid | Analysis Method | Sensitivity of Method Range (mU/mL) | Specificity of Assay |
|---|---|---|---|---|
| EPO-PHI-358 Pilot /Exploratory | Serum | RIA (RWJPRI)[23] | 7.8-125 | Detects both endogenous and exogenous EPO |
| EPO-PHI-359 Pilot /Exploratory | Serum | RIA (RWJPRI)[23] | 7.8-125 | Detects both endogenous and exogenous EPO |
| EPO-PHI-370 Supportive | Serum | RIA (PPD)[24] | 7.8-125 | Detects both endogenous and exogenous EPO |
| EPO-PHI-373 Pivotal | Serum | ELISA (PPD)[25] | 7.8-125 | Detects both endogenous and exogenous EPO |

FIG. 20

Mean ± SD Demographic and Baseline Parameters for Subjects Enrolled in Clinical Studies EPO-PHI-358 and EPO-PHI-359

| Parameter | EPO-PHI-358 (N=32) | EPO-PHI-359 (N=30) |
|---|---|---|
| Age (yr) | 35.7 ± 7.25 | 34.1 ± 6.76 |
| Weight (kg) | 76.7 ± 7.10 | 77.7 ± 8.83 |
| Height (cm) | 174.2 ± 7.69 | 174.7 ± 7.88 |
| Race | | |
| White | 8 (25%) | 9 (30%) |
| Black | 4 (13%) | 1 (3%) |
| Asian | 0 (0%) | 1 (3%) |
| Hispanic | 20 (63%) | 19 (63%) |

FIG. 21

Mean ± SD (%CV) Pharmacokinetic and Pharmacodynamic Parameters (Clinical Studies EPO-PHI-358 and EPO-PHI-359)

| Study | Dose | $C_{max}$ (mIU/mL) | $t_{max}$ (h) | $AUC^a$ (mIU·h/mL) | CL/F (mL/h/kg) | $t_{1/2}$ (h) | %RET$^b$ AUC (%·h) |
|---|---|---|---|---|---|---|---|
| EPO359 | 300 IU/kg | 429 ± 86 (20.0%) | 22.2 ± 8.1 (36.5%) | 20056 ± 4138 (20.6%) | 15.5 ± 3.1 (20.2%) | 68.2 ± 52.2 (76.6%) | 1280 ± 157 (12.3%) |
| EPO358 | 450 IU/kg | 1263 ± 290 (23.0%) | 15.6 ± 5.8 (37.0%) | 45498 ± 12342 (27.1%) | 10.4 ± 2.6 (24.9%) | 24.2 ± 3.2 (13.2%) | 1191 ± 164 (13.8%) |
| EPO359 | 600 IU/kg | 1263 ± 486 (38.5%) | 27.6 ± 9.1 (33.0%) | 55475 ± 16384 (29.5%) | 11.8 ± 4.2 (35.5%) | 29.3 ± 9.4 (32.0%) | 1224 ± 227 (18.5%) |
| EPO358 | 900 IU/kg | 2235 ± 599 (26.8%) | 22.2 ± 12.7 (57.0%) | 103154 ± 28024 (27.2%) | 9.36 ± 2.97 (31.7%) | 36.0 ± 13.5 (37.3%) | 1296 ± 274 (21.1%) |
| EPO359 | 1200 IU/kg | 2256 ± 710 (31.4%) | 26.4 ± 7.8 (29.4%) | 119932 ± 44217 (36.9%) | 11.2 ± 4.2 (37.7%) | 78.5 ± 95.4 (122%) | 1413 ± 315 (22.3%) |
| EPO358 | 1350 IU/kg | 3755 ± 879 (23.4%) | 23.4 ± 8.8 (37.8%) | 174193 ± 41417 (23.8%) | 8.23 ± 2.57 (31.3%) | 33.4 ± 2.4 (7.2%) | 1406 ± 146 (10.4%) |
| EPO358 | 1800 IU/kg | 4370 ± 1673 (38.3%) | 28.8 ± 7.8 (27.2%) | 258600 ± 101175 (39.1%) | 7.64 ± 2.22 (29.1%) | 32.4 ± 8.4 (25.9%) | 1679 ± 407 (24.2%) |
| EPO359 | 2400 IU/kg | 6819 ± 764 (11.2%) | 25.2 ± 6.2 (24.7%) | 429441 ± 32139 (7.5%) | 5.61 ± 0.44 (7.8%) | 43.6 ± 25.9 (59.5%) | 1720 ± 233 (13.5%) |
| EPO358 Wk 4 | 150 IU/kg t.i.w. | 252 ± 71 (28.0%) | NA | 16582 ± 4256 (25.7%) | 28.7 ± 7.8 (27.1%) | 25.9 ± 7.1 (27.2%) | |

FIG. 24

Mean ± SD (%CV) Pharmacokinetic and Pharmacodynamic Parameters (Clinical Studies EPO-PHI-358 and EPO-PHI-359)

| Study | Dose | $C_{max}$ (mIU/mL) | $t_{max}$ (h) | $AUC^a$ (mIU·h/mL) | CL/F (mL/h/kg) | $t_{1/2}$ (h) | %RET$^b$ AUC (%·h) |
|---|---|---|---|---|---|---|---|
| EPO358 Wk 1-4 | 150 IU/kg t.i.w. | | | | | | 1749 ± 406 (23.2%) |
| EPO359 Wk 1 | 600 IU/kg/wk | 1502 ± 384 (25.6%) | 21.6 ± 6.1 (28.5%) | 63439 ± 10893 (17.2%) | 9.70 ± 1.8 (18.1%) | 28.3 ± 7.5 (26.3%) | |
| EPO359 Wk 4 | 600 IU/kg/wk | 1278 ± 213 (16.6%) | 24.0 ± 8.7 (36.4%) | 50725 ± 6774 (13.4%) | 12.0 ± 1.6 (13.2%) | 28.1 ± 7.0 (24.9%) | |
| EPO359 Wk 1-4 | 600 IU/kg/wk | | | | | | 2220 ± 493 (22.2%) |

$^a$ AUC(0-168) during a dosing week for multiple dose regimens and AUC(0-672) during the 4 wk of study period for single doses.

$^b$ Percent reticulocyte AUC from time-zero to Day 29 after initiation of drug administration.

NA = not applicable

DEMOGRAPHIC DATA OF SUBJECTS IN CLINICAL STUDY EPO-PHI-370

| TREATMENT | GENDER | WEIGHT (kg) | AGE (yr) | BASELINE HEMOGLOBIN (g/dL) |
|---|---|---|---|---|
| 150 IU/kg t.i.w. | Male (N = 9) | 74.3 ± 8.5 (63.2-85.0) | 32.1 ± 5.5 (26.0-41.0) | 14.7 ± 0.8 (13.5-15.6) |
| | Female (N = 15) | 62.4 ± 10.3 (50.5-76.8) | 34.6 ± 7.3 (21.0-46.0) | 13.1 ± 0.9 (11.6-14.8) |
| | Overall (N = 24) | 66.8 ± 11.1 (50.5-85.0) | 33.7 ± 6.7 (21.0-46.0) | 13.7 ± 1.1 (11.6-15.6) |
| 40,000 IU q.w. | Male (N = 14) | 72.4 ± 7.0 (61.8-84.5) | 32.1 ± 8.6 (19.0-44.0) | 14.6 ± 0.6 (13.5-15.6) |
| | Female (N = 8) | 65.2 ± 7.8 (57.3-81.4) | 35.1 ± 9.9 (19.0-45.0) | 13.1 ± 0.7 (11.9-13.9) |
| | Overall (N = 22) | 69.8 ± 8.0 (57.3-84.5) | 33.2 ± 9.0 (19.0-45.0) | 14.1 ± 1.0 (11.9-15.6) |

FIG. 29

MEAN ± SD (%CV) PHARMACOKINETIC PARAMETERS (PROTOCOL EPO-PHI-370)

| Parameter | 150 (IU/kg t.i.w.) | 40,000 (IU q.w.) | RATIO[a] |
|---|---|---|---|
| $C_{max}$ (mIU/mL) | 191±100 (52.3%) | 785±427 (54.4%) | 4.11 |
| $C_{min}$ (mIU/mL) | 39±18 (45.9%) | 13±9 (73.1%) | 0.33 |
| $t_{max}$ (h) | ND | 18±5 (29.4%) | ND |
| AUC(0-168) (mIU·h/mL) | 13446±4374 (32.5%) | 30084±13516 (44.9%) | 2.24 |
| CL/F (mL/h/kg) | 37.1±12.3 (33.1) | 23.2±10.8 (46.5) | 0.63 |

[a] Parameter ratio of the mean values, 40,000 IU q.w./150 IU/kg t.i.w.
ND = Not Determined

FIG. 31

Mean ± SD (%CV) Pharmacodynamic Parameters Corrected for Baseline Value (Protocol EPO-PHI-370)

| Treatment Group | Auc(RETI)[a]<br>(%·d) | AUC(HEMO)[b]<br>(g·d/dL) | AUC(RBC)[c]<br>(x$10^{12}$cells·d/L) |
|---|---|---|---|
| 150 IU/kg t.i.w. | | | |
| Male | 56.8 ± 21.5 | 26.4 ± 11.6 | 12.0 ± 4.6 |
| (N = 9) | (37.8%) | (43.7%) | (37.8%) |
| Female | 66.6 ± 19.8 | 28.7 ± 18.6 | 12.3 ± 5.5 |
| (N = 15) | (29.7%) | (64.9%) | (44.9%) |
| All Subjects | 62.9 ± 20.5[d] | 27.9 ± 16.1 | 12.2 ± 5.1 |
| (N = 24) | (32.7%) | (57.8%) | (41.7%) |
| 40,000 IU q.w. | | | |
| Male | 75.5 ± 9.8 | 35.3 ± 11.2 | 14.1 ± 4.0 |
| (N = 14) | (12.9%) | (31.8%) | (28.6%) |
| Female | 80.3 ± 10.1 | 23.5 ± 11.5 | 10.9 ± 3.3 |
| (N = 8) | (12.5%) | (48.8%) | (30.6%) |
| All Subjects | 77.2 ± 9.9[d] | 31.0 ± 12.5 | 12.9 ± 4.0 |
| (N = 22) | (12.8%) | (40.3%) | (31.1%) |
| Ratio for All Subjects[e] | 1.23 | 1.11 | 1.06 |
| All Females[f] | 71.3 ± 18.0 | 26.9 ± 16.4 | 11.8 ± 4.9 |
| (N = 23) | (25.3%) | (61.0%) | (41.0%) |
| All Males[g] | 68.2 ± 17.7 | 31.8 ± 12.0 | 13.3 ± 4.3 |
| (N = 23) | (25.9%) | (37.6%) | (32.0%) |

FIG. 34

Mean ± SD Demographic Data of Subjects in Clinical Study EPO-PHI-373

| Treatment | Gender | Weight (kg) | Age (yr) | Baseline Hemoglobin (g/dL) |
|---|---|---|---|---|
| 150 IU/kg t.i.w. | Male (N = 9) | 72.1 ± 8.2 (64.5-90.5) | 26.4 ± 5.2 (21.0-37.0) | 14.0 ±0.4 (13.2-14.8) |
| | Female (N = 8) | 61.0 ± 4.8 (53.3-66.4) | 24.3 ± 3.5 (20.0-29.0) | 12.8 ± 0.7 (11.7-13.8) |
| | Overall (N = 17) | 66.9 ± 8.7 (53.3-90.5) | 25.4 ± 4.5 (20.0-37.0) | 13.4 ± 0.8 (11.7-14.8) |
| 40,000 IU q.w. | Male (N = 9) | 77.0 ± 12.8 (67.3-106) | 29.4 ± 5.5 (19.0-36.0) | 13.9 ± 0.5 (13.3-14.6) |
| | Female (N = 8) | 63.7 ± 8.8 (51.0-78.0) | 26.5 ± 7.5 (18.0-41.0) | 13.0 ± 0.8 (12.2-14.2) |
| | Overall (N = 17) | 70.7 ± 12.7 (51.0-106) | 28.1 ± 6.5 (18.0-41.0) | 13.5 ± 0.8 (12.2-14.6) |

FIG. 35

Mean ± SD Pharmacokinetic Parameters (Protocol EPO-PHI-373)

| Parameter | 150 (IU/kg t.i.w.) | 40,000 (IU q.w.) | Ratio[a] |
|---|---|---|---|
| $C_{max}$ (mIU/mL) | 143 ± 54 (37.8%) | 861 ± 445 (51.7%) | 6.02(13.2-14.8) |
| $C_{min}$ (mIU/mL) | 18 ± 9 (50.7%) | 3.8 ± 4.3 (114%) | 0.21 |
| $t_{max}$ (h) | ND | 16 ± 8 (45.6%) | ND |
| AUC(0-168) (mIU·h/mL) | 8587 ± 1521 (17.7%) | 25747 ± 9062 (35.2%) | 3.00 |
| CL/F (mL/h/kg) | 51.4 ± 10.1 (18.7%) | 24.7 ± 7.2 (29.1%) | 0.46 |

[a] Parameter ratio of the mean values, 40,000 IU q.w./150 IU/kg t.i.w.

ND = not determined

FIG. 37

Mean ± SD (%CV) Pharmacodynamic Parameters Corrected for Baseline Value (Protocol EPO-PHI-373)

| Treatment Group | Auc(RETI)[a] (%·d) | AUC(HEMO)[b] (g·d/dL) | AUC(RBC)[c] (x10$^{12}$·d/L) |
|---|---|---|---|
| 150 IU/kg t.i.w. | | | |
| Male | 55.1 ± 14.4 | 40.4 ± 13.0 | 13.4 ± 3.9 |
| (N = 9) | (23.1%) | (32.3%) | (29.3%) |
| Female | 59.6 ± 21.3 | 51.1 ± 10.9 | 16.4 ± 4.4 |
| (N = 8) | (35.7%) | (21.4%) | (26.7%) |
| All Subjects | 57.2 ± 17.5 | 45.4 ± 12.9 | 14.8 ± 4.3 |
| (N = 17) | (30.6%) | (28.5%) | (29.0%) |
| 40,000 IU q.w. | | | |
| Male | 58.8 ± 10.4 | 43.5 ± 11.6 | 13.6 ± 4.3 |
| (N = 9) | (17.7%) | (26.6%) | (31.3%) |
| Female | 68.4 ± 14.4 | 52.4 ± 15.0 | 16.9 ± 4.3 |
| (N = 8) | (21.1%) | (28.6%) | (25.5%) |
| All Subjects | 63.3 ± 13.0 | 47.7 ± 13.6 | 15.1 ± 4.5 |
| (N = 17) | (20.5%) | (28.6%) | (29.5%) |
| Ratio for All Subjects[d] | 1.11 | 1.05 | 1.02 |
| All Females[e] | 64.0 ± 18.1 | 51.7 ± 12.7g | 16.6 ± 4.2g |
| (N = 16) | (28.3%) | (24.5%) | (25.3%) |
| All Males[f] | 57.0 ± 12.3 | 41.9 ± 12.0g | 13.5 ± 4.0g |
| (N = 18) | (21.6%) | (28.7%) | (29.5%) |

FIG. 41

Mean = SD (%CV) Pharmacokinetic Parameters (Clinical Studies EPO-PHI-358, EPO-PHI-359, EPO-PHI-370, and EPO-PHI-373)

| Study | Dose | $C_{max}$ (mIU/mL) | $t_{max}$ (h) | $AUC^a$ (mIU·h/mL) | CL/F (mL/h/kg) | $t_{1/2}$ (h) |
|---|---|---|---|---|---|---|
| Single Subcutaneous Dose Administration | | | | | | |
| EPO359 | 300 IU/kg | 429 ± 86 (20.0%) | 22.8 ± 8.1 (36.5%) | 20056 ± 4138 (20.6%) | 15.5 ± 3.1 (20.2%) | 68.2 ± 52.2 (76.6%) |
| EPO358 | 450 IU/kg | 1263 ± 290 (23.0%) | 15.6 ± 5.8 (37.0%) | 45498 ± 12342 (27.1%) | 10.4 ± 2.6 (24.9%) | 24.2 ± 3.2 (13.2%) |
| EPO359 | 600 IU/kg | 1263 ± 486 (38.5%) | 27.6 ± 9.1 (33.0%) | 55475 ± 16384 (29.5%) | 11.8 ± 4.2 (35.5%) | 29.3 ± 9.4 (32.0%) |
| EPO358 | 900 IU/kg | 2235 ± 599 (26.8%) | 22.2 ± 12.7 (57.0%) | 103154 ± 28024 (27.2%) | 9.36 ± 2.97 (31.7%) | 36.0 ± 13.5 (37.3%) |
| EPO359 | 1200 IU/kg | 2256 ± 710 (31.4%) | 26.4 ± 7.8 (29.4%) | 119932 ± 44217 (36.9%) | 11.2 ± 4.2 (37.7%) | 78.5 ± 95.4 (122%) |
| EPO358 | 1350 IU/kg | 3755 ± 879 (23.4%) | 23.4 ± 8.8 (37.8%) | 174193 ± 41417 (23.8%) | 8.23 ± 2.57 (31.3%) | 33.4 ± 2.4 (7.2%) |
| EPO358 | 1800 IU/kg | 4370 ± 1673 (38.3%) | 28.8 ± 7.8 (27.2%) | 258600 ± 101175 (39.1%) | 7.64 ± 2.22 (29.1%) | 32.4 ± 8.4 (25.9%) |
| EPO359 | 2400 IU/kg | 6819 ± 764 (11.2%) | 25.2 ± 6.2 (24.7%) | 429441 ± 32139 (7.5%) | 5.61 ± 0.44 (7.8%) | 43.6 ± 25.9 (59.5%) |
| Multiple Subcutaneous Dose Administration | | | | | | |
| EPO358 Wk 4 | 150 IU/kg t.i.w. | 252 ± 71 (28.0%) | NA | 16582 ± 4256 (25.7%) | 28.7 ± 7.8 (27.1%) | 25.9 ± 7.1 (27.2%) |
| EPO359 Wk 1 | 600 IU/kg q.w. | 1502 ± 384 (25.6%) | 21.6 ± 6.1 (28.5%) | 63439 ± 10893 (17.2%) | 9.70 ± 1.8 (18.1%) | 28.3 ± 7.5 (26.3%) |
| EPO359 Wk 4 | 600 IU/kg q.w. | 1278 ± 213 (16.6%) | 24.0 ± 8.7 (36.4%) | 50725 ± 6774 (13.4%) | 12.0 ± 1.6 (13.2%) | 28.1 ± 7.0 (24.9%) |

FIG. 42

| Applicant: | The R.W. Johnson Pharmaceutical Research Institute | | | | |
|---|---|---|---|---|---|
| Drug: | Epoetin Alfa Once Weekly Dosing | | | | |
| NDA No.: | Insert NDA No. | | | | |

| Study | Dose | $C_{max}$ (mIU/mL) | $t_{max}$ (h) | $AUC^a$ (mIU·h/mL) | CL/F (mL/h/kg) | $t_{1/2}$ (h) |
|---|---|---|---|---|---|---|
| | | Single Subcutaneous Dose Administration | | | | |
| EPO370 Wk 4 | 150 IU/kg t.i.w. | 191 ± 100 (52.3%) | NA | 13446 ± 4374 (32.5%) | 37.1 ± 12.3 (33.1%) | 31.8 ± 13.4 (42.1%) |
| EPO370 Wk 4 | 40,000 IU q.w. | 785 ± 427 (54.4%) | 18 ± 5 (29.4%) | 30084 ± 13516 (44.9%) | 23.2 ± 10.8 (46.5%) | 39.3 ± 7.1 (18.1%) |
| EPO373 Wk 4 | 150 IU/kg t.i.w. | 143 ± 54 (37.8%) | NA | 8587 ± 1521 (17.7%) | 54.1 ± 10.1 (18.7%) | 19.4 ± 8.1 (41.5%) |
| EPO373 Wk 4 | 40,000 IU q.w. | 861 ± 445 (51.7%) | 16 ± 8 (45.6%) | 25,747 ± 9062 (35.2%) | 24.7 ± 7.2 (29.1%) | 15.0 ± 6.1 (40.9%) | a AUC(0-168) during a dose week for multiple dose regimens and AUC(0-672) during the 4-wk of study period for single doses.

NA = Not applicable

Demographic and Baseline Characteristics
(All Subjects in Protocol EPO-PHI-373)

| Characteristic | Epoetin Alfa 150 IU/kg t.i.w. (N=18) | Epoetin Alfa 40,000 IU q.w. (N=18) | Total (N=36) |
|---|---|---|---|
| Sex | | | |
| Male | 9 (50%) | 9 (50%) | 18 (50%) |
| Female | 9 (50%) | 9 (50%) | 18 (50%) |
| Age (years) | | | |
| Mean (SD) | 25.3 (4.34) | 27.7 (6.48) | 26.5 (5.57) |
| Median | 24 | 27.5 | 25.0 |
| Range | 20.0-37.0 | 18.0-41.0 | 18.0-41.0 |
| Weight (kg) | | | |
| Mean (SD) | 66.8 (8.47) | 70.3 (12.51) | 68.6 (10.67) |
| Median | 66.0 | 69.0 | 67.3 |
| Range | 53.3-90.5 | 51.0-105.5 | 51.0-105.5 |
| Height (cm) | | | |
| Mean (SD) | 171.9 (6.94) | 170.9 (8.86) | 171.4 (7.86) |
| Median | 172.8 | 169.5 | 171.8 |
| Range | 160.5-191.0 | 160.5-191.0 | 160.5-191.0 |
| Race | | | |
| White | 17 (94%) | 15 (83%) | 32 (89%) |
| Black | 1 (6%) | 2 (11%) | 3 (8%) |
| Other | 0 (0%) | 1 (6%) | 1 (3%) |

FIG. 47

SELECTED MEAN (SD) [%CV] PHARMACOKINETIC PARAMETERS (SUBJECTS IN THE EFFICACY POPULATION IN PROTOCOL EPO-PHI-373)

| Parameter | 150 IU/kg t.i.w. (n=17) | | 40,000 IU q.w. (n-17) | | Ratio[a] |
|---|---|---|---|---|---|
| | Mean (SD) | [%CV] | Mean (SD) | [%CV] | |
| $C_{max}$ (mIU/mL) | 143 (54) | [37.8%] | 861 (445) | [51.7%] | 6.02 |
| $C_{min}$ (mIU/mL) | 18 (9) | [50.7%] | 3.8 (4.3) | [114%] | 0.21 |
| $t_{max}$ (h) | ND | | 16 (8) | [45.6%] | ND |
| $AUC_{(0-168)}$ (mIU·h/mL) | 8587 (1521) | [17.7%] | 25747 (9062) | [35.2%] | 3.00 |
| CL/F (mL/h/kg) | 54.1 (10.1) | [18.7%] | 24.7 (7.2) | [29.1%] | 0.46 |

[a] Parameter ratio of the mean values, 40,000 IU q.w./150 IU/kg t.i.w.
ND = Not determined

FIG. 50

MEAN (SD) CHANGE FROM BASELINE IN PERCENT RETICULOCYTES (SUBJECTS IN THE EFFICACY POPULATION-PROTOCOL EPO-PHI-373)

| | Epoetin Alfa 150 IU/kg t.i.w. | | | Epoetin Alfa 40,000 IU/kg q.w. | | |
|---|---|---|---|---|---|---|
| | N | Mean (SD) | Range | N | Mean (SD) | Range |
| Baseline | 17 | 1.5 (0.59) | 0.9-2.9 | 17 | 1.4 (0.45) | 0.8-2.5 |
| Change from Baseline to Day | | | | | | |
| Day 3 | 17 | 1.1 (0.68) | -2.0-1.3 | 17 | 0.5 (0.51) | -0.3-1.8 |
| Day 5 | 17 | 1.1 (0.76) | -1.0-2.2 | 17 | 1.7 (0.56) | 0.5-2.7 |
| Day 8 | 17 | 3.1 (0.77) | 1.9-4.3 | 17 | 3.3 (0.97) | 2.0-5.3 |
| Day 10 | 17 | 3.2 (1.30) | 1.8-5.5 | 17 | 3.5 (1.26) | 1.4-6.8 |
| Day 12 | 17 | 2.7 (1.12) | 0.3-5.4 | 17 | 3.3 (0.74) | 2.0-5.5 |
| Day 15 | 17 | 2.6 (1.02) | 1.0-4.8 | 17 | 2.9 (0.76) | 1.6-4.9 |
| Day 17 | 17 | 2.5 (0.94) | -1.7-5.4 | 17 | 1.9 (0.42) | 1.3-2.7 |
| Day 19 | 17 | 1.9 (0.74) | -0.0-3.4 | 17 | 2.4 (0.53) | 1.7-3.6 |
| Day 22 | 17 | 2.1 (0.78) | -0.1-2.9 | 17 | 2.4 (1.00) | 0.7-4.5 |
| Day 24 | 17 | 2.0 (0.73) | 0.3-3.1 | 16 | 1.7 (0.82) | -0.0-3.2 |
| Day 26 | 17 | 1.9 (0.90) | -0.3-4.0 | 17 | 2.1 (0.47) | 1.0-2.7 |
| Day 29 | 17 | 1.7 (0.74) | -0.3-3.2 | 17 | 1.7 (0.46) | 1.0-2.7 |
| Last Visit | 17 | 1.7 (0.74) | -0.3-3.2 | 17 | 1.7 (0.46) | 1.0-2.7 |

FIG. 51

MEAN (SD) CHANGE FROM BASELINE IN HEMOGLOBIN (g/dL) (SUBJECTS IN THE EFFICACY POPULATION-PROTOCOL EPO-PHI-373)

| | Epoetin Alfa 150 IU/kg t.i.w. | | | Epoetin Alfa 40,000 IU/kg q.w. | | |
|---|---|---|---|---|---|---|
| | N | Mean (SD) | Range | N | Mean (SD) | Range |
| Baseline | 17 | 13.4 (0.81) | 11.7-14.8 | 17 | 13.5 (0.79) | 12.2-14.6 |
| Change from Baseline to Day | | | | | | |
| Day 3 | 17 | 0.2 (0.45) | -0.5-1.1 | 17 | 0.5 (0.52) | -0.5-1.5 |
| Day 5 | 17 | 1.3 (0.63) | -0.6-1.8 | 17 | 0.3 (0.37) | -0.4-0.8 |
| Day 8 | 17 | 0.7 (0.54) | -0.4-1.8 | 17 | 0.8 (0.47) | 1.0-1.7 |
| Day 10 | 17 | 0.8 (0.45) | -0.2-1.5 | 17 | 1.1 (0.56) | 0.2-2.4 |
| Day 12 | 17 | 1.1 (0.57) | 0.4-2.2 | 17 | 1.3 (0.65) | 0.1-2.4 |
| Day 15 | 17 | 1.5 (0.72) | 0.2-2.4 | 17 | 1.7 (0.73) | 0.2-2.7 |
| Day 17 | 17 | 2.0 (0.57) | 1.0-3.0 | 17 | 2.1 (0.62) | 1.0-3.2 |
| Day 19 | 17 | 2.2 (0.68) | 1.2-3.2 | 17 | 2.2 (0.69) | 1.2-3.2 |
| Day 22 | 17 | 2.7 (0.74) | 1.4-3.9 | 17 | 2.4 (1.00) | 0.7-4.7 |
| Day 24 | 17 | 2.9 (0.90) | 0.7-4.2 | 16 | 3.0 (0.70) | 1.6-4.0 |
| Day 26 | 17 | 3.0 (0.69) | 1.8-4.3 | 17 | 3.1 (0.74) | 1.9-4.4 |
| Day 29 | 17 | 3.1 (0.86) | 1.4-4.5 | 17 | 3.1 (0.84) | 1.8-4.6 |
| Last Visit | 17 | 3.1 (0.86) | 1.4-4.5 | 17 | 3.1 (0.84) | 1.8-4.6 |

FIG. 53

MEAN (SD) CHANGE FROM BASELINE IN RED BLOOD CELLS ($\times 10^{12}$/L) (SUBJECTS IN THE EFFICACY POPULATION-PROTOCOL EPO-PHI-373)

| | Epoetin Alfa 150 IU/kg t.i.w. | | | Epoetin Alfa 40,000 IU/kg q.w. | | |
|---|---|---|---|---|---|---|
| | N | Mean (SD) | Range | N | Mean (SD) | Range |
| Baseline | 17 | 4.4 (0.30) | 3.8-5.1 | 17 | 4.4 (0.26) | 4.0-4.8 |
| Change from Baseline to Day | | | | | | |
| Day 3 | 17 | 0.1 (0.16) | -0.2-0.4 | 17 | 0.2 (0.19) | -0.2-0.5 |
| Day 5 | 17 | 0.0 (0.18) | -0.2-0.4 | 17 | 0.1 (0.15) | -0.2-0.3 |
| Day 8 | 17 | 0.2 (0.21) | -0.2-0.8 | 17 | 0.2 (0.14) | 0.0-0.5 |
| Day 10 | 17 | 0.2 (0.17) | -0.1-0.5 | 17 | 0.4 (0.18) | 0.1-0.8 |
| Day 12 | 17 | 0.3 (0.21) | -0.1-0.7 | 17 | 0.4 (0.20) | -0.0-0.7 |
| Day 15 | 17 | 0.5 (0.29) | 0.0-0.9 | 17 | 0.5 (0.27) | -0.1-0.9 |
| Day 17 | 17 | 0.7 (0.20) | 0.3-1.0 | 17 | 0.7 (0.21) | 0.4-1.1 |
| Day 19 | 17 | 0.7 (0.24) | 0.3-1.1 | 17 | 0.7 (0.22) | 0.3-1.1 |
| Day 22 | 17 | 0.8 (0.20) | 0.5-1.2 | 17 | 0.8 (0.34) | 0.2-1.4 |
| Day 24 | 17 | 1.0 (0.28) | 0.3-1.3 | 16 | 0.9 (0.23) | 0.4-1.2 |
| Day 26 | 17 | 1.0 (0.18) | 0.7-1.3 | 17 | 0.9 (0.25) | 0.4-1.3 |
| Day 29 | 17 | 1.0 (0.27) | 0.5-1.4 | 17 | 1.0 (0.30) | 0.4-1.4 |
| Last Visit | 17 | 1.0 (0.27) | 0.5-1.4 | 17 | 1.0 (0.30) | 0.4-1.4 |

FIG. 55

MEAN (SD) [%CV] PHARMACODYNAMIC PARAMETERS CORRECTED FOR BASELINE VALUE
(EFFICACY POPULATION IN PROTOCOL EPO-PHI-373)

| TREATMENT GROUP | AUC(RETI)[a] (%·d) MEAN (SD) | [%CV] | AUC(HEMO)[b] (g·d/dL) MEAN (SD) | [%CV] | AUC(RBC)[c] (x10^12 ·d/L) MEAN (SD) | [%CV] |
|---|---|---|---|---|---|---|
| 150 IU/kg t.i.w. | | | | | | |
| Male (N=9) | 55.1 (14.4) | [26.1%] | 40.4 (13.0) | [32.2%] | 13.4 (3.9) | [29.3%] |
| Female (N=8) | 59.6 (21.3) | [35.7%] | 51.1 (10.9) | [21.4%] | 16.4 (4.4) | [26.7%] |
| All Subjects (N=17) | 57.2 (17.5) | [30.6%] | 45.4 (12.9) | [28.5%] | 14.8 (4.3) | [29.0%] |
| 40,000 IU q.w. | | | | | | |
| Male (N=9) | 58.8 (10.4) | [17.7%] | 43.5 (1 1.6) | [26.6%] | 13.6 (4.3) | [31.3%] |
| Female (N=8) | 68.4 (14.4) | [21.1%] | 52.4 (15.0) | [28.6%] | 16.9 (4.3) | [25.5%] |
| All Subjects (N=17) | 63.3 (13.0) | [20.5%] | 47.7 (13.6) | [28.6%] | 15.1 (4.5) | [29.5%] |
| Ratio for All Subjects[d] | 1.1 | | 1.05 | | 1.02 | |
| All Females[e] (N=16) | 64.0 (18.1) | [28.3%] | 51.7 (12.7) | [g] [24.5%] | 16.6 (4.2) | [g] [25.3%] |
| All Males[f] (N=18) | 57.0 (12.3) | [21.6%] | 41.9 (12.0) | [g] [28.7%] | 13.5 (4.0) | [g] [29.5%] |

%CV = percent coefficient of variation
[a] AUC of % reticulocytes over the one month study period and corrected for predose baseline value.
[b] AUC of hemoglobin over the one month study period and corrected for predose baseline value.
[c] AUC of red blood cells over the one month study period and corrected for predose baseline value.
[d] Ratios of 40,000 IU q.w. to 150 IU/kg t.i.w. mean parameter values for all subjects.
[e] Including all female subjects in both treatment groups.
[f] Including all male subjects in both treatment groups.
[g] Statistically different (p<0.05) between male and female subjects

FIG. 57

| Body System<br>  Preferred Term | Epoetin Alfa<br>150 IU/kg t.i.w.<br>(N=18) | | Epoetin Alfa<br>40,000 IU q.w.<br>(N=18) | |
|---|---|---|---|---|
| Any adverse event | 13 | (72%) | 12 | (67%) |
| Body as a whole - general disorders | 6 | (33%) | 7 | (39%) |
|   Pain | 4 | (22%) | 5 | (28%) |
|   Fatigue | 2 | (11%) | 1 | (6%) |
|   Enlarged abdomen | 1 | (6%) | 0 | (0%) |
|   Allergic reaction | 0 | (0%) | 1 | (6%) |
|   Back pain | 0 | (0%) | 1 | (6%) |
| Center & periph nerv syst disorders | 6 | (33%) | 6 | (33%) |
|   Headache | 5 | (28%) | 5 | (28%) |
|   Dizziness | 1 | (6%) | 2 | (11%) |
|   Hyperesthesia | 1 | (6%) | 0 | (0%) |
|   Hypertonia | 1 | (6%) | 0 | (0%) |
| Skin and appendage disorders | 6 | (33%) | 3 | (17%) |
|   Erythematous rash | 5 | (28%) | 2 | (11%) |
|   Rash | 2 | (11%) | 1 | (6%) |
|   Skin disorder | 0 | (0%) | 1 | (6%) |
|   Localized skin reaction | 1 | (6%) | 0 | (0%) |
| Gastro-intestinal system disorders | 4 | (22%) | 2 | (11%) |
|   Abdominal pain | 2 | (11%) | 0 | (0%) |
|   Nausea | 2 | (11%) | 0 | (0%) |
|   Constipation | 1 | (6%) | 0 | (0%) |
|   Diarrhea | 1 | (6%) | 0 | (0%) |
|   Gastroenteritis | 0 | (0%) | 1 | (6%) |
|   Gingivitis | 0 | (0%) | 1 | (6%) |
|   Toothache | 1 | (6%) | 0 | (0%) |
| Application site disorders | 5 | (28%) | 1 | (6%) |
|   Injection site bruising | 3 | (17%) | 1 | (6%) |
|   Application site reaction | 2 | (11%) | 0 | (0%) |
|   Injection site pain | 1 | (6%) | 0 | (0%) |
| Respiratory system disorders | 2 | (11%) | 1 | (6%) |
|   Upper respiratory tract infection | 2 | (11%) | 0 | (0%) |
|   Pharyngitis | 0 | (0%) | 1 | (6%) |
|   Rhinitis | 0 | (0%) | 1 | (6%) |
| Metabolic nutritional disorders | 1 | (6%) | 1 | (6%) |
|   Thirst | 1 | (6%) | 0 | (0%) |
|   Xerophthalmia | 0 | (0%) | 1 | (6%) |
| Musculo-skeletal system disorders | 2 | (11%) | 0 | (0%) |
|   Myalgia | 1 | (6%) | 0 | (0%) |
|   Skeletal pain | 1 | (6%) | 0 | (0%) |
| Psychiatric disorders | 0 | (0%) | 2 | (11%) |
|   Insomnia | 0 | (0%) | 1 | (6%) |
|   Somnolence | 0 | (0%) | 1 | (6%) |

FIG. 58

| Body System<br>Preferred Term | Epoetin Alfa<br>150 IU/kg t.i.w.<br>(N=18) | | Epoetin Afa<br>40,000 IU q.w.<br>(N=18) | |
|---|---|---|---|---|
| Heart rate and rhythm disorders | 0 | (0%) | 1 | (6%) |
| Palpitation | 0 | (0%) | 1 | (6%) |
| Female reproductive disorders | 1 | (11%)* | 0 | (0%) |
| Dysmenorrhea | 1 | (11%)* | 0 | (0%) |
| Other special senses disorders | 1 | (6%) | 0 | (0%) |
| Taste perversion | 1 | (6%) | 0 | (0%) |
| Vascular (extracardiac) disorders | 1 | (6%) | 0 | (0%) |
| Phlebitis | 1 | (6%) | 0 | (0%) |
| Vision disorders | 1 | (6%) | 0 | (0%) |
| Conjunctivitis | 1 | (6%) | 0 | (0%) |

* Percentages taken as a percentage of the

Mean (SD) Change from Baseline in Iron Profile
(All Subjects in Protocol EPO-PHI-373)

| | Epoetin Alfa 150 IU/kg t.i.w. | | | Epoetin Alfa 40,000 IU q.w. | | |
|---|---|---|---|---|---|---|
| | N | Mean | (SD) | N | Mean | (SD) |
| Serum Iron (µg/dL) | | | | | | |
| Baseline | 18 | 97.1 | (40.54) | 18 | 102.7 | (27.23) |
| Change from Baseline to Day 8 | 18 | 7.1 | (79.56) | 18 | 28.8 | (95.05) |
| Change from Baseline to Day 15 | 18 | 34.7 | (122.43) | 17 | 49.6 | (106.89) |
| Change from Baseline to Day 22 | 18 | 21.4 | (108.34) | 17 | 23.6 | (95.73) |
| Change from Baseline to Day 29 | 17 | -44.3 | (43.76) | 18 | 22.0 | (78.18) |
| Change from Baseline to Last Visit | 18 | -33.5 | (62.59) | 18 | 22.0 | (78.18) |
| Ferritin (ng/mL) | | | | | | |
| Baseline | 18 | 69.6 | (25.17) | 18 | 78.2 | (31.36) |
| Change from Baseline to Day 8 | 18 | -38.9 | (13.13) | 18 | -37.9 | (23.12) |
| Change from Baseline to Day 15 | 18 | -37.6 | (16.17) | 17 | -37.1 | (31.52) |
| Change from Baseline to Day 22 | 18 | -36.3 | (22.79) | 17 | -43.0 | (30.51) |
| Change from Baseline to Day 29 | 17 | -41.5 | (19.75) | 18 | -36.6 | (37.18) |
| Change from Baseline to Last Visit | 18 | -38.1 | (24.05) | 18 | -36.6 | (37.18) |
| Transferrin Saturation (%) | | | | | | |
| Baseline | 18 | 35.6 | (14.72) | 18 | 37.3 | (11.39) |
| Change from Baseline to Day 8 | 18 | -0.2 | (27.82) | 18 | 5.4 | (31.47) |
| Change from Baseline to Day 15 | 18 | 12.6 | (41.69) | 17 | 18.1 | (34.06) |
| Change from Baseline to Day 22 | 18 | 6.2 | (26.30) | 17 | 8.6 | (28.04) |
| Change from Baseline to Day 29 | 17 | -17.0 | (15.56) | 18 | -1.4 | (19.86) |
| Change from Baseline to Last Visit | 18 | -15.7 | (16.12) | 18 | -1.4 | (19.86) |

FIG. 59

SUBJECTS WITH HIGH BLOOD PRESSURE VALUES [a]

| SUBJECT | PRESTUDY | DAY 1 | DAY 8 | DAY 15 | DAY 22 | DAY 29 |
|---|---|---|---|---|---|---|
| Epoetin Alfa 150 IU/kg t.i.w. | | | | | | |
| 1005 | 119/69 | 129/72 | 119/62 | 140/87[b] | 127/70 | 121/72 |
| 2015 | 134/62 | 146/77[b] | 144/64[b] | 139/75 | 127/69 | 142/88[b] |

[a] As indicated by a systolic blood pressure ≥ 140 mmHg or a diastolic pressure ≥95 mmHg.
[b] Indicates a systolic blood pressure ≥ 140 mmHg.

FIG. 61

PHARMACOKINETIC PARAMETERS AFTER rHuEpo DOSING

|  | EPREX<br>*single dose* | PROLEASE |
|---|---|---|
| $ka1$ $(hr^{-1})$ | 0.0219 | 0.0084 |
| $ka2$ $(hr^{-1})$ | - | 0.0027 |
| fr1 | 0.1308 | 0.3643 |
| fr2 | - | 0.0782 |
| $kel$ $(hr^{-1})$ | - | 0.0027 |
| Vmax (IU/kg/hr) | 138.5 | - |
| Km (IU/L) | 20940 | - |
| Vd (L/kg) | 0.0558 | 0.2072 |
| Tau1 (hr) | 44 | 45.18 |
| Tau2 (hr) | - | 215.2 |
| F=0.3884+0.00024952*DOSE | | |

| For EPREX | |
|---|---|
| 150 IU/kg/t.i.w | 600 IU/kg/wk |
| 0.1193 | - |
| 10 | 32.15 |
| F=0.25 | |

FIG. 63

PHARMACODYNAMIC PARAMETERS AFTER rHuEpo DOSING
PHYSIOLOGICAL/LIFESPAN PARAMETERS ESTIMATED FROM SINGLE DOSE DATA

| | |
|---|---|
| TP1 | 88.17 |
| TP2 | 10.76 |
| *RL | 116.6 |
| **IC50 | 38.71 |
| TPO | 137.5 |

EPREX

| single dose | multiple dosing | |
|---|---|---|
| * (males) | males | females |
| ** 4.251 | 8.186 | 4.178 |
| 26.53 | 61.15 | 57.3 |

FIG. 64

PHARMACOKINETIC PARAMETERS IN MONKEYS

|  | EPREX |
|---|---|
| Vmax (IU/kg/hr) | 480.3 |
| Km (IU/L) | 35190 |
| Vd (L/kg) | 0.05689 |
| k12 (hr-1) | 0.1192 |
| k21 (hr-1) | 0.07916 |
| Tau (hr) | 10 |
| ka (hr-1) | 0.04427 |
| ka (hr-1)-lowest dose | 0.05255 |
| Fr | 0.6452 |
| F (400 IU/kg dose) | 0.2666 |
| F (1000 IU/kg dose) | 0.7348 |
| F (higher doses) | 1 |

FIG. 75

PHARMACODYNAMIC PARAMETERS IN MONKEYS

|  | EPREX |
|---|---|
| TP1 (h) | 70.38 |
| TP2 (h) | 14.95 |
| RL (h) | 141.6 |
| Smax | 3.133 |
| SC50 (IU/L) | 842.5 |

FIG. 77

PHARMACODYNAMIC PARAMETERS IN HUMANS

|  | EPREX |
|---|---|
| TP1 (h) | 88.17 |
| TP2 (h) | 10.76 |
| RL (h) | 116.6 |
| Smax | 4.251 |
| SC50 (IU/L) | 26.53 |
| TP0 (h) | 137.5 |
| $IC_{50}$ (x$10^{10}$ Reti/L) | 38.71 |

FIG. 80

PHARMACOKINETIC AND PHARMACODYNAMIC MODELING OF ERYTHROPOIETIN ADMINISTRATION

CROSS-REFERENCE TO RELATED APPLICATIONS

This application claims priority to provisional application Serial No. 60/133,418, filed May 11, 1999, the contents of which are incorporated herein by reference.

FIELD OF THE INVENTION

The present invention relates to systems and methods for obtaining optimized EPO dosage regimens for a desired pharmacodynamic/pharmacokinetic response.

BACKGROUND OF THE INVENTION

Erythropoietin (EPO) is the principal factor responsible for the regulation of red blood cell production during steady-state conditions and for accelerating recovery of red blood cell mass following hemorrhage. EPO is a glycoprotein hormone with a molecular mass of 30 KDa and is heavily glycosylated, which serves to protect the EPO molecule from rapid degradation in vivo. Serum EPO concentrations in humans normally range from 6 to 32 U/l (l), and the half-life ($t_{1/2}$) of EPO is reported to range from 2 to 13 hours with a volume of distribution close to plasma volume. As expected for a large sialoglycoprotein, less than 10% of EPO is excreted in the urine (see, e.g., Lappin et al., 1996. *Clin. Lab Haem.* 18:137–145.)

The primary site for EPO synthesis in adult organisms is the kidney; although the liver and bone marrow have also been implicated, the data remains inconclusive. The primary stimulus for increased EPO synthesis is tissue hypoxia, which results from decreased oxygen availability in the tissues. Hypoxia can result from the loss of large amounts of blood, destruction of red blood cells by radiation, or exposure to high altitudes. In addition, various forms of anemia cause hypoxia since red blood cells are responsible for oxygen transport in the body. In the normal state, an increased level of EPO stimulates the production of new red blood cells thereby raising the level of oxygen and reducing or eliminating the hypoxic condition.

The principal function of EPO is to act synergistically with other growth factors to stimulate the proliferation and differentiation of erythrocytic progenitor cells in the bone marrow leading to reticulocytosis and increased RBC numbers in the blood, a process also known as erythropoiesis (FIG. 1). During erythropoiesis, cell differentiation along the erythroid lineage occurs over a two week span in humans. The earliest progenitor is the BFU-E (Burst-Forming Unit-Erythroid), which is small and without distinguishing histologic characteristics. The stage after the BFU-E is the CFU-E (Colony Forming Unit-Erythroid), which is larger than the BFU-E and immediately precedes the stage where hemoglobin production begins. The cells that begin producing hemoglobin are the immature erythrocytes, which not only begin producing hemoglobin, but also start condensing their nuclei to eventually become mature erythroblasts. The mature erythroblasts are smaller than the immature erythrocytes and have a tightly compacted nucleus, which is expelled as the cells become reticulocytes. Reticulocytes are so named because these cells contain reticular networks of polyribosomes and as the reticulocytes lose their polyribosomes, they become mature red blood cells (RBCs).

Until recently, the availability of EPO has been very limited. Although the protein is present in human urine, excreted levels are too low to make this a practical source of EPO for therapeutic uses. The identification, cloning, expression of genes encoding EPO and EPO purification techniques, e.g., as described in U.S. Pat. Nos. 4,703,008, 5,389,541, 5,441,868, 5,614,184, 5,688,679, 5,888,774, 5,888,772, and 5,856,298, has made EPO readily available for therapeutic applications. A description of the purification of recombinant EPO (rHuEPO) from cell medium that supported the growth of mammalian cells containing recombinant EPO plasmids for example, is included in U.S. Pat. No. 4,667,016. This recombinant EPO has an amino acid sequence identical to that of human urinary erythropoietin, and the two are indistinguishable in chemical, physical and immunological tests. The expression and recovery of biologically active recombinant EPO from mammalian cell hosts containing the EPO gene on recombinant plasmids has made available quantities of EPO suitable for therapeutic applications. In addition, knowledge of the gene sequence and the availability of larger quantities of purified protein has led to a better understanding of the mode of action of this protein.

The biological activity of a protein is dependent upon its structure. In particular, the primary structure of a protein, i.e., its amino acid sequence, provides information that allows the formation of secondary (e.g., α-helix or β-pleated sheet) and tertiary (overall 3-dimensional folding) structures by a polypeptide during and after synthesis. Furthermore, not only is the biological activity of a protein governed by its structure, but also by modifications generated after the protein has been translated. Indeed, many cell surface proteins and secretory proteins are modified by one or more oligosacchride groups. This modification known as glycosylation, can dramatically affect the physical properties of proteins and can be important in protein stability, secretion, and subcellular localization. Proper glycosylation can be essential for biological activity.

Both human urinary derived and recombinant EPO (expressed in mammalian cells) having the amino acid sequence 1–165 of human EPO contain three N-linked and one O-linked oligosacchride chains which together comprise about 40% of the total molecular weight of the glycoprotein. The oligosacchride chains have been shown to be modified with terminal sialic acid residues. Enzymatic treatment of glycosylated EPO to remove all sialic acid residues results in a loss of in vivo activity, but does not affect its in vitro activity (Lowy et al., 1960, *Nature* 185:102; Goldwasser et al., 1974, *J. Biol. Chem.* 249:4202). This behavior has been explained by rapid clearance of asialoerythropoeitin from the circulation upon interaction with the hepatic asialoglycoprotein binding protein (Morrell et al., 1968, *J. Biol. Chem.* 243:155; Briggs et al., 1974, *Am. J. Physiol.* 227:1385; and Ashwell et al., 1978 *Methods of Enzymol.* 50:287). Thus, EPO possesses in vivo biological activity only when it is sialylated to avoid binding by the hepatic binding protein.

Deficient (or inefficient) EPO production relative to hemoglobin level is associated with certain forms of anemia. These include anemia of renal failure and end-stage renal disease, anemia of chronic disorders (chronic infections and rheumatoid arthritis), autoimmune disease, acquired immune deficiency disease (AIDS), and malignancy. Many of these conditions are associated with the generation of a factor that has been shown to be an inhibitor of EPO activity. Other anemias are clearly EPO-independent, and include aplastic anemia, iron deficiency anemia, the thalassemias, megaloblastic anemia, pure red cell aplasia, and myelodysplastic syndromes.

The measurement of EPO levels in human serum has clinical importance. Determination of EPO levels in patient serum can be useful in distinguishing those anemias and polycythemias that are associated with decreased or increased EPO levels from those that are not. Additionally, the demonstration of an inappropriately low level of serum EPO is a prerequisite for concluding that an anemic patient may benefit from treatment with exogenous EPO.

In clinical trials, Epoetin alfa has been evaluated in normal patients as well as in patients with various anemic conditions. Epoetin alfa induces a brisk haematological response in normal human volunteers, provided that adequate supplies of iron are available to support increased hemoglobin synthesis. A majority of trials have investigated the safety and effectiveness in the treatment of anemia associated with renal failure. In addition, Epoetin alfa may be used to correct anemia in other patient groups including anemia associated with platinum-based cancer chemotherapy, anemia associated with zidovudine therapy in patients with AIDS, and anemia associated with other drugs such as cisplatin. Also, the administration of Epoetin alfa has many other potential therapeutic applications: Epoetin alfa administration increases the capacity for autologous blood donation in patients scheduled to undergo surgery and attenuates the decrease in hemocrit often seen in untreated autologous donors; Epoetin alfa administration increases red blood cell recovery after allogeneic—but not autologous—bone marrow transplant; and administration of Epoetin alfa has been shown to improve the quality of life in individuals afflicted with rheumatoid arthritis An alternative application of EPO is for enhancing the performance of athletes by causing an increase in the hematocrit of the athlete. This augmentation in hematocrit increases the capacity of oxygen transported from the lungs to the exercising skeletal muscles. Since the synthesis of EPO by bioengineering, injecting athletes with EPO, also known as blood doping, has become popular in sports in general, and in particular, cycling (Scheen, A J., 1998. *Rev. Med. Liege* 53(8): 499–502).

Presently, there are a number of disadvantages associated as the standard EPO dosage regimen administered to patients. In specific indications, such as cancer, subjects are treated with 150 IU/kg of EPO three times per week. Thus, it remains an important goal to change the currently approved dosing schedule to a more convenient dosing schedule and regimen. It is expected that a less frequent administration will improve user acceptance and convenience. Moreover, the standard dosing regimens may not maximize the patient's physiological response; and standard dosing regimens may not be the most cost efficient.

Furthermore, there are a number of disadvantages associated with the route of EPO administration: regular intravenous administration is inconvenient for the patient; intravenous administration is impractical for individuals afflicted with certain conditions such as continuous ambulatory peritoneal dialysis and non-dialysis patients with restricted vascular access; the rapid dose delivery of rHuEPO via intravenous administration results in a lower bioavailability of rHuEPO for longer time periods and may not be as effective for stimulating production of RBC as desired.

Hence, for all of the reasons detailed above, a better route of administration and means for determining an effective dose and dosage regimen for EPO administration is needed.

Therefore, one aspect of the present invention is the development of a pharmacokinetic/pharmacodynamic (PK/PD) model for characterizing and predicting responses to rHuEPO thereby identifying the most efficient, cost effective, and/or convenient treatment regimens for patients. In a particular embodiment of the present invention, once-weekly or once every two weeks EPO administration is contemplated. Another aspect of the present invention provides a methodology to evaluate the pharmacokinetic and pharmacodynamic profiles of EPO after administration of two or more dosing regimens for comparison of clinical outcomes along with tolerance and safety parameters between the EPO dosing regimens. Associated business methods and computer systems are also contemplated.

SUMMARY OF THE INVENTION

A specific embodiment of the present invention may include a method for obtaining optimized EPO dosage regimens for a desired pharmacodynamic response, which can comprise choosing one or more EPO dosage regimens, then using a PK/PD model to determine the pharmacodynamic profile of one or more EPO dosage regimens, and finally selecting one of the EPO dosage regimens for administration to achieve the desired pharmacodynamic (PD) response based on the EPO profile. In an additional embodiment, the PD response can comprise one or more of the group consisting of reticulocyte number, RBC number, and hemoglobin level.

An alternate embodiment of the present invention may also be a method for obtaining optimized EPO dosage regiments for a desired pharmacodynamic response which comprises first selecting one or more desired pharmacodynamic responses, then using a PK/PD model to determine a EPO dosage regimen that provides the desired responses, and finally, selecting one of the EPO dosage regimens for administration to achieve the desired pharmacodynamic response. In an additional embodiment, the PD response can comprise one or more of the group consisting of reticulocyte number, RBC number, and hemoglobin level.

An additional preferred embodiment of the present invention can include a computer program, which can be used for obtaining optimized dosage regimens for a desired pharmacodynamic response. The computer program may comprise a computer code. In a further embodiment, the computer code describes a PK/PD model for EPO and allows the user to select one or more desired pharmacodynamic responses. The computer code then uses the PK/PD model to determine EPO dosage regimens that would provide the desired pharmacodynamic responses. The EPO dosage regimen may be administered as a weekly or once every two weeks, based upon body mass, dose. Preferably, the weekly EPO dose may comprise administering EPO at a dosing of 40,000 IU and the once every two weeks EPO dosing regimen may comprise administration of EPO at a dosing of about 80,000 to about 120,000 IU. In an additional embodiment, the PD response can comprise one or more of the group consisting of reticulocyte number, RBC number, and hemoglobin level.

An alternate preferred embodiment of the present invention may include a computer program for obtaining optimized dosage regimens for a desired pharmacodynamic response. In an additional embodiment, the computer program comprises a computer code. The computer code may allow the user to select one or more EPO dosage regimens. The computer code then uses the PK/PD model to determine a pharmacodynamic response based on the EPO dosage regimens selected.

A preferred embodiment of the present invention may include computer program for determining optimized EPO dosage regimens for a desired pharmacokinetic response comprising the steps of choosing one or more EPO dosage regimens, using the PK/PD model to determine the pharmacokinetic response of the EPO dosage regimens, and then selecting the desired EPO dosage regimen based on pharmacokinetic profile, in a specific embodiment, based upon one ore more EPO or EPO-like compounds. In an additional embodiment, the pharmacokinetic response may include serum EPO levels, bioavailability, and EPO threshold levels.

A further embodiment of the present invention may include a method for obtaining optimized EPO dosage regimens for a desired pharmacokinetic response comprising the steps of first selecting one or more desired pharmacokinetic responses, then using a PK/PD model to determine a EPO dosage regimen that provides one or more of the desired pharmacokinetic responses, and finally selecting the EPO dosage regimen that provides the desired pharmacokinetic responses.

An additional embodiment of the present invention can include a computer program for obtaining optimized EPO dosage regimens for a desired pharmacokinetic response which comprises a computer code that describes a PK/PD model for EPO. In a further embodiment, the computer code may allow the user to select of one or more pharmacokinetic responses, and then use the PK/PD model to determine one or more EPO dosage regimens that provide the desired pharmacokinetic responses.

An alternate preferred embodiment of the present invention may include a computer program for obtaining optimized dosage regimens for a desired pharmacokinetic response. In an additional embodiment, the computer program comprises a computer code. The computer code may allow the user to select one or more EPO dosage regimens. The computer code then uses the PK/PD model to determine a pharmacokinetic response based on the EPO dosage regimens selected. One or more EPO or EPO-like compounds may be contemplated for use.

Another preferred embodiment of the present invention comprises a variety of methods including a business method of providing to a consumer an EPO dosing regimen that comprises a first dose of EPO followed by a second dose of EPO to a patient. The second dose of EPO is preferably administered to the patient at a time point after the first dose that coincides with the PD profile resulting from the first dose of EPO. The PD profile may include, number of progenitor cells produced in respect to time, reticulocyte concentration in respect to time, RBC number produced in respect to time, and hemoglobin concentration in respect to time. Most preferably, the PD profile will be the reticulocyte profile for this regimen. The second dose of EPO is preferably administered to coincide with the reticulocyte profile, i.e., when reticulocyte production peaks. The second dose of EPO facilitates the maturation of young red cells in the circulation into mature RBCs.

A further embodiment of the present invention comprises a business method of providing to a patient an EPO dosing regimen that comprises a first dose of EPO followed by a second dose of EPO to a patient. The second dose of EPO is administered to the patient at a time after the first dose that coincides with the reticulocyte profile of the patient. The second dose may be administered within 6 to 10 days following the first EPO dose. Preferably, the second EPO will be administered 7 days subsequent to the first EPO dose.

The business method of the present application relates to the commercial and other uses, of the methodologies of the present invention. In one aspect, the business method includes the marketing, sale, or licensing of the present methodologies in the context of providing consumers, i.e., patients, medical practitioners, medical service providers, and pharmaceutical distributors and manufacturers, with the EPO dosing regimens provided by the present invention. These include once weekly and once every two weeks EPO dosing regimens.

Another preferred embodiment of the present invention provides a method for creating a pharmacokinetic model for subcutaneous (SC) EPO administration in patients. This method can comprise obtaining pharmacokinetic data from patients, choosing an equation based the PK data collected from the patients, and fitting the PK data to the equation. In addition, obtaining the PK data may comprise normalizing serum EPO concentration values from the collected PK data and creating serum EPO concentration time profiles based on the normalized data. In a further embodiment, the PK data may be normalized by first obtaining baseline serum EPO concentration values from the PK data by averaging predose serum EPO concentration values at a plurality of time points; next, obtaining serum EPO concentration values following SC EPO administration; then, obtaining normalized serum EPO concentration values by subtracting predose EPO concentration values from serum EPO concentration values; and, finally, calculating mean normalized serum EPO concentration values at each time point.

In an additional embodiment of the present invention, the PK equation may comprise selecting the Michaelis-Menten equation. The PK data may be fitted to the PK equation using, for example, ADAPT II software and an estimate of parameters may be obtained by utilizing the least-squares by Maximum likelihood method and the extended least squares model. In a further embodiment, the parameters may be selected from the group consisting of Vmax, Km, Vd, Fr, $\tau$ (lower doses), and $\tau$ (higher doses).

A further embodiment of the present invention provides a method for calculating the bioavailability of EPO following SC EPO administration. The method may comprise obtaining PK data, calculating the area under the serum EPO concentration curve (AUC) versus dose, normalizing AUC to dose, and finally, deriving an equation by performing a linear regression of the PK data.

Another preferred embodiment of the present invention provides a method for creating a pharmacodynamic (PD) model after SC EPO administration. This method may comprise normalizing serum EPO concentrations, obtaining PD data, choosing a PD model, obtaining an equation based on the PD model, and fitting the PD data to the PD equations. In an additional embodiment, normalizing the serum EPO concentrations may comprise obtaining baseline serum EPO concentration ($C_{bs}$) for each dose group by averaging predose serum EPO concentration values at a plurality of time points for each dose group, and then, adjusting $C_{bs}$ by adding $C_{bs}$ to serum EPO concentration predicted by PK model and where the adjusted $C_{bs}$ can be used as a forcing function for PD analysis.

In a further embodiment, the PD data may be obtained by determining the mean predose precursor cell, reticulocyte, and RBC number, and hemoglobin concentration, and then obtaining mean reticulocyte-, mean RBC-, and mean hemoglobin-versus time profiles according to EPO dose.

In an additional embodiment, the PD model may comprise a cell loss and production model. The PD data may be fitted to the model equation by using, for example, ADAPT II software, and following, both estimate and fixed parameters may be obtained by utilizing the least-squares by Maximum likelihood method and extended least squares model. Additionally, the estimated parameters can comprise Ks, $SC_{50}$, and TP, while the fixed parameters may include $R_L$, $RBC_L$, Hb, and threshold.

A further preferred embodiment of the present invention may provide a method for predicting a PD response in a patient following various doses of SC EPO. Moreover, this method may comprise selecting a dose and dosage regimen, and then determining the PD response based on that particular dose and dosage regimen via the PK/PD model. In an additional embodiment, the PD response can comprise one or more of the group consisting of reticulocyte number, RBC number, and hemoglobin level.

The present invention can address the requirements of patients that may have deficient or inefficient EPO production relative to hemoglobin level, which may be associated with certain forms of anemia. These may include, but are not limited to, anemia associated with end-stage renal or renal failure related anemia, platinum based cancer chemotherapy related anemia, AIDS drug therapy related anemia where the drugs may include cisplatin and zidovudine. Also, patients may be undergoing autologous transfusion prior to surgery, recovering from an allogenic bone marrow transplant, suffering from rheumatoid arthritis, or an athlete or others requiring or desiring increased RBC numbers and/or hemoglobin.

The PK/PD model of the present invention has many potential therapeutic applications. For example, a physician can use this PK/PD modeling system to determine the optimal EPO dosage regimen to administer to a patient in need of increased RBC numbers and/or hemoglobin. In particular, the physician would have the option of either determining an EPO dosage regimen based on the desired pharmacodynamic outcome or determining a pharmacodynamic response based on a specific EPO dosage regimen.

BRIEF DESCRIPTION OF THE FIGURES

FIG. 3: Pharmacokinetic parameters for intravenous and subcutaneous EPO doses.

FIG. 8: Bioavailability values for subcutaneous rHuEPO administration.

FIG. 13: Estimated and fixed pharmacodynamic parameters for subcutaneous EPO effects.

FIG. 17: Summary of Epoetin Alfa clinical pharmacokinetic studies contributing to pharmacokinetic and pharmacodynamic data for subjects in Clinical Studies EPO-PHI-358, EPO-PHI-359, EPO-PHI-370, and EPO-PHI-373.

FIG. 18A: Biopharmaceutics study summary for Clinical Study EPO-PHI-373.

FIG. 18B: Biopharmaceutics study summary for Clinical Study EPO-PHI-370.

FIG. 18C: Biopharmaceutics study summary for Clinical Study EPO-PHI-358.

FIG. 18D: Biopharmaceutics study summary for Clinical Study EPO-PHI-359.

FIG. 19: Summary of pharmacokinetic data for Clinical Studies EPO-PHI-358, EPO-PHI-359, EPO-PHI-370, and EPO-PHI-373.

FIG. 20: Summary of analytical methods for Clinical Studies EPO-PHI-358, EPO-PHI-359, EPO-PHI-370, and EPO-PHI-373.

FIG. 21: Mean±SD demographic and baseline parameters for subjects enrolled in Clinical Studies EPO-PHI-358 and EPO-PHI-359.

FIG. 24: Mean±SD (% CV) pharmacokinetic parameters (Clinical Studies EPO-PHI-358 and EPO-PHI-359).

FIG. 29: Demographic data of subjects in Clinical Study EPO-PHI-370.

FIG. 31: Mean±SD (% CV) pharmacokinetic parameters (Clinical Study EPO-PHI-370).

FIG. 34: Mean±SD (% CV) pharmacodynamic parameters corrected for baseline value (Clinical Study EPO-PHI-370).

FIG. 35: Mean±SD demographic data of subjects in Clinical Study EPO-PHI-373.

FIG. 37: Mean±SD (% CV) pharmacokinetic parameters corrected for baseline value (Clinical Study EPO-PHI-373).

FIG. 41: Mean±SD (% CV) pharmacodynamic parameters corrected for baseline value for subjects in Clinical Study EPO-PHI-373.

FIG. 42: Mean±SD (% CV) pharmacokinetic parameters corrected for baseline value for subjects in Clinical Studies EPO-PHI-358, EPO-PHI-359, EPO-PHI-370, and EPO-PHI-373.

FIG. 47: Demographic and baseline characteristics of the 34 subjects who completed the EPO study (EPO-PHI-373). 18 subjects were part of Group 1 who were administered an EPO dosing regimen of 150 IU/kg t.i.w. and 18 subjects were part of Group 2 who were administered EPO at 40,000 q.w. Demographic characteristics include sex, age (years), weight (kg), height (cm), and race.

FIG. 50: Mean (SD) [% CV] pharmacokinetic parameter values with data for individual subjects in Group 1 (150 IU/kg .i.w.) and Group 2 (40,000 IU q.w).

FIG. 51: Summaries of mean (SD) change from baseline in percent reticulocytes by study day for the efficacy population for all subjects in dosing Groups 1 (150 IU/kg t.i.w.) and Group 2 (40,000 IU q.w) for Clinical Study EPO-PHI-373.

FIG. 53: Summaries of mean (SD) change from baseline in hemoglobin (g/dL) by study day for the efficacy population for all subjects in Group 1 (150 IU/kg t.i.w.) and Group 2 (40,000 IU q.w) for Clinical Study EPO-PHI-373.

FIG. 55: Summaries of mean (SD) change from baseline in red blood cells ($\times 10^{12}$/L) by study day for the efficacy population for all subjects in Clinical Study EPO-PHI-373.

FIG. 57: Mean pharmacodynamic parameter values corrected for baseline value. % CV is the percent coefficient of variation. The notes are as follows: [a] AUC of % reticulocytes over the one month study period and corrected for predose baseline value; [b] AUC of hemoglobin over one month study period and corrected for predose baseline value; [c] AUC of red blood cells over one month study period and corrected for predose baseline value; [d] ratios of 40,000 IU q.w. to 150 IU/kg t.i.w. mean parameter value for all subjects; [e] including all female subjects in both treatment groups; [f] including all male subjects in both treatment groups; [g] statistically different (p<0.05) between male and female subjects.

FIG. 58: Treatment-emergent adverse events by preferred term for individual subjects in Clinical Study EPO-PHI-373.

FIG. 59: The mean changes from baseline in iron, ferritin, transferrin saturation, and other serum chemistry parameters by both treatment group and study day. Group 1 was administered 150 IU/kg t.i.w. EPO and Group 2 was administered 40,000 IU q.w. in Clinical Study EPO-PHI-373.

FIG. 61: Summary of the mean changes from baseline in vital sign measurements for individuals in Group 1 (150 IU/kg t.i.w.) in Clinical Study EPO-PHI-373.

FIG. 63: Pharmacokinetic parameters after rHuEPO dosing of EPREX® and PROLEASE®.

FIG. 64: Pharmacodynamic parameters after rHuEPO dosing. The reticulocyte data for males and females were analyzed separately. These parameters may reflect some slight pharmacodynamic differences based upon gender.

FIG. 75: PK parameters in monkeys.

FIG. 77: PD parameters in monkeys.

FIG. 80: PD parameters in humans.

DETAILED DESCRIPTION OF THE INVENTION

Figure 1:
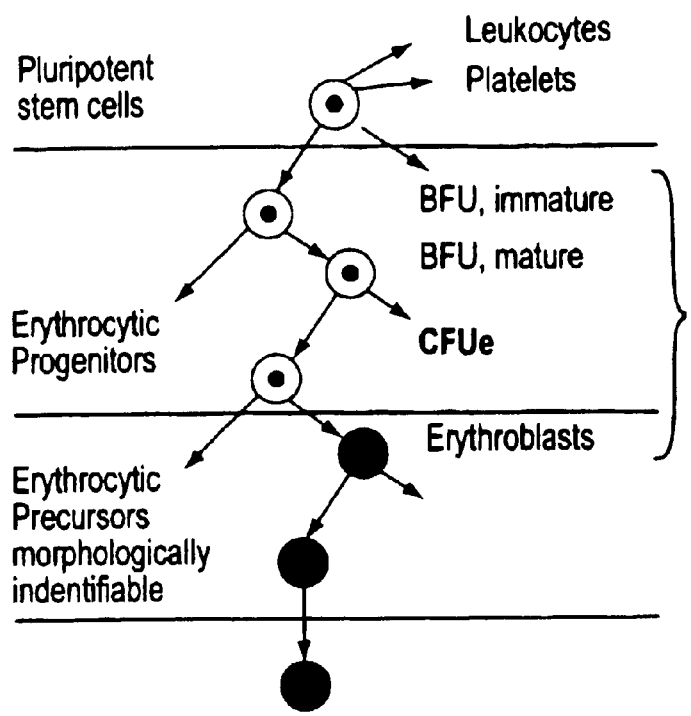
FIG. 1: Process of Erythropoiesis.

It is understood that the present invention is not limited to the particular methodology, protocols, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the present invention. All references cited herein are incorporated by reference herein in their entirety.

| DEFINITIONS | |
|---|---|
| a.m. | Ante meridiem, morning |
| AUC | Area under the concentration vs. time curve |
| $AUC_{(0-168)}$ | AUC of epoetin alfa concentration in serum from time 0 to 168 hour |
| AUC(RETI) | AUC of change in % reticulocytes from baseline |
| AUC(HEMO) | AUC of change in hemoglobin from baseline |
| AUC(RBC) | AUC of change in total red blood cell counts from baseline |
| BUN | Blood Urea Nitrogen |
| ° C. | Degrees centigrade |
| $C_{max}$ | Maximum concentration |
| $C_{min}$ | Predose trough concentration AUC from time 0 to 168 hour |
| CL/F | Clearance/bioavailability |
| cm | centimeter |
| CRF | Case Report Form |
| CV % | Coefficient of variation, relative standard deviation |
| d | Day |
| D | Dose (amount) |
| dL | Deciliter |
| g | Gram |
| h | Hour |
| Hb | Hemoglobin |
| Hct | Hematocrit |
| HIV | Human Immunodeficiency Virus |
| IRB | Institutional Review Board |
| I | Negative feedback mechanism |
| IV | Intravenous |
| kg | Kilogram |
| L | Liter |
| LDH | Lactate dehydrogenase |
| LOQ | Limit of Quantitation |
| ug | Microgram (also µg) |
| mg | Milligram |
| min | Minute |
| mL | Milliliter |
| N/A | Not Applicable/Available |
| ng | Nanogram |
| nm | Nanometer |
| NMR | Nuclear Magnetic Resonance |
| No. | Number |
| NS | Not statistically significant |
| OTC | Over-the-counter |
| q.w. | Once per week |
| QC | Quality control |
| r | Correlation coefficient |
| $r^2$ | Coefficient of determination |
| RBC | Red blood cell |
| REF | Reference |
| RETI | Reticulocyte |
| RIA | Radioimmunoassay |
| rHuEPO | Recombinant human erythropoietin |
| RWJPRI | The Robert Wood Johnson Pharmaceutical Research Institute |
| SC | Subcutaneous |
| SD | Standard deviation |
| SE | Standard error |
| SEM | Standard Error of the Mean |
| SGOT | Serum glutamic-oxaloacetic transaminase (AST) |
| SGPT | Serum glutamic-pyruvic transaminase (ALT) |
| $t_{max}$ | Time of maximum concentration |
| t.i.w. | Three-times-a-week |
| TIBC | Total iron binding capacity |
| $t_{1/2}$ | Elimination half-life |
| WBC | White Blood Cell |

| -continued | |
|---|---|
| DEFINITIONS | |
| WHOART | World Health Organization Adverse Reaction Terminology |

EPO, as defined herein, refers to any molecule that specifically stimulates terminal differentiation of red blood cells from hematopoietic stem cells and stimulates the production of hemoglobin. For example, but not to limit the scope of the present invention, EPO molecules may include small organic or inorganic molecules, synthetic or natural amino acid peptides, purified protein from recombinant or natural expression systems, or synthetic or natural nucleic acid sequences, or any chemical derivatives of the aforementioned. Specific examples of erythropoietin include, Epoetin alfa (EPREX®, ERYPO®), Novel erythropoiesis stimulating protein (NESP) (a hyperglycosylated analog of recombinant human erythropoietin (Epoetin) described in European patent application EP640619), human erythropoietin analog—human serum albumin fusion proteins described in the international patent application WO9966054, erythropoietin mutants described in the international patent application WO9938890, erythropoietin omega, which may be produced from an Apa I restriction fragment of the human erythropoietin gene described in U.S. Pat. No. 5,688,679, altered glycosylated human erythropoietin described in the international patent application WO9911781, PEG conjugated erythropoietin analogs described in WO9805363 or U.S. Pat. No. 5,643,575. Specific examples of cell lines modified for expression of endogenous human erythropoietin are described in international patent applications WO9905268 and WO9412650. A preferred form of EPO is purified, recombinant EPO. For example, purified, recombinant EPO is distributed under the trademarks of EPREX®, PROLEASE®, or ERYPO®. Specifically, Epoetin alfa (EPREX®, ERYPO®) is a sterile clear, colorless, aqueous solution for injection, that is provided in prefilled, single-use syringes containing either 4,000 or 10,000 IU epoetin alfa (a recombinant human erythropoietin) and 2.5 mg/ml human serum albumin in 0.4 ml (4,000 IU syringe) or 1.0 ml (10,000 IU syringe) of phosphate buffer.

EPO also includes those proteins that have the biological activity of human erythropoietin, as well as erythropoietin analogs, erythropoietin isoforms, erythropoietin mimetics, erythropoietin fragments, hybrid erythropoietin proteins, erythropoietin receptor agonists, renal erythropoietin, oligomers and multimers of the above, homologues of the above, and muteins of the above, regardless of the biological activity of the same, and further regardless of the method or synthesis or manufacture thereof including but not limited to naturally occurring, recombinant, synthetic, transgenic, and gene activated methods, e.g., EPO-like proteins. Such EPO and methodologies for production are described in, e.g., U.S. Pat. Nos. 5,716,644, 5,764,534, 5,916,597, 6,048,524, 5,994,127, 5,955,422, 5,856,298, 5,756,349, 5,621,080, 5,547,933, and 5,441,868.

SC EPO administration, as defined herein, refers to the delivery of a desired dosage of EPO via a medication delivery device. The medication delivery device can penetrate the epidermis of the individual to be treated, and results in introducing the desired dosage of EPO into the tissues of the individual. The delivery device of the present invention may include, but is not limited to any traditional hypodermic needle injectors, air-powered needle-less injectors, jet injectors, or gas-pressured needle-less injectors (see, e.g., U.S. Pat. Nos. 5,730,723, 5,891,086, 5,957,886, and 5,851,198).

Threshold level, as defined herein, refers to a serum EPO concentration at which serum EPO concentrations sustained above this level will promote the differentiation of young RBCs into mature RBCs. Conversely, serum EPO concentrations maintained below threshold level will not lead to the maturity of reticulocytes into RBCs.

A patient, as described herein, includes individuals who require due to a disease state, treatment regimen, or desire, an increase in hematocrit, RBC number, or oxygen capacity.

Infrastructure domain, as described herein, includes the operational aspects of the system which are largely transparent to the user of the system. Examples of infrastructure domain items include services which implement concurrency, transaction support, data structure support, and security services, etc.

Business domain, as described herein, includes all of the operations and logic concerning the actual functionality of the system as it regards the actual business models and methods being implemented by the system. For example, if the business model was providing and EPO dosing regimen and selling the dosed EPO, the business domain logic would include all of the aspects of running the business. This would include manufacturing, buying and selling EPO, checking and establishing credit for customers, etc. It is important to note that the business domain does not include support for infrastructure-related activities.

A preferred embodiment of the present invention describes a dosing regimen wherein EPO is administered about 40,000 IU/kg once a week for two consecutive weeks. The first dose of EPO facilitates the production of reticulocytes from RBC progenitor cells. The second dose of EPO is administered to coincide with the reticulocyte pharmacodynamic profile of the patient. The second dose of EPO will be administered 6–10 days following the initial dose, and preferably at the time when the reticulocyte concentration peaks following the first EPO dose.

This aspect of the present invention relates to the stimulation of the proliferation of erythroid progenitor cells by EPO and the release of reticulocytes in the blood circulation. After single dose administration, reticulocytes peaked at times ranging from 6 to 12 days and returned to predose levels at times up to 15 days. The lifespan of cells in reticulocyte stage is about 1 to 2 days in the blood circulation. Therefore, one skilled in the art would expect young red cells to appear in the blood circulation in about 7 to 14 days after dosing. It is hypothesized that EPO is required for the maturation of the young red cells into mature red cells during Days 7 to 14 after the initiation of the EPO therapy. Mature red cells have average life span of 120 days in healthy subjects. The life span of mature red cells could be shorter in patients of chronic anemia or other disease states.

Another preferred embodiment of the present invention comprises a dosing regimen wherein EPO is administered in a dosing cycle comprising two or more cycles, in which EPO is administered once a week for two consecutive weeks. The length of time between dosing cycles preferably coincides with the lifespan of RBCs. The lifespan of RBCs is typically 120 days, however this may time may vary due to a disease state or treatment regimen. Therefore, preferably, the subsequent cycle of EPO will preferably be administered 60–120 days following the previous dose.

A preferred embodiment of the present invention describes a pharmacokinetic model for serum EPO concentrations in healthy volunteers following intravenous (IV) and subcutaneous (SC) dosing as well as a pharmacodynamic model of SC EPO causing changes in reticulocyte, RBC numbers and Hb concentrations in blood. In addition, specific examples will follow utilizing the PK/PD models of the present invention. These include: determining expected differences in hemoglobin responses for various dosage regimens of rHuEPO; assessing the effects of subject body weight on the expected response to maintenance therapy with rHuEPO; and investigating whether cancer patients respond to the same extent as healthy volunteers to rHuEPO treatment.

Pharmacokinetic Model and Analysis

Data describing modeling and SC rHuEPO pharmacokinetics were obtained from clinical studies performed by The Robert Wood Johnson Pharmaceutical Research Institute (RWJPRI). This consisted of two comparable, open-label, randomized, parallel, placebo-controlled studies in healthy volunteers where rHuEPO was administered as eight single SC doses of EPREX®: 300, 450, 600, 900, 1200, 1350, 1800, 2400 IU/kg and as multiple dosage regimens: 150 IU/kg three times a week for four weeks and 600 IU/kg one per week for four weeks. Each treatment group had 5 subjects.

The measured rHuEPO concentrations after rHuEPO administration were corrected for baseline values because the radioimmunoassay used could not distinguish between endogenous EPO and rHuEPO. The baseline EPO concentration for each subject was determined by averaging the predose values (10, 20 and 30 min). This value was subtracted from the post-dose values at each time point to obtain the corrected serum rHuEPO concentration. The mean of the corrected concentrations for all subjects was used for data analysis. Any measurement below the limit of assay detection (7.8 IU/l) was not used as a data point. The intravenous data were also corrected for baseline EPO levels.

From preliminary analysis of IV data obtained from the literature, a one-compartment model was found to be adequate. The disposition of rHuEPO has been reported to be nonlinear mainly because of a dose-dependant decrease in clearance (see, e.g., Macdougall et al., 1991. *Clin. Pharmacokinet.* 20:99–113.). Therefore, the Michaelis-Menten function was used to describe rHuEPO disposition. The IV data for rHuEPO concentrations ($C_{EPO}$=Ap/Vd) versus time were fitted with the following equation:

$$\frac{dAp}{dt} = -\left(\frac{Vmax}{Km*Vd + Ap}\right)*Ap \qquad (1)$$

where Ap is the amount of rHuEPO in the body, Vmax is the capacity of the process, Km is the affinity constant or the plasma rHuEPO concentration at which the elimination rate reaches one-half Vmax, and Vd is the volume of distribution.

Figure 2:
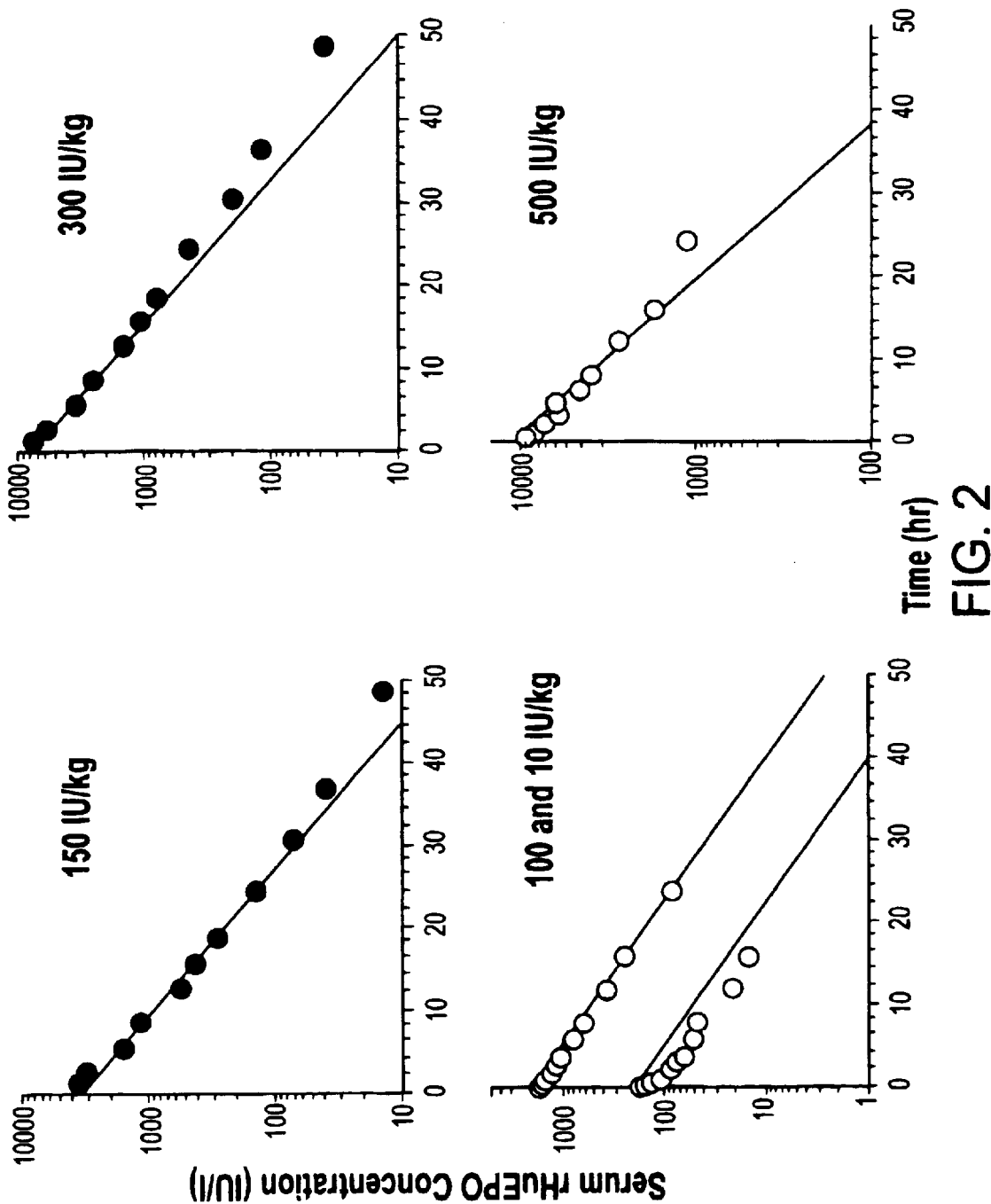
FIG. 2: Serum rHuEPO concentration versus time profiles after intravenous administration of five indicated dose levels. Data for the 150 and 300 IU/kg doses are the mean data from six healthy subjects while the other doses are single subject data. Circles are the data corrected for the baseline EPO concentrations while the solid lines are obtained from fitting the data to equations 1, 2 and 3, infra.

The IV concentration-time profiles for the various doses are shown in FIG. 2. A one-compartment model with nonlinear disposition was used to describe the kinetics of rHuEPO. Notably, a two-compartment model might better fit the IV data at early times; nonetheless, it would produce greater complexity in overall data fitting. Consequently, a one-compartment model was chosen as it gave acceptable fittings and served the purpose. Also, since rHuEPO is a 30 KDa protein, it can be expected to be restricted to the intravascular compartment, thus justifying the choice of a one-compartment model.

The parameters obtained by the fittings are listed in FIG. 3. The Vd (0.0558 L/kg) and Vmax/Km (i.e., CL at low doses: 0.0066 L/hr/kg) obtained are in the range of reported literature estimates (see e.g., Macdougall et al., supra and Lappin et al., 1996. *Clin. Lab Haem.* 18:137–1458.) The large Km value indicates that EPO disposition is only mildly non-linear and dose-dependant elimination would become important only at high doses. Studies in rats have suggested that binding of rHuEPO to receptors in bone marrow and spleen contribute to the saturable elimination of rHuEPO (see, e.g., Kato et al., 1997, *J. Pharmacol. Exp. Ther.* 283:520–27.).

Figure 4:
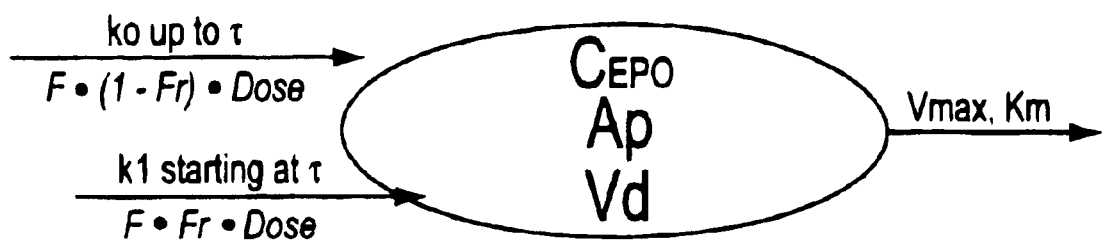
FIG. 4: Schematic representation of a pharmacokinetic model of the present invention used for analysis of plasma rHuEPO ($C_{EPO}$) versus time profiles. The symbols used are defined in the definitions section of the detailed description of the invention, infra.

The pharmacokinetics of SC EPO was found to be best characterized by a dual-absorption model with a fast zero-order input of most of the drug (87% of that absorbed) followed by slow first-order absorption of a small part of the drug (13% of that absorbed). The bioavailability was found to increase with dose (ranging 46 to 100%) contributing substantially to the nonlinearity in the kinetics. The differential equations for the model (FIG. 4) are shown as follows:

$$\frac{dAp}{dt} = ko(0 - \tau) + k_1(t > \tau) - \left(\frac{Vmax}{Km*Vd + Ap}\right)*Ap \quad (2)$$

where $ko = 0$ when $t > \tau$ $ko = \frac{F*(1 - Fr)*Dose}{\tau}$ when $0 < t \leq \tau$ $k_1 = 0$ when $t \leq \tau$ and $k_1 = ka*F*Fr*Dose*e^{-(ka*(t-\tau))}$ when $t > \tau$ The rHuEPO was assumed to be 100% bioavailable on IV administration. The bioavailability after SC dosing is represented by the parameter F. Accordingly, the amount of rHuEPO associated with the first-order process is given by F*Fr*Dose while that absorbed by the zero-order process is given by F*(1-Fr)*Dose.

All fittings were done using the ADAPT II software (see, e.g., Argenio et al., 1998. ADAPT II User's Guide, Biomedical Simulations Resource, University of Southern California, Los Angeles), although any appropriate software also could have been employed. Estimation of parameters was done using least-squares fitting by the Maximum Likelihood method and the extended least-squares variance model used is given by:

$$V(1) = \text{Inter}^2 * Y(1)^{sigma} + 0.0001 \text{ where } Y(1) = Ap/Vd$$

Simultaneous fitting of the eight single SC doses and five IV dose levels was performed. During initial fittings, Vmax, Km, Vd, ka, Fr and variance parameters were kept constant across doses while T and F were allowed to vary with dose. Results indicated that τ could be fixed as a single value up to the 1350 IU/kg dose whereas for the last two doses, a higher τ value was optimal. Bioavailability F was found to increase proportionately with dose in the range of doses tested and was described by a linear equation ($r^2$=0.9713) as follows:

$$F = 0.3884 + 0.00024952*Dose \quad (3)$$

For linear regression, the F value for the 450 IU/kg dose was excluded as it appeared to be an outlier. Final fittings were done using this function to set F values across doses and τ was fixed to be 44 hours for all doses except the last two for which τ was set as 60 hours. This made it possible to describe all the data using a single set of parameters for Vmax, Km, Vd, ka, Fr, and the variance parameters. The 600 IU/kg/week multiple dosing data were simulated using the same parameters with F set to 60% as it gave optimal fittings. For the 150 IU/kg t.i.w. regimen, F was fixed at 25%. In addition, for this low dose, it was necessary to increase the Vd (0.1193 l/kg) and set the τ as 18 hrs.

Figure 5A:
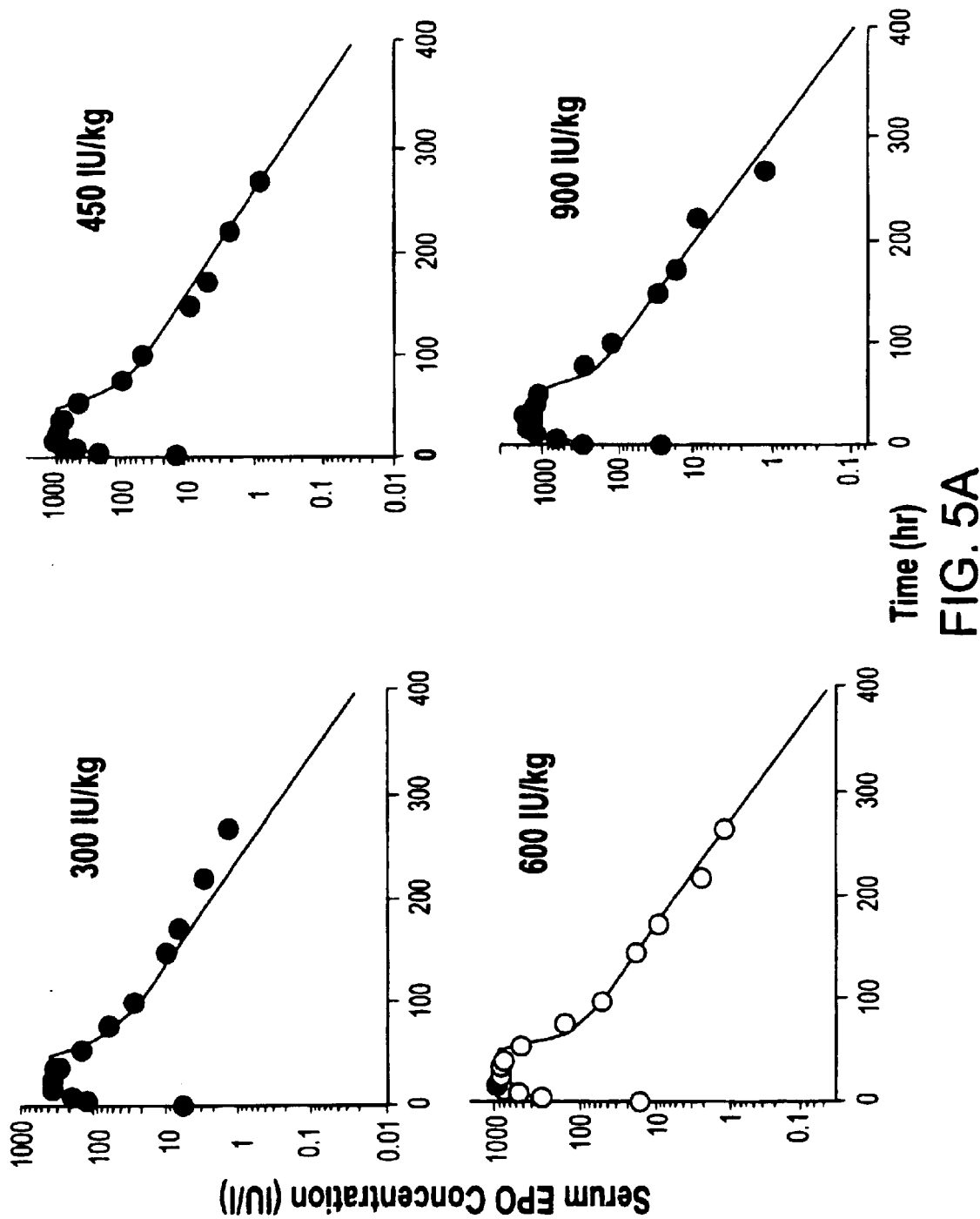
FIG. 5A: Serum rHuEPO concentration versus time profiles after subcutaneous administration of 300, 450, 600, and 900 IU/kg doses. Data points for each dose are the mean values of five healthy subjects. The data are corrected for baseline EPO concentrations while the solid line is obtained from fitting the data to equations 1, 2 and 3.
Figure 5B:
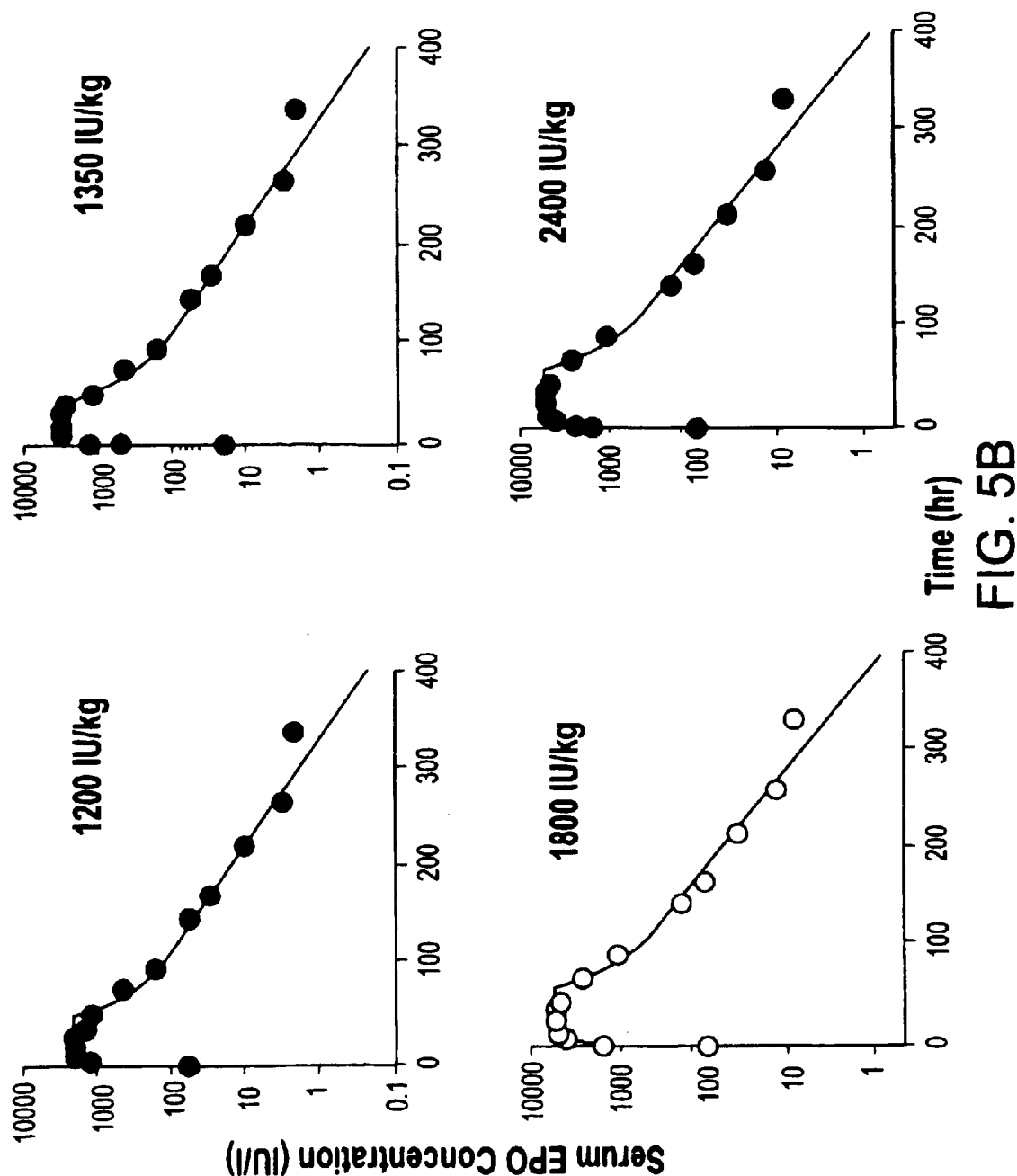
FIG. 5B: Serum rHuEPO concentration versus time profiles after subcutaneous administration of 1200, 1350, 1800, and 2400 IU/kg doses. Data points for each dose are the mean values of five healthy subjects. The data are corrected for baseline EPO concentrations while the solid line is obtained from fitting the data to equations 1, 2 and 3.

FIGS. 5A and 5B show the mean rHuEPO concentration-time profiles for the different single SC doses. Visual inspection of the SC data clearly indicates flip-flop kinetics since the terminal slope is much flatter compared to the IV monoexponential decline. Hence, a first-order absorption rate constant was assigned to capture the terminal phase. The data also shows that rHuEPO concentrations rapidly reach the peak Cmax within one day, thereby indicating that there must be a faster absorption process as well. This rapid upcurve was accounted for by a zero-order input process. The terminal slopes across all of the doses were found to be parallel indicating that a single first-order absorption rate ka could account for this phase for all doses. The fraction of dose associated with the slow first-order absorption process was only 13.1%. Thus, the majority of the bioavailable dose is rapidly absorbed within 2–3 days by the zero-order component. The first-order absorption rate ka accounts for a slow continuous release of rHuEPO from the subcutaneous site. A similar dual-absorption rate model was used to characterize the absorption kinetics of another macromolecule, IL-10, following SC dosing (see, e.g., Radwanski et al., 1998. *Pharm. Res.* 15:1895–1902.)

Figure 6:
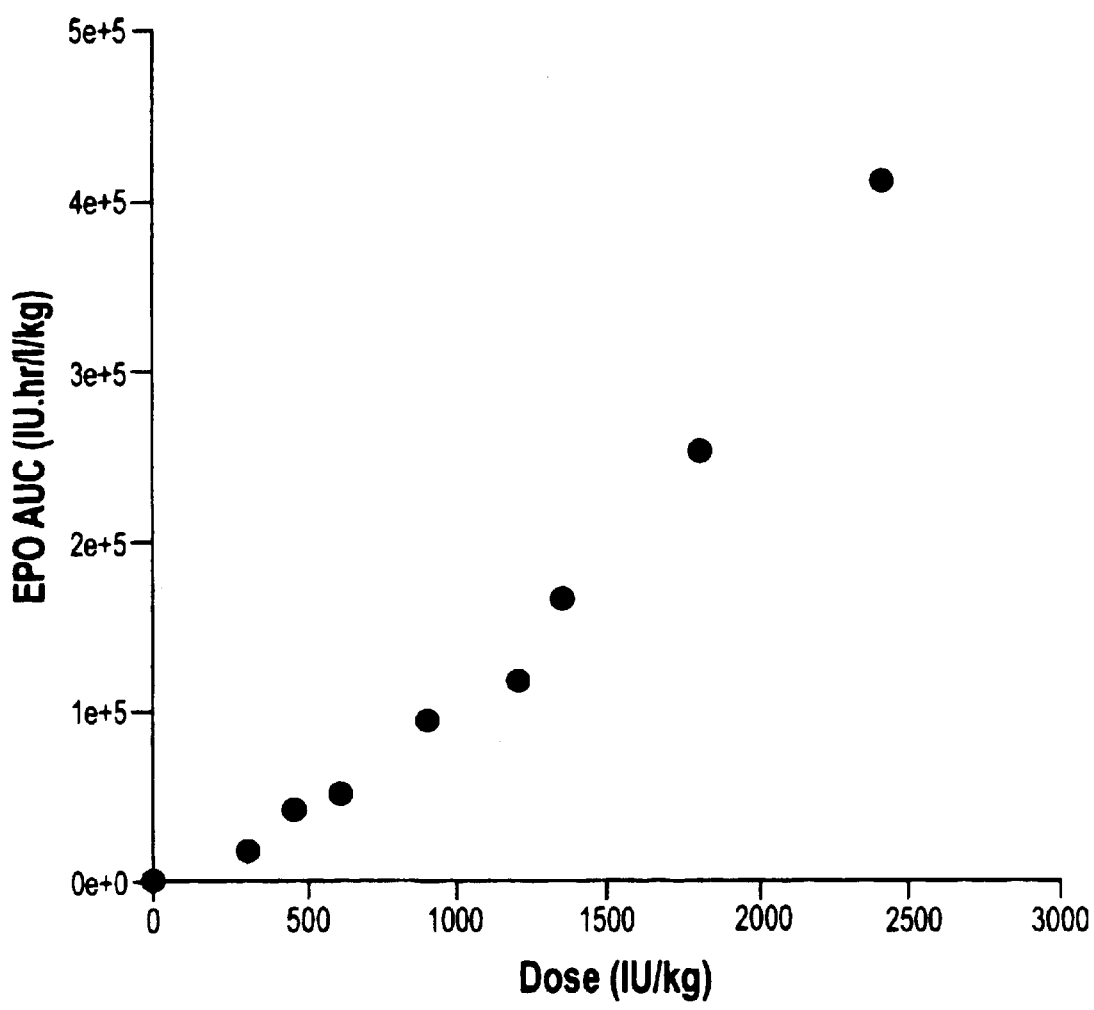
FIG. 6: Area under the serum rHuEPO concentration-time curve (AUC) versus dose after subcutaneous administration of the eight dose levels indicated in FIGS. 4A and 4B. The AUC was calculated by the Spline method.
Figure 7:
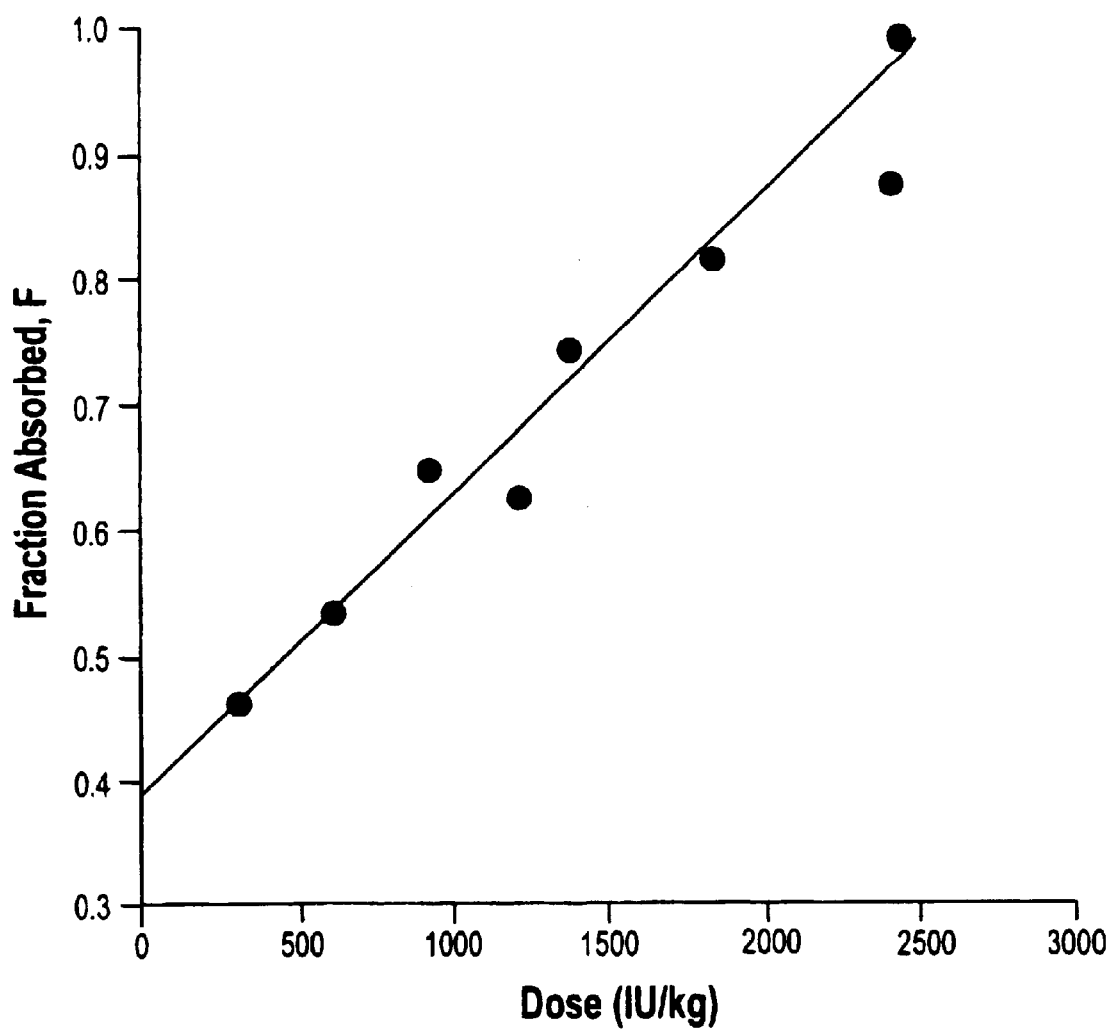
FIG. 7: Bioavailability (F) of the rHuEPO versus dose after subcutaneous administration of the eight indicated dose levels. The F values were obtained from the initial fittings of the pharmacokinetic data to the model as explained in the text. Linear regression yielded a $r^2$ of 0.9713, slope of 0.00024952, and an intercept of 0.3884.

FIG. 6 provides the plot of AUC versus dose for the different single SC doses. The greater than proportional increase in AUC with increasing dose indicates that either CL or bioavailability or both are changing with dose. Elimination of rHuEPO was found to be only very mildly non-linear. On the other hand, F was found to increase linearly with dose (FIG. 7) and turned out to be the main factor responsible for the disproportionate increase in AUC with SC dose. At the last two highest doses, reduced CL was also contributing to non-linearity. FIG. 8 lists the F values for all the doses obtained by deconvolution and by fitting the data from individual doses to the proposed model. The estimates obtained using both methods are very similar, thus indicating that the pharmacokinetic model of the present invention can adequately account for the nonlinearity due to changing values of F.

The cause of the incomplete and nonlinear bioavailability of SC rHuEPO is not known. For example, the protein IL-10 exhibits only 42% bioavailability on SC dosing with loss assumed to be due to the effects of proteolytic enzymes (see, e.g., Id.). In turn, these enzymes may be saturable at higher concentrations of peptide or protein substrates. The dual absorption process may be due to the role of the lymphatics in controlling access of macromolecules after SC dosing. The rapid early absorption phase may be caused by leakage of a major part of the dose into local blood vessels while the later phase may be related to slow entry via the lymphatic system.

Figure 9:
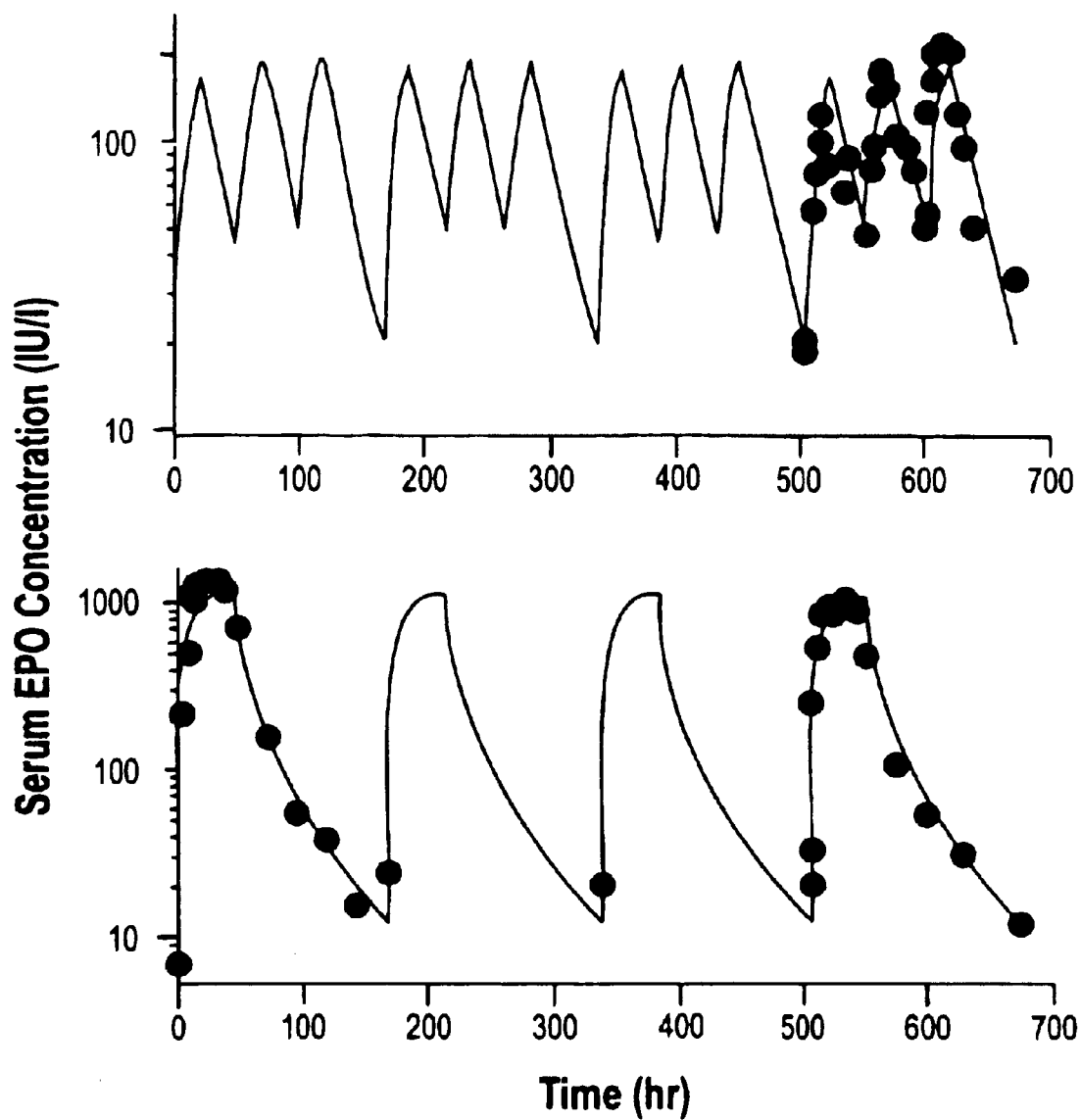
FIG. 9: Serum rHuEPO concentration versus time profiles during multiple-dosing regimens of 150 IU/kg t.i.w. (top) and 600 IU/kg/week (bottom). Solid circles represent mean data while lines are model-predicted values.

Simulations of rHuEPO concentrations versus time for the 150 IU/kg t.i.w. and 600 IU/kg/week multiple-dosing regimens are shown in FIG. 9. The pharmacokinetic model of the present invention, with most of the parameters fixed to the value obtained from fittings of the single doses, accurately describes the multiple dosing data. For the lower multiple-dosing regimen of 150 IU/kg, the Vd had to be increased. This may be due to non-linearities involved in distribution when the bioavailable amount is so low. The same change in Vd may also facilitate a better fitting of the 10 IU/kg IV dose where the maximum concentrations are in the same range.

Pharmacodynamic Model and Analysis

Data describing the pharmacodynamics of reticulocytes, RBC numbers, and Hb levels in blood were obtained from clinical studies performed by RWJPRI. This consisted of two comparable, open-label, randomized, parallel, placebo-controlled studies in healthy volunteers where rHuEPO was administered at eight single SC doses of EPREX®: 300, 450, 600, 900, 1200, 1350, 1800, 2400 IU/kg and as multiple dosage regimens: 150 IU/kg three times a week for four weeks and 600 IU/kg one per week for four weeks. Each treatment group had 5 subjects. The pharmacodynamic end points measured were the number of reticulocytes, RBCs in blood, and hemoglobin count.

The pharmacodynamic data were described using a cell production and loss model, which describes the changes in cell numbers with time after rHuEPO administration. According to this model, all cells involved in the process of erythropoiesis are assumed to be produced in a zero order fashion (k0): they live for a fixed time period at the end of which they die or are converted to other cells. As a result, the cells are lost at a rate which is exactly equal to the rate at which they were born, except that their elimination is delayed by a time period which is equal to the life-span of the cell. It is assumed that the lifespan of any single set of cells is constant with respect to time and is the same for each cell of that type.

Figure 10:
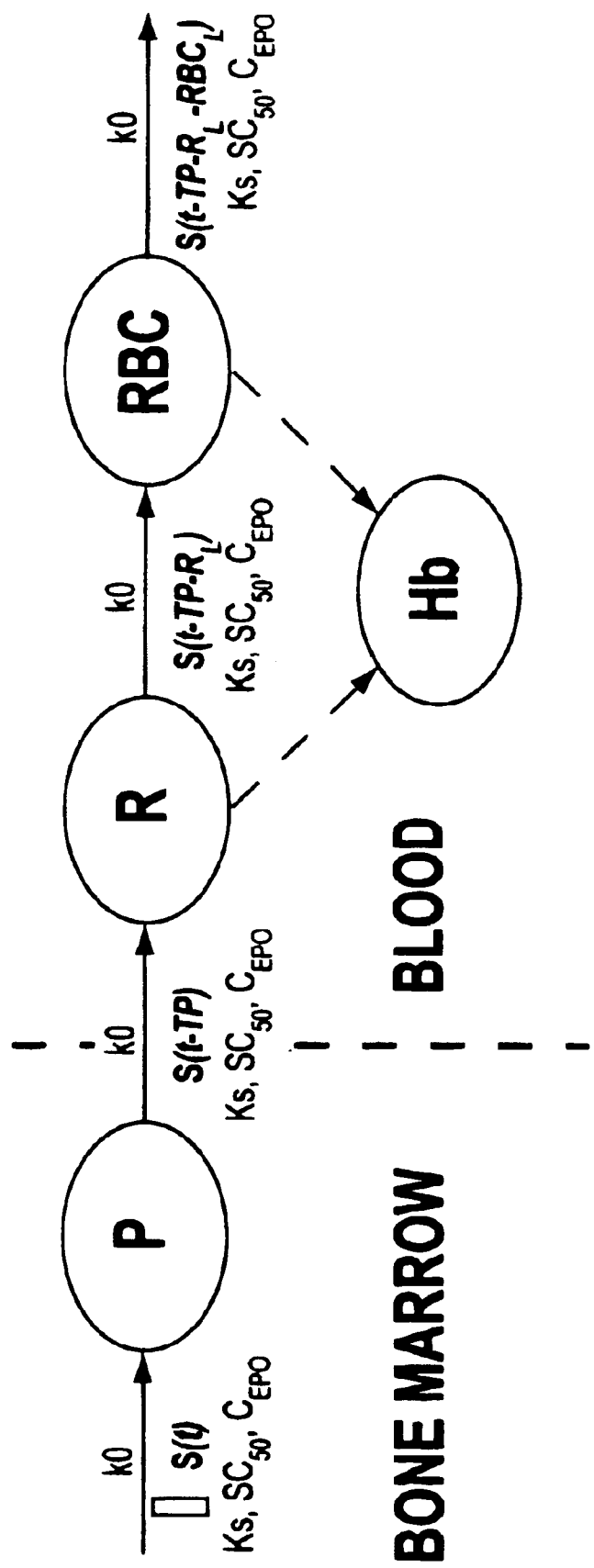
FIG. 10: Schematic representation of the pharmacodynamic model used for analysis of reticulocyte, RBC, and hemoglobin concentrations. Symbols are defined in the definition section of the detailed description of the present invention, infra.

FIG. 10 provides a schematic representation of a PD model of the present invention. The life spans of each precursor cell (TP), reticulocyte ($R_L$), and red blood cell ($RBC_L$) are indicated. The compartments reflect the pools of erythroid progenitor cells (P), reticulocytes (R), red blood cells (RBC) and hemoglobin (Hb) in the blood. Stimulation of erythropoiesis by the administered rHuEPO (Cp(t)) is given by the Hill function (S(t)) acting on the production of precursor cells in the marrow.

The differential equations for the model are as follows:

$$dP/dt = k0[S(t) - S(t-TP)] \quad (4)$$

$$dR/dt = k0[S(t-TP) - S(t-TP-R_L)] \quad (5)$$

$$dRBC/dt = k0[S(t-TP-R_L) - S(t-TP-R_L-RBC_L)] \quad (6)$$

where $$S(t) = \frac{S_{max} * (Cp(t) + C_{bs})}{SC_{50} + Cp(t) + C_{bs}} \quad (7)$$

$$S(t-TP) = \frac{S_{max} * (Cp(t-TP) + C_{bs})}{SC_{50} + Cp(t-TP) + C_{bs}} \quad (8)$$

$$S(t-TP-R_L) = \frac{S_{max} * (Cp(t-TP-R_L) + C_{bs})}{SC_{50} + Cp(t-TP-R_L) + C_{bs}} \quad (9)$$

$$S(t-TP-R_L-RBC_L) = \frac{S_{max} * (Cp(t-TP-R_L-RBC_L) + C_{bs})}{SC_{50} + Cp(t-TP-R_L-RBC_L) + C_{bs}} \quad (10)$$

$S_{max}$ is the maximum possible stimulation of reticulocyte production by rHuEPO and $SC_{50}$ is the plasma concentration of rHuEPO which can cause one-half maximum stimulation. The parameter Ks is defined as $Ks = k0*S_{max}$ and it signifies the maximum possible production rate of cells upon stimulation by rHuEPO.

The $SC_{50}$ was also used as a threshold rHuEPO concentration for formation of RBC from reticulocytes. It was assumed that when rHuEPO concentrations fall below this limit, the reticulocytes are not converted to erythrocytes. For this process, the stimulation function for model equation (6) was adjusted as follows:

If $Cp(t) \leq SC_{50}$, then $Cp(t-TP-R_L) = 0$ \quad (11)

and $Cp(t-RBC_L) \leq SC_{50}$, then $Cp(t-TP-R_L-RBC_L) = 0$ \quad (12)

The baseline conditions (steady-state levels) are defined as follows:

$$\frac{dPss}{dt} = 0, \quad \frac{dRss}{dt} = 0 \quad \text{and} \quad \frac{dRBCss}{dt} = 0 \quad (13)$$

As a result, the initial condition itself defines the steady-state levels.

$$Pss = P(0), Rss = R(0) \text{ and } RBCss = RBC(0) \quad (14)$$

The precursor steady-state conditions can be defined in explicit form as follows:

$$Pss = kin*TP \quad (15)$$

Since the baseline condition for the precursor compartment is unknown, a value of $14*10^{10}$ cells/L/hr was assigned using the above equation and literature estimates of $K_{in}$ (19).

The change in hemoglobin levels was modeled by simply using a proportionality factor $Hb_{cell}$, which represents the hemoglobin content per cell (reticulocyte or RBC).

$$Hb(t) = Hb_{cell} * \text{No.cells}(t) \quad (16)$$

As depicted in FIG. 1, erythropoiesis involves a cascade of events. The precursor compartment in the model is representative of all cells in the bone marrow involved in this process which are eventually converted to reticulocytes. The time TP thus serves as an average length of time taken for the earliest precursor cell stimulated by rHuEPO to undergo the cascade of differentiation processes to finally get converted to a reticulocyte. In other words, it accounts for the time delay seen for reticulocytosis to be initiated by rHuEPO. Once a reticulocyte is formed, it exists for a time equal to $R_L$ at which point it is converted to a RBC. It is assumed that the primary way by which a reticulocyte could be lost is by conversion to an erythrocyte, except for the subthreshold condition. The model does not account for random destruction of cells such as bleeding. Hence, the production and elimination rate of all these cells can be represented by a single zero-order rate constant k0. Once an RBC is produced, it in turn survives for a period of $RBC_L$ days after which it disappears from blood.

The transformation of a reticulocyte to RBC occurs partly in the bone marrow and partly in the blood over a period of 72 hours (see, e.g., Jusko, 1994. Clin. Pharmacol. Ther. 56:406–19.) Reticulocytes are formed in the marrow and by diapedesis, they pass into the circulation where these immature cells develop for a period of 24–48 hr before being transformed to erythrocytes (see, e.g., Guyton, 1996. Textbook of Medical Physiology, W. B. Saunders, Philadelphia.) Since rHuEPO is known to stimulate the premature release of reticulocytes from the marrow, it was assumed that these newly born cells spend their whole life span of 72 hours in the blood under rHuEPO stimulation. Consequently, the life span of reticulocyte, $R_L$ was fixed to be 72 hours. The RBC life span, $RBC_L$ was fixed to be 120 days and the Hb content per cell was fixed to be 29.5 pg/cell based on literature values (see, e.g., Jusko, supra and Guyton, supra.) Both reticulocytes and RBC are assumed to contribute to the overall Hb content of blood.

Furthermore, the new cell production (rate Ks) and loss model was used to obtain estimates of the $SC_{50}$ and Ks. Reticulocytes and red blood cells were assumed to have 3 day (72 hour) and 120 day (2880 hour) life-spans. The time lag in appearance of reticulocytes in blood was estimated by introduction of a precursor compartment representing the progenitor cells. A Ks value of 0.3709×1010 cells/L/hr was obtained yielding roughly an $S_{max}$ of 2 which reflects a moderate maximum stimulation of erythropoiesis. The $SC_{50}$ value obtained was 23 IU/L indicating that low serum rHuEPO concentrations were sufficient to maintain stimulation. A threshold concentration assumed equal to $SC_{50}$ of rHuEPO was found to be essential for conversion of reticulocytes to erythrocytes in the blood. Single doses of rHuEPO up to 900 IU/kg were incapable of maintaining rHuEPO levels above this threshold during the time of RBC production. This explains the lack of increase in RBC numbers in spite of stimulation in reticulocyte production after administration of the four lower single SC doses, consequently yielding only a very slight change in Hb for a brief period of time. Also, the threshold concept explains the better responsiveness of Hb levels to rHuEPO multiple-dosage regimens, which caused a significant improvement in Hb levels. The parallel nature of the study produced variability in responses to different rHuEPO doses, but a single set of parameters provided reasonable characterization of responses to the range of doses and regimens.

Figure 11:
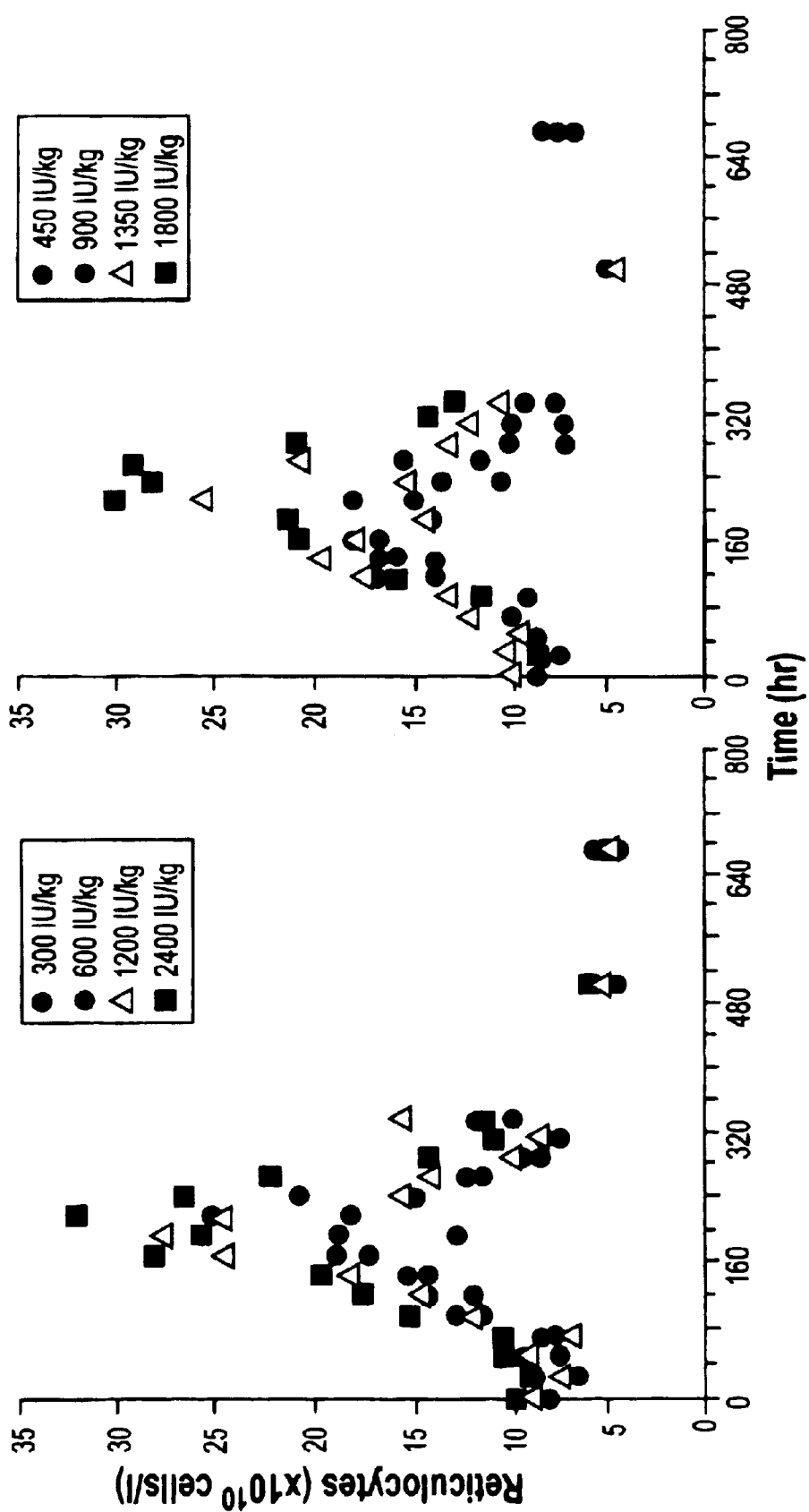
FIG. 11: Mean reticulocyte count versus time profiles for the eight indicated subcutaneous rHuEPO dose levels.

FIG. 11 shows the mean reticulocyte number versus time profiles for all single SC doses. The reticulocyte counts slightly increase compared to predose levels immediately at the first sampling point. This level is maintained for 3–4 days after which they steadily start rising till the peak is reached around 200–300 hour. Then, counts start declining rapidly with an apparent half-life of 25 hours to reach baseline levels by day 22 (528 hours).

Figure 12A:
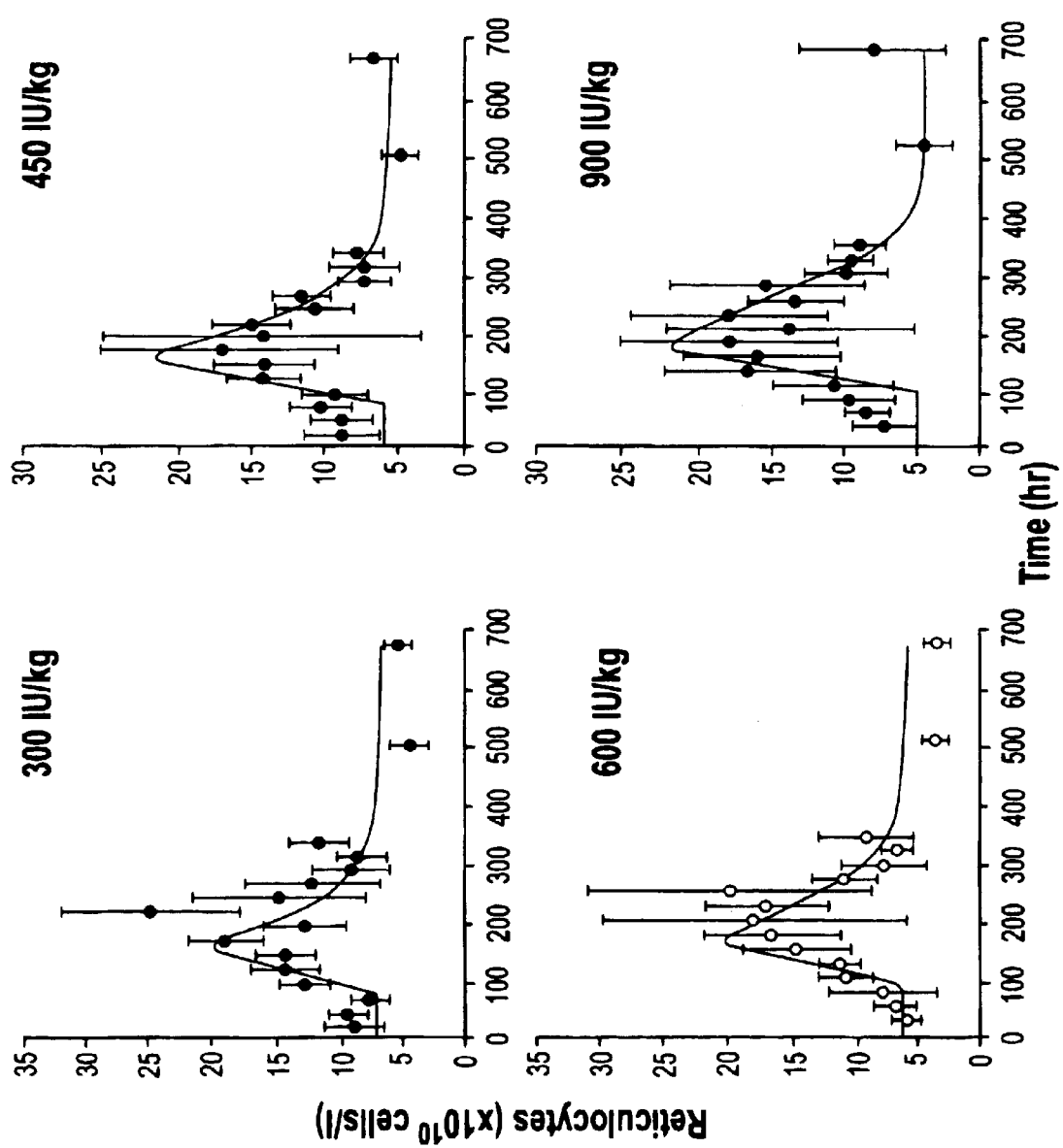
FIG. 12A: Reticulocyte number versus time profiles after subcutaneous administration of 300, 450, 600, and 900 IU/kg doses. Data for each dose are mean values from five healthy subjects. Symbols indicate the experimental data while the solid lines were obtained from fitting the data to equations 4, 5, 6, and 7, infra.
Figure 12B:
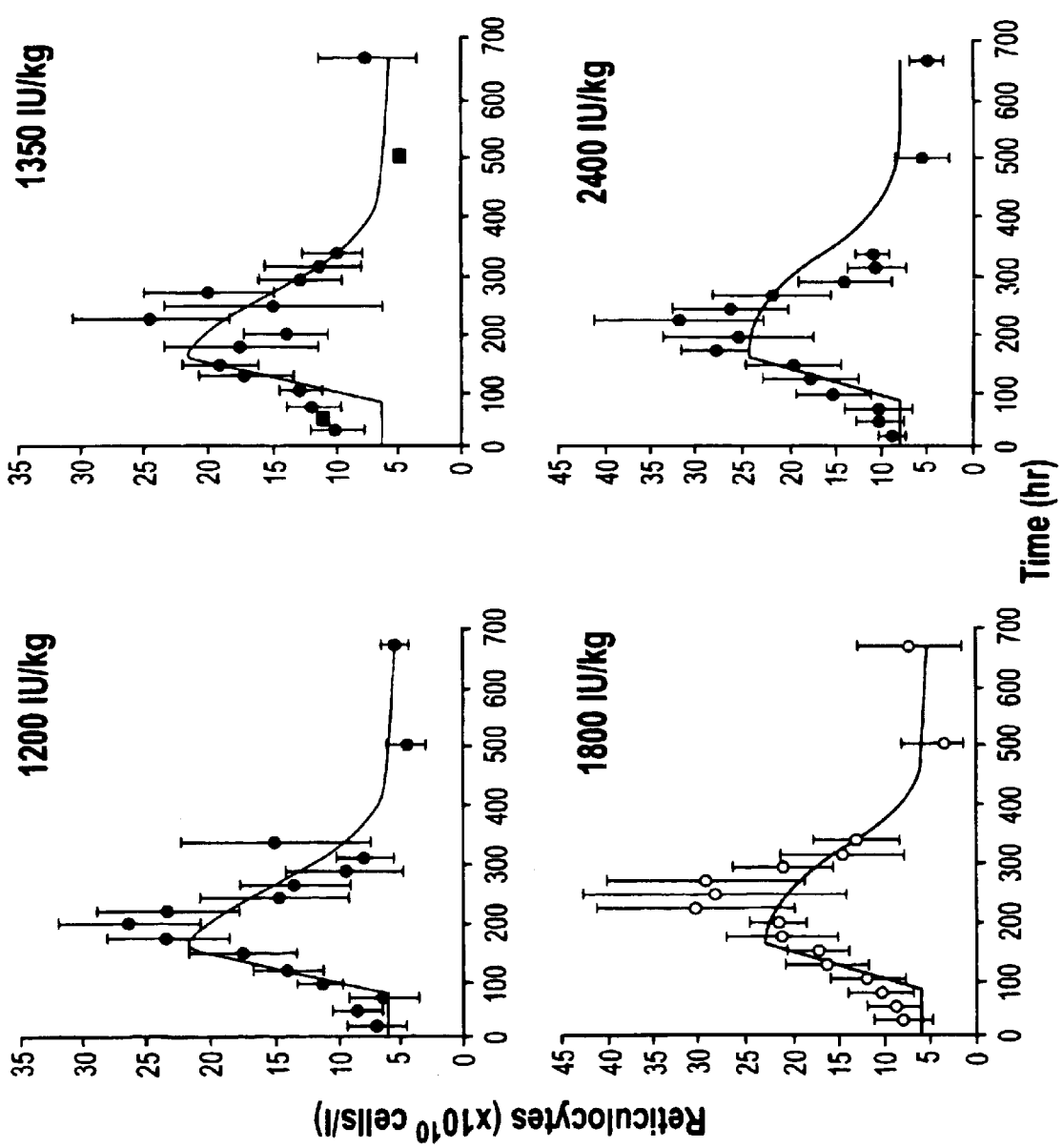
FIG. 12B: Reticulocyte number versus time profiles after subcutaneous administration of 1200, 1350, 1800, and 2400 IU/kg doses. Data for each dose are mean values from five healthy subjects. Symbols are the experimental data while the solid lines were obtained from fitting the data to equations 4, 5, 6 and 7.

The data and model fittings are shown in FIGS. 12A and 12B. Parameter estimates obtained by fitting the pharmacodynamic equations to the data are presented in FIG. 13. A Ks of $0.3709 \times 10^{10}$ cells/L/hr was obtained which translates to $4.451 \times 10^{10}$ cells/day assuming a blood volume of 5 L. It is known that 1% of all RBC are destroyed daily and replaced by reticulocytes in healthy humans yielding an erythrocyte production rate (k0) of $2-3 \times 10^{11}$ cells/day. Therefore, the estimated $S_{max}$ is 1.5–2.2 which indicates that rHuEPO can produce a maximum 2.5 to 3.2-fold increase in the zero-order production rate of reticulocytes, a relatively modest degree of stimulation which accounts for the slow and limited rise in blood.

The $SC_{50}$ of 22.58 IU/L obtained reflects the serum rHuEPO concentration needed to cause half-maximal stimulation. As long as rHuEPO serum concentrations are maintained above this value, the cell counts should remain above baseline. Normal erythrocytic progenitor cells, regardless of origin, express less than 1000 EPO-receptors on the cell surface. Binding of EPO to this receptor causes signal transduction events which ultimately lead to stimulation of the differentiation and proliferation of erythrocytic progenitors in the bone marrow (see, e.g., Lappin, supra.) In addition, EPO accelerates the release of reticulocytes from the marrow leading to increased serum reticulocyte and erythrocyte numbers (Id.). The slight increase in levels of reticulocytes seen after the zero time point may be caused due to the early release of immature reticulocytes from the marrow which is not accounted for by the model at these early times.

The low $SC_{50}$ value of 22.58 IU/L obtained reflects the fact that there are low numbers of receptor sites on erythropoietic cells which may be readily saturated so that high doses with rapid delivery may lead to considerable wastage of the bioavailable rHuEPO. An increase in dose or slower delivery facilitates rHuEPO levels being maintained above the $SC_{50}$ for a longer time and so there is an increase in the extent and duration of stimulation of reticulocyte production. This concept explains the results of two recent clinical studies that show that SC rHuEPO is more effective than IV dosing for stimulating production of erythrocytes. In spite of lower bioavailability, the SC doses with prolonged absorption results in more efficient stimulation of RBC production (see, Kaufmann, et al., 1998. *N. Engl. J. Med.* 339:578–83 and Besarab, et al., 1992. *Am. Soc. Nephrol.* 2:1405–12.)

FIGS. 12A and 12B show that the pharmacodynamic data for some dose levels are quite variable, which is reflected by the inconsistencies in the extent of stimulation with increasing dose. For instance, the 600 and 1200 IU/kg doses produce slightly higher numbers of cells compared to the 900 and 1350 IU/kg doses. The pattern of return, however, to baseline seems to be similar across doses. In any case, the models of the present invention capture the trend of responses, considering the variable nature of the data and the fact that one single set of parameters could adequately describe the pharmacodynamic data from all doses. It would be possible to obtain better fittings of the data from each dose level by allowing Ks and $SC_{50}$ to vary for each group. This would be reasonable since these were parallel dose groups, but then the parameters would have to be averaged for purposes of generalization.

Figure 14:
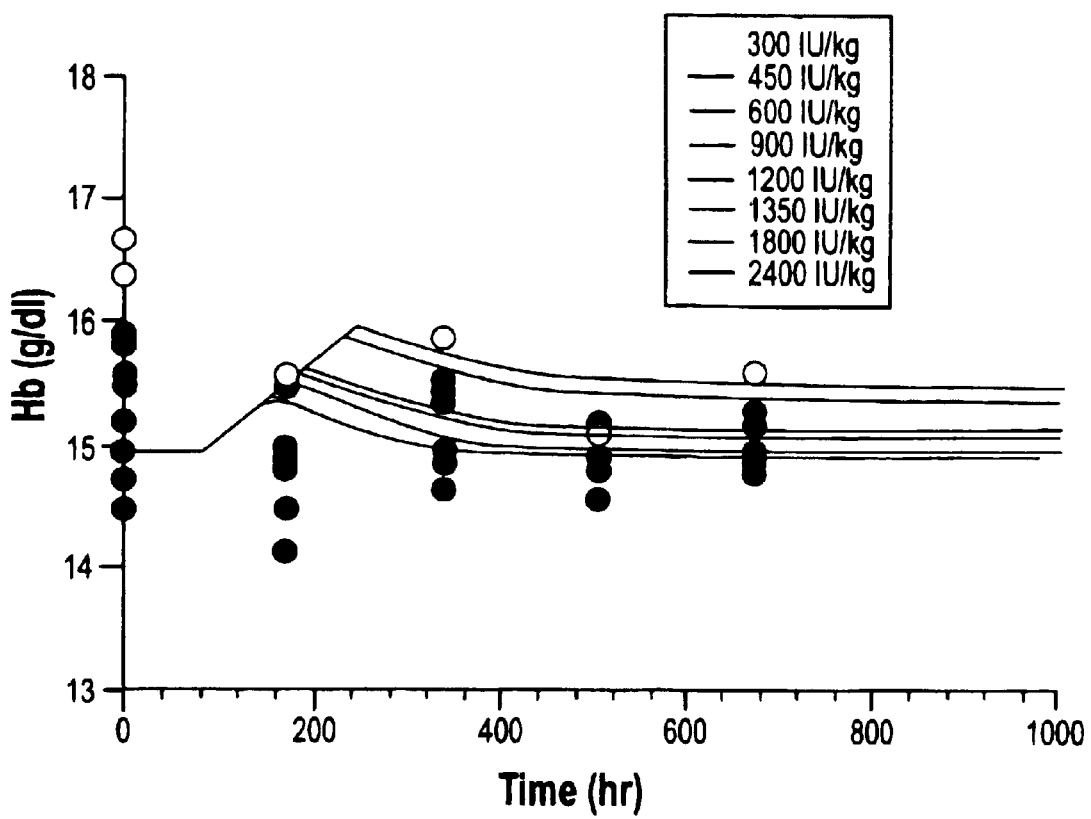
FIG. 14: Hemoglobin concentration versus time profiles after single subcutaneous administration of the eight indicated dose levels of rHuEPO. Closed circles are the mean data while solid lines are the model predictions.

FIG. 14 shows the Hb response versus time after the 8 single SC doses and the simulations. There is very little, if any, change in the Hb levels and this could be explained by the fact that rHuEPO concentrations fall close to the threshold limit by 7 days, thus preventing the conversion of newly formed reticulocytes to RBC. The slight elevation in Hb levels are therefore solely caused by increase in reticulocyte numbers for doses up to 900 IU/kg, after which there are modest increases in RBC also contributing to the consistently higher Hb levels. This threshold concept might explain the dose-dependant increase in reticulocyte response without significant increases in hematocrit or hemoglobin responses after single intravenous doses up to 1000 IU/kg in healthy volunteers as reported by Flaharty et al., supra.

Figure 15:
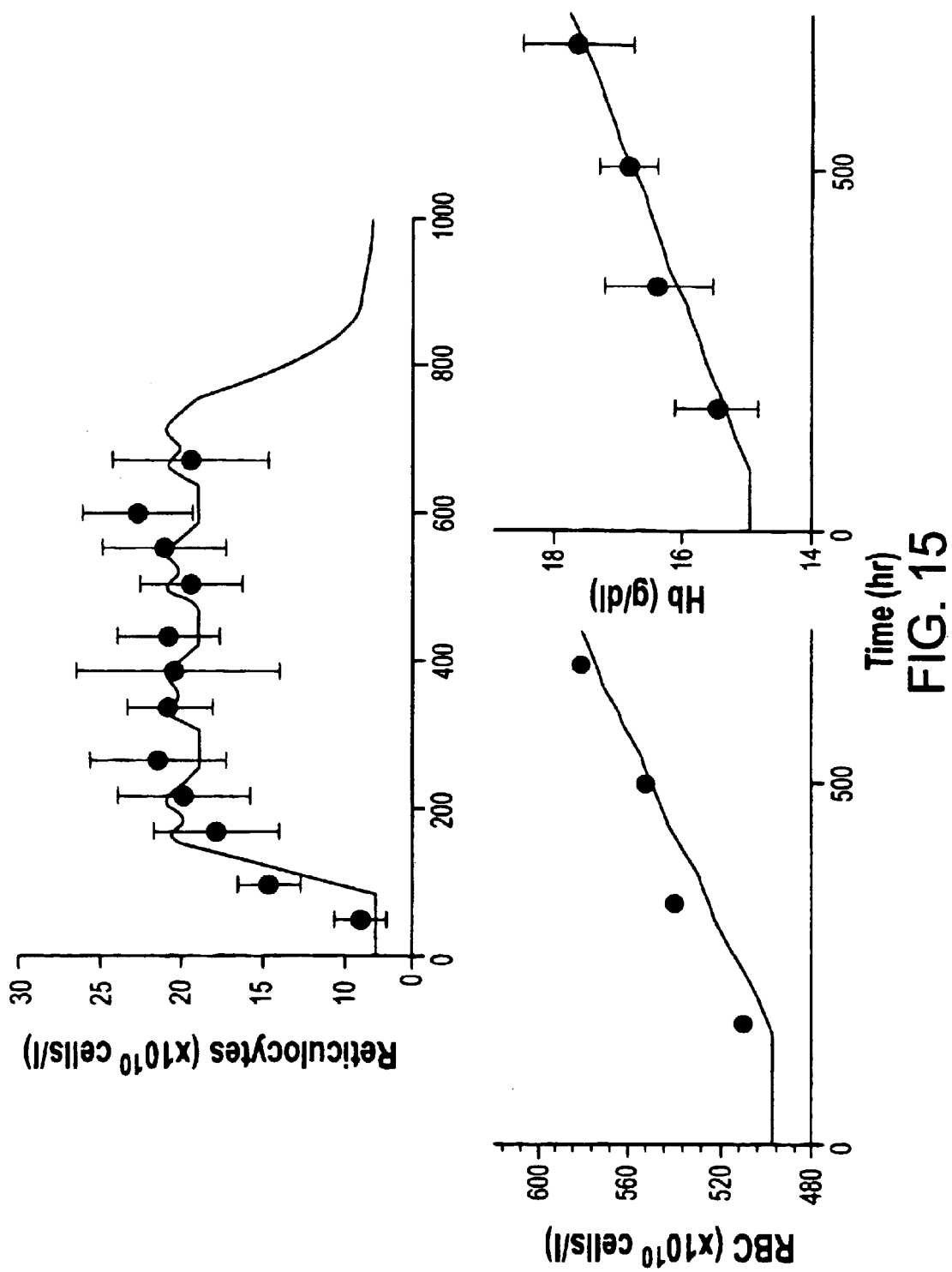
FIG. 15: Reticulocyte, RBC, and hemoglobin responses after multiple subcutaneous dosing of 150 IU/kg t.i.w. rHuEPO. Solid circles represent measured data and the solid lines are the model-predictions.
Figure 16:
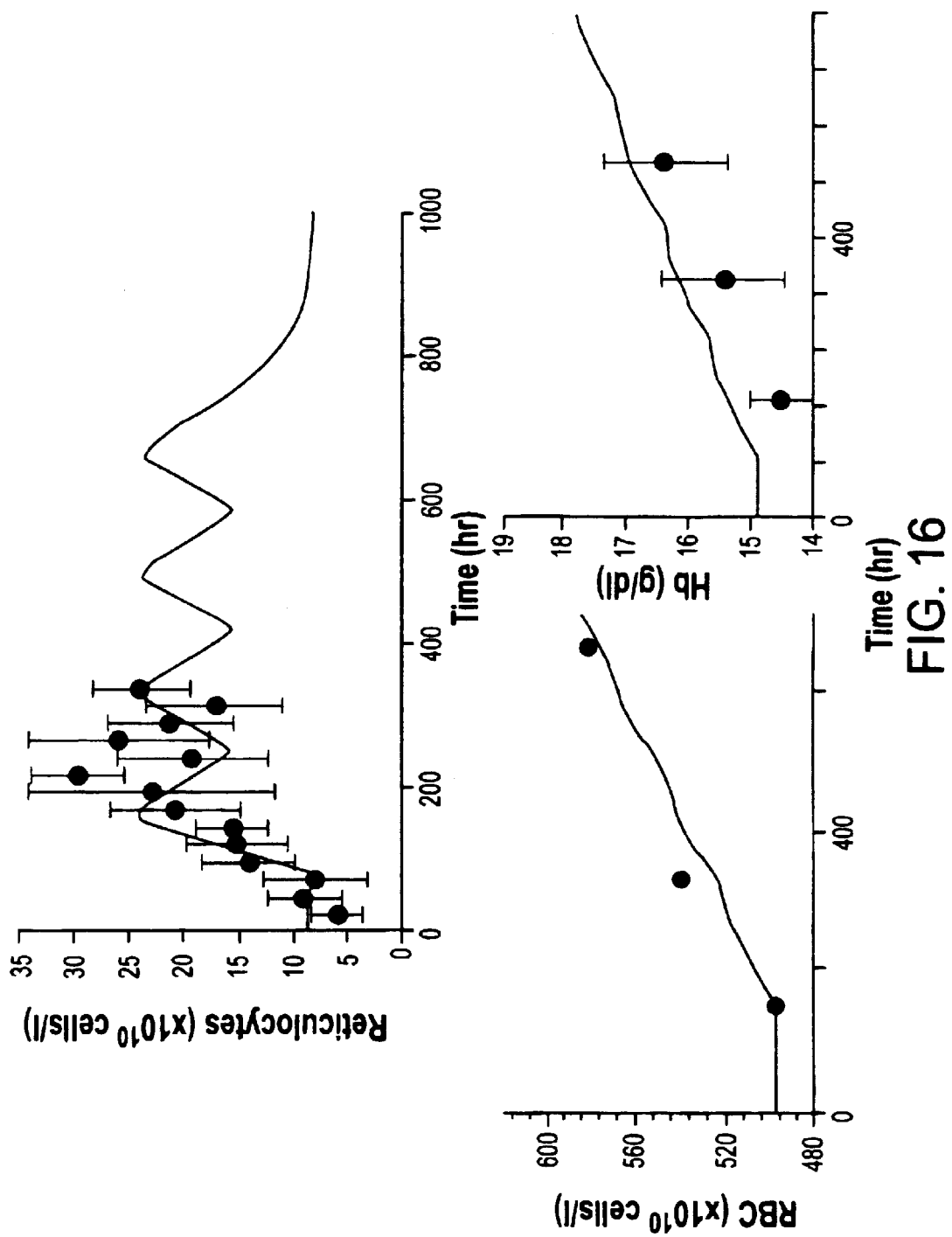
FIG. 16: Reticulocyte, RBC, and hemoglobin responses after multiple dosing of 600 IU/kg/week rHuEPO. Solid circles represent measured data and the solid lines are the model-predictions.

FIGS. 15 and 16 show the model output for the change in reticulocyte, RBC and Hb counts after multiple SC dosing of rHuEPO. The pharmacodynamic responses for both the dosage regimens are captured. The rHuEPO concentrations are maintained above the threshold for most of the period of time, giving the reticulocytes a chance to get converted to RBC, which is reflected as a steady increase in Hb levels after multiple-dosing in contrast to the single doses. The fittings of the different single SC doses and simulations of the multiple SC doses show that maintaining the rHuEPO concentrations above the $SC_{50}$ by administration of several smaller doses tends to enable a continuous increase in Tib levels as opposed to giving the same total dose as a single shot. In the latter case, the concentrations fall below the $SC_{50}$ much sooner causing a diminished reticulocyte response and more importantly, an ineffective Hb response.

In conclusion, the PK/PD models of the present invention demonstrate the importance of dose, dosage regimen, and route of administration in controlling rHuEPO responses and can be used as a valuable tool for designing optimal rHuEPO doses and time of readministration for various conditions. In addition, the present invention provides a computer-based system to tailor the dosage and schedule of the EPO treatment such that the patient receives optimum benefit in terms of, for example, increased hemoglobin and reticulocyte production, or to provide a dosage regimen, for example, once-weekly or once every two weeks, that suits the patient's needs.

Business Method

In a particular embodiment of the present invention, a business method relating to providing a dosing regimen of EPO and sale of the dosed EPO may be implemented. In a specific embodiment, that method may be implemented through the computer systems of the present invention. For example, a user (e.g. a health practitioner such as a physician or a pharmacist) may access the computer systems of the present invention via a computer terminal and through the Internet or other means. The connection between the user and the computer system is preferably secure.

In practice, the user may input, for example, information relating to a patient such as the patient's disease state, hematocrit, hemoglobin concentration, and other factors relating to the patient's reticulocyte and/or RBC count, such as the desired or optimal reticulocyte or RBC count. The computer system may then, through the use of the resident computer programs, provide one or more appropriate EPO dosing regimens for the patient. The computer program, via the user interface, may also provide pricing and cost comparisons for different EPO or EPO-like drugs, in conjunction with, or separate from, appropriate dosing regimens for those EPO or EPO-like drugs.

A computer system in accordance with a preferred embodiment of the present invention may be, for example, an enhanced IBM AS/400 mid-range computer system. However, those skilled in the art will appreciate that the methods and apparatus of the present invention apply equally to any computer system, regardless of whether the computer system is a complicated multi-user computing apparatus or a single user device such as a personal computer or workstation. Computer system suitably comprises a processor, main memory, a memory controller, an auxiliary storage interface, and a terminal interface, all of which are interconnected via a system bus. Note that various modifications, additions, or deletions may be made to the computer system within the scope of the present invention such as the addition of cache memory or other peripheral devices.

The processor performs computation and control functions of the computer system, and comprises a suitable central processing unit (CPU). The processor may comprise a single integrated circuit, such as a microprocessor, or may comprise any suitable number of integrated circuit devices and/or circuit boards working in cooperation to accomplish the functions of a processor. The processor suitably executes the PK/PD modeling computer programs of the present invention within its main memory.

In a preferred embodiment, the auxiliary storage interface allows the computer system to store and retrieve information from auxiliary storage devices, such as magnetic disk (e.g., hard disks or floppy diskettes) or optical storage devices (e.g., CD-ROM). One suitable storage device is a direct access storage device (DASD). A DASD may be a floppy disk drive which may read programs and data from a floppy disk. It is important to note that while the present invention has been (and will continue to be) described in the context of a fully functional computer system, those skilled in the art will appreciate that the mechanisms of the present invention are capable of being distributed as a program product in a variety of forms, and that the present invention applies equally regardless of the particular type of signal bearing media to actually carry out the distribution. Examples of signal bearing media include: recordable type media such as floppy disks and CD ROMS, and transmission type media such as digital and analog communication links, including wireless communication links.

The computer systems of the present invention may also comprise a memory controller, through use of a separate processor, which is responsible for moving requested information from the main memory and/or through the auxiliary storage interface to the main processor. While for the purposes of explanation, the memory controller is described as a separate entity, those skilled in the art understand that, in practice, portions of the function provided by the memory controller may actually reside in the circuitry associated with the main processor, main memory, and/or the auxiliary storage interface.

Furthermore, the computer systems of the present invention may comprise a terminal interface that allows system administrators and computer programmers to communicate with the computer system, normally through programmable workstations. It should be understood that the present invention applies equally to computer systems having multiple processors and multiple system buses. Similarly, although the system bus of the preferred embodiment is a typical hardwired, multidrop bus, any connection means that supports bidirectional communication in a computer-related environment could be used.

The main memory of the computer systems of the present invention suitably contains one or more computer programs relating to the PK/PD modeling of EPO administration and an operating system. Computer program in memory is used in its broadest sense, and includes any and all forms of computer programs, including source code, intermediate code, machine code, and any other representation of a computer program. The term "memory" as used herein refers to any storage location in the virtual memory space of the system. It should be understood that portions of the computer program and operating system may be loaded into an instruction cache for the main processor to execute, while other files may well be stored on magnetic or optical disk storage devices. In addition, it is to be understood that the main memory may comprise disparate memory locations.

Other objectives, features and advantages of the present invention will become apparent from the following specific examples. The specific examples, while indicating specific embodiments of the invention, are provided by way of illustration only. Accordingly, the present invention also includes those various changes and modifications within the spirit and scope of the invention that may become apparent to those skilled in the art from this detailed description.

EXAMPLE 1

Human Pharmacokinetics and Bioavailability for EPO

The following example of the present invention provides a summary of the PK/PD data that support a 40,000-IU q.w. dosing regimen. The data are derived from both the literature and four clinical studies conducted by RWJPRI, Raritan, N.J. Three studies were conducted under Investigational New Drug BB-IND-23 18, and one study was conducted in the UK. A brief overview of the studies is given in FIG. 17.

The clinical pharmacokinetic studies included in this technical summary are described FIGS. 18A–18D, and the pharmacokinetic data from these studies are summarized in FIG. 19. The analytical methods used for the determination of EPO concentration in serum are summarized, infra, and FIG. 20.

Clinical Study EPO-PHI-373 (FIG. 17) provides the data to support the 40,000 IU once weekly dosing regimen. Clinical Study EPO-PHI-370 (FIG. 17), which has a similar design as Clinical Study EPO-PHI-373.

In Clinical Study EPO-PHI-370, there were randomization issues, fluctuating hemoglobin levels, and many subjects were iron-deficient at initial. Error in the randomization at the study site resulted in an unequal distribution of males and females in each treatment group, and contributed to an imbalance in mean baseline hemoglobin values. A review of hematology values revealed a substantial fluctuation in hemoglobin for a number of subjects between screening and baseline evaluations. Further investigation revealed laboratory inconsistencies relating to equipment calibration. To appropriately confirm the positive findings of this study, it was decided that a repeat study would be conducted. Clinical Study EPO-PHI-373 was the repeat of Clinical Study EPO-PHI-370.

Clinical Studies EPO-PHI-358 (FIG. 17) and EPO-PHI-359 (FIG. 17) are two pilot studies conducted to investigate the dose-proportionality of EPO and to obtain preliminary pharmacokinetic and pharmacodynamic information after different single and multiple doses.

General Analytical Methods for in vivo Studies

Summary

Bioanalytical methods were developed and validated to support the clinical program for EPO conducted by RWJPRI, Raritan, N.J. The original method used to determine EPO concentrations in human serum was a radioimmunoassay (RIA) (RWJPRI Study Nos DM92001 and DM96023). This method was successfully transferred to PPD Development (PPD), Richmond Va., the Contract Research Organization which conducted the analysis of the supportive clinical study (EPO-PHI-370). This RIA method was fully cross-validated with an enzyme-linked immunosorbent assay (ELISA) at PPD for the analysis of the pivotal study (EPO-PHI-373). To test the comparability between the RIA and the ELISA, a set of 16 pooled human subject samples was prepared by RWJPRI and analyzed at PPD in both the ELISA and RIA. The ELISA provided improvements in accessibility of reagents, time of analysis and extended range of standard curve without loss of sensitivity.

Assay Type

A radioimmunoassay was used for the quantitation of EPO to support Clinical Studies EPO-PHI-358, EPO-PHI-359 (conducted at RWJPRI) and EPO-PHI-370 (conducted at PPD). An ELISA was used for the quantitation of EPO in Clinical Study EPO-PHI-373 (conducted at PPD).

The RIA method was originally developed by Diagnostic Systems Laboratories (DSL), Webster, Tex., for the quantitative determination of EPO and the results were compared to those obtained with a RWJPRI method. The commercially available RIA is a double-antibody, competitive method that uses a rabbit polyclonal antiserum to human urinary EPO as the primary antibody and an $^{125}$I-labeled human urinary EPO as tracer. The procedure follows the basic principle of radioimmunoassay whereby there is competition between a radioactive and a nonradioactive antigen for a fixed number of antibody binding sites. The amount of $^{125}$I-labeled EPO bound to the antibody is inversely proportional to the concentration of EPO present in the serum. The separation of free and bound antigen is easily and rapidly achieved by using an accelerated double antibody polyethylene glycol system. The major in-house modification of the DSL kit was substitution of recombinant human EPO for urinary EPO in standards and spiked quality control samples. Standard concentrations used in the assay were 7.8, 15.6, 31.3, 50, 62.5, 100, and 125 mU/mL. This exact method was transferred to and validated by PPD.

The Immunochemistry Department of PPD validated the ELISA for determination of EPO concentrations in human serum. This ELISA is a direct, double-antibody sandwich assay developed by R&D Systems, Inc, Minneapolis, Minn., for the quantitative determination of EPO concentrations in plasma or serum. Microtiter wells, precoated with monoclonal (murine) antibody specific for r-HuEPO are used to capture EPO. The bound EPO is labeled with anti-EPO polyclonal (rabbit) antibody and horseradish peroxidase (conjugate). An optical signal is produced with the addition of tetramethylbenzidine/buffered hydrogen peroxide (substrate). The amount of color generated is directly proportional to the concentration of EPO in sample or standard. The major in-house modification of the R&D kit was use of in-house recombinant human EPO in standards and spiked quality control samples. Standard concentrations used in the assay were 7.8, 15.6, 31.3, 50, 62.5, 100, 125, and 250 mU/mL.

Range of Standard Curves

The RIA used for the Clinical Studies EPO-PHI-358, EPO-PHI-359, and EPO-PHI-370 had a standard curve range of 7.8 to 125 mU/mL using a 0.1-mL sample aliquot. The precision of the standard curve at RWJPRI was ≦5.8% and at PPD, ≦10.8%. The ELISA used to assay clinical samples from Clinical Studies EPO-PHI-373 demonstrated a concentration range of 7.8 to 250 mU/mL using a 0.1-mL sample aliquot with a precision of ≦5.3%.

Lower Limit of Quantitation

The lower limit of quantitation (LLOQ), the lowest measurable standard concentration which could be accurately and precisely quantified, was 7.8 mU/mL in both the RIA and the ELISA.

Quality Controls

Quality control samples (QCs) for both methods were prepared in blank serum to reflect the expected concentrations in the study. QC concentrations assayed during the validation of the RIA at RWJPRI were 35, 60 100, 300, 1000, and 2000 mU/mL. QC concentrations assayed during the validation of the RIA at PPD were 100, 500, 2000, and 5000 mU/mL. The QC concentrations for the ELISA were 7.8, 20, 100, 500, 2000, and 5000 mU/mL. At least three levels of QCs in human serum were assayed with study samples during daily sample analysis.

A set of 16 pooled human serum samples from a previous clinical study was prepared by RWJPRI and the blinded samples were shipped to PPD to be assayed in both the RIA and the ELISA. The relative percent difference (RPD) calculated between the values obtained by both methods was determined to be 15.8% (for the lowest level of QC) or better.

Dilutional linearity was also demonstrated since the expected concentrations of some samples were above the highest standard curve concentration. During the validation of the RIA at RWJPRI linearity upon dilution was established using serial 1:30- to 1:256-fold dilutions of QC samples. At PPD dilutional linearity was demonstrated during RIA validation with 1:20- to 1:200-fold dilutions in QC samples and from 1:20- to 1:100-fold dilutions in in vivo samples from one subject with high EPO concentrations. During the ELISA validation the dilutional linearity was established using 1:50-1:100-, and 1:200-fold dilutions of the 5000-mU/mL QC.

Recovery

The assay was run without sample extraction, therefore recovery assessment was not required.

Accuracy and Precision

In the RIA, the intra-assay accuracy (percent difference between measured concentration and target concentration) ranged from 102.7 to 127% at RWJPRI and 95.5 to 100.3% at PPD. The interassay accuracy ranged from 81.7 to 109.8% at RWJPRI and 100 to 105.6% at PPD. In the ELISA the intra-assay accuracy ranged from 87.9 to 109.9% and the interassay accuracy ranged from 83.6 to 116%.

In the RIA, the intra-assay precision (percent coefficient of variation) was ≦8.2% at RWJPRI and ≦5.3% at PPD. The interassay precision was ≦15.1% at RWJPRI and ≦7.2% at PPD. In the ELISA, the intra-assay precision was ≦10% and the interassay precision was ≦12.9%.

Stability

The stability of EPO in human serum was demonstrated for 20 months at −20° C., at room temperature for 2 hours and during four freeze/thaw cycles.

Data Analysis and Acceptability Criteria

A validated four parameter logistic curve was used to determine unknown serum sample concentrations of EPO from the standard curve in both assays. The data from the RIA performed at RWJPRI was reduced using Micromedic software (ICN Biomedicals, Inc., Costa Mesa, Calif.). The data from the RIA and the ELISA performed at PPD was reduced using the PPD Development Oracle 7.3 proprietary RICORA database. The RIA assays were acceptable when the QCs were within 20% of nominal and the difference between the count per minutes of the replicates was ≦6%. The ELISA assays were acceptable when the QCs were within 20% for both accuracy and precision.

Summaries of Individual Studies

Pilot Exploratory Studies, EPO-PHI-358 and EPO-PHI-359

Clinical Study EPO-PHI-358 and Clinical Study EPO-PHI-359 were two pilot exploratory studies designed to investigate the dose-proportionality of EPO after SC administration. Because of the similarity in study design, data from the two studies were pooled to maximize the dose range for pharmacokinetic and pharmacodynamic analyses.

The objective of Clinical Study EPO-PHI-358 was to determine the pharmacokinetic and pharmacodynamic profiles of EPO after a single 450-, 900-, 1350-, or 1800-IU/kg subcutaneous dose of EPO and to compare these profiles to that of the typical 150-IU/kg t.i.w.×4-week dosing regimen. The objective of Clinical Study EPO-PHI-359 was to determine the PK and PD profiles of EPO after a single 300-, 600-, 1200-, or 2400-IU/kg SC dose of EPO and to compare these profiles to that of the 600-IU/kg q.w.×4-week dosing regimen. There was a placebo group in each study.

The EPO formulation used in these two studies was a 40,000 IU/mL, preservative-free phosphate buffered solution containing 2.5 mg/mL human serum albumin, 5.84 mg/mL sodium chloride, 1.164 mg/mL sodium phosphate monobasic dihydrate, and 2.225 mg/mL sodium phosphate dibasic dihydrate (Formulation No. FD-22512-000-J-45; Product Lot 5C903J; date of manufacture, March 1995). The placebo formulation used in these two studies was a preservative-free phosphate buffered solution containing 2.5 mg/mL human serum albumin, 5.84 mg/mL sodium chloride, 1.164 mg/mL sodium phosphate monobasic dihydrate, and 2.225 mg/mL sodium phosphate dibasic dihydrate (Formulation No. FD-22512-000-ABX-45; Product Lot 5C902J; date of manufacture, March 1995).

Both studies were open-label, randomized, placebo controlled, parallel-group, single-center studies. Thirty-two healthy subjects were enrolled in Clinical Study EPO-PHI-358 and 30 subjects completed the study and were included in the PK/PD analyses. Thirty subjects were enrolled and completed the Clinical Study EPO-PHI-359. Demographic data of the subjects in these two studies are listed in FIG. 21.

Frequent serial blood samples were collected for serum EPO determination during Weeks 1 and 4 for the 600-IU/kg q.w. dosing regimen and during Week 4 for the 150-IU/kg t.i.w. dosing regimen. Weekly predose blood samples for serum EPO determination were also collected. For the single dose groups, serial blood samples for serum EPO determination were taken over the 4-week study period. Blood samples were also collected for determination of percent reticulocytes (% RETI), total red blood cells (RBC), and hemoglobin (HEMO) in blood during the 4-week study period.

Sample analyses for serum EPO were performed at RWJPRI, Raritan, N.J. A RIA kit procedure manufactured by DSL and modified at RWJPRI was used for the determination of EPO concentrations in serum. This method and its validation are described in Section 4. Pharmacokinetic and pharmacodynamic parameters were summarized by descriptive statistics. Mean serum EPO concentration-time profiles for subjects in Clinical Studies EPO-PHI-358 and EPO-PHI-359 are shown in FIGS. 22 and 23, respectively.

Figure 22:
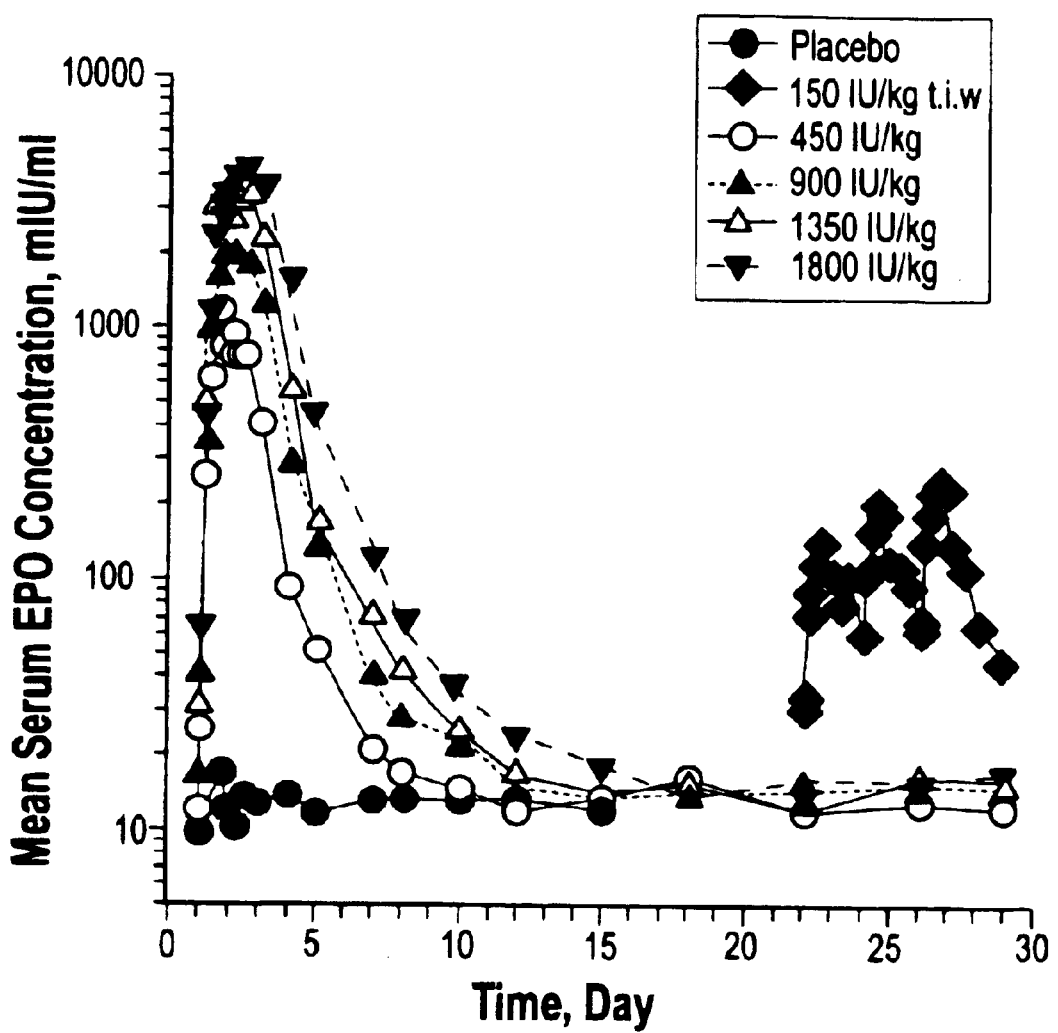
FIG. 22: Mean serum Epoetin Alfa concentration-Time profiles (uncorrected for baseline EPO) for subjects in Clinical Study EPO-PHI-358.
Figure 23:
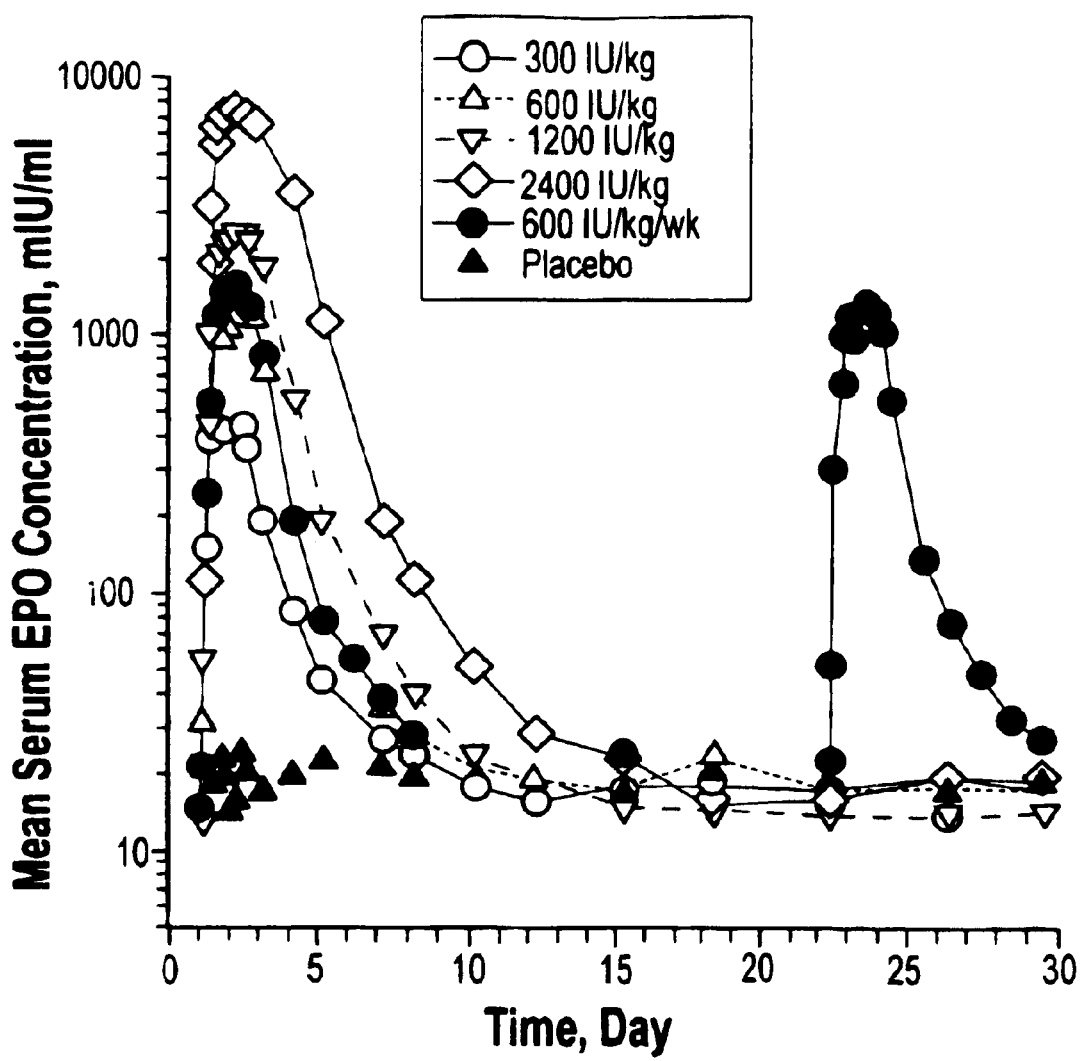
FIG. 23: Mean serum Epoetin Alfa concentration-Time profiles (uncorrected for baseline EPO) for subjects in Clinical Study EPO-PHI-359.

While serum EPO concentrations after single dose administrations declined to the endogenous EPO level by Day 15, the 150-IU/kg t.i.w. dosing regimen was able to maintain serum EPO concentrations above the pre-dose endogenous EPO level throughout the treatment period (FIG. 22). The mean predose endogenous EPO concentration for this group of subjects was 14±4 mIU/mL, and the mean trough concentrations (corrected for baseline EPO) before the first, second, and third doses during the fourth dosing week were 19±9, 48±18, and 52±25 mIU/mL, respectively. There was an accumulation of serum EPO during dosing as the $C_{max}$ after the first, second, and the third doses in the last dosing week ranged from 128 to 163, 141 to 214, and 152 to 334 mIU/mL, respectively. The 600-IU/kg once per week dosing regimen maintained serum EPO levels above the predose endogenous EPO level up to 5 to 6 days in a dosing week (FIG. 23). The mean predose endogenous EPO level in these subjects was 13±3 mIU/mL, and the mean steady-state trough EPO concentration (corrected for baseline EPO) was 11±5 mIU/mL. This dose regimen attained a higher $C_{max}$ than the 150-IU/kg t.i.w. dosing regimen, although the predose trough concentrations were near the endogenous EPO level. $C_{max}$ values for the 600-IU/kg q.w. regimen during Weeks 1 and 4 ranged from 1203 to 2148 and 920 to 1489 mIU/mL, respectively. The mean±SD pharmacokinetic and pharmacodynamic parameter values are listed in FIG. 24.

Figure 25:
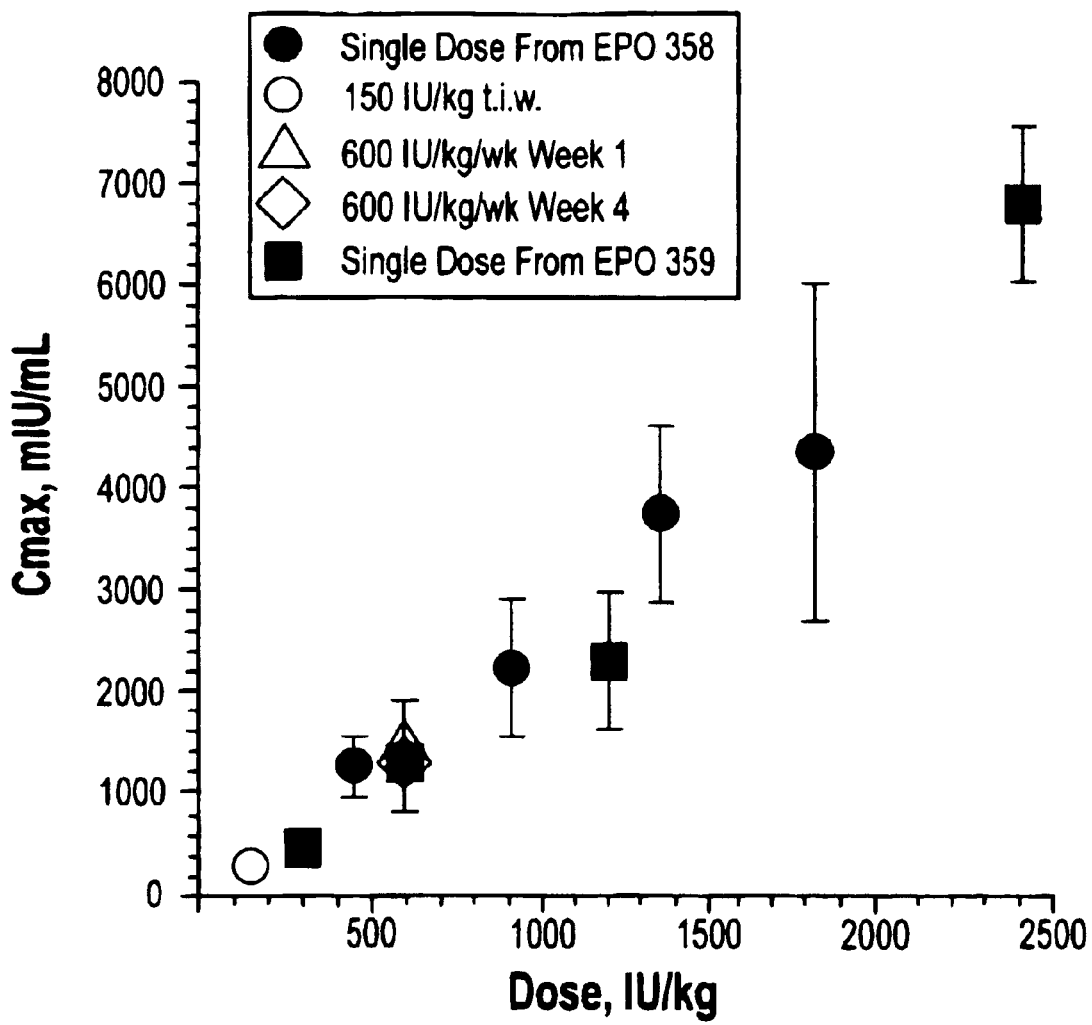
FIG. 25: Relationship between mean±SD $C_{max}$ and dose for subjects receiving single or multiple SC dose regimens in Clinical Studies EPO-PHI-358 and EPO-PHI-359.
Figure 26:
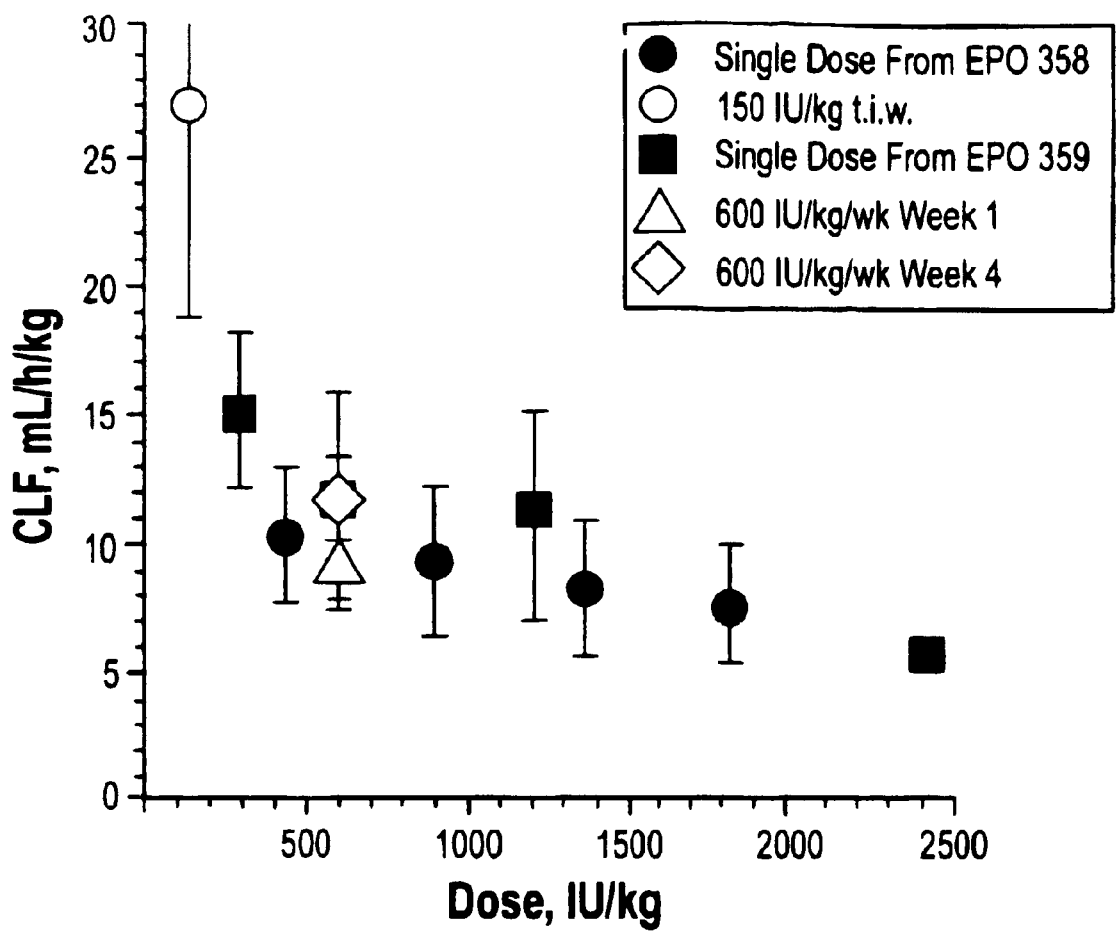
FIG. 26: Relationship between mean±SD CL/F and dose for subjects receiving single or multiple SC dose regimens in Clinical Studies EPO-PHI-358 and EPO-PHI-359.

There was a linear relationship between mean $C_{max}$ and dose with correlation coefficient=0.982 (FIG. 25), suggesting that the absorption rate of EPO from the injection site was independent of dose. On the other hand, the relationship between AUC and dose was a curvilinear one such that clearance (CL/F) decreased with increasing doses (FIG. 26).

Figure 27:
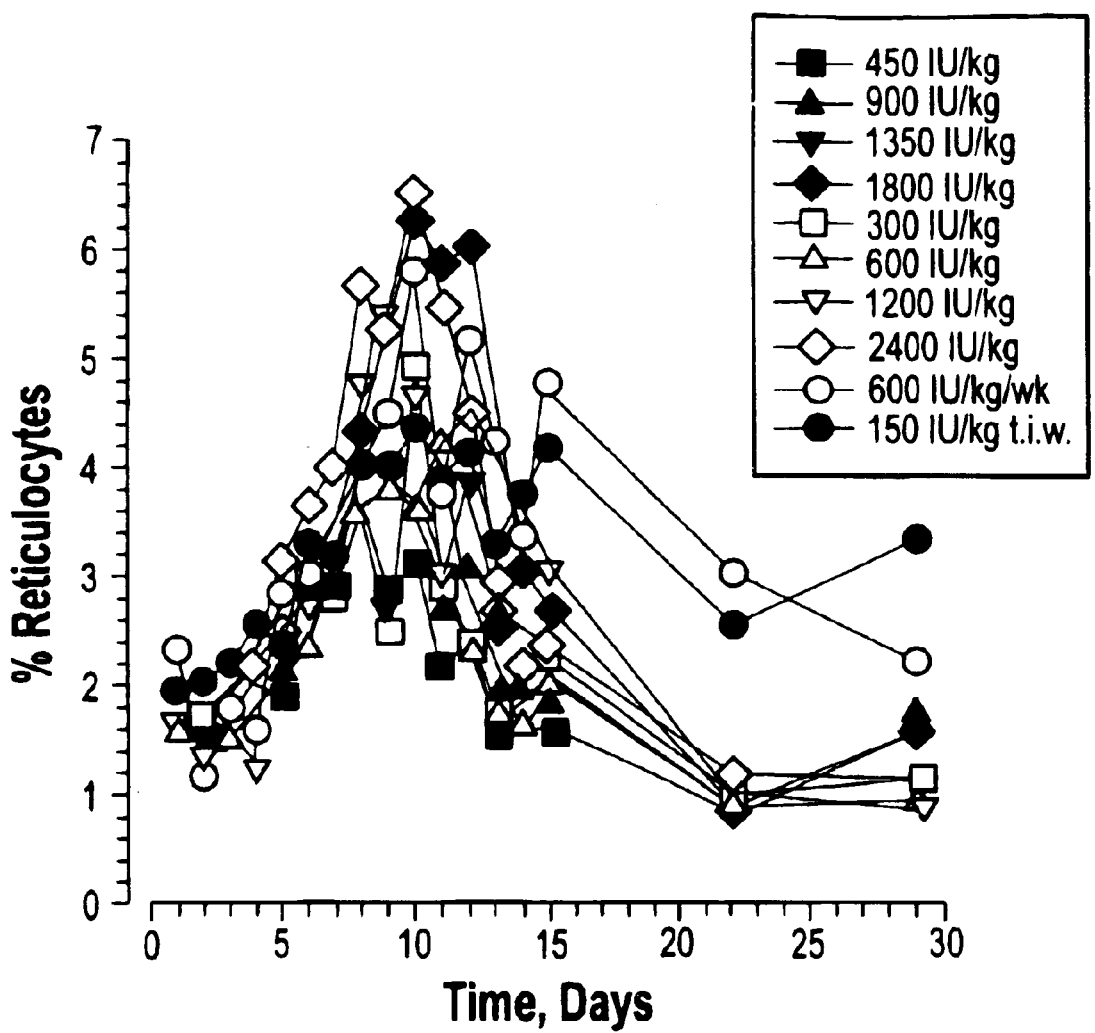
FIG. 27: Mean percent reticulocyte-time profiles for the four week study period (Clinical Studies EPO-PHI-358 and EPO-PHI-359).

Mean percent reticulocyte-time profiles during the 4-week study period are shown in FIG. 27. Percent reticulocytes in blood reached their maximum values on approximately Day 10 after drug administration for both single and multiple doses. While the percent reticulocytes in blood after single dose administrations declined to the predose baseline values by Day 15, the percent reticulocytes in blood after the two multiple dosing regimens (150 IU/kg t.i.w. and 600 IU/kg q.w.) were maintained well above the predose baseline values for up to Day 30. This observation is not unexpected as the normal lifespan of cells in the reticulocyte stage is around 3.5 days in the marrow and 1 to 2 days in the blood circulation (Hillman, supra). EPO exerts its biological effects by binding to a specific cell-surface receptor on its target erythroid progenitor cells in bone marrow, the colony-forming unit-erythroid (CFU-E) and the burst-forming unit-erythroid (BFU-E) (Dessypris et al., 1984, *Br. J. Haematol.,* 56:295–306 and Wu et al., 1995, *Cell,* 83:59–67). These erythroid progenitor cells eventually mature into reticulocytes which are then released into blood circulation. Data from these two studies indicate that reticulocytes produced from stimulation by a single dose of EPO appeared in the blood circulation in about 7 to 10 days. With a lifespan of 1 to 2 days in blood circulation, one would expect reticulocytes produced from stimulation by a single dose to disappear from blood circulation by Day 15. Therefore, a continuous production of reticulocytes requires EPO in serum to be maintained continuously (such as after 150-IU/kg t.i.w. dosing regimen) or intermittently (such as after the 600-IU/kg q.w. dosing regimen) above the endogenous EPO concentration.

For the single dose data, there was a trend for increase in mean AUC of percent reticulocytes (AUC[UNCORR RETI]) as the mean AUC of EPO [AUC(Day 0–29)] increases (serum EPO concentration corrected for predose EPO level and AUC value was calculated over a 4-week period). Compared to single dose data of similar AUC(Day 0–29) values, multiple dose data have higher mean AUC (UNCORR RETI) values. The data, therefore, suggest that multiple dosing of EPO is more efficient in stimulating the production of reticulocytes than a single dose.

Figure 28:
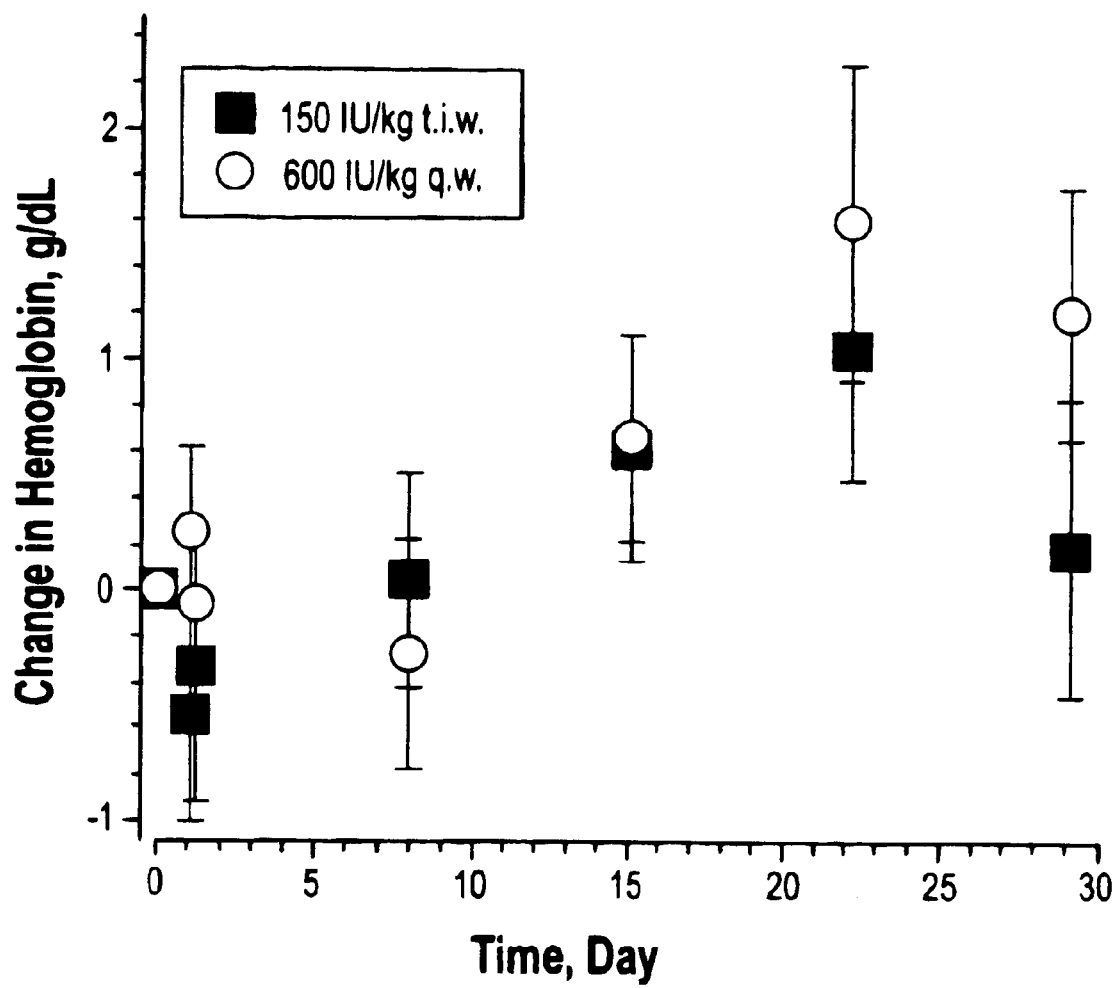
FIG. 28: Mean±SC change in hemoglobin from baseline profiles after 150 IU/kg t.i.w. (N=5) and 600 IU/kg q.w (N=5) Epoetin Alfa for four weeks (Clinical Studies EPO-PHI-358 and EPO-PHI-359).

Despite an EPO AUC-related increase in the production of reticulocytes, there were no apparent increases in hemoglobin levels after single dose administration. The reason for the lack of increase in hemoglobin level after single dosing is not known at this time. On the other hand, both multiple dose regimens were able to deliver a steady rise in hemoglobin levels, and the patterns of the change in hemoglobin from baseline were similar for the two multiple dose regimens (FIG. 28).

In conclusion, the results from this study show that pharmacological response to EPO is a function of dose and dosing regimen. The absorption rate of EPO after SC administration was independent of dose. Clearance of EPO was dose-dependent, decreasing with increasing dose. There was an increasing trend of response (AUC[UNCORR RETI]) with AUC(Day 0–29) for single doses. A continuous pharmacological response (a continuous production of reticulocytes and sustained elevation of hemoglobin) requires EPO serum concentration to be maintained continuously (such as after 150-IU/kg t.i.w. dosing regimen) or intermittently (such as after the 600-IU/kg q.w. dosing regiment) above endogenous EPO levels.

Clinical Study Epo-PHI-370

The primary objective of this study was to evaluate the pharmacokinetic profile of EPO after administration of 150 IU/kg t.i.w. or 40,000 IU q.w. and to demonstrate that the two dosing regimens deliver similar clinical outcomes using hemoglobin as a measure of clinical effectiveness. Secondary objectives were to assess the pharmacodynamic profiles of EPO after administration of 150 IU/kg t.i.w. or 40,000 IU q.w., and to compare tolerance and safety parameters between the two EPO dosing regimens.

EPO used in this study was formulated as a sterile, colorless, preservative-free, citrated-buffered solution, in single-use vials. The EPO 10,000 IU/mL (Formula No. FD-22512-000 C-45, Lot D000123) was used in the 150-IU/kg t.i.w. arm, and the EPO 40,000 IU/mL (Formula No. FD-22512-000 AC-45, Lot D000175) was used in the 40,000-IU q.w. arm.

This was a single-center, open-label, parallel-design, randomized study conducted in 49 healthy subjects (49 enrolled and analyzed for safety; 46 completed the study and were analyzed for PK/PD). Subjects were randomized to two treatment groups and received EPO as either the standard cancer regimen (150 IU/kg s.c. t.i.w.) or a weekly fixed dose regimen (40,000 IU s.c. q.w.) for four weeks. Blood samples were drawn at predose on Days 1, 8, 15, and during Week 4 for determination of serum EPO concentrations. Blood samples were also drawn at baseline (Day 1) and at specific time points over the 4-week study period for determination of percent reticulocytes, hemoglobin, and total red blood cell counts.

Of the 46 subjects who were analyzed for PK/PD, 24 subjects (9 males and 15 females) were enrolled in the 150-IU/kg t.i.w. arm and 22 subjects (14 males and 8 females) were enrolled in the 40,000-IU q.w. arm. Demographic data and baseline hemoglobin of these subjects are listed in FIG. 29.

Sample analyses for serum EPO were performed at PPD Development, Richmond, Va. A RIA kit procedure manufactured by DSL and modified at RWJPRI, was used for the determination of EPO concentrations in serum.

The sample size of this study was not based on statistical considerations. Summary statistics were provided by treatment group and day for pharmacodynamic parameters; mean, standard deviation, median, range, and standard error were calculated. To compare the PD profiles of EPO after 150 IU/kg t.i.w. and 40000 IU q.w., analysis of variance models appropriate for two way layout were fit to the data, with one of the PD parameters of interest (log-transformed AUC of percent reticulocytes, hemoglobin, and total red blood cell counts) as the dependent variable and treatment, gender, and gender by treatment as fixed effects. Since the gender by treatment interaction effect was found to be not significant for all three parameters, reduced models without the interaction term were fitted to the data and the treatment and gender effects were tested at the 5% level using the residual error term. The ratio of the means from 40000 IU/week to 150 IU/kg t.i.w. and the ratio of the means from females to males were estimated using the geometric least square means obtained from the ANOVA models.

Figure 30:
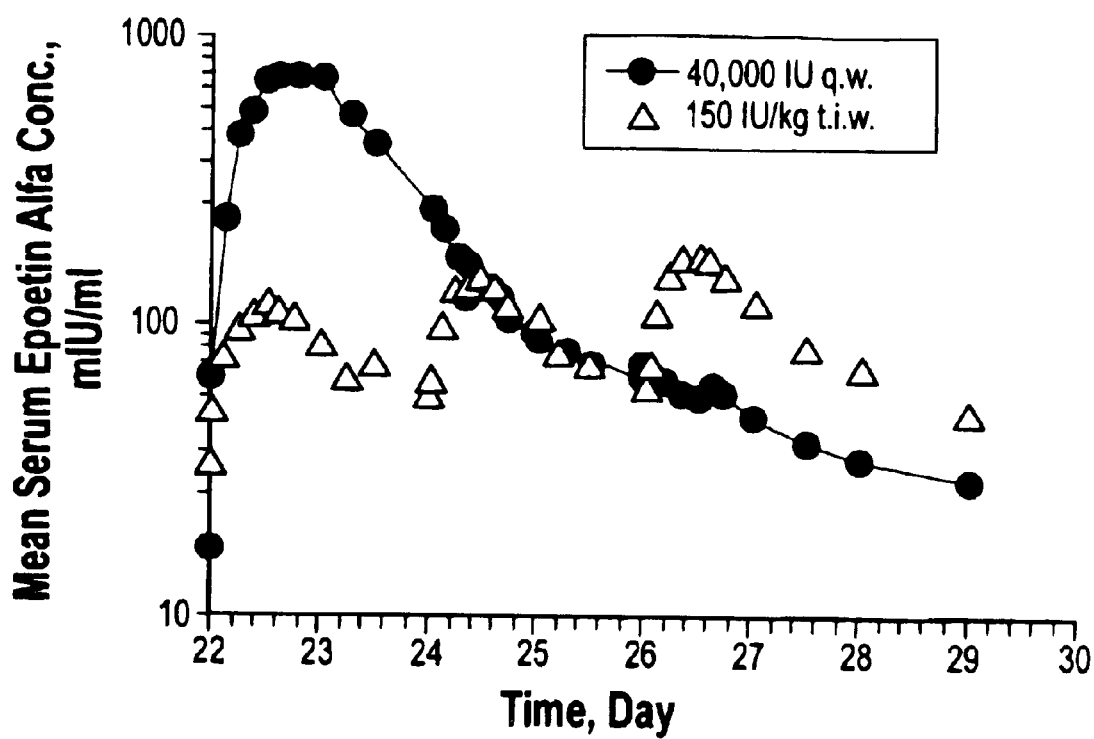
FIG. 30: Mean serum concentration-time profiles of Epoetin Alfa (uncorrected for Baseline EPO) in healthy subjects after receiving 150 IU/kg t.i.w. (N=24) or 40,000 IU q.w (N=22) during the fourth dosing week (Clinical Study EPO-PHI-370).

Mean serum EPO concentration-time profiles (uncorrected for predose endogenous EPO level) for the 150-IU/kg t.i.w. and the 40,000-IU q.w. groups during Week 4 of the study period are shown in FIG. 30.

During Week 4 of the 150-IU/kg t.i.w. dosing regimen, EPO peak serum concentrations (corrected for baseline EPO) ranged from 78 to 447 mIU/mL (mean $C_{max}$=191+100 mIU/mL) to trough concentrations of 7.3 to 88 mIU/mL (mean trough concentration ($C_{min}$)=39±18 mIU/mL). During Week 4 of the 40,000-IU q.w. dosing regimen, serum EPO peak concentrations (corrected for baseline EPO) ranged from 197 to 1992 mIU/mL (mean $C_{max}$=785±427 mIU/mL) and were achieved at times ranging from 9 to 24 hours (mean $t_{max}$=18±5 hours), then declined multi-exponentially to trough levels ranging from values below the quantification limit of the analytical method (7.8 mIU/mL) to 44 IU/mL (mean trough concentration on Day 29=19±10 mIU/mL) at the end of the dosing week on Day 29. The mean $C_{min}$ over the four week study period was 13±9 mIU/mL. The terminal phase of the two dosing regimens seemed to be in parallel with mean half-life values of 31.8±13.4 (N=13) and 39.3±7.1 (N=3) hours for the 150-IU/kg t.i.w. and the 40,000-IU q.w. dosing regimens, respectively.

Mean (SD) (% CV) pharmacokinetic parameter values are listed in FIG. 31.

Bioavailability of the 40,000-IU q.w. dosing regimen relative to that obtained after the 150-IU/kg t.i.w. dose regimen was calculated using the following formula:

$$\frac{AUC(0-168) \text{ of } 40,000 \text{ IU q.w.}}{AUC(0-168) \text{ of } 150 \text{ IU/kg t.i.w.}} \times \frac{450}{40,000/\text{mean body weight}} \times 100\%$$

Mean body weight was calculated using data from subjects who completed the study.

Bioavailability of EPO after the 40,000-IU q.w. dosing regimen relative to that after the 150-IU/kg t.i.w. dosing regimen was 176%.

Figure 32:
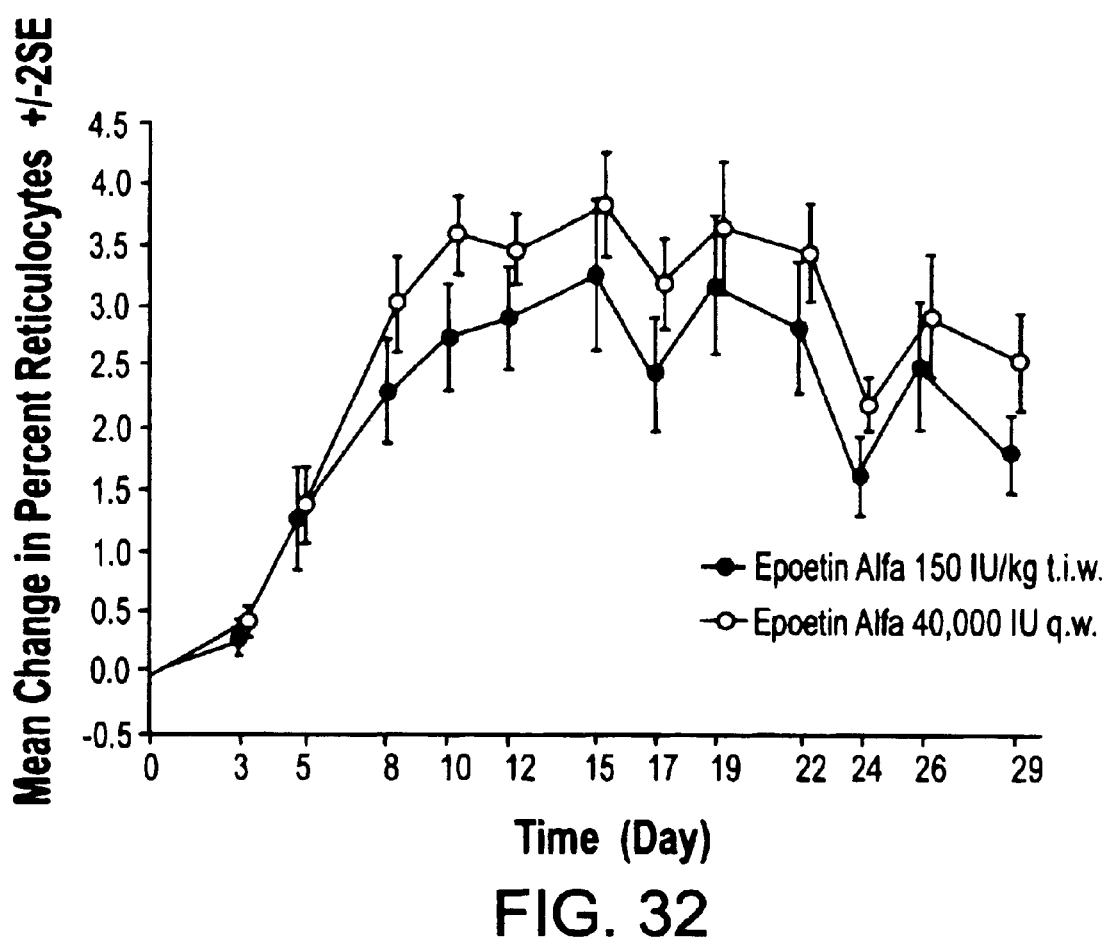
FIG. 32: Profile of mean change from baseline in percent reticulocytes.
Figure 33:
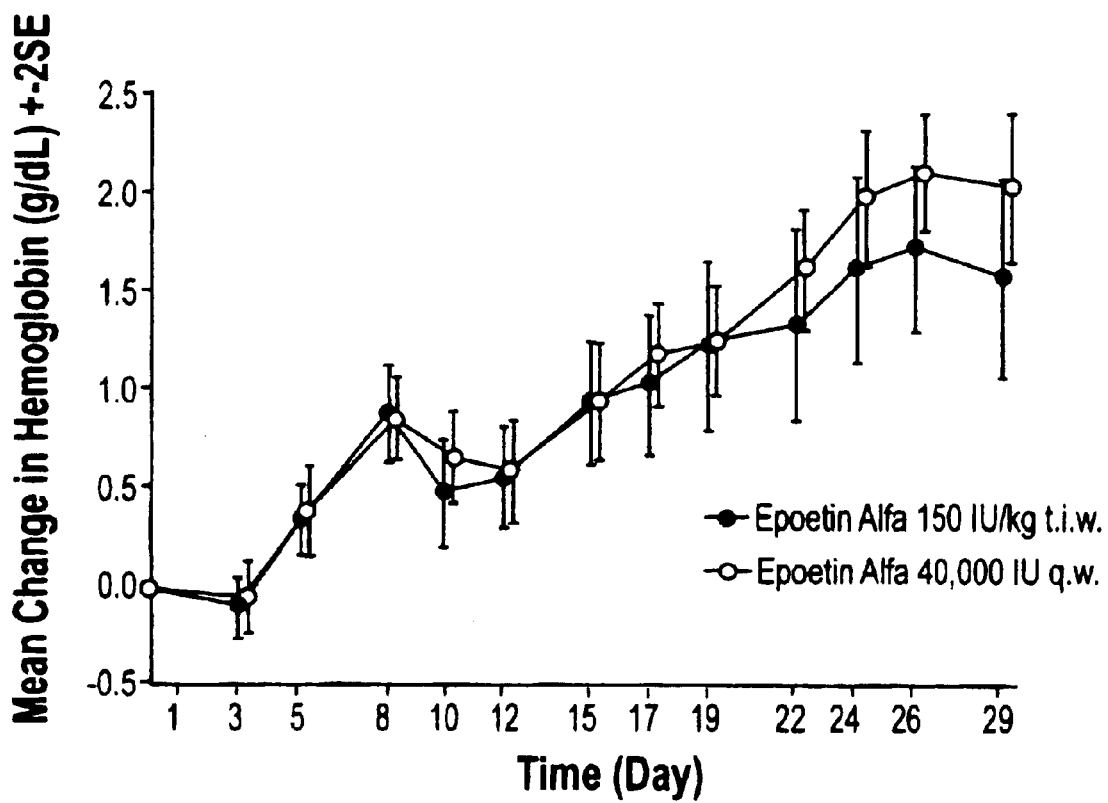
FIG. 33: Profile of mean change form baseline in hemoglobin (g/dl).

Linear plots of mean change from baseline versus study day for percent reticulocytes and hemoglobin concentrations are presented in FIGS. 32 and 33, respectively. Mean pharmacodynamic parameter values (corrected for baseline value) are presented in FIG. 34. The dynamic responses of the two dosing regimens were similar despite the fact that serum EPO AUC for the 40,000-IU q.w. dosing regimen was larger than that for the 1 50-IU/kg t.i.w. dosing regimen. There were no statistically significant differences in the AUC of hemoglobin and the AUC of red blood cells between the two dosing regimens, although the AUC of percent reticulocytes after the 40,000-IU q.w. dosing regimen was statistically larger ($p<0.05$) than that after the 150-IU/kg t.i.w. dosing regimen. There were no statistically significant differences in the AUC of percent reticulocytes, the AUC of hemoglobin, and the AUC of red blood cells between male and female subjects.

The time profiles of changes in hemoglobin and total red blood cells over the one month study period were similar between the two dosing regimens despite the differences in exposure (i.e. AUC[0–168]) of EPO in serum and despite a higher production of reticulocytes (as measured by area under the curve) for the 40,000-IU q.w. regimen. The AUCs of hemoglobin and total red blood cell over the one month study period were similar for two dosing regimens. There were no differences in pharmacodynamic responses for male and female subjects in this study.

Although the data of this study suggest that the hemoglobin responses after the 150-IU/kg t.i.w. and the 40,000-IU q.w. dosing regimens were similar and that the two dosing regimens can be used interchangeably, there were randomization issues, fluctuating hemoglobin levels at the study entry, and many subjects were iron-deficient at initiation (as indicated by transferrin saturation values). Error in the randomization at the study site resulted in an unequal distribution of males and females in each treatment group, and contributed to an imbalance in mean baseline hemoglobin values. To appropriately confirm the positive findings of this study, it was decided that a repeat study would be conducted (Clinical Study EPO-373).

Clinical Study EPO-PHI-373

The primary objective of this study was to evaluate the PK profile of EPO after administration of 150 IU/kg t.i.w. or 40,000 IU q.w. and to demonstrate that the two dosing regimens deliver similar clinical outcomes. Secondary objectives were to assess the PD profiles of EPO after administration of 150 IU/kg t.i.w. or 40,000 IU q.w., and to compare tolerance and safety parameters between the two EPO dosing regimens.

EPO used in this study was formulated as a sterile, colorless, preservative-free, phosphate-buffered solution, in single-use vials. The EPO 10,000 IU/mL (Formula No. FD-22512-000-T-45, Lot 99KS077) was used in the 150-IU/kg t.i.w. arm, and the EPO 40,000 IU/mL (Formula No. FD-22512-000-AA-45, Lot 99KS091) was used in the 40,000-IU q.w. arm.

This was a single-center, open-label, parallel-design, randomized study conducted in 36 healthy subjects (36 enrolled and analyzed for safety; 34 completed the study and were analyzed for PK/PD). Subjects were randomized to two treatment groups and received EPO as either the standard cancer regimen (150 IU/kg s.c. t.i.w.) or a weekly fixed dose regimen (40,000 IU q.w.) for four weeks. Blood samples were drawn at predose on Days 1, 8, 15, and during Week 4 for determination of serum EPO concentrations. Blood samples were also drawn at baseline (Day 1) and at specific time points over the 4-week study period for determination of percent reticulocytes, hemoglobin, and total red blood cell counts.

Of the 34 subjects who were analyzed for PK/PD, 17 subjects (nine males and eight females) were enrolled in the 150-IU/kg t.i.w. arm and 17 subjects (nine males and nine females) were enrolled in the 40,000-IU q.w. arm. Demographic data and baseline hemoglobin of these subjects are listed in FIG. 35.

An ELISA kit, manufactured by R&D Systems, Inc. (R&D), Minneapolis, Minn., modified at RWJPRI and cross validated with the original RIA at PPD Development, Richmond, Va., was used for the determination of EPO concentrations in serum.

The sample size of this study was not based on statistical considerations. Summary statistics were provided by treatment group and day for pharmacodynamic parameters; mean, standard deviation, median, range, and standard error were calculated. To compare the pharmacodynamic profiles of EPO after 150 IU/kg t.i.w. and 40000 IU q.w., analysis of variance models appropriate for two way layout were fit to the data, with one of the pharmacodynamic parameters of interest (log-transformed AUC of percent reticulocytes, hemoglobin, and total red blood cell counts) as the dependent variable, and treatment, gender and gender by treatment as fixed effects. Since the gender by treatment interaction effect was found to be not significant for all three parameters, reduced models without the interaction term were fitted to the data and the treatment and gender effects were tested at the 5% level using the residual error term. The ratio of the means from 40000 IU/week to 150 IU/kg t.i.w. and the ratio of the means from females to males were estimated using the geometric least square means obtained from the ANOVA models.

Figure 36:
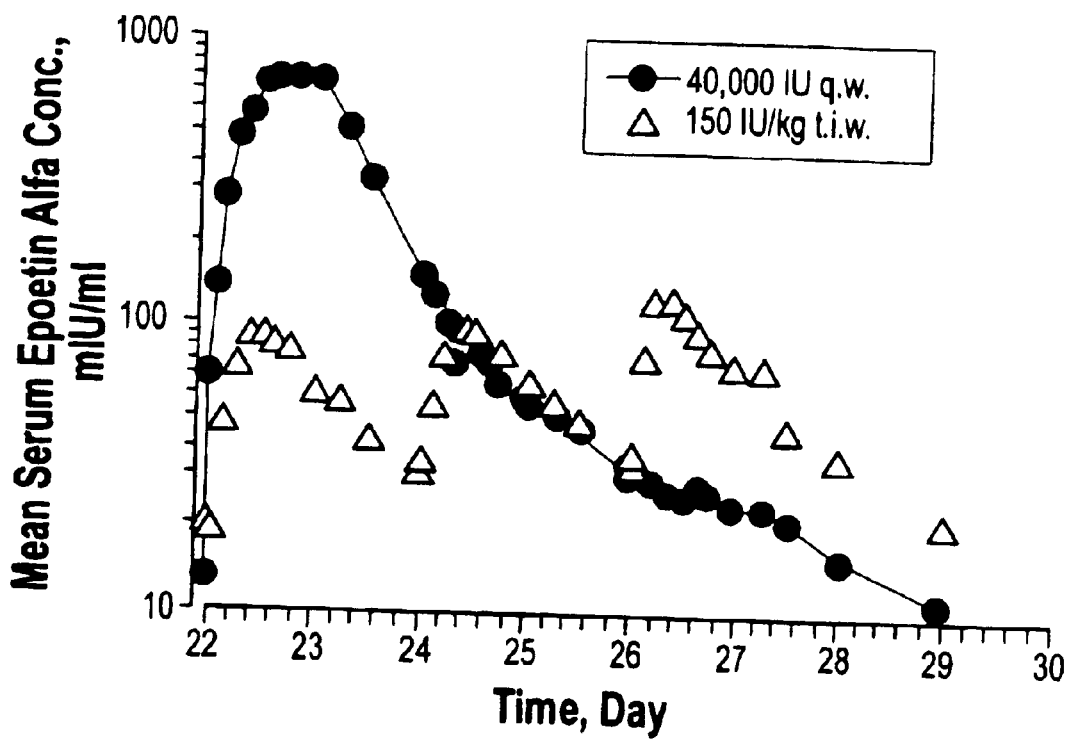
FIG. 36: Mean serum concentration-time profiles of Epoetin Alfa (uncorrected for Baseline EPO) in healthy subjects after receiving 150 IU/kg t.i.w. (N=17) or 40,000 IU q.w (N=17) during the fourth dosing week (Clinical Study EPO-PHI-373).

Mean serum EPO concentration-time profiles (uncorrected for predose endogenous EPO level) for the 150-IU/kg t.i.w. and the 40,000-IU q.w. groups during Week 4 of the study period are shown in FIG. 36.

During Week 4 of the 150-IU/kg t.i.w. dosing regimen, EPO concentrations in serum (corrected for baseline EPO) ranged from peak concentrations of 75 to 284 mIU/mL (mean $C_{max}=143\pm54$ mIU/mL) to trough level values ranging from values below the quantification limit of the analytical method (7.8 mIU/mL) to 40 IU/mL (mean trough concentration ($C_{min})=18\pm9$ mIU/mL). During Week 4 of the 40,000-IU q.w. dosing regimen, serum EPO concentrations (corrected for baseline EPO) reached peak concentrations (mean $C_{max}=861\pm445$ mIU/mL) at times ranging from 1 to 24 hours (mean $t_{max}=16\pm8$ hours), then declined multi-exponentially to trough level values ranging from values below the quantification limit of the analytical method (7.8 mIU/mL) to 5.9 mIU/mL (mean trough concentration on Day 29=2.0±1.5 mIU/mL) at the end of the dosing week on Day 29. Mean $C_{min}$ of the 40,000 IU q.w. during the 4-week study period was 3.8±4.3 mIU/mL. The terminal phase of the two dosing regimens seemed to be in parallel with mean half-life values of 19.4±8.1 hours (n=9) and 15.0±6.1 hours (n=9) for the 150-IU/kg t.i.w. and the 40,000-IU q.w. dosing regimens, respectively.

Mean (SD) (% CV) pharmacokinetic parameter values are listed in FIG. 37.

Bioavailability of the 40,000-IU q.w. dosing regimen relative to that obtained after the 150-IU/kg t.i.w. dose regimen was calculated using the following formula:

$$\frac{AUC(0-168) \text{ of } 40{,}000 \text{ IU q.w.}}{AUC(0-168) \text{ of } 150 \text{ IU/kg t.i.w.}} \times \frac{450}{40{,}000/\text{mean body weight}} \times 100\%$$

Mean body weight was calculated using data from subjects who completed the study.

Bioavailability of EPO after the 40,000-IU q.w. dosing regimen relative to that after the 150-IU/kg t.i.w. dosing regimen was 239%.

Figure 38:
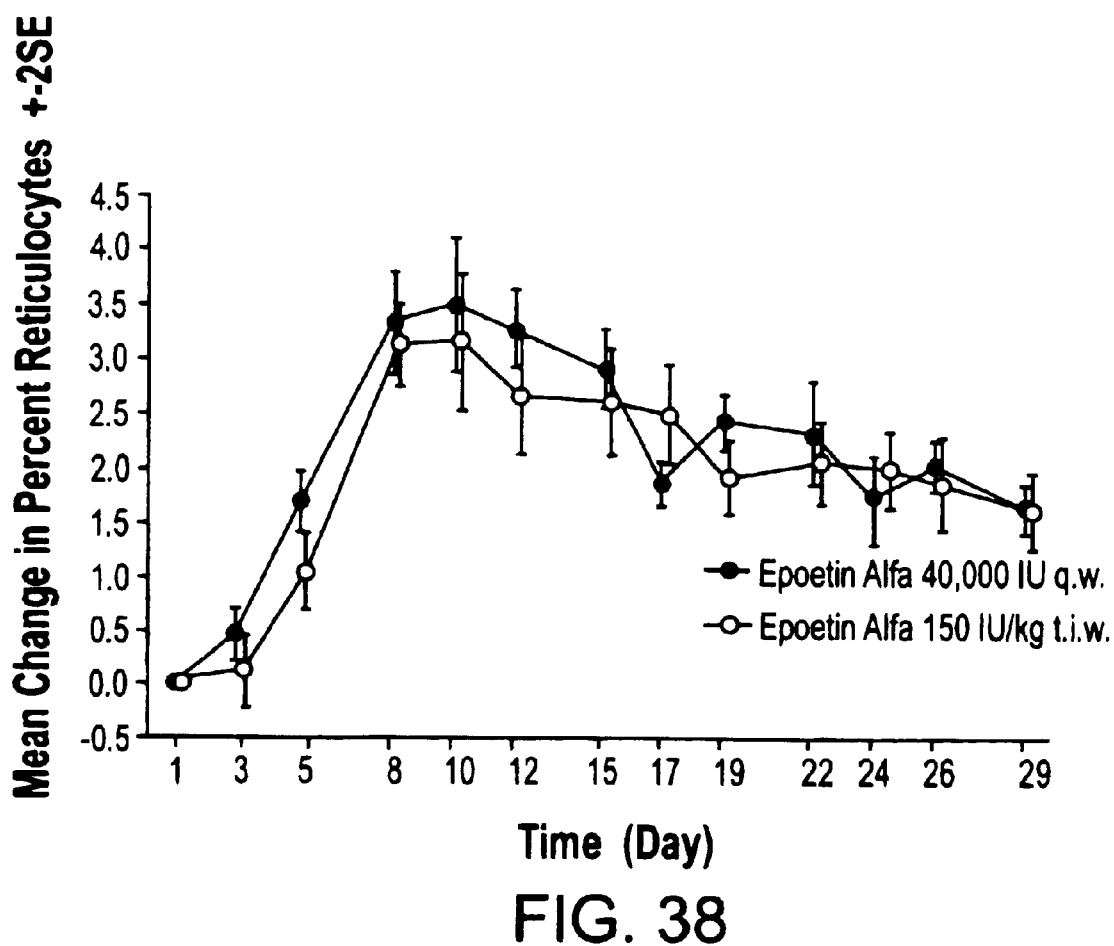
FIG. 38: Profile of mean change from baseline in percent reticulocytes for subjects in Clinical Study EPO-PHI-373.
Figure 39:
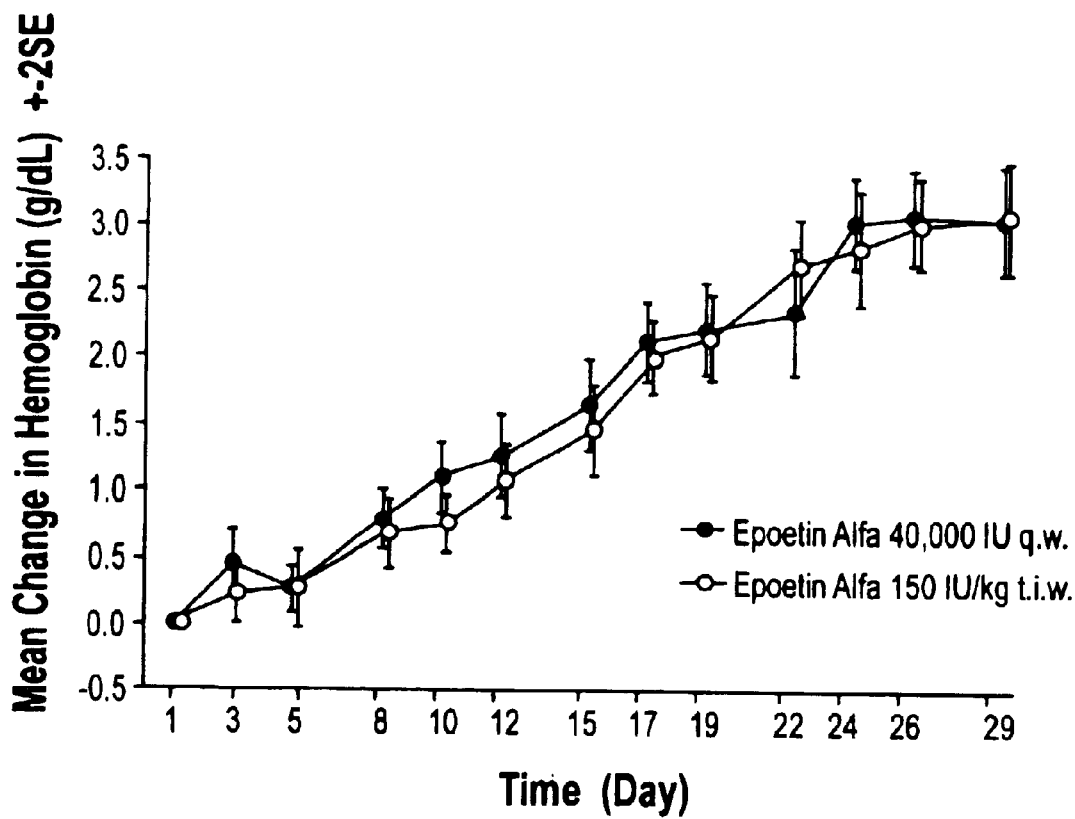
FIG. 39: Profile of mean change from baseline in hemoglobin (g/dl) for subjects in Clinical Study EPO-PHI-373.
Figure 40:
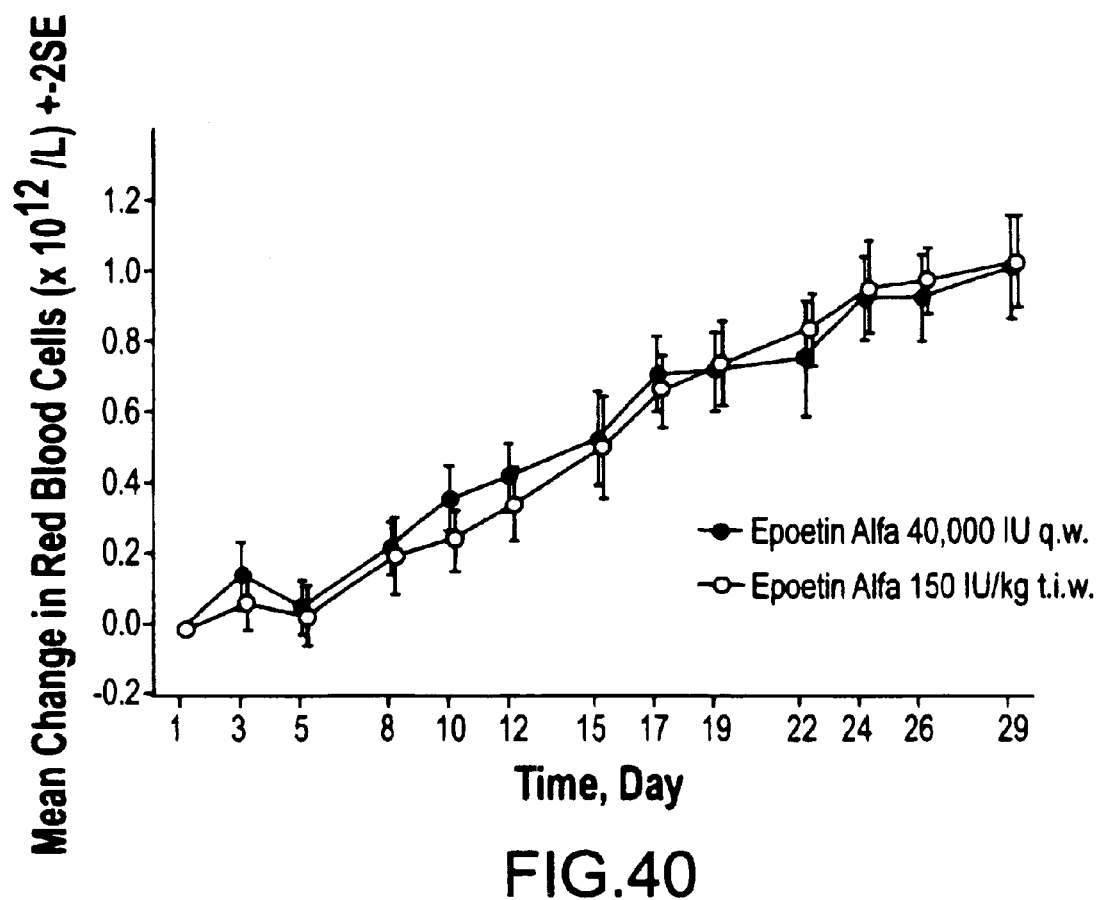
FIG. 40: Profile of mean change from baseline total red blood cells ($\times 10^{12}$/l) for subjects in Clinical Study EPO-PHI-373.

Linear plots of mean change from baseline versus study day for percent reticulocytes, hemoglobin concentrations, and total red blood cell counts are presented in FIGS. 38, 39, and 40, respectively.

Mean pharmacodynamic parameter values (corrected for baseline value) are presented in FIG. 41. The dynamic responses of the two dosing regimens were similar despite the fact that serum EPO AUC for the 40,000-IU q.w. dosing regimen was larger than that for the 150-IU/kg t.i.w. dosing regimen. There were no statistically significant differences in the AUC of percent reticulocytes, AUC of hemoglobin, and AUC of red blood cells between the two dosing regimens. There were no statistically significant differences (p>0.05) in the AUC of percent reticulocytes between male and female subjects. However, the AUC of hemoglobin and the AUC of red blood cells were statistically (p=0.038 and 0.042, respectively) larger in females than in males. These differences were not clinically significant.

The time profiles of changes in percent reticulocytes, hemoglobin, and total red blood cells over the one month study period were similar between the two dosing regimens despite the differences in exposure of EPO in serum (in terms of AUC[0–168]). In addition, there were no statistically significant differences (p>0.05) in AUC of percent reticulocytes, AUC of hemoglobin, and AUC of total red blood cells over the one month study period between the two dosing regimens. There were no differences in pharmacodynamic responses between male and female subjects in this study. The data of this study indicate that the hemoglobin responses after the 150-IU/kg t.i.w. and the 40,000-IU q.w. dosing regimens were similar, thereby justifying that the two dosing regimens can be used interchangeably.

In conclusion, there was an expected difference in total exposure of EPO in serum after the 150-IU/kg t.i.w. and the 40,000-IU q.w. dosing regimens. The hemoglobin responses were similar, thereby justifying that the two dosing regimens can be used interchangeably. Thus, the present studies show that a once-weekly EPO dosing regimen can be used. This regimen overcomes the disadvantages associated with the commonly used dosing regimens. In a preferred embodiment, a 40,000 IU dose is contemplated based upon these clinical studies. The present invention also contemplates a once every two weeks dosing regimen, e.g., at a EPO dose of 80,000 to 120,000 IU. In a specific embodiment, a once every two weeks dose of EPO is used.

Results
Pharmacokinetics After IV Administration

After IV administration in healthy volunteers or patients with impaired renal function, r-HuEPO is distributed in a volume comparable to the plasma volume, and plasma concentrations decay with mean half-life values ranging from 4 to 11.2 hours which have been reported to be shortened after repeated administrations (Macdougall et al., 1991, *Clin. Pharmacokinet.*, 20:99–113). There were dose-proportional increases in $C_{max}$ and AUC values following single intravenous doses of 50 to 1000 IU/kg in healthy subjects (Flaharty et al., 1990, *Clin. Pharmacol. Ther.*, 47:557–64), and clearance (CL) was reported to be independent of dose after single bolus intravenous administration of 10-, 100-, and 500-IU/kg doses in healthy subjects, with respective mean values of 5.89±1.53, 7.02±1.14, and 6.88±1.19 mL/h/kg (Veng-Pendersen et al., 1995, *J. Pharma. Sci.*, 84(6):760–767). However, clearance was also reported to be higher after a single intravenous 10-IU/kg dose (13.1 mL/h/kg) than after that after single intravenous doses of 100 and 500 IU/kg in healthy subjects (respectively CL=7.9 and 6.2 mL/h/kg) (Widness et al., 1996, *J. Appl. Physiol.*, 80(1):140–148).

Pharmacokinetics After SC Administration

A summary of pharmacokinetic parameters after SC administration from Clinical Studies EPO-PHI-358, EPO-PHI-359, EPO-PHI-370, and EPO-PHI-373 is given in FIG. 42.

After single or weekly SC administration, serum EPO concentrations reached maximum value in times ($t_{max}$) ranging from 9 to 36 hours. The mean $t_{max}$ was similar for different single doses and ranged from 15.6±5.8 to 28.8±7.8 hours. There was a linear relationship between mean $C_{max}$ and dose (correlation=0.982), suggesting that the absorption rate of EPO from the injection site was independent of dose. On the other hand, the relationship between AUC and dose was a curvilinear one such that clearance (CL/F) decreased with increasing doses (Cheung et al., 1998, *Clin. Pharmacol. Ther.*, 64:412–423). Data from Clinical Studies EPO-PHI-373 and EPO-PHI-370 indicate that the 150-IU/kg t.i.w. dosing regimen had a higher CL/F value than the 40,000-IU q.w. weekly dosing regimen and data in Clinical Studies EPO-PHI-358 and EPO-PHI-359 indicate that the 150-IU/kg t.i.w. dosing regimen had a higher CL/F value than the 600-IU/kg q.w. dosing regimen.

As indicated in FIG. 42, EPO decays at a much slower rate after SC administration than after IV administration. Half-life values ranged from 15.9 to 221 hours after single SC doses of 300 to 2400 IU/kg, and mean half-life values after the 150-IU/kg t.i.w. and 40,000-IU q.w. dosing regimens were 19.4±8.1 and 15.0±6.1 hours, respectively. The half-life values were independent of dose in the dose range studied. The longer half-life value observed after SC administration compared to IV administration is probably a reflection of the absorption half-life from subcutaneous tissues.

While serum EPO concentrations after single dose administrations declined to the endogenous EPO level by Day 15 (earlier for the lower doses), the 150-IU/kg t.i.w. dosing regimen was able to maintain serum EPO concentrations above the a predose endogenous EPO level throughout the treatment period (Cheung, supra). The weekly dosing regimens of 600 IU/kg/mL and 40,000 IU q.w. maintained serum EPO levels above the predose endogenous EPO level up to 5 to 6 days in a dosing week (Cheung, supra). These weekly dosing regimens attained a higher $C_{max}$ than the 150-IU/kg t.i.w. dosing regimen, although the predose trough concentrations were near the endogenous EPO level.

Pharmacodynamics of EPO After SC Administration

After single (300 to 2400 IU/kg) or multiple (150 IU/kg t.i.w., 600 IU/kg q.w., or 40,000 IU q.w.) SC administrations of EPO, percent reticulocytes began to increase by Days 3 to 4. Percent reticulocytes after single dose administrations reached their maximum values at Days 6 to 12 (Cheung, supra), whereas percent reticulocytes after multiple dose regimens reached peak values at times ranged from Day 8 to the last blood sample point on Day 29 (Cheung, supra). All multiple dose regimens stimulated modest, but sustained increases in percent reticulocytes (approximately 2 to 7%) which were maintained above the predose baseline values through Days 22 to 29, while the percent reticulocytes after single dose administrations declined to baseline values by Days 15 to 22 (Cheung, supra).

Figure 43:
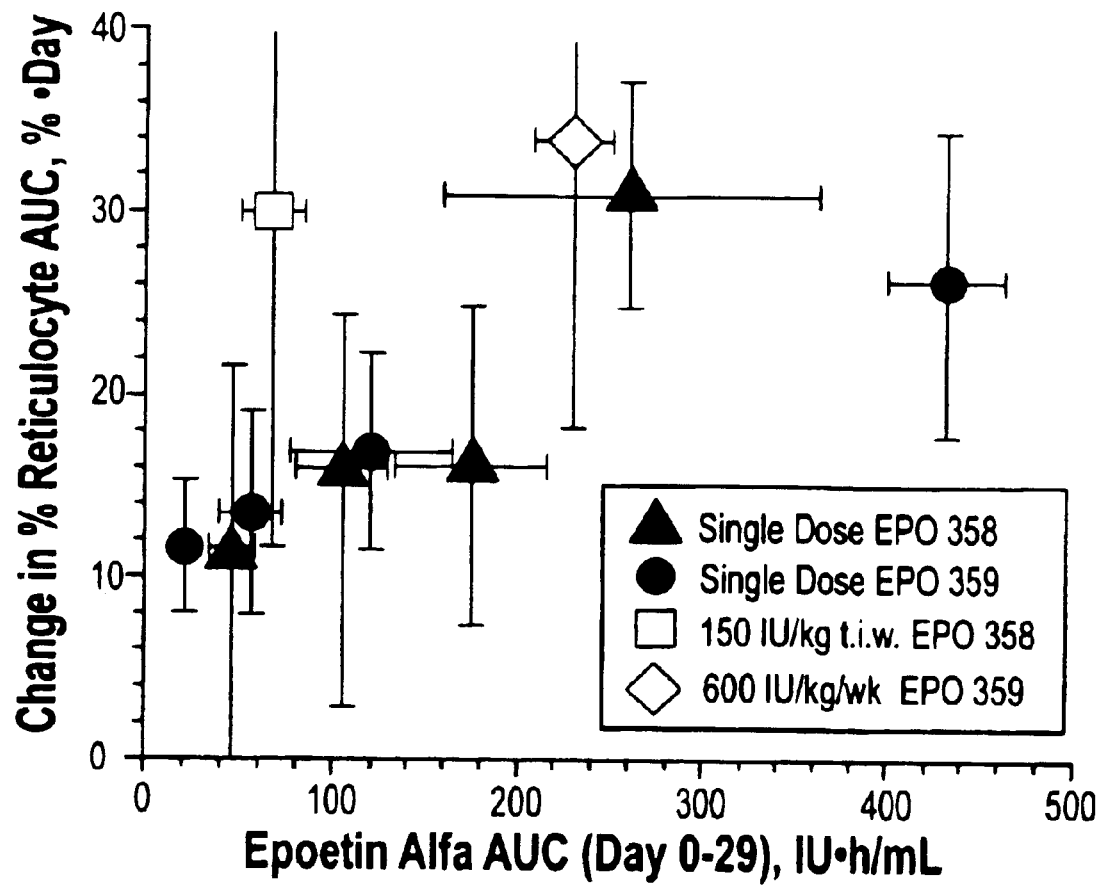
FIG. 43: Mean AUC of change in percent reticulocytes as a function of AUC (Day 0–29) of Epoetin Alfa (Clinical Studies EPO-PHI-358 and EPO-PHI-359).
Figure 44:
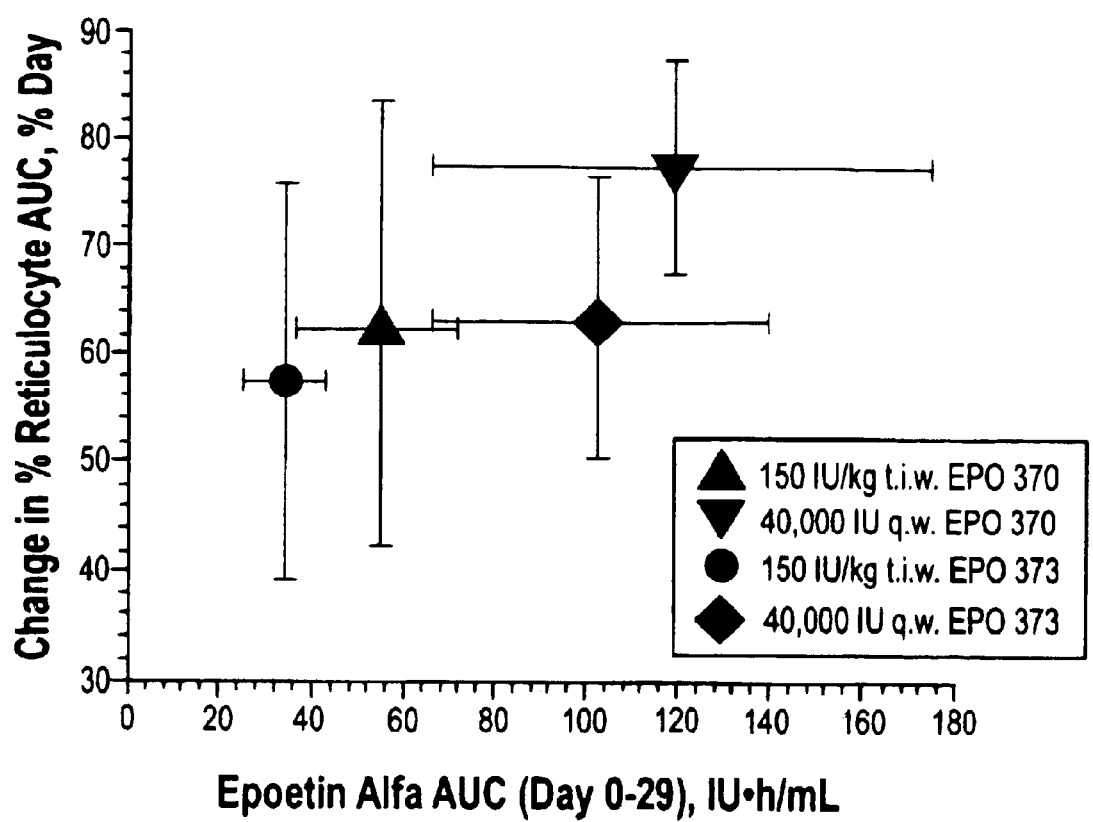
FIG. 44: Mean AUC of change in percent reticulocytes as a function of AUC (Day 0–29) of Epoetin Alfa (Clinical Studies EPO-PHI-370 and EPO-PHI-373).

The relationship between mean AUC of the change (from baseline) in percent reticulocyte [AUC(RETI)] and mean AUC of EPO (corrected for predose endogenous EPO level) [AUC(Day 0–29)] is shown in FIG. 43 for data in Clinical Studies EPO-PHI-358, EPO-PHI-359, and in FIG. 44 for data in Clinical Studies EPO-PHI-370 and EPO-PHI-373. The AUC values for both change in percent reticulocyte from baseline and EPO were calculated over a four-week period. The AUC(RETI) values in Clinical Studies EPO-PHI-358 and EPO-PHI-359 can not be compared to those in Clinical Studies EPO-PHI-370 and EPO-PHI-373 as the times of sample collection for reticulocytes were different. The sampling schedule was less frequent in Clinical Studies EPO-PHI-358 and EPO-PHI-359, and the AUC(RETI) values could have been underestimated. Data from Clinical Studies EPO-PHI-358 and EPO-PHI-359 indicated that, for the single dose data, there was a trend of increase in mean AUC(RETI) as the mean AUC(Day 0–29) of EPO increases. For the multiple dose regimens based on data from Clinical Studies EPO-PHI-370 and EPO-PHI-373, there is also a trend of increase in mean AUC(RETI) as the mean AUC (Day 0–29) of EPO increases.

The total EPO administered in one month for the 150-IU/kg t.i.w. regimen was 1800 IU/kg, and for the 600-IU/kg q.w. regimen was approximately 2400 IU/kg. Although the 150-IU/kg t.i.w. regimen had a much smaller EPO AUC(Day 0–29) value than the 1800-IU/kg single dose regimen, they had similar mean AUC(RETI) values. Similarly, the 600-IU/kg q.w. regimen had a much smaller EPO AUC(Day 0–29) value than the 2400-IU/kg single dose regimen, but they also had similar mean AUC(RETI) values. Thus, EPO (per unit AUC exposure) after multiple dosing is more efficient in producing reticulocytes than after a single dose.

Figure 45:
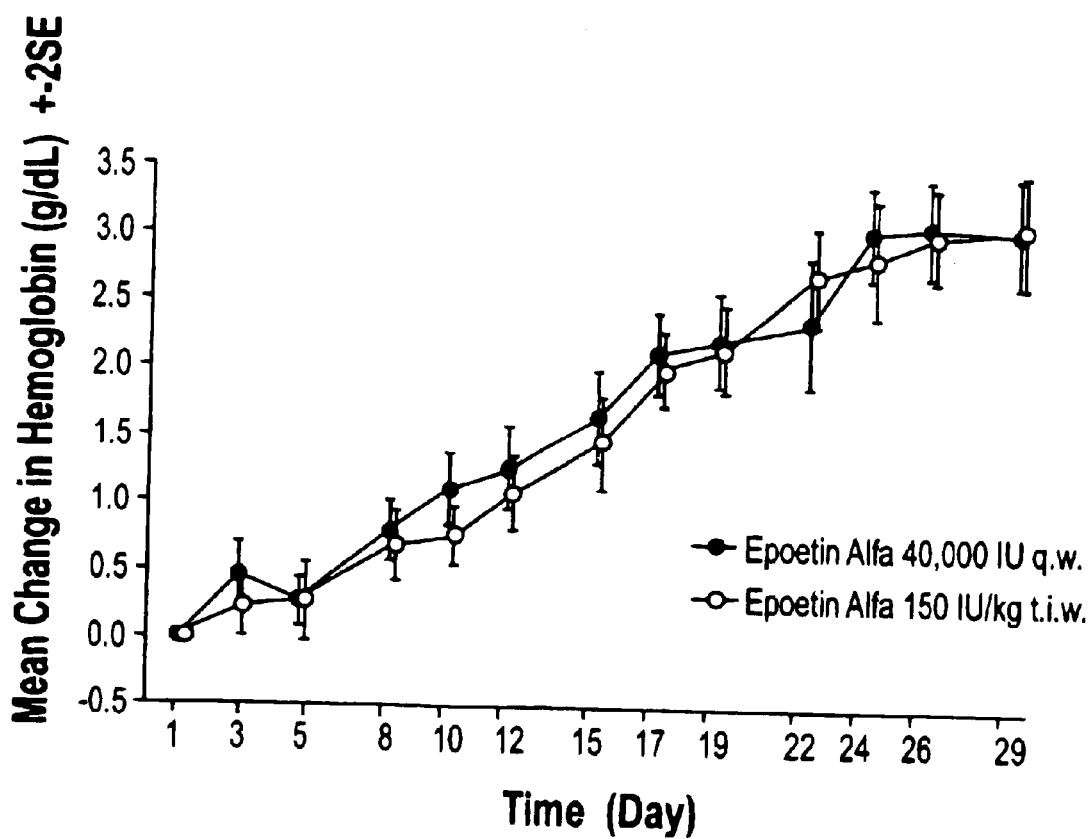
FIG. 45: Profile of mean change from baseline in hemoglobin (g/dl) for subjects in Clinical Study EPO-PHI-373.
Figure 46:
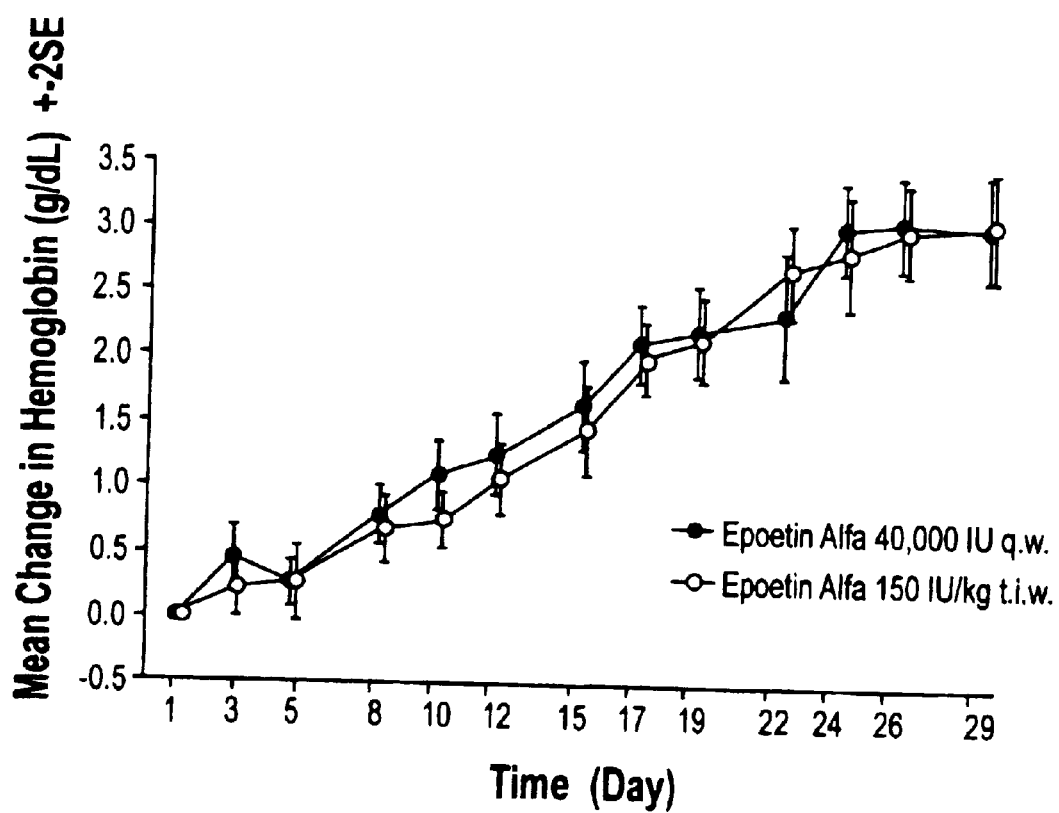
FIG. 46: Profile of mean change from baseline in hemoglobin (g/dl) for subjects in Clinical Study EPO-PHI-370.

Despite an EPO AUC-related increase in the production of reticulocytes, there were no apparent increases in hemoglobin after single dose administration. On the other hand, multiple dose regimens were able to deliver a steady rise in hemoglobin, and the patterns of the rise in hemoglobin were similar between the 150-IU/kg t.i.w. and 40,000-IU q.w. dosing regimens as demonstrated in the pivotal Clinical Study EPO-PHI-373 (FIG. 45) and the supportive Clinical Study EPO-PHI-370 (FIG. 46), and were similar between the 150-IU/kg t.i.w. and 600-IU/kg q.w. regimens as demonstrated in the pilot Clinical Studies EPO-PHI-358 and EPO-PHI-359. The lack of hemoglobin response after single dosing is not known at this time. There are two possible explanations for this: the increase in reticulocytes after single doses (maximum increase of percent reticulocytes after 2400-IU/kg single dose=6.6%) might not have been sustained for long enough to lead to any substantial increase in hemoglobin; and it has been hypothesized that the survival of young red blood cells depends on the continuous presence of EPO in the blood circulation (Alfrey et al., 1997, *The Lancet,* 349:1389–1390). After single dose administration, reticulocytes peaked at times ranging from 6 to 12 days and returned to predose levels at times up to 15 days. The lifespan of cells in reticulocyte stage is about 1 to 2 days in the blood circulation (Hillman et al., 1967, *Sem Haematol.,* 4(4):327–336).

Therefore, one would expect young red cells to appear in the blood circulation about 7 to 14 days after dosing. By then, EPO concentrations after single dose administration were at the endogenous level, which may have resulted in death of the young red cells due to the absence of sufficient EPO in the blood circulation to sustain their survival. On the other hand, EPO concentrations were maintained above the endogenous level continuously after the t.i.w. dosing regimen or intermittently after the weekly dosing regimen, and therefore the survival of young red cells was sustained, leading to a continuous rise in hemoglobin during the study period.

Consequently, to sustain the survival of a large number of pharmacologically produced young red cells, serum EPO concentrations have to be above the endogenous level.

Conclusion

In conclusion, data from these four Phase 1 studies in healthy subjects indicate that the pharmacokinetics and pharmacodynamics of EPO in humans are nonlinear after SC administration. The data from these studies also clearly demonstrate the 150-IU/kg t.i.w. dosing regimen delivered similar hemoglobin response as the 40,000-IU per week dosing regimen, thereby justifying that the two dosing regimens can be used interchangeably. Accordingly, EPO is administered about 40,000 IU/kg once a week for two consecutive weeks. The first dose of EPO facilitates the production of reticulocytes from RBC progenitor cells. The second dose of EPO is administered to coincide with the reticulocyte pharmacodynamic profile of the patient. The second dose of EPO will be administered 6–10 days following the initial dose, and preferably at the time when the reticulocyte concentration peaks following the first EPO dose.

EXAMPLE 2

Evaluation of EPO PK/PD Profile After Administration of 150 IU/kg t.i.w. and 40,000 IU q.w In specific indications, such as cancer, subjects are treated with 150 IU/kg epoetin alfa t.i.w. Thus, it remains an important goal to change the currently approved dosing schedule to a more convenient (i.e., once per week or once every two weeks) dosing schedule and regimen. A less frequent administration will improve user acceptance and convenience.

The pharmacokinetic and pharmacodynamic properties of the multiple dosing regimen of epoetin alfa have been defined in the previous example (EPO-PHI-358 and EPO-PHI-359). The data suggest that 150 IU/kg t.i.w. and 600 IU/kg/week dosing regimens have similar pharmacodynamic responses (e.g., a rise in hemoglobin). Therefore, epoetin alfa can potentially be administered as a weekly per kilogram dose. Since 600 IU/kg is equivalent to 42,000 IU for a 70-kg person, the present study was conducted to demonstrate that a fixed dosing regimen of 40,000 IU per week delivered a comparable pharmacodynamic response as the approved dosing regimen of 150 IU/kg t.i.w.

The primary objective of this study was to evaluate the pharmacokinetic profile of epoetin alfa after administration of 150 IU/kg t.i.w. or 40,000 IU q.w., and to demonstrate that the two dosing regimens deliver similar clinical outcomes.

The secondary objectives were to assess the pharmacodynamic profiles of epoetin alfa after administration of 150 IU/kg t.i.w. or 40,000 IU q.w., and to compare tolerance and safety parameters between the two epoetin alfa dosing regimens.

Thirty-six healthy adult volunteers (18 males and 18 females) were enrolled into this open-label, parallel-design, randomized, single-center study. Subjects were to be between the ages of 18 and 45 years old with hemoglobin levels between 12.0 and 14.0 g/dL, inclusive, for females and between 13.0 and 14.0 g/dL, inclusive, for males. Subjects were screened for study eligibility based on inclusion and exclusion criteria and randomized to one of two treatment groups. Group 1 received the standard cancer regimen of 150 IU/kg of SC EPO, t.i.w. for four weeks. Group 2 received a weekly fixed dose regimen of 40,000 IU epoetin alfa s.c.q.w. for four weeks.

Subjects were to receive daily oral iron supplementation during the study (two capsules of Ferro-Grad® each containing 105 mg of elemental iron).

Blood samples were drawn at baseline and at specific time points during the study for the determination of serum erythropoietin concentrations, complete blood count (CBC), including percent reticulocytes, hemoglobin concentrations, and hematocrit values. Safety evaluations were based on the incidence and type of treatment-emergent adverse events, changes in clinical laboratory tests (hematology and chemistry), vital sign measurements, and physical examination results. In addition, serum iron, calculated transferrin saturation, and ferritin concentrations were monitored during the study.

Safety was based on the incidence and severity of treatment-emergent adverse events, and on changes from prestudy in physical examination findings, vital sign measurements, and clinical laboratory parameters.

The protocol was amended after all subjects were initiated. The amendment clarified inclusion and exclusion criteria, concomitant therapy, laboratory parameters, urinalysis, vital sign measurements, and the dosing regimen for the 40,000 IU q.w. group.

Three subjects randomized to the 150 IU/kg t.i.w. group and one subject in the 40,000 IU q.w. group had hemoglobin entry criteria marginally above the limit specified in the inclusion/exclusion criteria (14.0 g/dL), but were included in the study. Subjects 2012, 2015, and 2016 in the 150 IU/kg t.i.w. group had screening hemoglobins of 14.1 g/dL; subject 2018 in the 40,000 IU q.w. group had a screening hemoglobin of 14.2 g/dL. Four subjects in the 40,000 IU q.w. group had screening ferritin values below the limit of 45 ng/mL specified in the exclusion criteria: subject 1006 had a screening value of 40 ng/mL, subject 1010 had a screening value of 43 ng/mL, and subjects 1015 and 2011 had screening values of 44 ng/mL. One subject in each treatment group (subject 2015 in the 150 IU/kg group and subject 2014 in the 40,000 IU group) had screening transferrin saturation values of 19%, slightly below the inclusion criteria of >20%. Subject 2002 (40,000 IU) weighed 0.1 kg above the maximum value allowed by protocol inclusion criteria for someone his height. Additionally, subject 2016 (150 IU/kg t.i.w.) took herbal sleeping tablets four days prior to initiation of epoetin alfa therapy.

Study Drug Information

Epoetin alfa was formulated as a sterile, colorless, preservative-free, phosphate-buffered solution, supplied in single-use vials. Commercial product was used in this study, and it was commercially labeled. The epoetin alfa 10,000 IU/mL solution was Formula No. FD 22512-000-T-45, Lot No. 99KS077, and the epoetin alfa 40,000 IU/mL solution was Formula No. FD 22512-000-AA-45, Lot No. 99KS091.

Dosage and Administration

Subjects were admitted to the investigator's facility at least 12 hours prior to the administration of study medication on Day 1. Subjects were fasted for at least ten hours prior to dosing on Day 1; water was available ad libitum. Subjects were randomly assigned and received one of two study medications as follows:

| Group | Treatment |
|---|---|
| Group 1 (N = 18) | Standard Cancer Regimen 150 IU/kg of epoetin alfa s.c. t.i.w. for four weeks |
| Group 2 (N = 18) | Weekly Fixed Dose Regimen 40,000 IU of epoetin alfa s.c. q.w. for four weeks |

For Dose Group 1, the volume of injection for a 70 kg subject was approximately 1.0 mL.
For Dose Group 2, the volume of injection was exactly 1 mL.

If, at any time during the treatment phase, the hemoglobin for any subject equalled or exceeded 18.0 g/dL, a second sample was drawn to confirm the first finding. If confirmed, phlebotomy was done to reduce the hemoglobin level; initially, one unit of blood was to be removed. The hemoglobin was measured again once the subject was stabilized. If the hemoglobin level was still 18.0 g/dL or greater, another 0.5 to one unit of blood was to be removed, and the hemoglobin measured. Any phlebotomized subject was discontinued from epoetin alfa therapy and underwent the required completion evaluations and procedures.

The 10,000 IU/mL formulation of epoetin alfa was used for Group 1 (Standard Cancer Regimen), and the 40,000 IU/mL formulation of epoetin alfa was used for Group 2 (Weekly Fixed Dose Regimen).

Concomitant Therapy

Subjects were instructed to take no medications (prescription, over-the-counter (OTC), herbal, or "natural") beginning two weeks prior to the first dose of study drug and thereafter for the entire duration of the study. In case of headache or flu-like symptoms, paracetamol could be administered. If the administration of any medication became necessary, it was to be reported on the appropriate case report form (CRF) and source document.

Subjects received daily oral iron supplementation during the study (two capsules of Ferro-Grad® each containing 105 mg of elemental iron.

Study Evaluations

Time and Events Schedule

The study was divided into three phases: screening, treatment, and completion/early withdrawal. Subjects were evaluated for their eligibility during the screening period (procedures performed within two weeks of study drug administration). Subjects were randomly assigned to one of the two treatment groups and then entered the treatment phase. Subjects were confined within the clinic at least 12 hours prior to the administration of study drug on Day 1, and remained confined for at least 24 hours after dosing, until all tests were performed. Subjects were fasted at least ten hours prior to dosing on Day 1, but received water ad libitum. The treatment phase consisted of study drug administration (dosing on Days 1, 3, 5, 8, 10, 12, 15, 17, 19, 22, 24, and 26 for the 150 IU/kg t.i.w. group and on Days 1, 8, 15, and 22 for the 40,000 IU q.w. group). On Day 22, a second confinement period began with the administration of epoetin alfa and continued for at least 144 hours post-dosing. Evaluations of pharmacokinetic, pharmacodynamic, and safety parameters were performed on all subjects at periodic intervals during the 28-day treatment phase. Study completion evaluations and procedures were performed on Day 29, or upon early withdrawal from the study.

Pharmacokinetic Evaluations

Sample Collection and Handling

Venous blood samples, 2.5 mL each, were collected by direct venipuncture into vacuum tubes for the determination of serum erythropoietin concentration from the 150 IU/kg epoetin alfa t.i.w. group (Group 1) at the following time points:

Day 1: 30, 20, and 10 minutes prior to the initial dose of study medication.

Days 8 and 15: immediately prior to dosing.

Days 22 and 24: immediately prior to dosing and at 0.5, 3, 6, 9, 12, 15, 18, 24, 30, and 36 hours post-dosing.

Day 26: immediately prior to dosing and at 0.5, 3, 6, 9, 12, 15, 18, 24, 36, 48 and 72 hours post-dosing.

Blood samples for the determination of serum erythropoietin concentration from the 40,000 IU q.w. group (Group 2) at the following time points:

Day 1: 30, 20, and 10 minutes prior to the initial dose of study medication.

Days 8 and 15: immediately prior to dosing.

Days 22–28: immediately prior to dosing and at 0.5, 3, 6, 9, 12, 15, 18, 24, 30, 36, 48, 48.5, 51, 54, 57, 60, 63, 66, 72, 78, 84, 96, 96.5, 99, 102, 105, 108, 111, 114, 120, 126, 132, 144, and 168 hours post Day 22 epoetin alfa administration.

Samples were allowed to clot at room temperature for approximately 20 minutes and then centrifuged for ten minutes at 1200 rpm in a refrigerated centrifuge. Serum was dispensed into a prelabeled polypropylene vial. The samples were frozen at −20 C. and were stored frozen at this temperature until analyzed.

Analytical Procedures

Sample analyses for serum epoetin alfa were performed at PPD development, Richmond, Va. An enzyme-linked immunosorbent assay (ELISA) kit procedure manufactured by R&D Systems, Inc., (R&D), Minneapolis, Minn., and modified at RWJPRI, was used for the determination of erythropoietin concentrations in serum. The commercially available ELISA is a direct, double-antibody sandwich assay. Microtiter wells, precoated with a mouse monoclonal antibody specific for rHuEPO, are used to capture EPO. The bound EPO is labeled with anti-EPO polyclonal (rabbit) antibody and horseradish peroxidase. An optical signal is produced with the addition of substrate. The major in-house modification of the R&D kit was use of in-house recombinant human erythropoietin in standards and spiked quality control samples.

Standard concentrations used in the assay were 7.8, 15.6, 31.3, 50, 62.5, 100, 125 and 250 mIU/mL. Sensitivity, defined as the lowest standard giving acceptable precision, was 7.8 mIU/mL and the assay range was extended to 5,000 mIU/mL via quality control dilutions.

Pharmacokinetic Parameters

Serum concentrations of erythropoietin were measured. The pharmacokinetic parameters $C_{max}$, $t_{max}$, $C_{min}$, $AUC_{(0-468)}$, CL/F, and $t_{1/2}$ were measured by model-independent methods.

Pharmacodynamic Analysis

Pharmacodynamic parameters included measurement of changes from baseline in percent reticulocytes, red blood cells, and hemoglobin concentrations and their relationship to serum erythropoietin concentrations.

Safety Evaluations

Adverse Events

Treatment-emergent adverse events were defined as any noxious or unintended events observed during clinical investigation that were new in onset or aggravated in severity or frequency, including pathologic findings that required medical intervention, including additional diagnostic procedures or alteration of study therapy.

Each subject was observed throughout the study beginning with the first dose for possible adverse events. Adverse event reports were identified by voluntary subject reporting. The investigator recorded on the subject's CRF any treatment-emergent adverse events regardless of their relationship to study drug. Adverse events were characterized according to date of onset, severity (marked, moderate, or mild), relationship to study drug (very likely, probable, possible, doubtful, or not related), action taken regarding study therapy (none, dose reduced, drug stopped temporarily, or drug stopped permanently), and whether or not the event was serious. Information on concomitant therapy and outcome was also recorded.

Serious adverse events were defined as those that were fatal or immediately life-threatening, required or prolonged inpatient hospitalization, caused persistent or significant disability or incapacity, or were congenital anomalies, birth defects, or overdoses. The investigator was instructed to report all serious adverse events immediately to RWJPRI. The investigator was to collect information on serious adverse events for up to 35 days after the last assessment on Day 29. Safety data were also reviewed for potentially serious adverse events; these were considered to be those that were sufficiently severe or alarming to require medical intervention.

Clinical Laboratory Tests

Sample analyses for clinical laboratory tests were performed at Havenfern Laboratories, Berks, UK. Blood samples, including hemoglobin, hematocrit, percent reticulocytes, red blood cells (RBC), mean corpuscular volume (MCV), mean corpuscular hemoglobin (MCH), mean corpuscular hemoglobin concentration (MCHC), and platelets were drawn during screening and on Days 1, 3, 5, 8, 10, 12, 15, 17, 19, 22, 24, 26, and 29, between 8 and 10 AM, if possible. The screening CBC also included total erythrocyte count and total leukocyte count with differential.

Serum chemistry samples were drawn at screening and termination (Day 29); parameters included glucose, calcium, sodium, potassium, chloride, phosphorus, blood urea nitrogen (BUN), total bilirubin, creatinine, total protein, cholesterol, albumin, uric acid, alkaline phosphatase, serum glutamic-oxaloacetic transaminase (SGOT; aspartate aminotransferase (AST), serum glutamic-pyruvic transaminase (SGPT; alanine aminotransferase (ALT), and lactic dehydrogenase (LDH).

Blood samples for iron parameters (serum iron, total iron binding capacity (TIBC), and ferritin levels) were drawn during screening and on Days 8, 15, 22, and 29. Transferrin saturation was calculated as iron/total iron binding capacity.

Urine testing was performed via dipstick. If the blood or leukocyte esterase was positive (1+ or greater) and/or protein or nitrate was trace or greater, a urine specimen was to be sent to the central laboratory for microscopic examination.

Other Safety Observations

Vital Signs

Vital sign measurements of sitting blood pressure, pulse rate, and oral temperature were recorded at the screening visit, prior to study drug administration on Days 1, 8, 15, and 22, and on Day 29 (termination). Respiration rate and body weight measurements were taken at screening and termination; height measurement was obtained only at the screening visit.

Physical Examinations

Physical examinations were performed at the screening visit and on Day 29.

Data Quality Assurance

Before the study site was selected, the investigator, study site personnel, and facility were evaluated by clinical RWJPRI personnel. The protocol and statement of informed consent were reviewed and approved by the investigator's Ethics Committee (EC) before initiation of the study. Case report forms were reviewed for accuracy and completeness by RWJPRI personnel during the periodic on-site monitoring visits.

Discrepancies in the data were resolved with the investigator or designees. The data were entered into the RWJPRI data base and appropriate computer edit programs were run to verify the accuracy of the data base.

Statistical Methods

The sample size of this study was not based on statistical considerations. Therefore, the analysis is descriptive; no statistical tests were performed on pharmacokinetic parameters. Summary statistics, including mean, standard deviation, median, and range were provided by treatment group for hematology, serum chemistry, and vital sign measurements.

The primary objectives (i.e., to evaluate the pharmacokinetic profile of epoetin alfa after administration of 150 IU/kg t.i.w. or 40,000 IU q.w., and to demonstrate that the two dosing regimens deliver similar clinical outcomes, using hemoglobin as a measure of clinical effectiveness) was addressed by descriptive comparison of pharmacokinetic parameters obtained after study drug administration.

Pharmacokinetics

The following pharmacokinetic parameters were calculated by model independent methods using the WinNonlin software, Version 1.1 (Scientific Consulting, Incorporation, Apex, N.C.):

Peak serum concentration ($C_{max}$): the observed maximum serum concentration during the fourth week of the dosing period for the 150 IU/kg t.i.w. dosing regimen and the 40,000 IU q.w. dosing regimen.

Time to $C_{max}$ ($t_{max}$): the time at which $C_{max}$ occurs. $T_{max}$ was not reported for the epoetin alfa t.i.w. treatment group because $C_{max}$ occurred randomly at any one of the three doses during the fourth dosing week.

Mean predose trough concentration ($C_{min}$). $C_{min}$ for the 150 IU/kg t.i.w. regimen was estimated by averaging the predose trough concentrations on Days 22, 24, and 26, and the concentration at 72 hours after the last dose on Day 26. $C_{min}$ for the 40,000 IU q.w. regimen was estimated by averaging the predose concentration on Days 8, 15, 22, and the concentration at 168 hours after the last dose on Day 22.

Area under the serum concentration-time curve from time zero to the last blood sampling time $AUC_{(0-168)}$ during the last dosing week for epoetin alfa 40,000 IU q.w. and 150 IU/kg t.i.w.: calculated using the linear trapezoidal rule.

Clearance after SC administration (CL/F): calculated by dividing dose (per kg) by $AUC_{(0-168)}$.

Terminal elimination half-life ($t_{1/2}$): computed from 0.693/elimination rate constant. The elimination rate constant was estimated by linear regression of consecutive data points in the terminal linear region of the log-linear concentration-time plot. A minimum of three data points were used in the regression. The $t_{1/2}$ values were not reported for those regressions with a correlation coefficient (r) less than 0.975 (or $r^2 < 0.95$).

The mean, standard deviation, and coefficient of variation of the pharmacokinetic parameters were calculated for each treatment.

The pharmacokinetic parameters were calculated using serum erythropoietin concentrations corrected for predose endogenous erythropoietin levels. Postdose serum concentration values were corrected for predose baseline erythropoietin concentrations by subtracting from each of the values the mean baseline erythropoietin concentration determined from the samples collected at 30, 20, and 10 minutes before dosing. Predose serum erythropoietin concentrations were not included in the calculation of mean value if they were below the quantification limit of the assay. If the concentration values of all three of a subject's predose samples were below the quantification limit of the assay, then the quantification limit of the assay, 7.8 mIU/mL was assigned as the mean baseline erythropoietin concentration for that subject. Actual blood drawn times (in hour relative to the time of the first dose) were used in the calculation of pharmacokinetic parameters.

Bioavailability of the 40,000 IU q.w. dosing regimen relative to that obtained after the 150 IU/kg t.i.w. dose regimen was calculated using the following formula:

$$\frac{AUC_{(0-168)} \text{ of } 40{,}000 \text{ IU q.w.}}{AUC_{(0-168)} \text{ of } 150 \text{ IU/kg t.i.w.}} \times \frac{450}{40{,}000/\text{mean body weight}^*} \times 100\%$$

*Mean body weight of subjects in the 40,000 IU q.w. group who completed the study Pharmacodynamics Summary statistics including mean, standard deviation, median, range, and standard error were provided by treatment group and day for percent reticulocytes and hemoglobin concentrations. Calculations were based on subjects who completed the study. Baseline, Days 1, 3, 5, 8, 10, 12, 15, 17, 19, 22, 24, 26, and 29 were summarized; "windowing" was performed to include laboratory test results in the summaries if a subject did not have data collected at the day(s) specified. Changes from baseline were summarized by treatment group and day. Linear plots of mean change from baseline values versus study day were generated for reticulocytes, hemoglobin, and ferritin.

Pharmacokinetics/Pharmacodynamics

Nominal times (in day relative to the first dose on Day 1) as stated in the protocol were used in the calculation of pharmacodynamic parameters. The following pharmacodynamic parameters were calculated by model independent methods using the WinNonlin software, Version 1.1 (Scientific Consulting, Incorporation, Apex, N.C.):

Area under the serum concentration-time curve of percent reticulocytes from time zero to 672 hours (Day 29) post-initiation of dosing [AUC(RETI)] was calculated using the linear trapezoidal rule. AUC(RETI) was estimated using percent reticulocyte values corrected for predose percent reticulocyte value. The mean of the −10 minute and −30 minute predose measurements was used as the predose percent reticulocyte value. For those corrected percent reticulocyte data with negative values, a zero value was used in the estimation of AUC(RETI).

Area under the serum concentration-time curve of hemoglobin from time zero to 672 hours (Day 29) post-initiation of dosing [AUC(HEMO)] was calculated using the linear trapezoidal rule. AUC(HEMO) was estimated using hemoglobin values corrected for predose hemoglobin value. The mean of the −10 minute and −30 minute predose measurements was used as the predose hemoglobin. For those corrected hemoglobin data with negative values, a zero value was used in the estimation of AUC(HEMO).

Area under the serum concentration-time curve of total red blood cell count (RBC) from time zero to 672 hours (Day 29) post-initiation of dosing [AUC(RBC)] was calculated using the linear trapezoidal rule. AUC(RBC) was estimated using RBC values corrected for predose RBC value. The mean of the −10 minute and −30 minute predose measurements was used as the predose RBC. For those corrected RBC data with negative values, a zero value was used in the estimation of AUC(RBC).

The 40,000 IU q.w. to 150 IU/kg t.i.w. ratios of AUC (RETI), AUC(HEMO), and AUC(RBC) were determined.

Safety

The safety evaluations were based upon the type and incidence of adverse events reported by the subjects and changes in physical examinations, clinical laboratory data, and vital signs. Treatment-emergent adverse events were classified by body system, preferred term, and included term. Adverse events were coded in accordance with the World Health Organization Adverse Reaction Terminology (WHOART) dictionary where the included term is the description most closely related to the investigator's terminology, the preferred term is a group of closely related included terms, and the body system is a broad category including related preferred terms. Treatment-emergent adverse events were summarized by body system and preferred term and presented as individual subject data listings.

Clinical laboratory data and vital signs were summarized and presented as individual subject data listings.

Data Storage

The protocol, report, and raw data from this study are stored in the Document Management, Information Management department of RWJPRI. The data can be found in the project notebook maintained for Drug Metabolism Study DM00009.

Study Duration

Dosing and serum sample collection for both groups were conducted during the period from 21 February 2000 through 29 March 2000. Validation of the erythropoietin serum assay occurred between 21 Jan. 2000 and 3 Feb. 2000. Serum samples were analyzed during the period from 24 Mar. 2000 through 4 Apr. 2000.

Results

Demographic and Baseline Characteristics

Thirty-six healthy adults (18 subjects per group) were enrolled in this study and were randomly assigned to one of two treatment groups. Overall, the majority of subjects (89%) were white, and the mean age was 26.5 years (range 18–41 years). The mean body weight of subjects in the 40,000 IU q.w. group was slightly higher (70.3 kg) compared to the 150 IU/kg t.i.w. group (66.8 kg), with the rest of the baseline and demographic characteristics being very similar between the two groups.

Demographic and baseline characteristics of the 34 subjects who completed the study are presented in FIG. 47. There were no notable differences from the overall study population.

Study Completion/Withdrawal Information

Subjects were considered to have completed the study if they participated for the full duration (29 days) of the study. In addition, the subject must have taken all required doses of the study drug, they must have been compliant with the blood sampling procedures, and they must have undergone Day 29 evaluations and procedures. The efficacy population included subjects receiving all required doses who completed the study. The efficacy population was used for pharmacokinetic and pharmacodynamic data analyses.

94% of the subjects in both groups completed the study. One subject (1014) in the epoetin alfa 150 IU/kg group withdrew on Day 15 of the study due to an adverse event (persistent headaches), and one subject (1006) in the epoetin alfa 40,000 IU q.w. group withdrew on Day 10 (subject choice). These subjects were not included in the efficacy population.

Analytical Results

Pharmacokinetic Results

Figure 48:
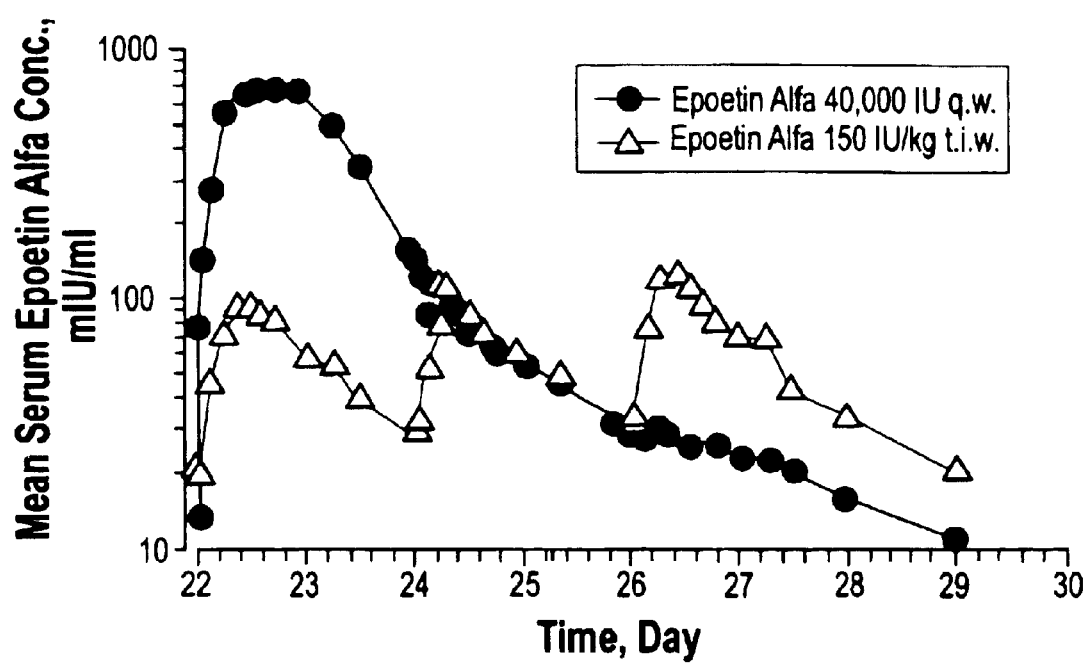
FIG. 48: Serum epoetin alfa concentrations uncorrected for predose endogenous erythropoietin concentrations for subjects in Group 1 (150 IU/kg t.i.w.) designated by triangles and Group 2 (40,000 IU q.w) denoted by circles.
Figure 49:
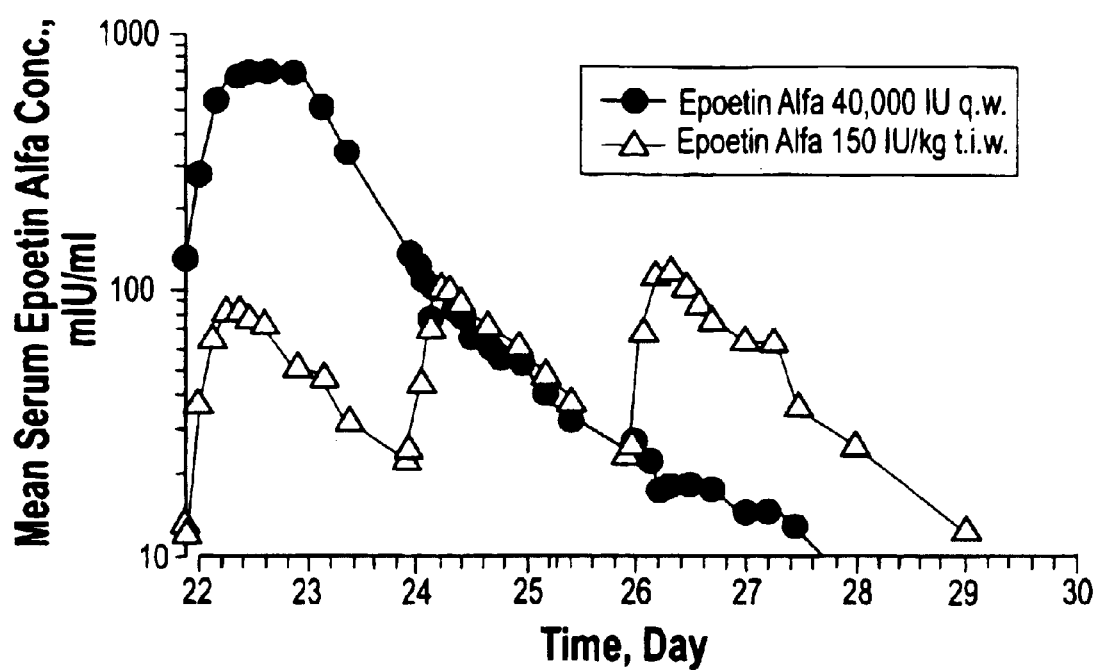
FIG. 49: Serum epoetin alfa concentration data corrected for predose endogenous erythropoietin concentrations for subjects in Group 1 (150 IU/kg t.i.w.) designated by triangles and Group 2 (40,000 IU q.w.) designated by circles.

FIG. 48 illustrates the mean serum epoetin alfa concentration-time profiles (uncorrected for predose endogenous erythropoietin level) for the 150 IU/kg t.i.w. and the 40,000 IU q.w. groups during Week 4 of the study period. The mean serum erythropoietin concentration-time profiles corrected for predose endogenous erythropoietin level are shown in FIG. 49.

The mean (SD) pre-dose endogenous erythropoietin alfa concentrations for subjects in the 150 IU/kg t.i.w. and 40,000 IU q.w. regimen groups were 8 (0.4) and 9 (2) mIU/mL, respectively. During Week 4 of the 150 IU/kg t.i.w. dosing regimen, erythropoietin concentrations in serum (corrected for baseline erythropoietin) ranged from peak concentrations of 75 to 284 mIU/mL [mean (SD) $C_{max}$=143 (54) mIU/mL] to trough level values ranging from values below the quantification limit of the analytical method (7.8 mIU/mL) to 40 IU/mL [mean (SD) trough concentration ($C_{min}$)=18 (9) mIU/mL]. During Week 4 of the 40,000 IU q.w. dosing regimen, serum erythropoietin concentrations (corrected for baseline erythropoietin) reached peak concentrations [mean (SD) $C_{max}$=861 (445) mIU/mL] at times ranging from 1 to 24 hours [median $t_{max}$=15 (range, 1–24) hours], then declined multi-exponentially to trough level values ranging from values below the quantification limit of the analytical method (7.8 mIU/mL) to 5.9 mIU/mL [mean (SD) trough concentration on Day 29=2.0 (1.5) mIU/mL) at the end of the dosing week on Day 29. Mean (SD) $C_{min}$ of the 40,000 IU q.w. during the four week study period was 3.8 (4.3) mIU/mL. The terminal phase of the two dosing regimens seemed to be in parallel with mean (SD) half-life values of 19.4 (8.1) hours (n=9) and 15.0 (6.1) hours (n=9) for the 150 IU/kg t.i.w. and the 40,000 IU q.w. dosing regimens, respectively.

Mean (SD) [% CV] pharmacokinetic parameter values are presented in FIG. 50. Bioavailability of epoetin alfa after the 40,000 IU q.w. dosing regimen relative to after the 150 IU/kg t.i.w. dosing regimen was 239%.

Pharmacodynamic Results

The mean changes from baseline in percent reticulocytes, hemoglobin concentrations, and red blood cell values are summarized by treatment group and study day in FIGS. 51, 53, and 55, respectively. Mean change from baseline for pharmacodynamic results is presented only for subjects who completed the study.

Figure 52:
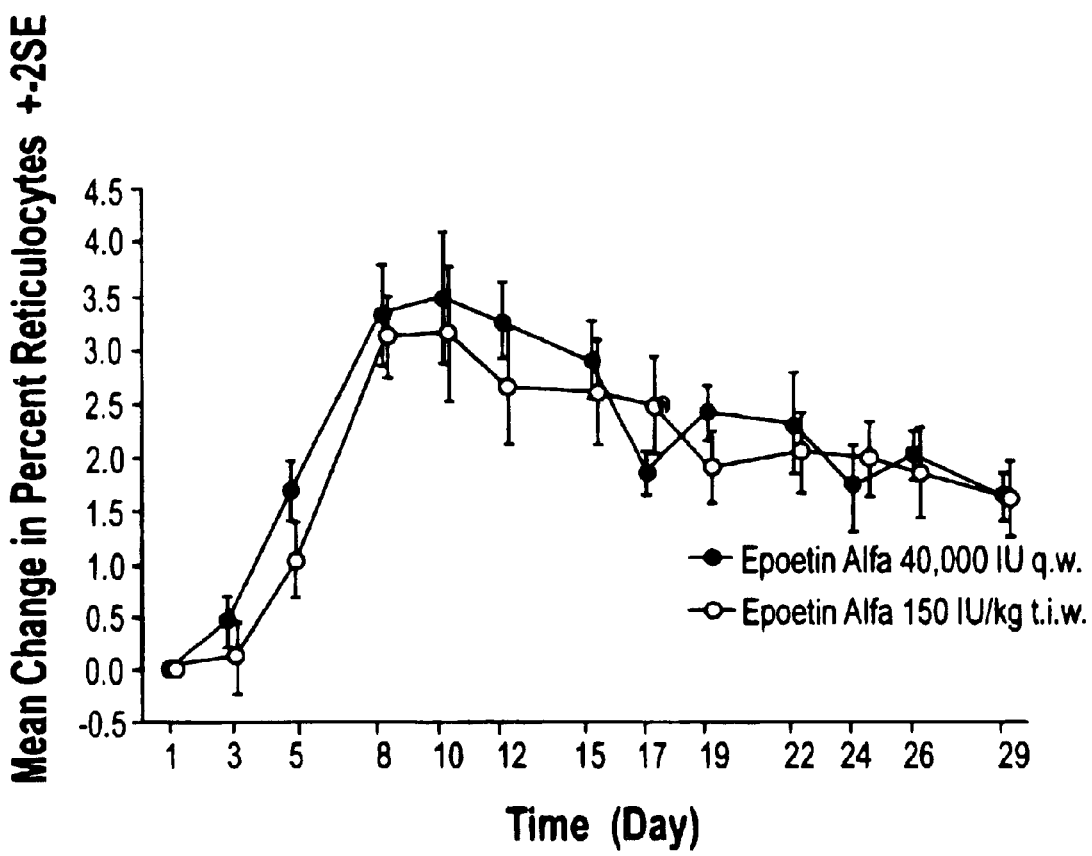
FIG. 52: Profile of mean (SD) change from baseline in percent reticulocytes by study day for the efficacy population for all subjects. The open circles represent Group 1 (150 IU/kg t.i.w.) and the closed circles represent Group 2 (40,000 IU q.w). The parameters obtained are listed in FIG. 51.
Figure 54:
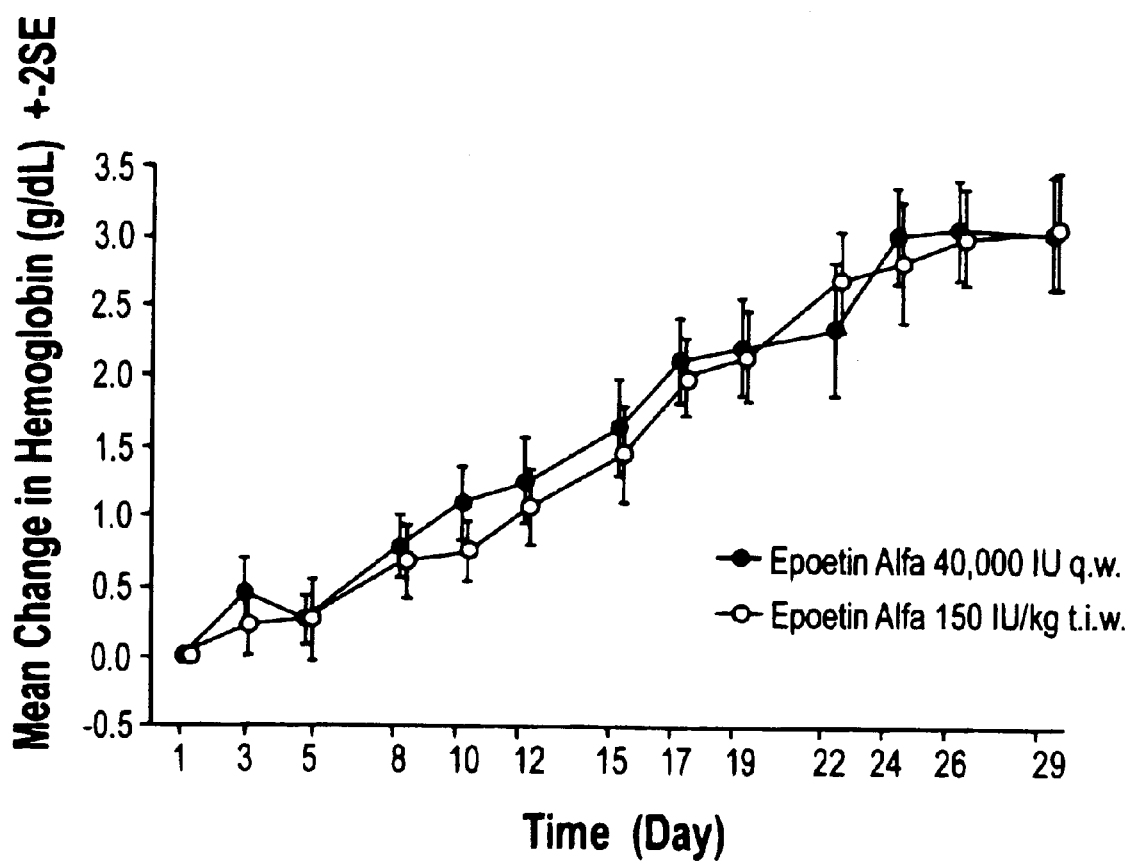
FIG. 54: Profile of mean (SD) change from baseline in percent hemoglobin (g/dL) by study day for the efficacy population for all subjects. The open circles represent Group 1 (150 IU/kg t.i.w.) and the closed circles represent Group 2 (40,000 IU q.w). The parameters obtained are listed in FIG. 53.
Figure 56:
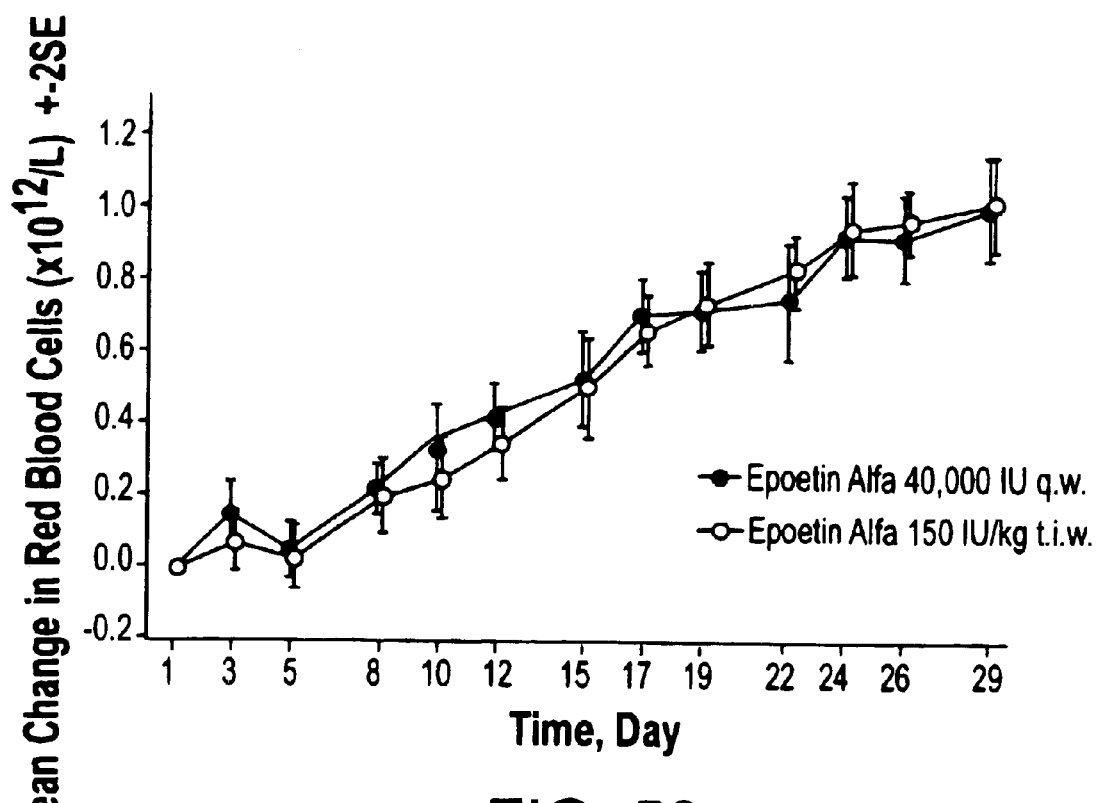
FIG. 56: Profile of mean (SD) change from baseline in red blood cells ($\times 10^{12}$/L) by study day for the efficacy population for all subjects. The open circles represent Group 1 (150 IU/kg t.i.w.) and the closed circles represent Group 2 (40,000 IU q.w). The parameters obtained are listed in FIG. 55.

Linear plots of mean change from baseline versus study day for percent reticulocytes, hemoglobin concentrations, and red blood cell values are presented in FIGS. 52, 54, and 56, respectively.

Percent Reticulocytes

In both groups, mean change in percent reticulocytes increased through Day 10 and gradually declined through Day 29 (FIGS. 51 and 52).

Hemoglobin

Mean hemoglobin at baseline was equivalent in the two dosage groups, 13.4 g/dL in the 150 IU/kg t.i.w. group and 13.5 g/dL in the 40,000 IU q.w. group. In both treatment groups, mean change from baseline for hemoglobin values increased through Day 26 (FIGS. 53 and 54). Mean change from baseline in hemoglobin for the 40,000 IU q.w. group mirrored the change in the epoetin alfa 150 IU/kg t.i.w. group. Overall, both groups exhibited a 3.1 g/dL increase from baseline through Day 29.

Red Blood Cells

The mean change from baseline in red blood cell values is illustrated in FIGS. 55 and 56. In both treatment groups, mean change from baseline for red blood cell values increased through Day 24. Mean change from baseline in red blood cell values for the 40,000 IU q.w. group mirrored the change in the epoetin alfa 150 IU/kg t.i.w. group. Overall, both groups exhibited a $1.0 \times 10^{12}$/L increase from baseline through Day 29.

Pharmacokinetic/Pharmacodynamic Results

Mean pharmacodynamic parameter values (corrected for baseline value) are presented in FIG. 57. The dynamic responses of the two dosing regimens were similar despite the fact that serum erythropoietin AUC for the 40,000 IU q.w. dosing regimen was larger than that for the 150 IU/kg t.i.w. dosing regimen. There were no statistically significant differences (p>0.05) in the AUC of % reticulocytes, AUC of hemoglobin, and the AUC of red blood cells between the two dosing regimens. There were no statistically significant differences (p>0.05) in the AUC of percent reticulocytes between male and female subjects. However, the AUC of hemoglobin and the AUC of red blood cells were statistically (p=0.038 and 0.042, respectively) larger in females than in males. These differences were not clinically significant.

Safety Results

Extent of Exposure

Thirty-four (94%) of the subjects participating in the study received all doses of study drug (either epoetin alfa 150 IU/kg t.i.w. [12 doses] or epoetin alfa 40,000 IU q.w. [four doses]). One subject (1014) randomized to the epoetin alfa 150 IU/kg t.i.w. group withdrew from the study due to an adverse event (persistent headaches) after receiving six doses of study drug. In the 40,000 IU q.w. group, one subject (1006) chose to withdraw after receiving two doses of study drug.

With one exception, all subjects received daily oral iron supplementation as per protocol; subject 2008 (40,000 IU q.w.) discontinued oral iron supplementation on Day 19 of the study. With one exception, all women continued with the method of birth control practiced prestudy (as per protocol); subject 1010 (epoetin alfa 40,000 IU q.w.) discontinued oral birth control eleven days before study initiation.

Adverse Events

All treatment-emergent adverse events are summarized in FIG. 58. Overall, 13 (72%) of 18 subjects administered epoetin alfa 150 IU/kg t.i.w. had an adverse event compared with 12 (67%) of 18 subjects administered epoetin alfa 40,000 IU q.w. The majority of treatment-emergent adverse events were mild in severity with minor qualitative differences between the two groups.

The most frequently reported adverse events were pain (22% 150 IU/kg, 28% 40,000 IU q.w.), headache (28% both groups), and erythematous rash. Five (28%) of 18 subjects receiving epoetin alfa 150 IU/kg t.i.w. exhibited an erythematous rash at the cannula site in the forearm, compared with two (11%) of 18 subjects receiving epoetin alfa 40,000 IU q.w. All events were assessed by the investigator to be unrelated to epoetin alfa therapy.

Summary of All Adverse Events

Deaths, Other Serious Adverse Events, and Other Significant Adverse Events

There were no deaths or serious adverse events during the course of the study. One subject (1014) administered epoetin alfa 150 IU/kg t.i.w. discontinued the study due to an adverse event (persistent headaches) on Day 15 of the study. The headaches were assessed by the investigator as very likely to be related to epoetin alfa administration.

Subject 2007 (150 IU/kg t.i.w., a 28-year-old white male, had a hemoglobin level of 18.0 g/dL on Day 26. Repeat hemoglobin evaluation later that day revealed a level of 17.6 g/dL. On Day 29, the subject's hemoglobin level was 18.2 g/dL; repeat evaluation on Day 31 revealed a hemoglobin level of 18.4 g/dL. The subject was then phlebotomized as specified in the protocol; 450 mL of blood were removed. The subject completed the study on Day 29 and hemoglobin levels were subsequently monitored for safety; evaluations on Days 32 and 39 revealed hemoglobin levels of 17.7 g/dL and 16.9 g/dL, respectively.

Concomitant medications used during the study for the treatment of adverse events included: paracetamol for headache (subjects 1014, 2004 [150 IU/kg] and 1011, 2008 [40,000 IU]), tooth pain (subject 2004 [150 IU/kg]), neck pain (subject 2010 [150 IU/kg]), period pain (subject 1013 [150 IU/kg]), gastric flu (subject 1011 [40,000 IU]), cold (subject 1013 [150 IU/kg]), and pain at cannulae sites (subject 1008 [150 IU/kg]); and normal saline and chloramphenicol (subject 2004 [150 IU/kg]) for ocular inflammation.

Clinical Laboratory Evaluation

Laboratory Values Over Time

The mean changes from baseline in iron, ferritin, and transferrin saturation are summarized in FIG. 59. There were no consistent patterns in iron values or transferrin saturation that would indicate that either treatment resulted in clinically significant abnormalities.

Figure 60:
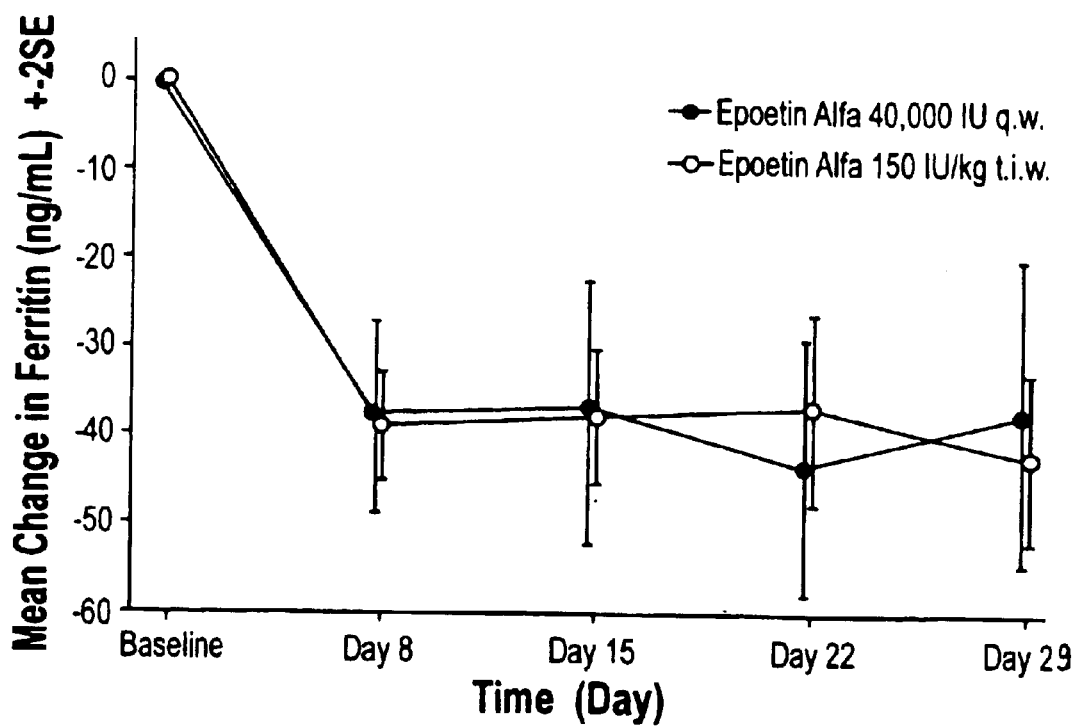
FIG. 60: The profile of mean change from baseline in iron, ferritin (ng/mL) by both treatment group and study day for Clinical Study EPO-PHI-373. Group 1(150 IU/kg t.i.w.) is designated by open circles and Group 2 (40,000 IU q.w) is designated by closed circles. The parameters obtained for ferritin are listed in FIG. 59.

The patterns reflected in ferritin changes, which were similar between groups, reflect expected use of iron stores for the production of hemoglobin (FIG. 60). The fluctuating serum iron levels in both groups were not considered clinically meaningful.

As FIG. 60 illustrates, mean change from baseline in ferritin values decreased through Day 8 and remained low through Day 29, indicating continued erythropoiesis through this period. There was no notable difference between the two groups in mean change from baseline ferritin values.

Individual Subject Changes

There were no individual subject changes recorded as an adverse event during the course of the study.

Other Safety Observations

Vital Signs

A summary of the mean changes from baseline in vital sign measurements by study day for individual subject data are presented in FIG. 61. There were no clinically significant changes in mean vital sign measurements for either treatment group and no significant differences between groups.

Two subjects administered epoetin alfa 150 IU/kg t.i.w. exhibited systolic blood pressure values at or above the upper limit of 140 mmHg; none of these events were considered by the investigator to be clinically significant, and none were recorded as adverse events.

Physical Findings

There were no clinically significant changes from baseline in physical examinations.

Safety Conclusions

Epoetin alfa administered t.i.w. at 150 IU/kg or q.w. at 40,000 IU was safe and well tolerated by healthy subjects in this study. There were no clinically important treatment-emergent adverse events in either treatment group. The majority of treatment-emergent adverse events were mild in severity with minor qualitative differences between the two groups. No subject died during the study, and there were no serious adverse events reported. One subject administered epoetin alfa 150 IU/kg t.i.w. was phlebotomized on Day 31 of the study, due to high hemoglobin levels. Subsequent monitoring of hemoglobin levels in this subject revealed no further elevation in hemoglobin levels. One subject receiving epoetin alfa 150 IU/kg t.i.w. withdrew from the study due to an adverse event (persistent headaches). There were no clinically significant changes noted in clinical laboratory test values, mean vital sign measurements, or physical examinations for either group; there were also no apparent differences in the results between the two groups.

Summary and Discussion

Following administration of epoetin alfa 40,000 IU q.w., $C_{max}$ values were six times and $AUC_{(0-168)}$ values were three times that of the 150 IU/kg t.i.w. dosing regimen. Clearance after the 150 IU/kg t.i.w. dosing regimen was higher than that after the 40,000 IU q.w. dosing regimen. The time profiles of changes in percent reticulocytes, hemoglobin, and total red blood cells over the one month study period were similar between the two dosing regimens despite the differences in exposure of epoetin alfa in serum [in terms of $AUC_{(0-168)}$]. In addition, there were no statistically significant differences (p>0.05) in AUC of percent reticulocytes, AUC of hemoglobin, and total red blood cell over the one month study period between the two dosing regimens. Although the differences in AUC of hemoglobin and AUC of total red blood cells between male and female subjects were statistically significant, these differences were not considered clinically meaningful. The data of this study clearly indicate that the hemoglobin responses after the 150 IU/kg t.i.w. and the 40,000 IU q.w. dosing regimens were similar.

There was an expected difference in total exposure of epoetin alfa in serum after the 150 IU/kg t.i.w. and the 40,000 IU q.w. dosing regimens. Hemoglobin responses were similar, suggesting that the two dosing regimens can be used interchangeably.

EXAMPLE 3

Comparison of PK/PD Parameters After Administration of EPREX® and PROLEASE®

Figure 62:
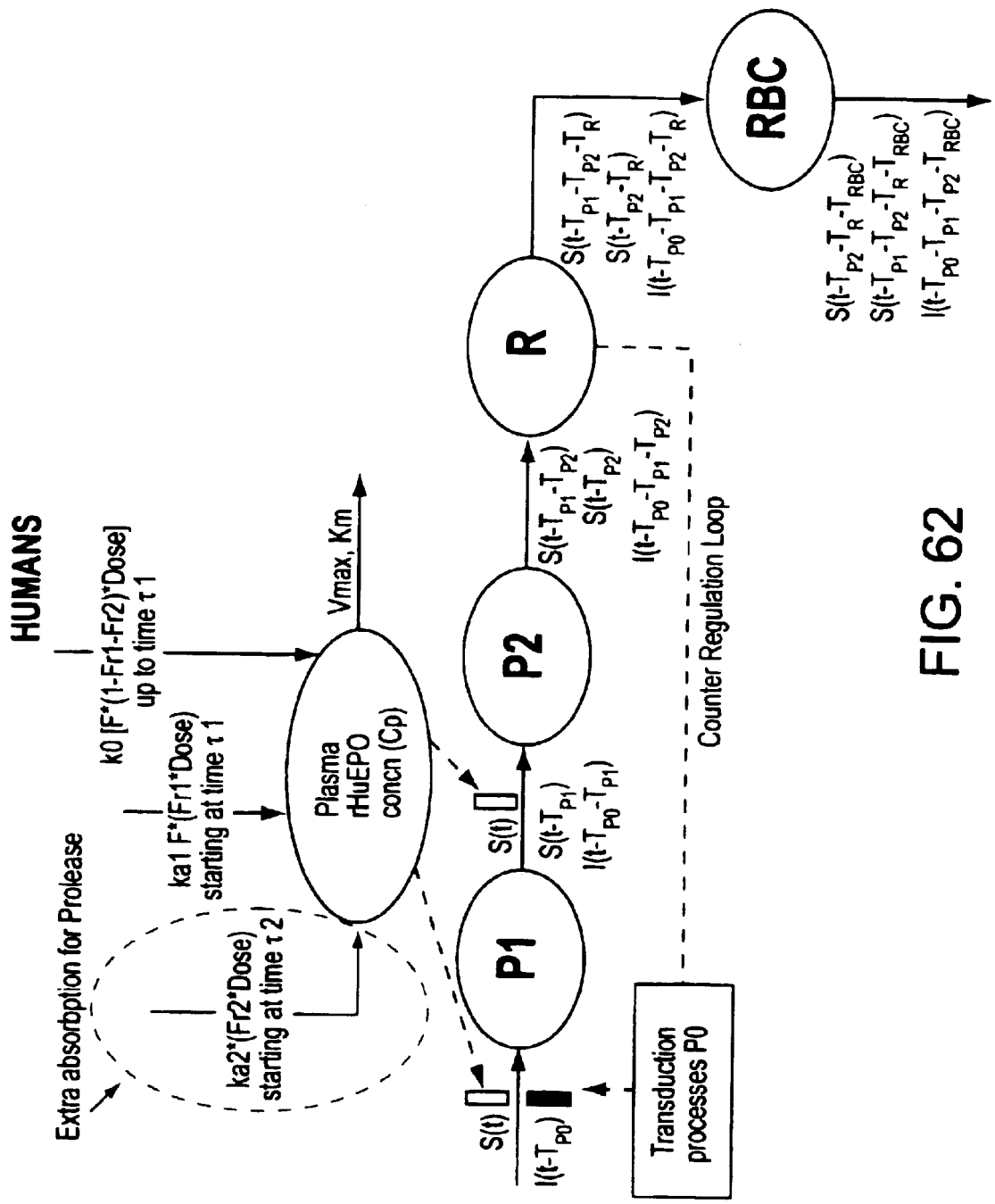
FIG. 62: Schematic representation of the model for erythropoiesis stimulating effects of rHuEPO.

FIG. 62 is a schematic representation of the model for erythropoiesis stimulating effects of rHuEpo. This model was used to estimate the kinetic and dynamic parameters for rHuEpo responses after administration of 8 single doses of EPREX® as well as the kinetic parameters after single dose PROLEASE® administration.

Pharmacokinetics

The pharmacokinetics of 600 IU/kg/wk EPREX® administered for 4 weeks was simulated using parameters obtained from the simultaneous fitting of the eight single doses. Only the Tau and Fr values were estimated. For the INT-57 cancer regimen of 150 IU/kg/t.i.w, the F, Tau, and Vd values were fixed as indicated in FIG. 63 based on previous estimations from the earlier study (EPO 358/359). The pharmacokinetics for single dose PROLEASE® (2400 IU/kg) were estimated and these parameters were used to simulate the multiple dose regimen of 1800 IU/kg/month. The same sets of kinetic parameters were used to characterize profiles for both males and females, since preliminary runs did not show significant differences in the estimated parameters based on gender.

Pharmacodynamics

Figure 65:
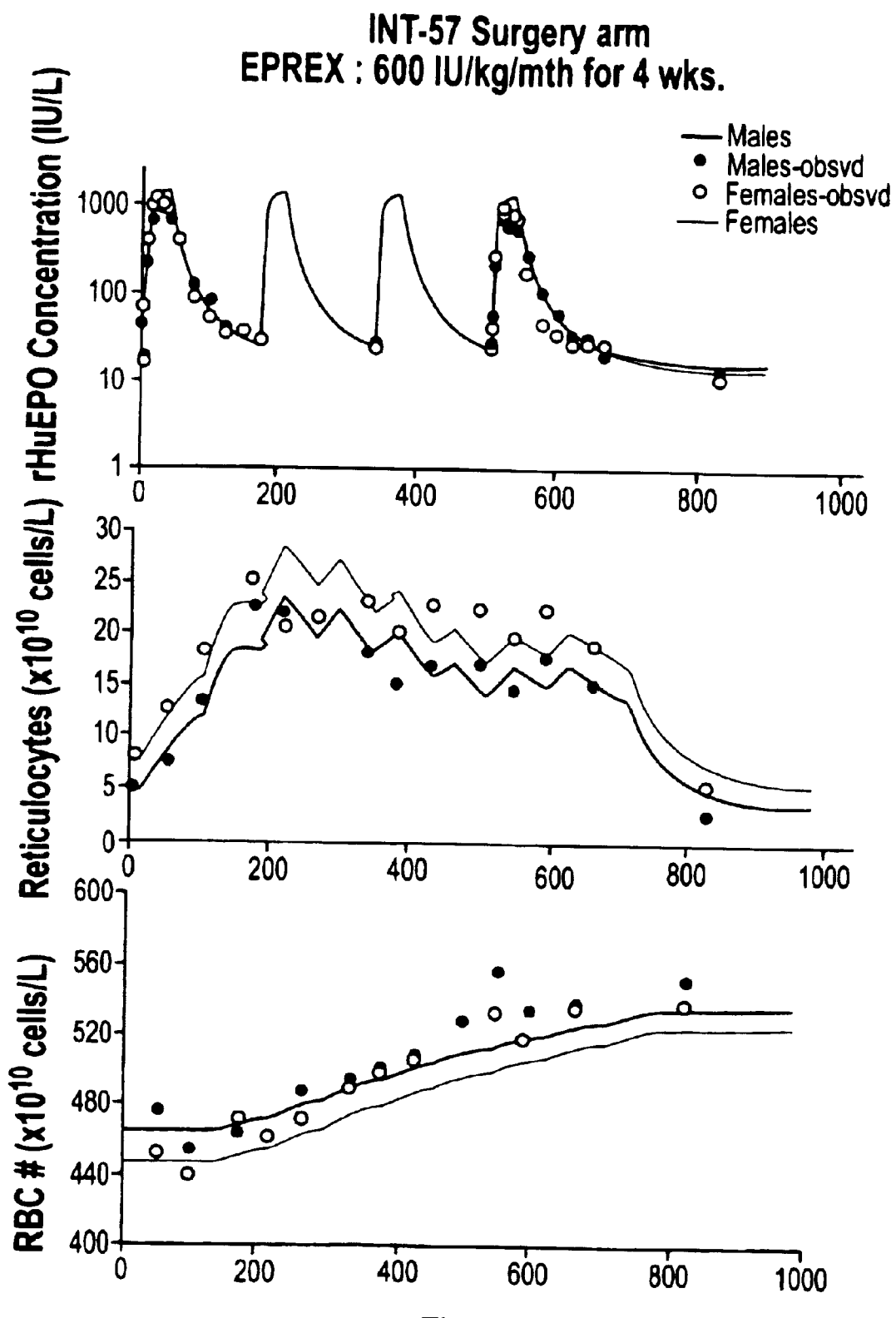
FIG. 65: Profile of pharmacodynamic parameters after administration of 600 IU/kg/t.i.w. EPREX® for 4 weeks. The mean rHuEPO concentration-time, reticulocyte concentration-time, and RBC concentration-time profiles are shown. The male subjects are designated by the closed circles while the female subjects are designated with open circle.

The kinetics was fixed and used as a forcing function for driving the dynamic responses. Predose values were fixed as baseline levels for reticulocytes and the mean of the 48 and 96-hour values were fixed as baseline for RBC. Lifespan parameters obtained from single dose estimation for EPREX® were fixed for further multiple dose fittings. The Smax and $SC_{50}$ were estimated for the reticulocyte response after the multiple dose 600 IU/kg/wk surgery regimen. As reported in FIG. 64, these parameters do not seem to change very appreciably considering the variability in the responses. The difference may simply reflect the fact that this was a different Phase I study from the single dose study, conducted on a new set of volunteers. Moreover, these set of parameters seem to well characterize the 150 IU/kg/t.i.w. cancer regimen too based on the simulations shown in FIGS. 65 and 66. The reticulocyte data for males and females were analyzed separately since the estimated Smax and SC50 from the data on male subjects did not describe the responses for females well enough. As seen from FIG. 68, these parameters were different when estimated separately for females, though it would be hard to judge whether the difference is appreciable. These parameters may reflect some slight pharmacodynamic differences based on gender since all the data was obtained from a single study which might be expected to have lower variability.

The estimated EPREX® parameters were used to simulate the responses for both the single and double dose PROLEASE® regimens. Simulations using the models of the present invention were performed for males and females separately according to the parameters estimated for the respective genders from EPREX® estimations. Further, the RBC responses were simulated based on the parameters generated using the reticulocyte data, and the erythrocyte response seems to be characterized well in all the cases for both EPREX® and PROLEASE®.

Figure 66:
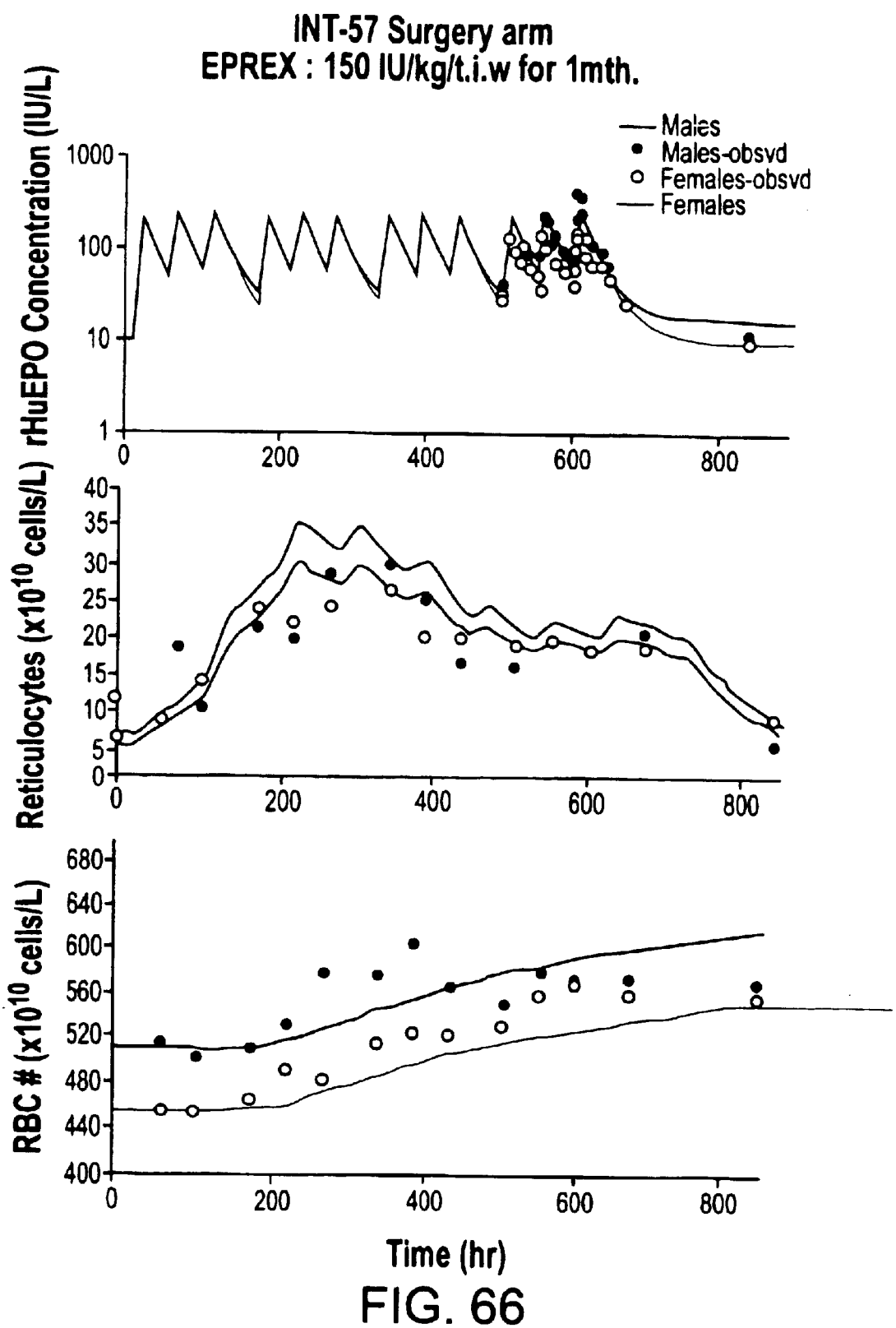
FIG. 66: Profile of pharmacodynamic parameters after administration of 150 IU/kg/t.i.w. EPREX® for 1 month. The mean rHuEPO concentration-time, reticulocyte concentration-time, and RBC concentration-time profiles are shown. The male subjects are designated by the closed circles while the female subjects are designated with open circle.
Figure 67:
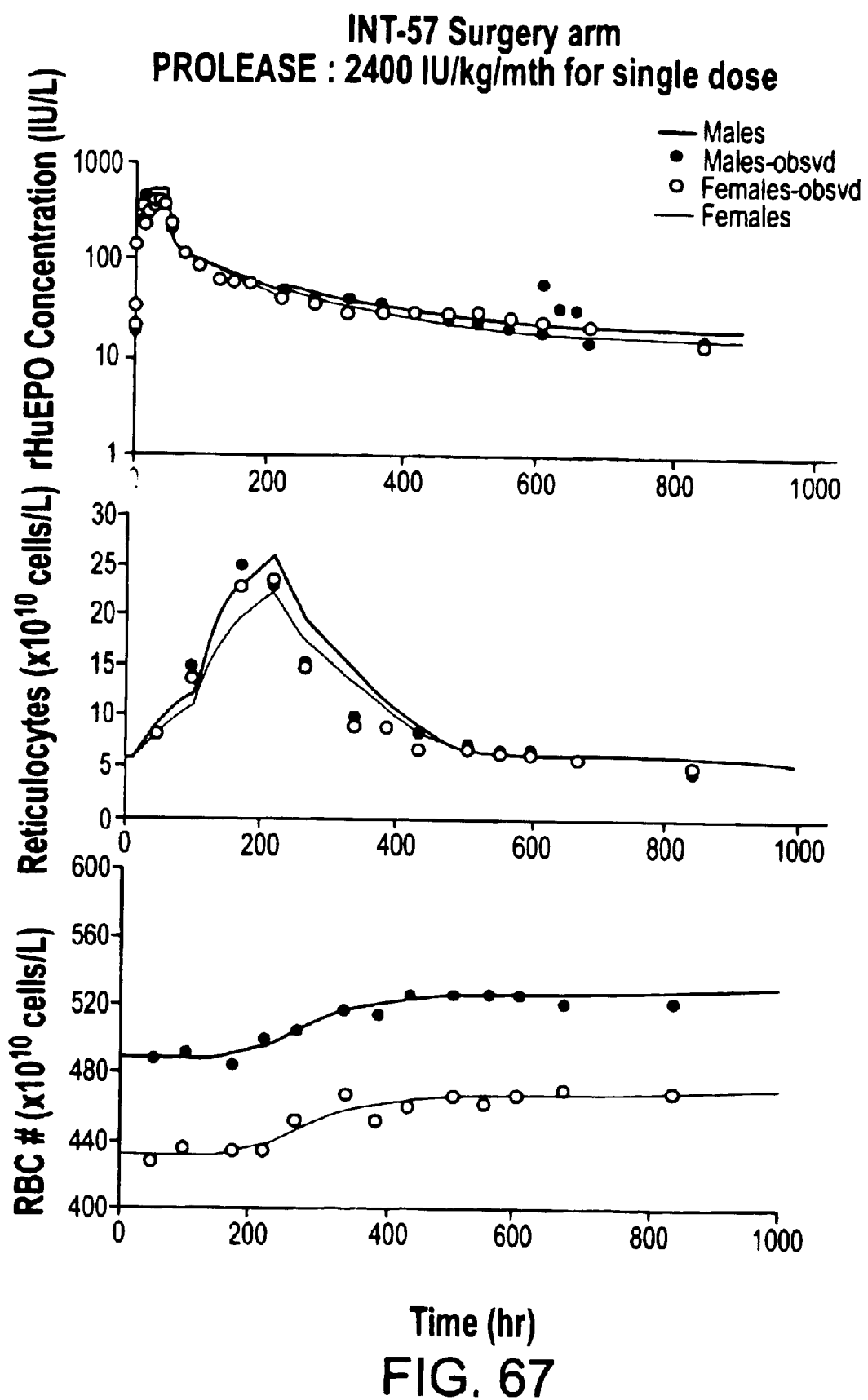
FIG. 67: Profile of pharmacodynamic parameters after administration of PROLEASE® at 2400 IU/kg/mth single dose. The mean rHuEPO concentration-time, reticulocyte concentration-time, and RBC concentration-time profiles are shown. The male subjects are designated by the closed circles while the female subjects are designated with open circle.

Based on the simulations as shown in FIGS. 66 and 67, it can be seen that the same set of dynamic parameters can well describe responses to both the formulations Hence, it can be concluded that EPREX® and PROLEASE® seem to be pharmacodynamically equivalent. The models of the present invention predict that the differences in the responses between the two formulations may be accounted for completely by the altered kinetics. Indeed, the models of the present invention may be used to compare the PK/PD characteristics of new forms and versions of EPO and EPO-like compounds with those currently available to provide the patient with the most beneficial treatment regimen.

EXAMPLE 4

Comparison of Different Dosing Regimens of rHuEPO.

The standard dosage regimens for chronic administration of rHuEPO are 150 IU/kg/t.i.w. and 600 IU/kg/week. There may be savings in cost and added convenience if patient therapy involved less frequent dosing. Therefore, the differences in hemoglobin responses for various dosage regimens of rHuEPO were examined using the models of the present invention to characterize and predict responses to rHuEPO which offer the most efficient treatment regimens.

The production/loss pharmacodynamic model along with the dual absorption pharmacokinetic model of the present invention was used. Parameters obtained from fittings of rHuEPO dynamics in healthy volunteers (FIG. 3 and FIG. 13) were used for simulations of the different dosage regimens. A baseline EPO concentration of 40 IU/L was fixed for the simulations in all cases. The ADAPT II program was used for all simulations.

Figure 68:
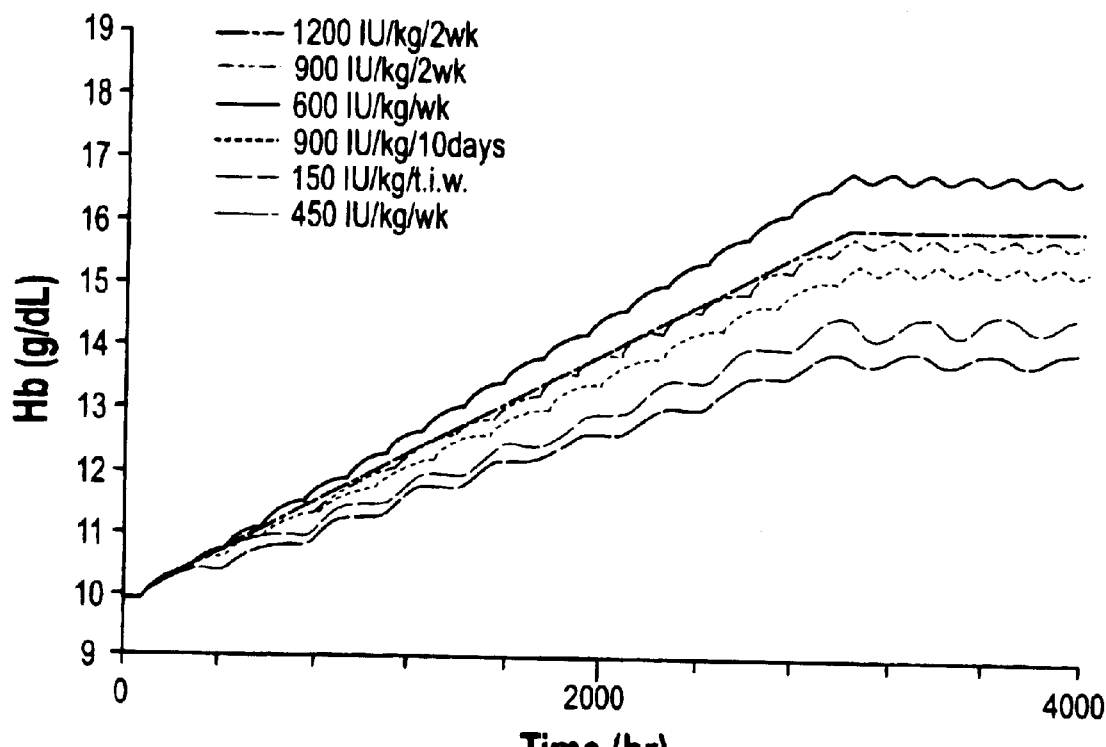
FIG. 68: Simulations of hemoglobin levels after administration of different doses/regimens of rHuEPO.

FIG. 68 shows the simulated hemoglobin response versus time profiles for several different doses and dosing regimens of rHuEPO. All regimens produce a continual rise in Hb concentrations until steady-state is reached around 126 days (3024 hr). The dose of 600 IU/kg/wk seems to produce the maximum increase in Hb levels. This dose and regimen can keep the rHuEPO concentrations above the threshold of 23 IU/L for most periods of time causing continual increases in cell counts ultimately producing higher steady-state levels of Hb. The same total dose of 1200 IU/kg given every 2 weeks produces responses which are much lower because the rHuEPO concentrations fall below threshold before most of the reticulocytes are converted to erythrocytes. Moreover, the succeeding doses of rHuEPO are also not given soon enough to elevate the concentrations above the threshold as would occur with every week dosing.

A similar argument can be made in comparing the 450 IU/kg/wk regimen to the 900 IU/kg every 2 weeks dosing. The 150 IU/kg t.i.w. dosing is equivalent to the 450 IU/kg/wk dosing regimen in terms of the total dose delivered but the dynamic profiles after thrice a week dosing yield a slightly better Hb response. As expected, the 900 IU/kg/10 days dosing schedule yields a steady-state response profile (56% increase) better than the 1200 IU/kg/2 wk (48% increase) but lower than the 600 IU/kg/wk (71% increase) regimen.

When treatment is continued for a substantial length of time, the true steady-state responses attained appear to differ with the various dosage and regimens. These differences in steady state response, however, are not as apparent with the short term treatment regimen, which causes only slight elevations in Hb levels (e.g., an increase by 1 unit), except for the 600 IU/kg/week treatment, which causes a consistently higher Hb response in comparison to the other regimens. The simulations, using the models of the present invention, show that as the time for readministration is decreased, greater and steadier increases in Hb can be achieved with the same total dose. Frequent dosing helps to keep the rHuEPO concentrations above the threshold facilitating formation of RBC from reticulocytes. The erythrocytes, having a 40 times longer life-span than that of reticulocytes, persist in blood for a much longer time resulting in steady increases in Hb levels. Also, it is seen that the change in response seen with more frequent administration also depends on the dose chosen. Switching from an every other week regimen to a weekly dosing schedule affects the 600 IU/kg dose more than the 450 IU/kg dose. Though better in terms of the steady-state response achieved, thrice a week dosing may not be preferable over weekly dosing for the same total dose because the extent to which there is improvement in response is not great enough compared to the inconvenience of more frequent dosing. Hence, for the dosage regimens tested, a once-weekly 600 IU/kg/dose of EPO is shown to provide the desired PK/PD response.

Indeed, the models of the present invention can provide any desired dosing regimen, such as less than once daily, to less than once weekly to less than once every two, three, or four weeks, depending on the EPO used and the desired PK/PD response. Thus, the models of the present invention are not limited to use with any particular type of EPO or any specific type of dosage regimen, and can be modified and used with any type of EPO.

EXAMPLE 5

Effects of 40,000 IU/wk Dosing of rHuEPO in Relation to Patient Body Weight.

The need for repeated rHuEPO administration causes dosing based on body weight to be inconvenient and time consuming. A switch from this practice to dosing a definite amount irrespective of subject body weight would facilitate clinical use of rHuEPO. Hence, simulations were performed with the models of the present invention in an attempt to reveal the extent of changes in expected RBC and hemoglobin response profiles with body weight alterations. It was intended to use these simulations to provide insight as to whether this change in the mode of dosing is justifiable from a theoretical perspective.

The production/loss pharmacodynamic model along with the dual absorption pharmacokinetic model of the present invention was used. Parameters obtained from fittings of rHuEPO dynamics in healthy volunteers (FIG. 3 and FIG. 13) were used for simulations of the different dosage regimens. A baseline EPO concentration of 40 IU/L was fixed for the simulations in all cases. The ADAPT II program was used for all simulations.

Figure 69:
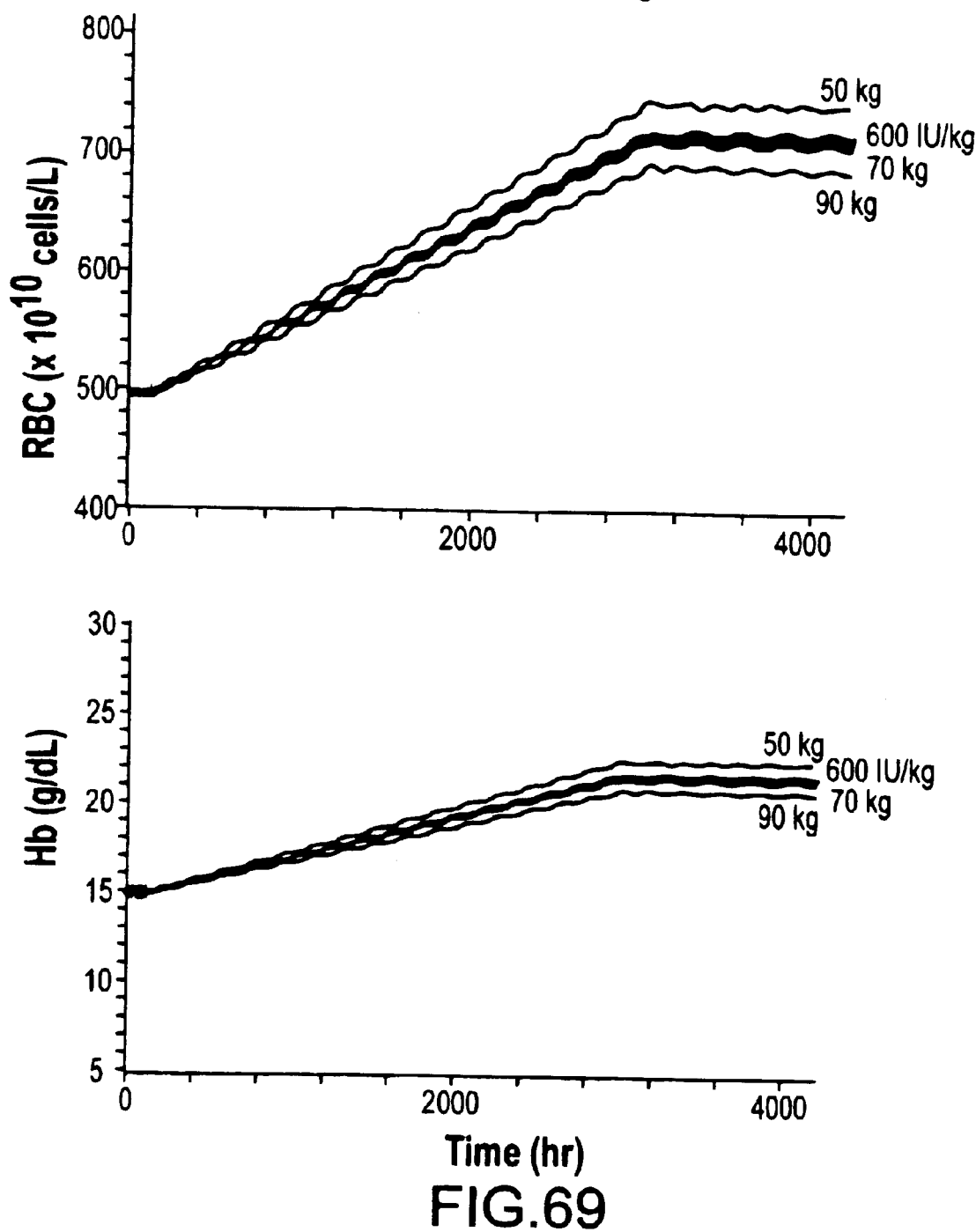
FIG. 69: Simulations of hemoglobin and RBC response versus time profiles for the EPO dose regimen of 600 IU/kg/wk for 24 weeks in comparison to giving a total dose of 40,000 IU/wk of rHuEPO to subjects with body weights of 50, 70 and 90 kg.
Figure 70A:
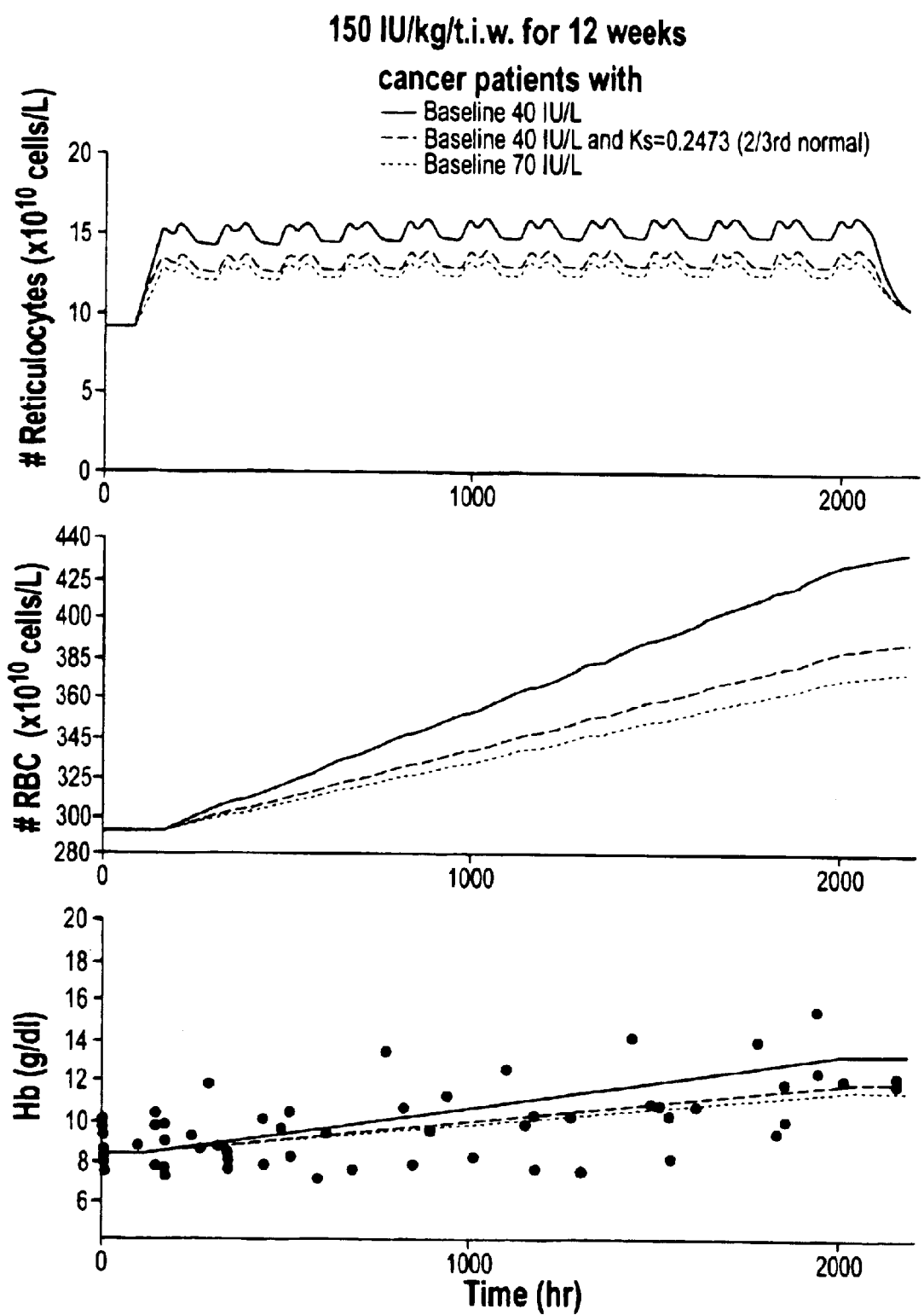
FIG. 70A: Simulations of reticulocyte, RBC, and hemoglobin response versus time profiles in cancer patients for the EPO dose regimen of 150 IU/kg/t.i.w. for 12 weeks.
Figure 70B:
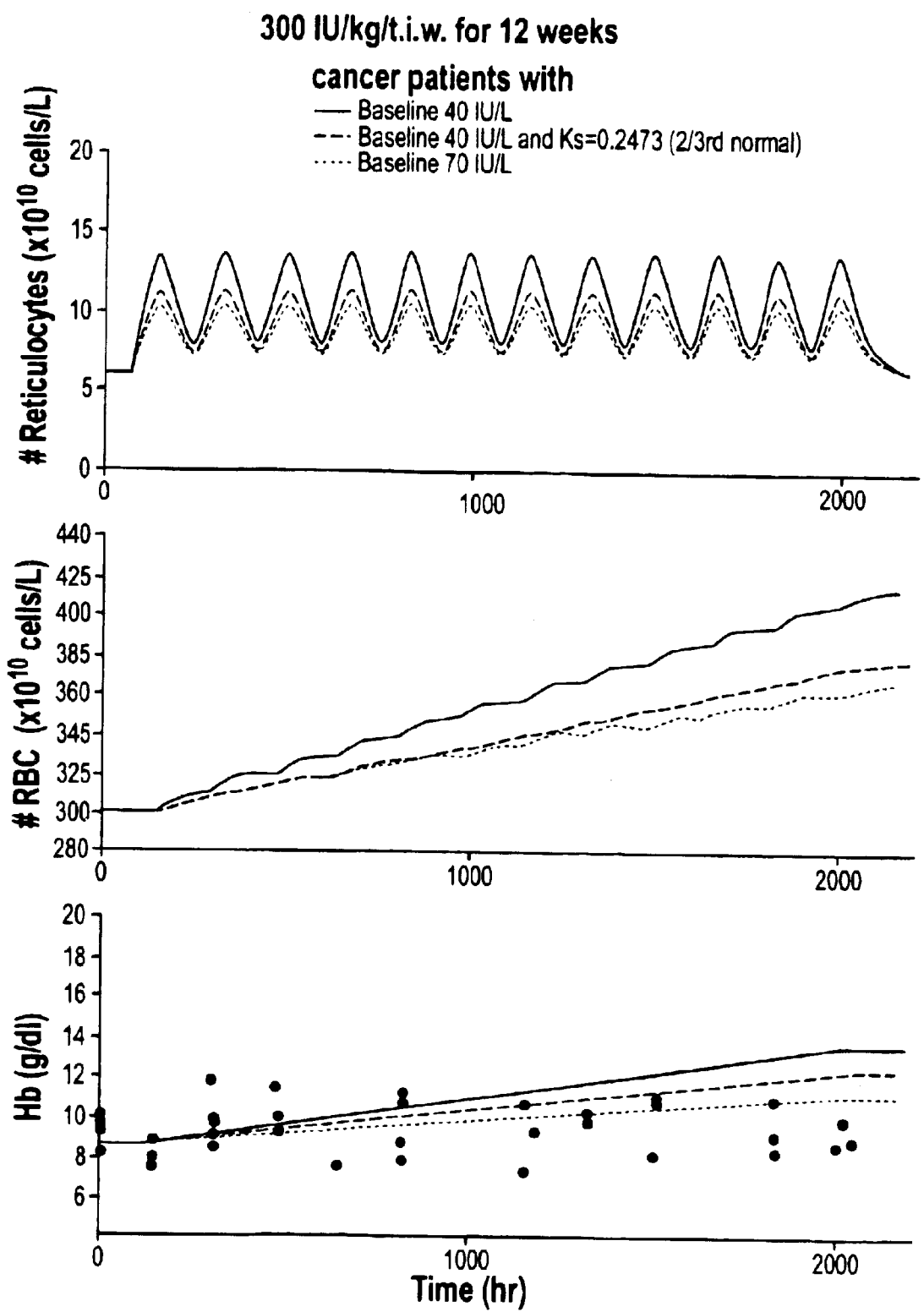
FIG. 70B: Simulations of reticulocyte, RBC, and hemoglobin response versus time profiles in cancer patients for the EPO dose regimen of 300 IU/kg/t.i.w. for 12 weeks.
Figure 70C:
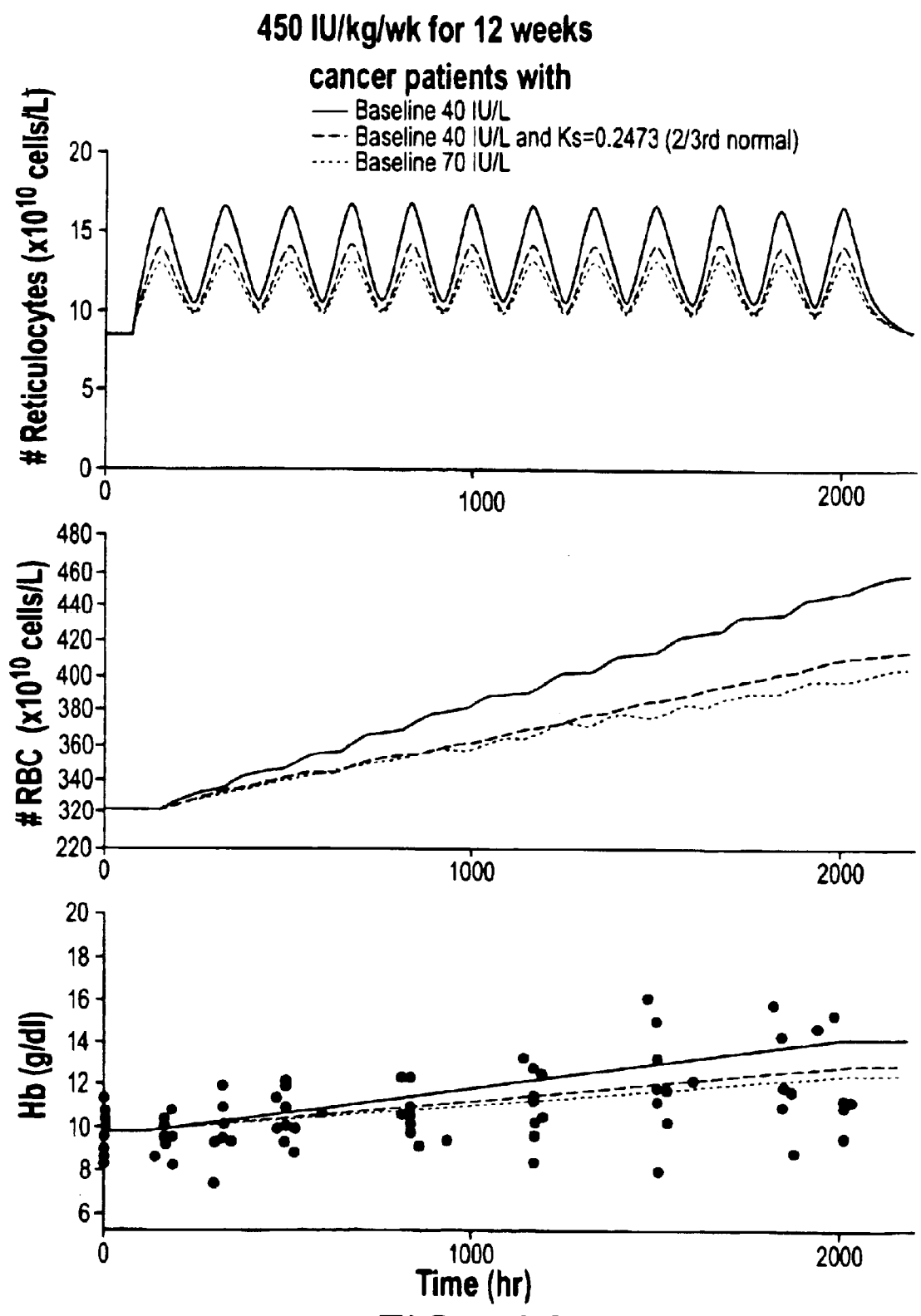
FIG. 70C: Simulations of reticulocyte, RBC, and hemoglobin response versus time profiles in cancer patients for the EPO dose regimen of 450 IU/kg/t.i.w. for 12 weeks.
Figure 70D:
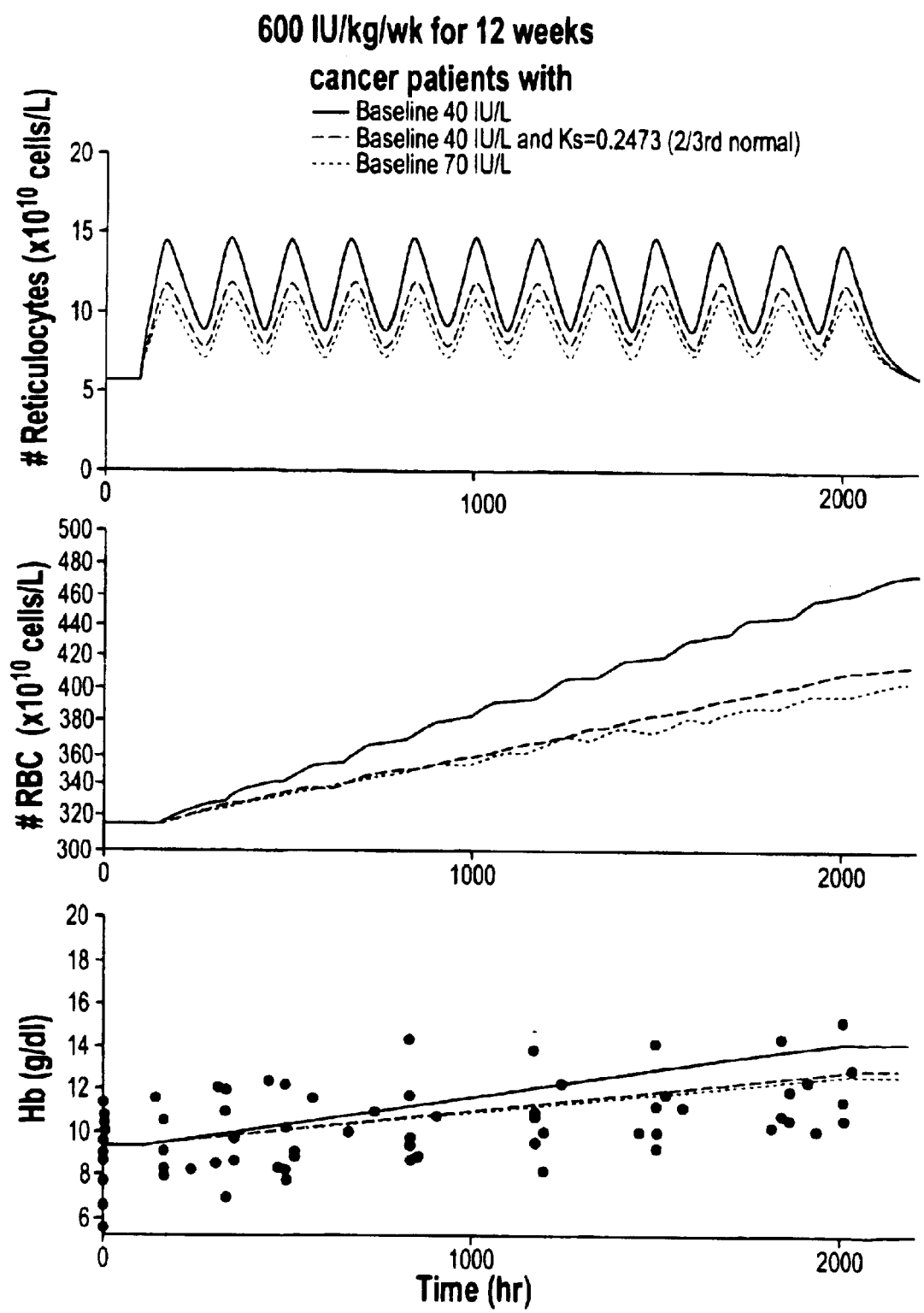
FIG. 70D: Simulations of reticulocyte, RBC, and hemoglobin response versus time profiles in cancer patients for the EPO dose regimen of 600 IU/kg/t.i.w. for 12 weeks.
Figure 70E:
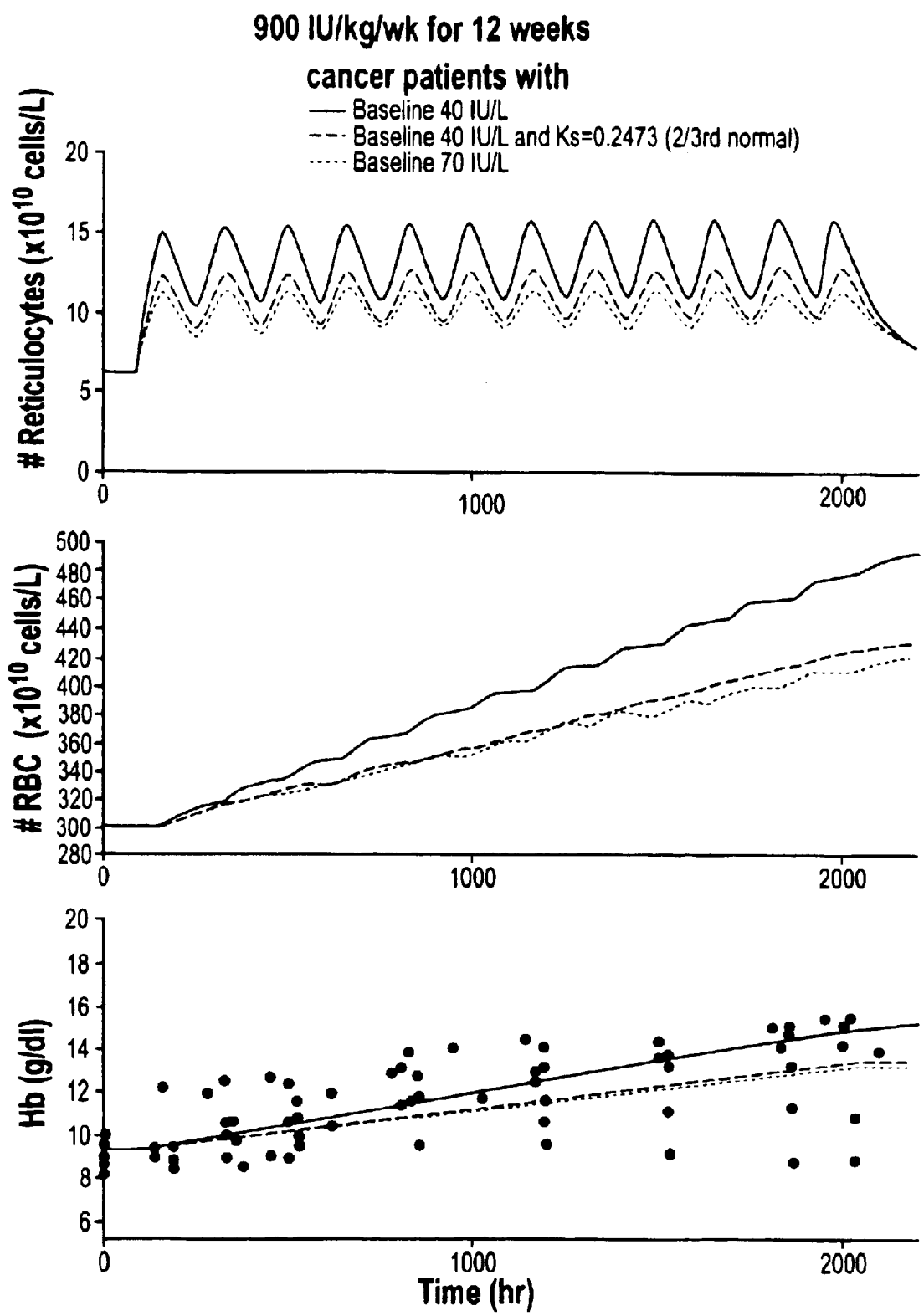
FIG. 70E: Simulations of reticulocyte, RBC, and hemoglobin response versus time profiles in cancer patients for the EPO dose regimen of 900 IU/kg/t.i.w. for 12 weeks.

The effects of subject body weight on the expected response to maintenance therapy with rHuEPO is depicted in FIG. 69. FIG. 69 shows the simulated RBC and Hb response versus time profiles for the regimen of 600 IU/kg/wk for 24 weeks (4032 hr) in comparison to giving a total dose of 40000 IU/wk to subjects with body weights of 50, 70 and 90 kg. Both RBC and Hb show continual increases over the duration of rHuEPO administration. The dose of 40000 IU/wk resembles the 600 IU/kg/wk dosing regimen assuming that most subjects have a 70 kg weight.

A change in body weight affects the volume of distribution (Vd). The rHuEPO has a Vd of 0.0558 L/kg, which is very close to plasma volume. As body weight increases, Vd (L) increases causing the maximum rHuEPO concentrations attained to become lower. A change in body weight also affects the clearance parameter Vmax (IU/hr/kg). There is an increase in Vmax (IU/hr) with increase in body weight leading to an increase in clearance (Vmax/(Km+$C_{EPO}$)) of rHuEPO. As both Vmax and Vd are affected to the same extent, the elimination rate constant (i.e., k at lower concentrations) remains unchanged. In any case, body weight differences appear not to affect the kinetics to a significant extent because the terminal slope after SC administration is in fact governed by the absorption kinetics and with the $SC_{50}$ being very low, the terminal slope principally governs the extent of response.

The simulations show that the steady-state levels of RBC counts and Hb counts are slightly different based on body weight. The time to reach steady-state, however, is also long and therefore, the Hb responses at early times such as 4 weeks do not differ very much (16.46, 16.33 and 16.19 g/dl for 50, 70 and 90 kg subjects versus 16.35 g/dl for 600 IU/kg/wk dosing).

Therefore, the data derived from the models of the present invention show that differences in body weight over the 50 to 90 kg range do not contribute substantially to rHuEPO kinetics and dynamics. Therefore, dosing based on body weight might not be optimal, nor imperative and a change from dosing on a body weight basis to a standard regimen of 40,000 IU/wk irrespective of body weight, is reasonable and convenient. The 40,000 and 650 IU doses are not meant to be absolute and contemplate a range of values in the dose that can be administered to a patient and provide the same or similar effect. Indeed, "about" 40,000 or 650 IU contemplates a range of values that provide the same or similar effect to a patient and contemplates ranges of, in a particular embodiment, +/−1 to 20% of the IU value.

EXAMPLE 6

Assessment of rHuEPO Dynamics in Cancer Patients

Cancer patients undergoing chemotherapy are often anemic. Inadequate endogenous EPO production is believed to be one of the factors responsible for the anemic condition in these patients, and administration of rHuEPO at a dose of 150 IU/kg three times a week (t.i.w.) has been shown to prove beneficial in correcting the anemia. Though this regimen gives adequate responses and is most commonly used, the frequent dosing required makes it inconvenient and it might not be the best one. Therefore, an optimal dose of rHuEPO, which can be given on a weekly regimen to yield comparable increases in hemoglobin levels as the current thrice a week regimen, was sought. The PK/PD models of the present invention using data from normal subjects was used to quantitatively compare the responses in cancer patients and explain possible causes of differences, if any, in the dynamics. The study also provides an opportunity to validate the models of the present invention so that they could be reliably used for predictive purposes in the future.

The data for the cancer patients was obtained from RWJPRI. This was an open-label, randomized, controlled, parallel group, multicenter study carried out in 150 anemic cancer patients having solid tumors and receiving platinum-containing chemotherapy (cisplatin or carboplatin). Different dose levels of PROCRIT® (Epoetin alfa, Amgen) which included weekly SC doses of 300, 450, 600, 900 IU/kg and an SC dose of 150 IU/kg t.i.w. were administered to 5 groups of subjects (25 patients per group) for a period of 12 weeks. The control group received no treatment. Patients were required to be 18 years of age or older, have prestudy Hb≦10 g/dl, corrected reticulocyte counts≦3%, platelets≧25,000 cells/mm³, creatinine≦2.0 mg/ml, negative stool occult blood, no evidence of hemolysis, and normal serum folate and Vitamin $B_{12}$ levels. Also, only those subjects that had not required blood transfusion one month prior to randomization and that were not iron-deficient were included in the study. The hemoglobin count was measured as the primary pharmacodynamic end point.

The parameters obtained from fittings of the kinetic and dynamic data for normal volunteers were used to simulate responses after administration of the different doses and regimens of rHuEPO to the cancer patients. The production/loss pharmacodynamic model along with the dual absorption kinetic model of the present invention was used. Parameters obtained from fittings of the rHuEPO dynamics in healthy volunteers (FIG. 3 and FIG. 13) along with a baseline EPO concentration of 40 IU/L were used as a starting point for simulations of the different dosage regimens, and the effects of changing various parameters on the responses were investigated. The ADAPT II program was used for all the simulations.

FIGS. 70A–70E show the hemoglobin data and simulations of reticulocytes, RBC and Hb responses for anemic cancer patients who were given different doses and regimens of rHuEPO. As seen in the figures, the patients seem to respond favorably to therapy in general with continual increases in Hb concentrations. There is only a very slight response associated with the 300 IU/kg dosage regimen. With increases in the weekly dose, there seems to be an increase in the extent of response. The highest dose of 900 IU/kg/week, however, does not produce considerably higher increases in Hb levels than the 600 IU/kg/wk dose. The data show that a weekly regimen of 600 IU/kg produces responses slightly better than the 150 IU/kg t.i.w. regimen. It can also be seen from the figures that the simulations using parameters from healthy subjects predict responses that are higher compared to those actually observed in cancer patients. Differences in the kinetics and/or dynamics of rHuEPO in cancer patients compared to healthy subjects can explain the cause of these altered response profiles. Simulations were therefore performed altering selected parameters in the pharmacodynamic model to explain these differences.

Erythroid hypoplasia of the bone marrow, decreased RBC survival, and decreased reticulocytosis are reported (see, e.g., Abels, 1992. *Semin. Oncol.* 19:29–35) to be some of the possible causes of anemia in chronic disease. Anticancer drug therapy is also thought to be one of the principal causes of anemia in these patients. (see, e.g., Matsumoto, et al., 1990. *Br. J. Pharmacol.* 75:463–68.) A reduction in the Ks value by ⅓rd, indicating a lowered intrinsic production rate of cells and/or a lower $S_{max}$ could explain the diminished responses as seen in the simulations. Cancer patients have baseline EPO concentrations, which are higher than normal, but inappropriately low for the degree of anemia. (see, e.g., Case, et al., 1993. *J. Natl. Cancer Inst.* 85:801–806 and Miller, et al., 1990. *N. Engl. J. Med.* 322:1689–99. The baseline EPO concentrations are reported to range from lower than 40 to higher than 500 U/L (see, e.g., Ludwig, et al., 1994. *Blood* 84:1056–63, Case et al., supra, Abels, supra, and Miller et al., supra) depending on the severity and type of anemia associated with the cancer and chemotherapy. Baseline EPO levels greater than 500 IU/1 have been reported to indicate unresponsiveness to rHuEPO therapy. (see, e.g., Ludwig et al., supra.)

Increasing the baseline EPO concentrations in the model to 70 U/L, signifying a decreased sensitivity of the system to EPO, shifted the response-time profiles down and gave a better fit of the data. Since dosing was done every week, concentrations remained well above the threshold allowing the conversion of most reticulocytes to erythrocytes. Therefore, a change in the threshold did not significantly help in shifting the curves, which suggests that reticulocyte-RBC conversion process may not be significantly affected in these patients. Under normal conditions, erythrocytes live for a period of 2880 hours and according to the production/loss model, the true steady-state is reached one life-span after the beginning of production of new erythrocytes. Any reduction in RBC life span would cause this steady state to be reached at an earlier time and be lower in these patients. This possibility was not demonstrated because the dosing was not carried out long enough to allow attainment of true steady-state under normal conditions in the study. As mentioned earlier, another possible cause of diminished responses in cancer patients could be differences in the pharmacokinetics of rHuEPO. In healthy volunteers, rHuEPO undergoes flip-flop kinetics after SC administration causing concentrations to stay above baseline for prolonged periods of time allowing continued stimulation of the production of new cells. The slow first-order input via lymphatics was assumed to contribute to this phenomenon and any alterations in the physiological functioning of the lymphatics due to the disease state and chemotherapy may abate the slow delivery leading to lower responses.

Although the weekly regimen of 600 IU/kg requires a higher total dose compared to 150 IU/kg t.i.w., it produces better Hb responses in cancer patients and is a more convenient dosing schedule for rHuEPO maintenance therapy. Therefore, a change from the current regimen to 600 IU/kg/wk might be preferable according to the models of the present invention. The PK/PD model developed can account for differences in responses due to disease conditions such as cancer, and the simulations predict that a lower Ks value and/or higher baseline EPO levels with or without alterations in the pharmacokinetics of rHuEPO could be responsible for the blunted responses seen in these patients.

With reference to the preceding detailed description and specific examples, one skilled in the art will understand that the PK/PD modeling system of the present invention may be used in a variety of situations. For example, a practitioner may want to adjust the EPO dosage regimen to achieve a desired pharmacokinetic response in a patient, such as serum EPO concentration. The practitioner can use the systems of the present invention to accomplish this result. Alternatively, the practitioner may want a specific pharmacodynamic response in patient, such as a specific increase in hemoglobin levels. The practitioner can use the systems of the present invention to determine which EPO dosage regimen will be capable of achieving the desired result. In another aspect, the practitioner may want to determine what type of pharmacokinetic and pharmacodynamic outcome will result from a specific EPO dosage regimen. Again, the practitioner will be able to use the PK/PD models of the present invention to make this determination.

EXAMPLE 7

Immunogenicity of EPO in Dogs During One-Month Dosing Regimens

This study was designed to evaluate the immunogenicity of EPO formulations in immunosuppressed and non-immunosuppressed beagle dogs. Pharmacodynamics and pharmacokinetic profiles of EPO formulations were examined.

Regulatory Compliance

Good Laboratory Practice (GLP): This study was not conducted in strict compliance with the U.S. Food and Drug Administration's GLP Regulations for Nonclinical Laboratory Studies (21 CFR, Part 58), yet was performed according to the protocol and applicable Oread standard operating procedures.

Animal Care and Use: Animal studies were conducted in accordance with the NRC "Guide for the Care and Use of Laboratory Animals", (Revised 1996) and the USDA "Laboratory Animal Welfare Act, Aug. 24, 1966, Pub.L.89–544 and subsequent amendments. Oread Met/PK is an AAALAC accredited facility.

Identification and Source

Formulations:

EPREX®, one 2000 IU/mL and one 10,000 IU/mL Saline as control

Storage

EPO formulations were stored refrigerated (~4° C.) protected from light when not used on study. Unused formulations were returned to RWJPRI following dosing or destroyed.

| Study Animals | |
| --- | --- |
| Species: | Dog |
| Strain: | Beagle |
| Sex: | Male |
| Source: | Harlan Sprague Dawley, Inc. Indianapolis, Indiana 46299 |
| Age at Dosing: | 8–9 months |
| Target Weight at First Dosing: | 9–12 kg |
| Identification Method: | Tattoo applied by animal supplier |
| Number on Study: | 18 (N = 3 dogs/group) |

Housing

Dogs were group housed by treatment group within kennels in a dog holding room and acclimated to handling and sample collection prior to dose administration. Quarantine were at least 5 days prior to dose administration. At the end of the quarantine period, the health of all animals was confirmed by study personnel. During the study/collection period, the dogs remained in group housing unless necessary due to health conditions. Kennels were labeled with the animals' and protocol numbers.

Environmental Conditions

Animal rooms were maintained at 23±3° C. with a relative humidity of 50±15% and a 12-hour light/dark cycle. There was at least 10 room air changes per hour.

Diet and Water

Dogs had access to Purina Certified Canine Diets #5007 and water ad libitum when on study. Results of food analysis (certificate of analysis provided by the vendor) and water analysis (dissolved solids, microbial content, selected elements, heavy metals, and chlorinated hydrocarbons) were maintained in the raw data file. No contaminants were reasonably expected to be present in feed or water at levels sufficient to interfere with the results of the study.

Justification of Dose and Species

The dose was selected based on existing data obtained from formulations evaluated in previous studies. This study was conducted in immunosuppressed and nonimmunosuppressed beagle dogs to evaluate the immunogenicity of EPO formulations, and the PK/PD profiles of two dosing regimens. The number of dogs that were used was the minimum number necessary to provide scientifically valid results. No acceptable in vitro models were available. Purpose bred beagle dogs are routinely used for the conduct of pharmacokinetic, pharmacodynamic, and toxicological studies to meet regulatory requirements.

Study Design

Summary

Beagle dogs (N=3 dogs/group, 6 groups) were randomly assigned to treatment groups. On Day-2, three groups of dogs were administered a single oral dose of cyclosporin (25 mg/kg). Thereafter, the three groups of dogs received a daily maintenance dose of cyclosporin (10 mg/kg). Two dosing regimens with EPREX® and vehicle were examined in immunosuppressed and nonimmunosuppressed dogs. All formulations and vehicle were administered subcutaneously (sc) either daily or weekly. At designated times over a four-week period, blood samples were collected. The injection site was monitored daily and body weights obtained weekly. Dogs were euthanized or donated to another research institute following the last collections.

Preparation and Test Formulations Dose Administration

Day 1

Test formulations were initially administered to the dogs on Day 1 (see table below). All formulations were administered at the volume specified in the following table.

Dose were drawn-up into a syringe fitted with appropriate gauge needle. The SC dose was administered in the dorsal region. Dose sites were clipped prior to dosing and marked with indelible ink.

| Group | Treatments | Immuno-suppressed | EPO Dose (IU/kg) | Volume (mL/kg) | Frequency | Dose Route |
| --- | --- | --- | --- | --- | --- | --- |
| 1 | EPREX ® | Yes | 50 | 25[1] | Daily | SC |
| 2 | EPREX ® | No | 50 | 25[1] | Daily | SC |
| 3 | EPREX ® | Yes | 600 | 60[2] | Weekly | SC |
| 4 | EPREX ® | No | 600 | 60[2] | Weekly | SC |
| 5 | Saline | Yes | NA | 60 | Weekly | SC |
| 6 | Saline | No | NA | 60 | Weekly | SC |

[1]Based on EPREX ® formulation containing 2000 IU EPO/mL.
[2]Based on EPREX ® formulation containing 10,000 IU EPO/mL.
NA indicates not applicable.

Observations, Sample Collection, and Processing

Dogs and injection sites were monitored daily. Any abnormal appearance or behavior was noted and evaluated. Body weights were recorded once weekly.

At designated primary time points (see below), approximately 2 mL of blood were collected via the jugular vein into heparinized Vacutainers® (Becton Dickinson, Franklin Lakes, N.J.). In case of jugular vein failure, blood was collected via the cephalic vein and noted. The primary blood collection, obtained prior to cyclosporin administration, was used to harvest plasma. The blood was placed on ice, centrifuged (1500×g, 10 min, ~4° C.), and plasma collected. Plasma was frozen at −20 C. for shipment.

At the secondary blood collection, approximately 2 mL of blood collected using a Vacutainer® containing EDTA, was obtained in the morning and placed on ice. The secondary collection was stored at ~4° C. as whole blood and used for reticulocyte, hemoglobin, and total red blood cell measurements.

Primary Blood Collection Time Points:

| | |
|---|---|
| Groups 1 & 2 (daily EPREX ®): | Predose, 1, 3, 8, 12, 16 and 24 h on Days 1 and 28, and predose on Days 3, 7, 14, 21, and 24. |
| Groups 3–6 (weekly EPREX ® or saline): | Predose, 1, 3, 8, 12, 24, 48, 72, and 96 h on Days 1 and 22, and predose on Days 7 and 14. |
| Secondary Blood Collection Time Points: | |
| All Groups: | Predose on Days 1, 3, 7, 10, 14, 17, 21, 24 and 28. |

As necessary during the study, additional serum samples were collected to assess renal and liver function. Within 24 h of the last sample collection, dogs were euthanized with an intravenous overdose of barbiturate euthanasia solution or donated to another research facility.

Sample Analysis

Collected whole blood (on EDTA) was analyzed for reticulocytes, hemoglobin, and total red blood cells.

Figure 71:
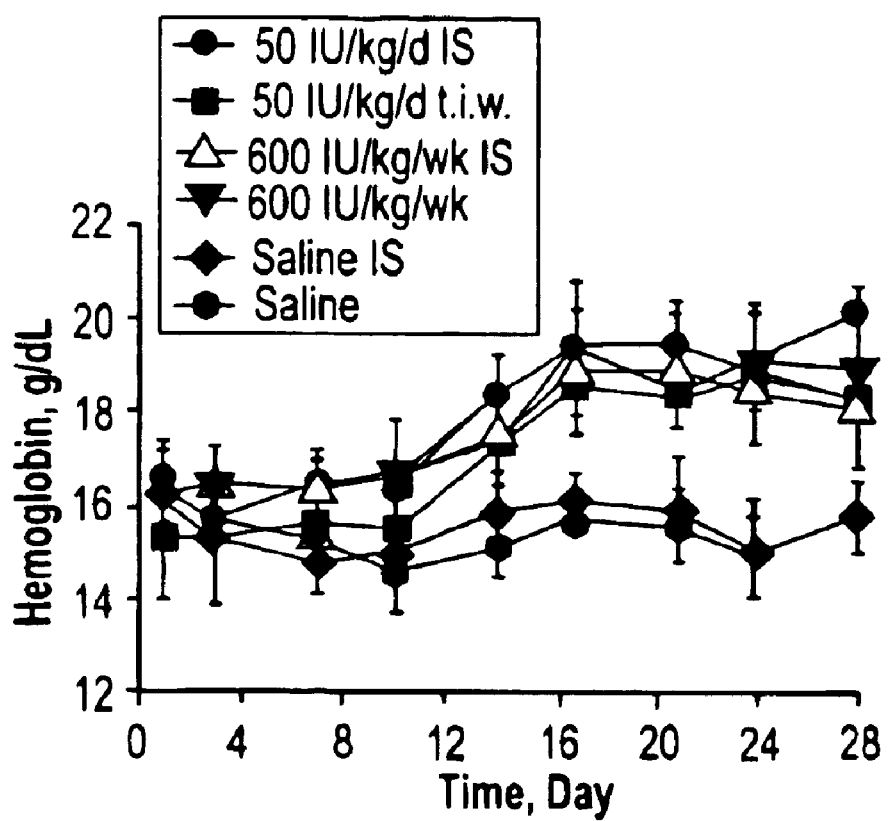
FIG. 71: Mean hemoglobin time concentration profiles by day for immunosuppressed (IS) and non-immunosuppressed dogs. The closed circles represent EPO administered at 50 IU/kg/d IS dogs, the closed squares represent EPO administered at 50 IU/kg/d t.i.w. for non-IS dogs, the open triangle represents EPO administered at 600 IU/kg/wk for IS dogs, the closed triangles represent EPO administered at 600 IU/kg/wk for non-IS dogs, the closed diamonds represent saline control for IS dogs, and the shaded octagons represent the saline control for non-IS dogs.
Figure 72:
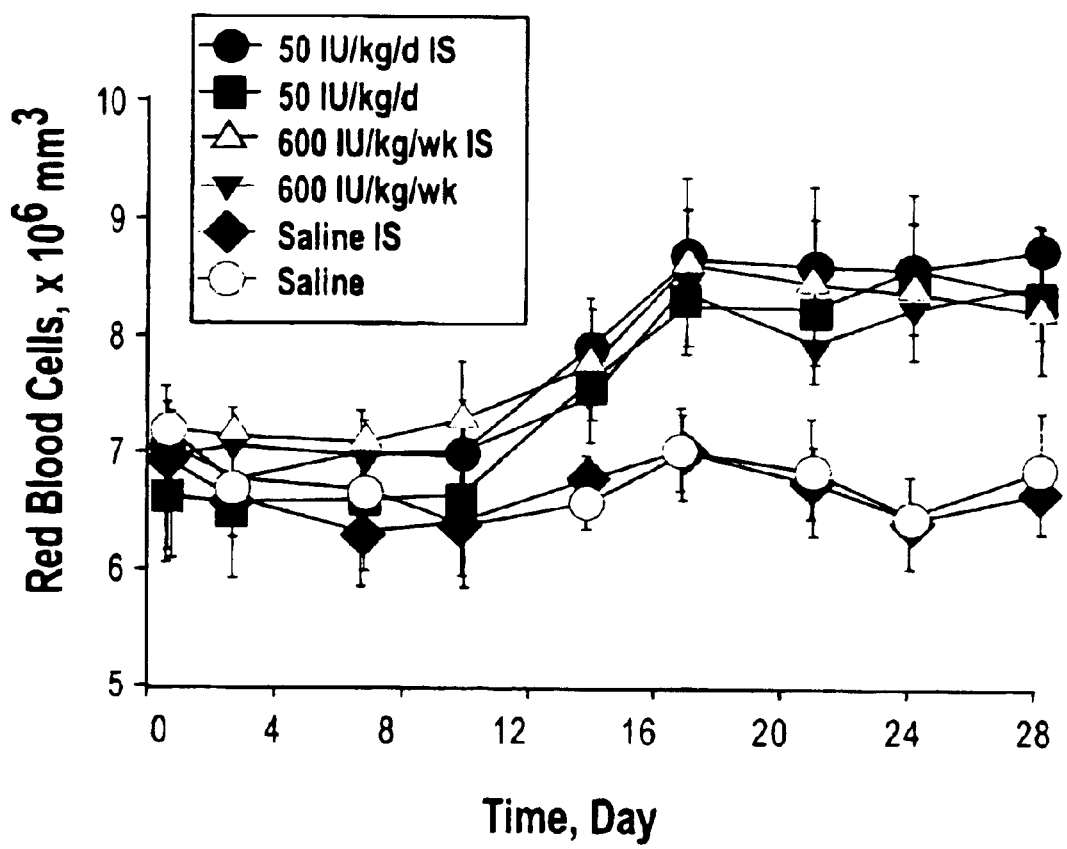
FIG. 72: Mean red blood cell time-concentration profiles by day for immunosuppressed and nonimmunosuppressed dogs. The closed circles represent EPO administered at 50 IU/kg/d IS dogs, the closed squares represent EPO administered at 50 IU/kg/d t.i.w. for non-IS dogs, the open triangle represents EPO administered at 600 IU/kg/wk for IS dogs, the closed triangles represent EPO administered at 600 IU/kg/wk for non-IS dogs, the closed diamonds represent saline control for IS dogs, and the shaded octagon represent the saline control for non-IS dogs.

Results:

The results from this study are presented in FIGS. 71 and 72. The results from this study indicate that the dynamic responses (patterns of rise in hemoglobin and red blood cells) over the 4 week study period are similar after the dosing regimens of 50 IU/kg/day and 600 IU/kg/week in immunosuppressed or non-immunosuppressed dogs.

EXAMPLE 8

PK/PD Modeling of Recombinant Human EPO After Three IV and Six SC Dose Administrations in Male Cynomolgus Monkeys Objectives:

The purpose of this study was to utilize the PK/PD model of the present invention to characterize the pharmacokinetics (PK) and pharmacodynamics (PD) profiles of rHuEpo in terms of increased reticulocyte, red blood cell and hemoglobin counts in blood after IV administration of three single doses and SC administration of six single doses of rHuEpo (EPREX®) in male cynomolgus monkeys.

Methods:

Data were obtained from two studies performed by RWJPRI (Sbi Study Nos 0876-49 and 0875-49 and RWJPRI Study Nos DM99146 and DM99124, Dec. 1999). One study was a parallel group study performed in 12 male cynomolgus monkeys (Sbi Study No 0876-49 and RWJPRI Study No. DM99146, Dec. 1999). Monkeys were divided into 4 groups, one group being the control while the other three being injected intravenously with 500, 2000 and 4000 IU/kg of EPREX®. Blood samples were drawn predose and up to 48 hours for measuring rHuEpo concentrations. The other study was a parallel group study done in 21 male cynomolgus monkeys which were divided into 7 groups with 3 monkeys per group Sbi Study No. 0875-49 and (RWJPRI Study No. DM99124, Dec. 1999). The control group received subcutaneously sterile saline while the remaining six groups were administered 400, 1000, 2400, 5000, 20000 and 40000 IU/kg of EPREX® subcutaneously. Animals were assigned so as to have a uniform body weight distribution across groups. Blood samples were drawn predose and at various times after administration up to day 28 for rHuEpo concentrations as well as reticulocyte, erythrocyte and hemoglobin counts. The mean data were used for this analysis.

Figure 73:
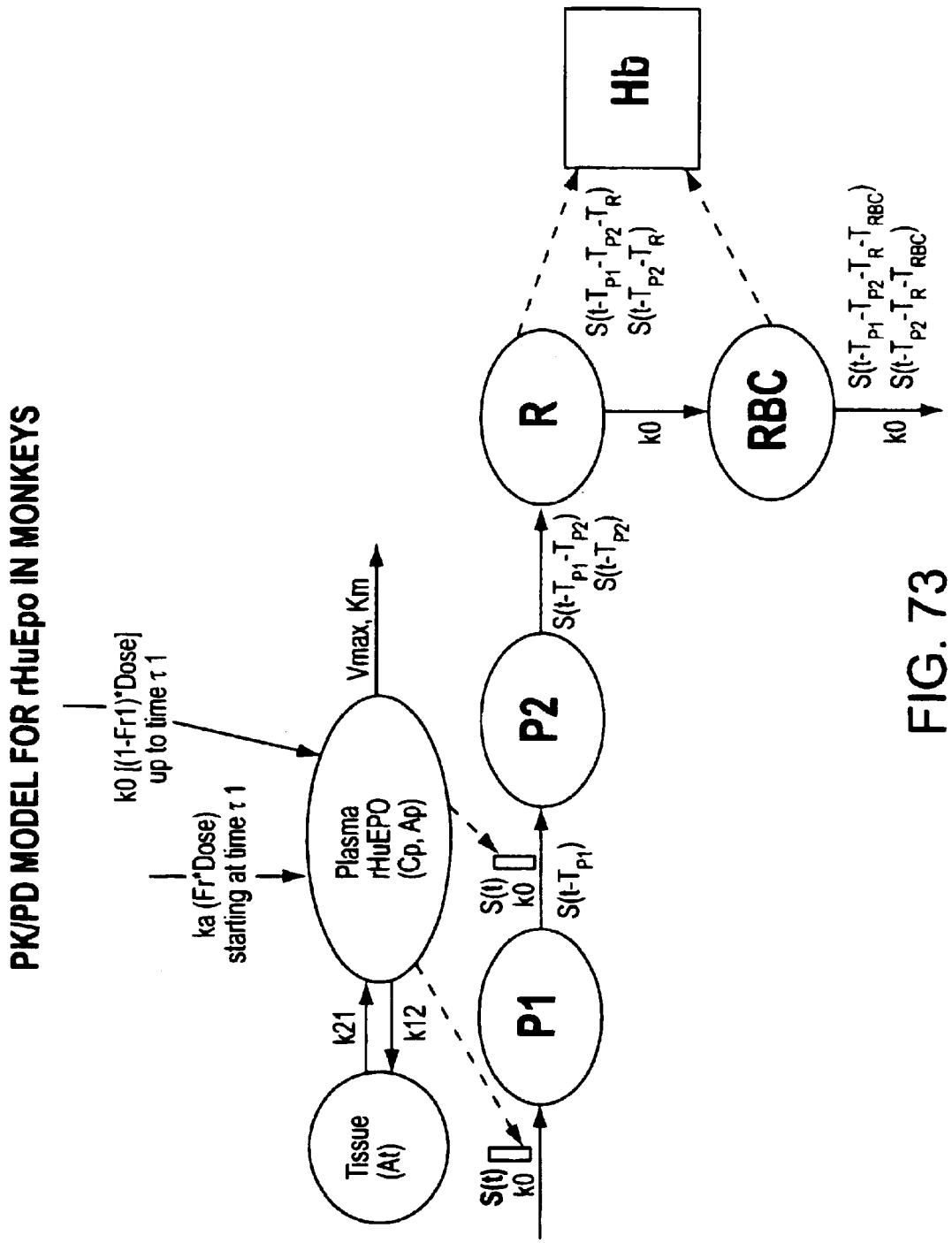
FIG. 73: PK/PD model for rHuEPO in monkeys.

Model: A Schematic Representation of the PK/PD Model is Depicted in FIG. 73.

Pharmacokinetics: A 2-compartment model was chosen to account for the polyexponentiality in the kinetic profiles upon IV administration. Non-compartmental analysis indicated non-linearity in the kinetics, which was modeled using the Michaelis-Menten disposition function. A dual absorption kinetic model with a rapid zero-order input of a fraction of the dose followed by a slow first-order input of the remainder was used to characterize the absorption of rHuEpo upon SC administration. The six single SC doses as well as the three IV doses were fitted simultaneously to this model to obtain a common set of parameters to characterize all the data.

The differential equations used for modeling the intravenous kinetics were:

$$\frac{dAp}{dt} = -Vmax \cdot Ap/(Km \cdot Vd + Ap) - k12 \cdot Ap + k21 \cdot At$$

$$\frac{dAt}{dt} = k12 \cdot Ap - k21 \cdot At$$

The SC data were modeled with the following equations:

$$\frac{dAp}{dt} = ko(0 - \tau_1) + k_1(t > \tau_1) - Vmax \cdot Ap/(Km \cdot Vd + Ap) - k12 \cdot Ap + k21 \cdot At$$

$$\frac{dAt}{dt} = k12 \cdot Ap - k21 \cdot At$$

where $ko = 0$ when $t > \tau_1$ $ko = \dfrac{F \cdot (1 - Fr) \cdot Dose}{\tau_1}$; when $0 < t \leq \tau_1$ $k_1 = 0$ when $t \leq \tau_1$ and $k_1 = ka \cdot F \cdot Fr \cdot Dose \cdot e^{-(ka \cdot (t - \tau_1))}$ when $t > \tau_1$ Ap represents the amount of drug in the plasma while At represents the drug in the peripheral compartment (i e, tissue). The microconstants k12 and k21 are first order rates of transfer between the central (plasma) and peripheral compartments. Vmax and Km are the Michaelis-Menten constants representing the capacity of the process and concentration at which one-half Vmax are reached. The Fr is the fraction of the dose associated with the first-order pathway of absorption k1. The time period (tau1) for the zero-order input (ko) was fixed to 10 hours based on the data and initial runs. A single first-order rate of absorption ka could describe all the doses except the lowest dose (400 IU/kg) for which a separate ka was estimated. The bioavailability F appeared to change with dose and was estimated for the lowest two doses and fixed to 100% for the remaining doses.

The catenary aging pharmacodynamic model (FIG. 73) with two precursor cell compartments having different lifespans was used for modeling the pharmacodynamics of EPREX®. Stimulation of production was assumed to occur at the production rates of both precursor compartments. The k0 represents the zero order production rate of cells while $T_R$ and $T_{RBC}$ stand for the lifespans of the reticulocyte and red blood cells.

The baseline rHuEpo concentrations were assumed to be zero and hence the baseline reticulocyte level was given by k0 $T_R$. The differential equation used for estimation purposes were as follows:

$$\frac{dR}{dt} = k0 \cdot \big((1 + S(t - TP2)) \cdot (1 + S(t - TP1 - TP2)) - (1 + S(t - TP2 - T_R)) \cdot (1 + S(t - TP1 - TP2 - T_R))\big)$$

where the stimulation function is given by the Hill equation, with gamma fixed to 1.

$$S(t) = \frac{Smax \cdot (C_{EPO})^\gamma}{SC_{50}^\gamma + (C_{EPO})^\gamma}$$

The reticulocyte numbers after administration of the six dose levels of EPREX® were fitted to the above equation to get a single set of dynamic parameters characterizing the data across all the doses. The parameters for the kinetic model were fixed and used as the forcing function for the dynamics. The predose reticulocyte counts were fixed to be the steady-state baseline values.

The dynamic parameters obtained from the reticulocyte fittings were used to simulate the RBC numbers and hemoglobin levels for all the doses. The 48 hour RBC count was used as the baseline while the hemoglobin content per cell was fixed for each group from the ratio of the predose hemoglobin count to the predose total number of cells (RBC+reticulocytes) for that group.

The differential equations used for simulation purposes were as follows:

$$\frac{dRBC}{dt} = k0 \cdot \left( \begin{array}{l} (1 + S(t - TP2 - T_R)) \cdot (1 + S(t - TP1 - TP2 - T_R)) - \\ (1 + S(t - TP2 - T_R - T_{RBC})) \cdot (1 + S(t - TP1 - TP2 - T_R - T_{RBC})) \end{array} \right)$$

$$Hb_t = Hb_{cell} \cdot (RBC_t + R_t)$$

Figure 74:
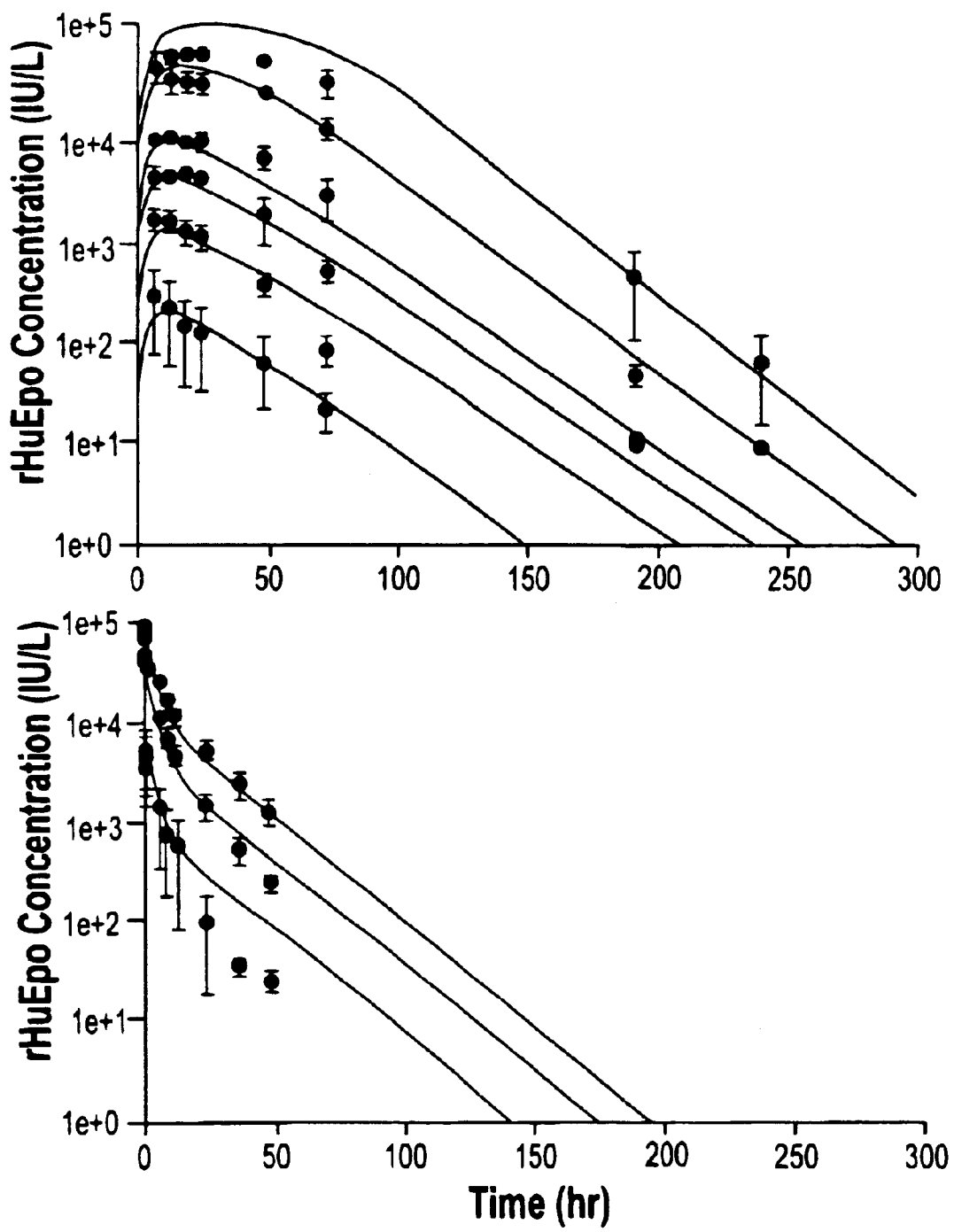
FIG. 74: The fittings for the rHuEpo concentration-time profiles after administrations of three single intravenous doses and six single subcutaneous doses of EPREX®. The parameters obtained are listed in FIG. 75.

Results:

FIG. 74 shows the fittings for the rHuEpo concentration-time profiles after administrations of three single intravenous doses and six single SC doses of EPREX®. The parameters obtained are listed in FIG. 75. The two compartment kinetic model with non-linear disposition could adequately capture the multiphasic IV kinetic profiles although the terminal phase for the lowest dose seems to be slightly overestimated. A high Km value was estimated which indicates that the non-linearity in disposition is mild and would be prominent only at high doses. The central volume of distribution Vd was estimated to 57 ml/kg, which is close to the blood volume. For the SC administrations, the bioavailability substantially increased with dose with the lowest dose showing a bioavailability of 26.8% and the next higher dose 73%. The lowest dose has a slightly different ka value compared to the rest of the doses. It can be inferred from the parameter estimates that a major fraction of the bioavailable dose follows the slow first-order pathway. The zero-order route of entry seems to be fast and accounts for a smaller fraction (35.5%) of the bioavailable dose.

Figure 76A:
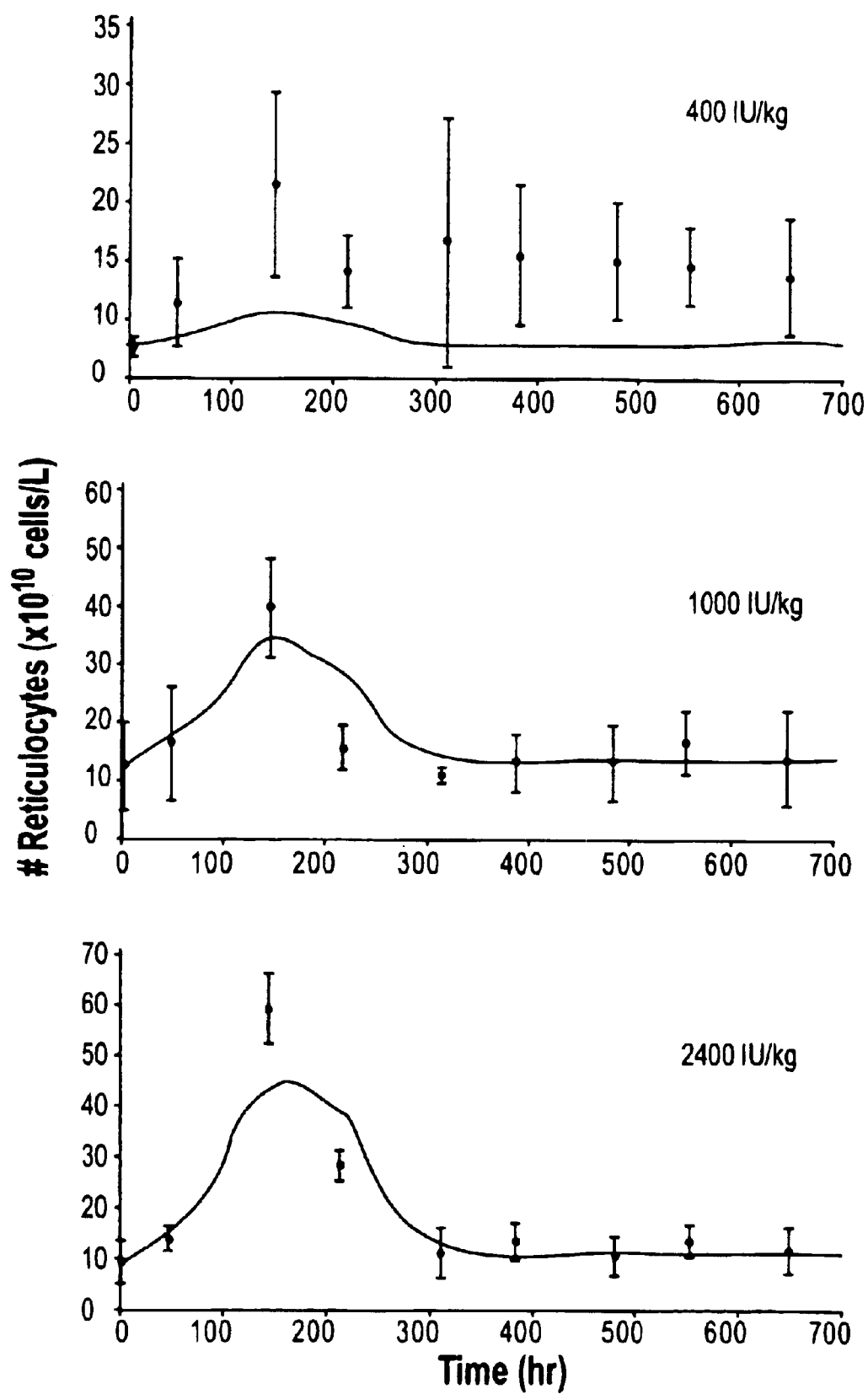
FIG. 76A: Mean reticulocyte concentration-time profiles for the 400 IU/kg, 1000 IU/kg, and 2400 IU/kg dosing regimens.
Figure 76B:
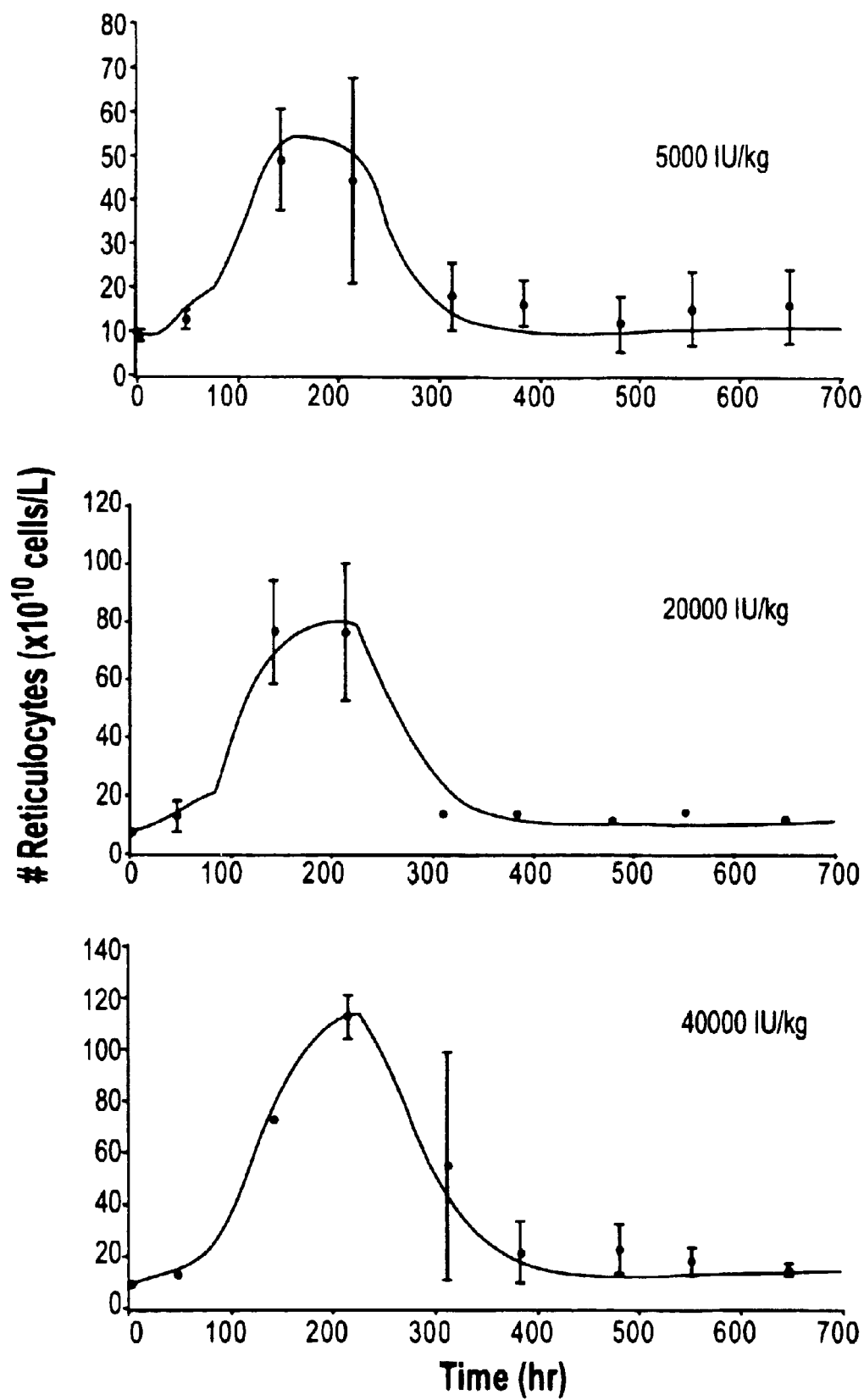
FIG. 76B: Mean reticulocyte concentration-time profiles for the 5000 IU/kg, 20,000 IU/kg, and 40,000 IU/kg dosing regimens.
Figure 78A:
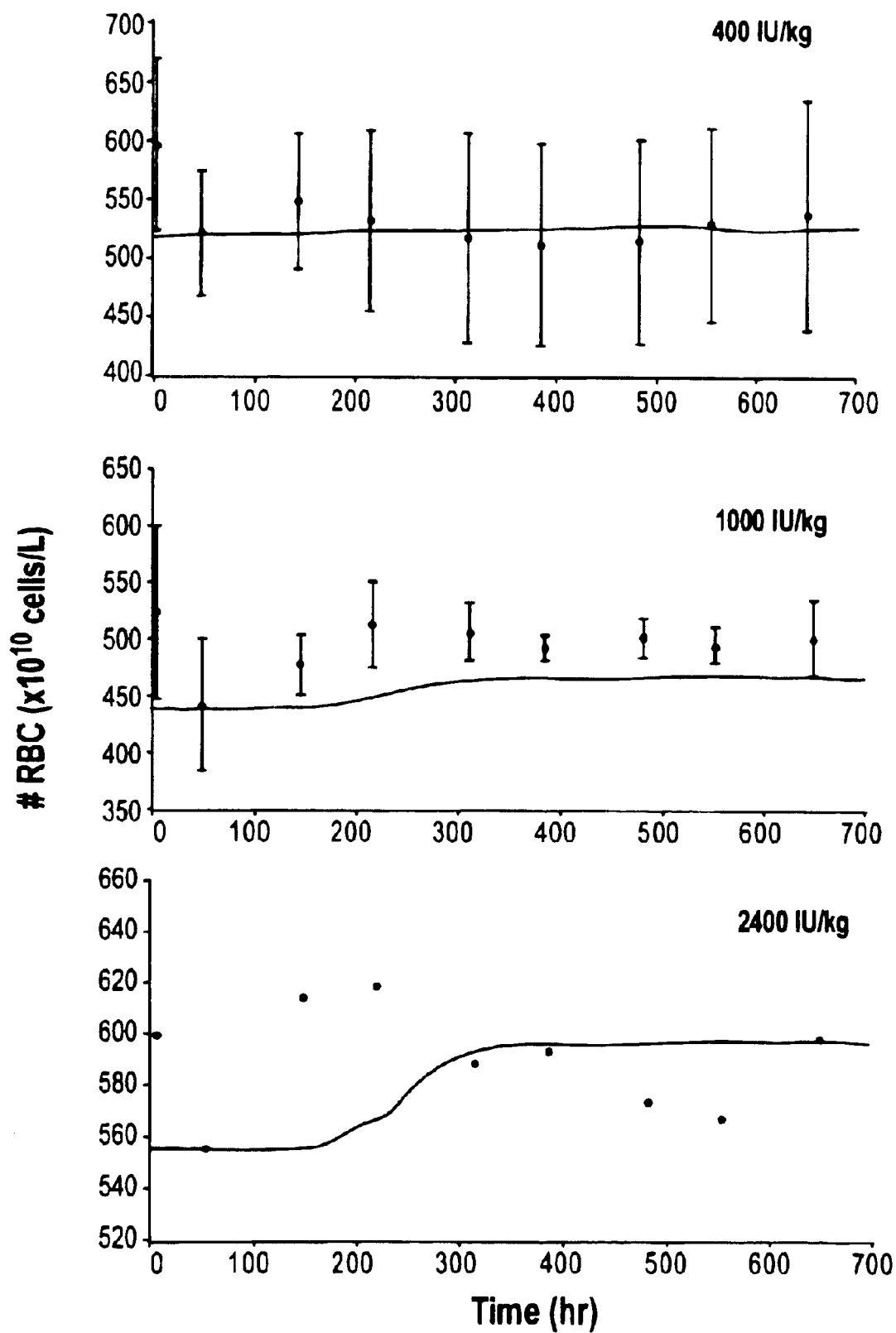
FIG. 78A: Mean RBC concentration-time profiles for the 400 IU/kg, 1000 IU/kg, and 2400 IU/kg dosing regimens.
Figure 78B:
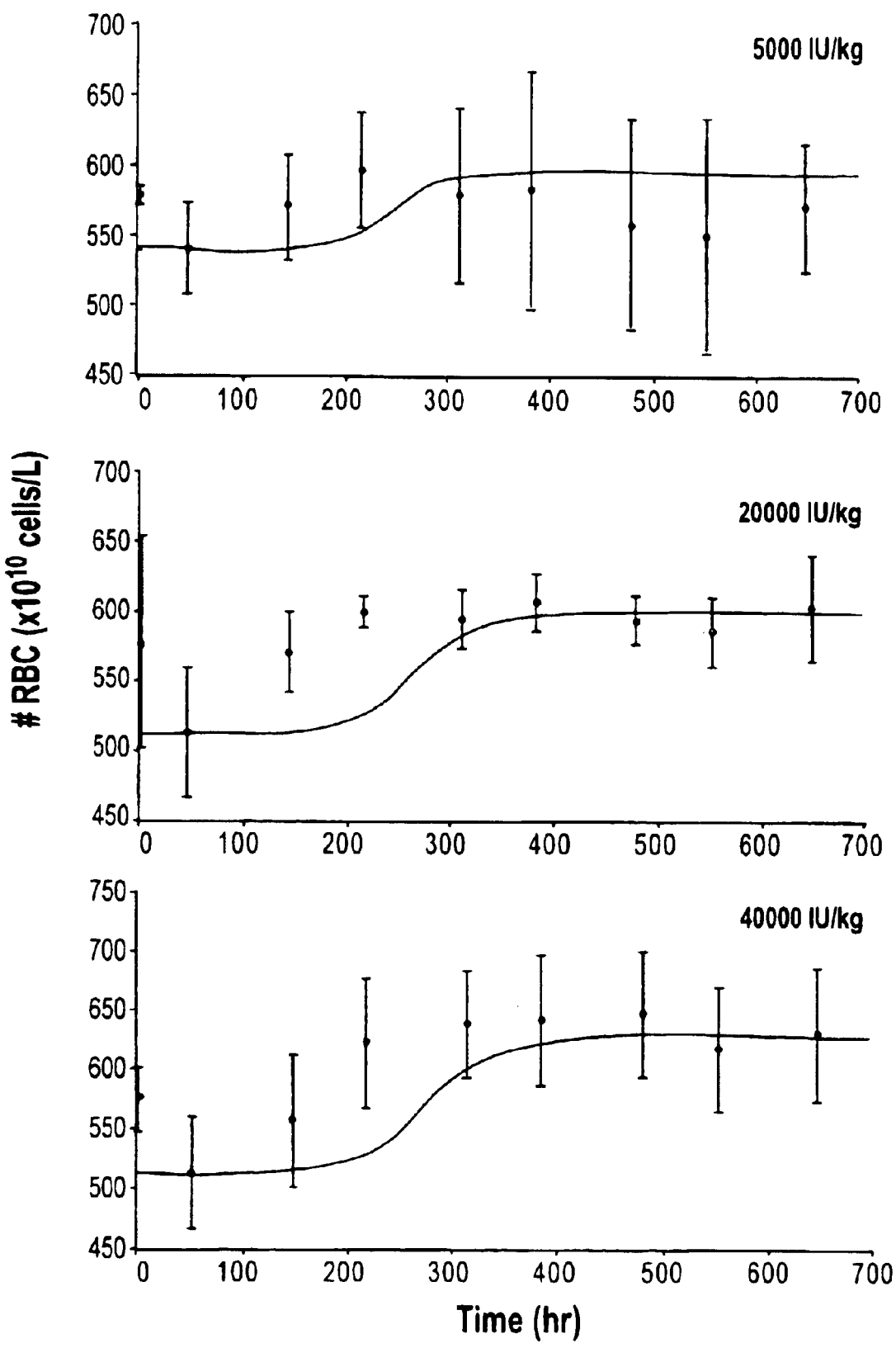
FIG. 78B: Mean RBC concentration-time profiles for the 5000 IU/kg, 20,000 IU/kg, and 40,000 IU/kg dosing regimens.
Figure 79A:
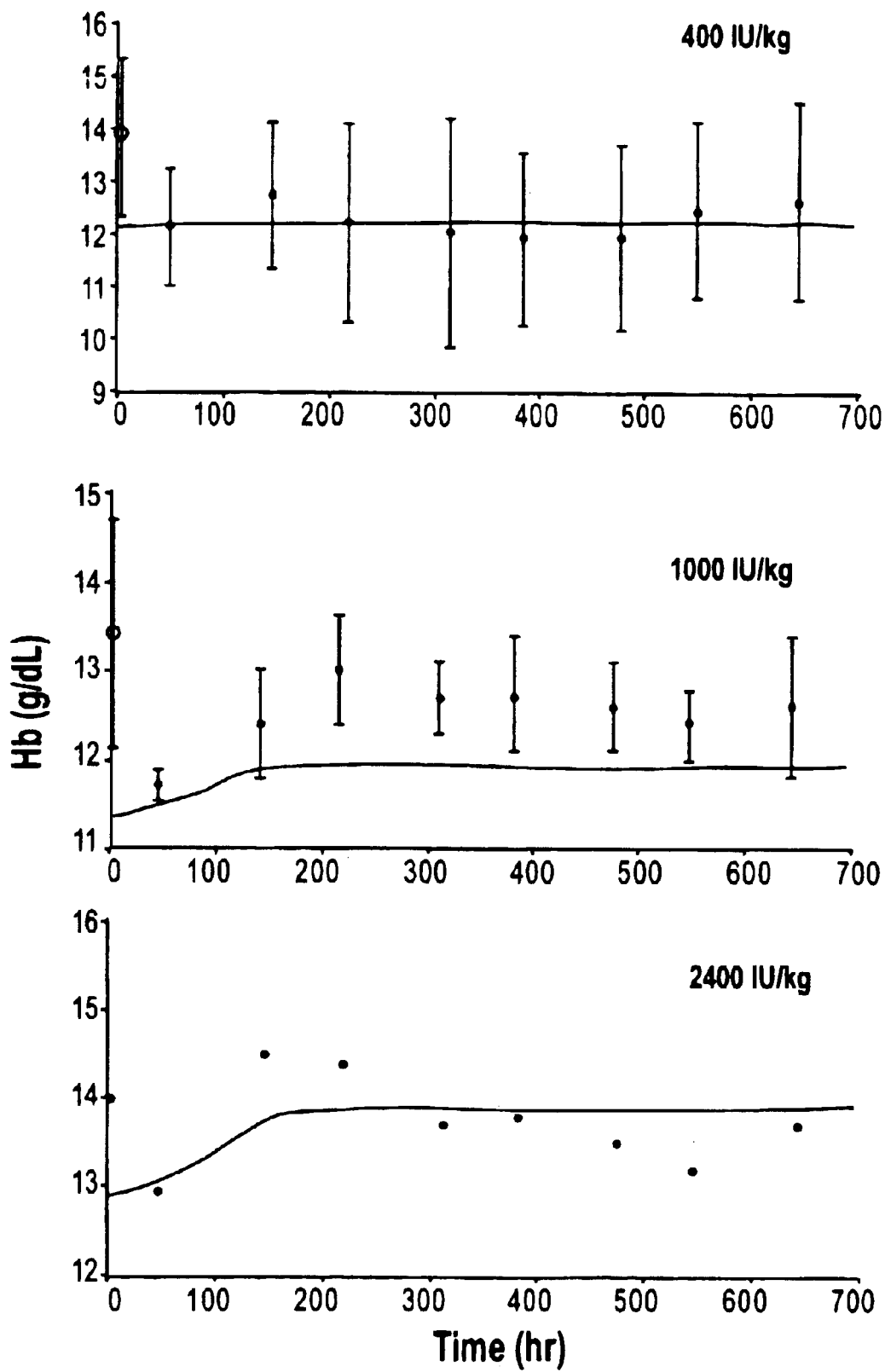
FIG. 79A: Mean hemoglobin concentration profiles for the 400 IU/kg, 1000 IU/kg, and 2400 IU/kg dosing regimens.
Figure 79B:
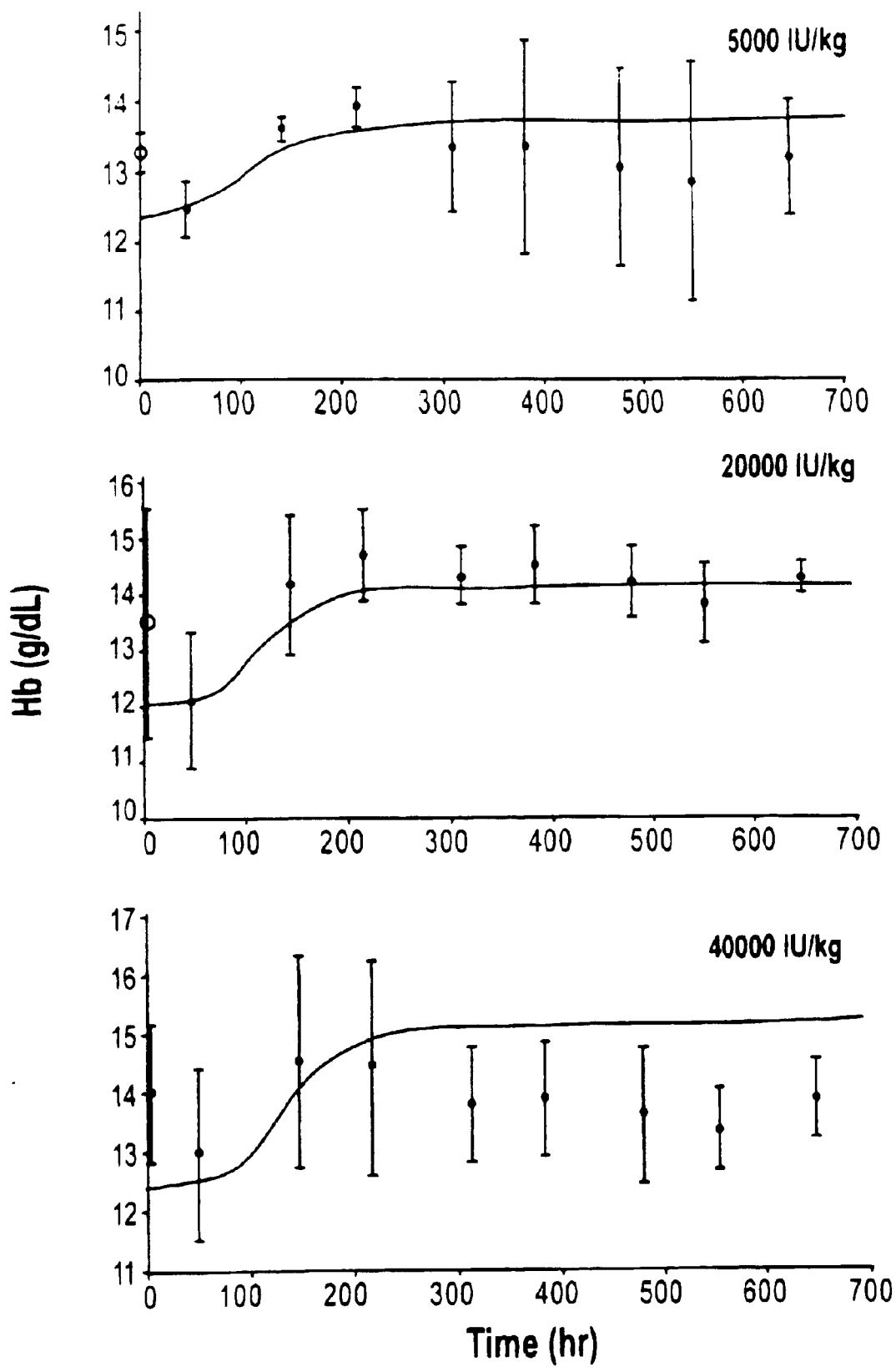
FIG. 79B: Mean hemoglobin concentration profiles for the 5,000 IU/kg, 20,000 IU/kg, and 40,000 IU/kg dosing regimens.

The reticulocyte fittings are shown in FIGS. 76a, 76b, and 77 lists the pharmacodynamic parameters estimated. The lag time which is accounted for by the second precursor compartment TP2 was small (~15 hr). The estimated reticulocyte lifespan was close to 6 days. The Smax, which signifies the maximum possible increase in production rate, was 3.133 whereas a high $SC_{50}$ value of 842.5 IU/L was estimated. FIGS. 78a and 78b show the simulations for the RBC numbers and FIGS. 79a and 79b are simulations for the hemoglobin response.

Figure 81:
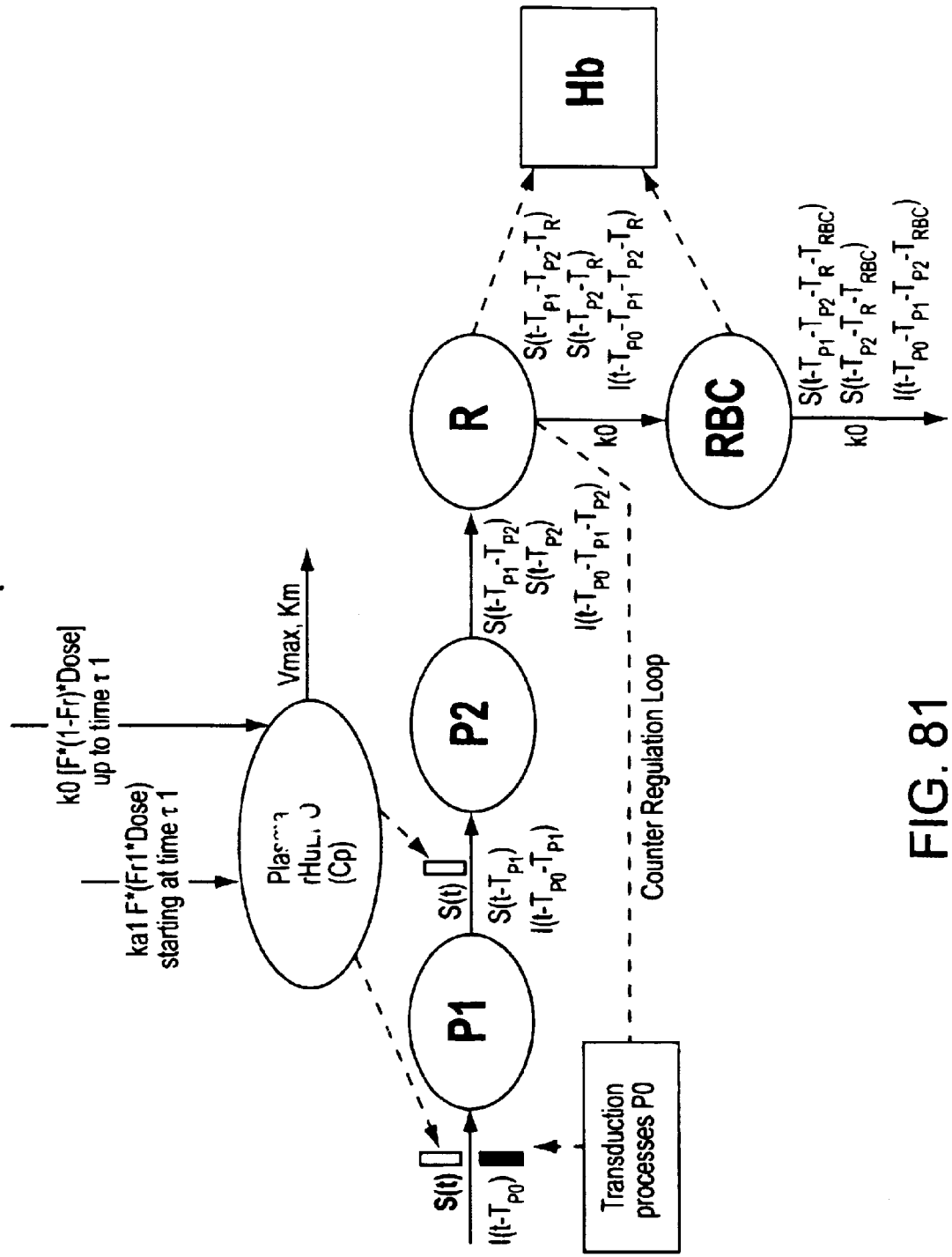
FIG. 81: PK/PD model for rHuEPO in humans.

FIG. 80 shows the pharmacodynamic parameters obtained after administration of EPREX® in healthy humans. The pharmacokinetic model was simplified from a 2-compartment to a 1-compartment model based on the IV concentration-time profiles. The pharmacodynamic model was extended by employing control of cell production by endogenous EPO levels and an extra component accounting for the body's natural feedback mechanism was also included (FIG. 81). This was done by assuming that reticulocytes cause a feedback inhibition of their own production by reducing the production rate of the earliest cells represented by the P1 compartment. It was also assumed that it takes a time of TP0 hours for this inhibition to take effect. The inhibition was modeled using the Hill function. A comparison of the pharmacodynamic parameter estimates between monkeys and humans shows that the compartment lifespan parameters are very similar between these species. The Smax and the SC50 values seem to differ between species, but this might be due to the added complexity of counter-regulation and baseline Epo concentrations in the model for rHuEpo effects on reticulocytes in human.

Discussion:

Pharmacokinetics: Upon IV administration, the kinetics followed a biexponential decline, which was captured using a two-compartment model with non-linear disposition. The primary site of action of rHuEpo is the bone marrow, which is a highly perfused tissue, and so the peripheral compartment in the model may only represent some non-specific binding of rHuEpo. The terminal phase for the lowest dose was overestimated which could be due to unavailability of concentration measurements for the later time points or possibly a different kinetic behavior in the range of this dose. Similar to humans, the estimated Vd was very close to the blood volume in monkeys, and the kinetics were mildly non-linear as indicated by the high Km value.

After SC administration, the peak concentrations of rHuEpo were attained within one day and rHuEpo remained in circulation for a much longer time compared to that after IV administration due to the occurrence of the flip-flop phenomenon with ka governing the terminal phase. These data patterns were acceptably captured using a multiphase absorption model. The initial concentrations for the highest SC dose were slightly overestimated. However, this should be acceptable considering the fact that a single set of parameters was used to describe all the dose levels. Our dual absorption kinetic model can be used to explain the different pathways for absorption of the drug from the SC site. The rapid zero-order input of a part of the dose may be explained by a direct entry via blood vessels in the subcutaneous site to the blood. On the other hand, another fraction of the dose can be assumed to enter the lymphatics and undergo a slow process of first-order absorption from the lymph to the blood. This would also explain the 10-hour time lag for start of the first order absorption. The bioavailability increased with dose and was 100% for doses of 2400 IU/kg and higher. This same dual absorption model well characterized the SC kinetics in human and showed a similar trend of increasing bioavailability with dose. However, unlike in monkeys, the model predicted a major fraction of the dose to be absorbed via the zero-order pathway in humans.

Pharmacodynamics: The reticulocyte counts started rising within 48 hours and peaked around 10 days after which they started dropping and returned to baseline levels by 20 days. Our catenary-aging model seems to characterize the data well. Simulations in FIGS. 78a, 78b, 79a and 79b show that the reticulocyte dynamics can be readily used to predict the change in RBC numbers as well as hemoglobin counts.

The exact mode of action of erythropoietin is still not fully understood. The primary action of rHuEpo was thought to be stimulation of the proliferation of early progenitor cells. However, there is evidence from studies on experimental animals that erythropoietin acts on the differentiated erythroblasts as well (Krantz et al., *Erythropoietin and the regulation of erythropoesis*, 1970, The University of Chicago Press). This school of thought has led to the proposal that rHuEpo acts on the mature erythroblasts to give rise to an early 24-hour reticulocyte response followed by a macrocytosis due to an additional effect on normoblasts. Based on this theory, we developed the mechanistic catenary-aging model with rHuEpo stimulation occurring at two precursor cell populations, which might represent the erythroblasts and the earlier progenitor cells.

Erythroblasts are known to undergo 2 to 5 cell divisions with a mean maturation or turnover time of 11 to 48 hours depending on the species (Id., Aplen et al., 1959, *Ann. N.Y. Acad. Sci.*, 77:753, Osgood, E., 1954, *Blood*, 9:1141, and Fliedner et al., 1959, *Acta. Haematol.*, 22:65). Our model predicts that there is an 15 hr lag time before the newly produced reticulocytes are actually released into circulation, and this reflects the erythroblast maturation time.

The estimated reticulocyte lifespan is 6 days. In humans, the normal lifespan of cells in the reticulocyte stage is around 3.5 days in the marrow and I to 2 days in the blood (Hillman et al., 1967, *Sem. Haematol.*, 4(4): 327). However, in animal models of severe anemia, it has been demonstrated that the marrow reticulocyte pool is shifted to the circulation (Id., and Bessis et al., 1973, *Living blood cells and their ultrastructure*, Verlag New York-Heidelberg-Berlin). These displaced marrow reticulocytes take up to 3 days longer than normal reticulocytes to produce erythrocytes. Hence we could expect that the average lifespan of reticulocytes estimated by our model reflects the sum of the maturation times in the marrow and blood.

It has been reported in literature that in humans, it takes an average of 5 days for an erythroid precursor to form a reticulocyte in the marrow (Krantz et al., supra). This time actually reflects the sum of the times a cell spends in the P1 and P2 compartments, which was estimated to be 85 hours.

In conclusion, the rHuEPO kinetics and dynamics seems to be fairly similar across species (monkey and human) and the models of the present invention can well approximate the kinetics and dynamics of rHuEpo effects and gives realistic estimates of the cell aging time parameters.

Various modifications and variations of the described examples and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in related fields are intended to be within the scope of the following claims.

We claim:

1. A method comprising the step of:
   administering at least one EPO dose to a patient according to an EPO dosing regimen, wherein said regimen maintains at least a serum EPO concentration above a predose level for about 5 to about 30 days between EPO doses.

2. The method of claim 1, wherein said serum EPO concentration is sufficient to increase production of red blood cells.

3. The method of claim 2, wherein said serum EPO concentration is sufficient to maintain increased red blood cell production for at least one week.

4. The method of claim 2, wherein said serum EPO concentration is sufficient to maintain increased red blood cell production for at least two weeks.

5. The method of claim 1, wherein said EPO dosing regimen comprises administering EPO once a week.

6. The method of claim 5, wherein said once weekly EPO dosing regimen comprises administering a dose of EPO in the range of about 300 IU/kg to about 2400 IU/kg.

7. The method of claim 5, wherein said once weekly EPO dosing regimen comprises administering a dose of EPO in the range of about 30,000 IU to about 54,000 IU.

8. The method of claim 1, wherein said EPO dosing regimen comprises administering a dose of EPO once every two weeks.

9. The method of claim 8, wherein said once every two weeks EPO dosing regimen comprises administering a dose of EPO in the range of about 900 IU/kg to about 1200 IU/kg.

10. The method of claim 1, wherein said EPO dosing regimen comprises administering EPO once every ten days.

11. The method of claim 10, wherein said once every ten days EPO dosing regimen comprises administering a dose of EPO of about 900 IU/kg.

12. The method of claim 1, 3, 4, 5, 8, or 10, wherein said EPO dosing regimen comprises administering EPO selected from the group consisting of epoietin alpha and darbepoietin alpha.

13. The method of claim 1, wherein said EPO dosing regimen comprises administering EPO selected from the group consisting of novel erythropoeisis stimulating protein (NESP), human erythropoietin analog, and erythropoietin omega.

14. The method of claim 1, wherein said EPO dosing regimen comprises administering proteins having EPO biological activity.

15. The method of claim 14, wherein said proteins having EPO biological activity are selected from the group consisting of erythropoietin analogs, erythropoietin isoforms, and renal erythropoietin.

16. The method of claim 1, wherein said EPO dosing regimen comprises administering EPO derived from the group consisting of naturally occurring EPO, recombinant EPO, and synthetic EPO.

17. The method of claim 1, wherein said patient has anemia.

18. The method of claim 17, wherein said anemia comprises EPO concentration related anemia.

19. The method of claim 18, wherein said anemia is selected from the group consisting of end-stage renal failure, renal failure related anemia, and dialysis related anemia.

20. The method of claim 17, wherein said anemia comprises cancer chemotherapy related anemia.

21. The method of claim 17, wherein said anemia comprises AIDS drug therapy related anemia.

22. The method of claim 17, wherein said anemia comprises drug related anemia.

23. The method of claim 22, wherein said drug is selected from the group consisting of cisplatin and carboplatin.

24. The method of claim 22, wherein said drug is zidovudine.

25. The method of claim 1, wherein said patient is undergoing blood donation.

26. The method of claim 1, wherein said patient has received a bone marrow transplant.

27. The method of claim 1, wherein said patient has rheumatoid arthritis.

28. The method of claim 1, wherein said EPO dosing regimen comprises administering EPO via a route selected from the group consisting of intravenous administration, subcutaneous administration, and parental administration.

29. The method of claim 1, wherein said EPO dosing regimen comprises administering EPO having a modified glycosylation pattern.

30. The method of claim 29, wherein said EPO having a modified glycosylation pattern comprises darbepoietin alpha.

* * * * *

Disclaimer

6,747,002 B2 — Wing Cheung, Warren, NJ (US); David Gibson, Bassersdorf (CH); Christine Cote, Skillman, NJ (US); and Els Vercammen, Dietlikon (CH). PHARMACOKINETIC AND PHARMACODYNAMIC MODELING OF ERYTHROPOIETIN ADMINISTRATION. Patent dated Jun. 8, 2004. Disclaimer filed September 17, 2013, by the assignee, Janssen Pharmaceuticals, Inc.

Hereby disclaim the complete claims 1-7, 12 and 14-28 of said patent.

*(Official Gazette, November 12, 2013)*

(12) INTER PARTES REVIEW CERTIFICATE (22nd)
United States Patent
Cheung et al.

(10) Number: US 6,747,002 K1
(45) Certificate Issued: Jul. 16, 2014

(54) PHARMACOKINETIC AND PHARMACODYNAMIC MODELING OF ERYTHROPOIETIN ADMINISTRATION

(75) Inventors: Wing Cheung; David Gibson; Christine Cote; Els Vercammen

(73) Assignee: Janssen Pharmaceuticals, Inc.

Trial Number:

IPR2013-00365 filed Jun. 19, 2013

Petitioner: Hospira, Inc.

Patent Owner: Janssen Pharmaceuticals, Inc.

Inter Partes Review Certificate for:

Patent No.: 6,747,002
Issued: Jun. 8, 2004
Appl. No.: 09/569,612
Filed: May 10, 2000

The results of IPR2013-00365 are reflected in this inter partes review certificate under 35 U.S.C. 318(b).

INTER PARTES REVIEW CERTIFICATE
U.S. Patent 6,747,002 K1
Trial No. IPR2013-00365
Certificate Issued Jul. 16, 2014

AS A RESULT OF THE INTER PARTES REVIEW PROCEEDING, IT HAS BEEN DETERMINED THAT:

Claims 1-7, 12 and 14-28 are disclaimed.

\* \* \* \* \*